US012516051B1

(12) United States Patent
Chen et al.

(10) Patent No.: US 12,516,051 B1
(45) Date of Patent: Jan. 6, 2026

(54) SMALL MOLECULE DEGRADERS AND FLUORESCENT PROBES OF PXR

(71) Applicant: St. Jude Children's Research Hospital, Inc., Memphis, TN (US)

(72) Inventors: Taosheng Chen, Germantown, TN (US); Andrew Huber, Collierville, TN (US); Young-Hwan Jung, League City, TX (US); Yongtao Li, Changsha (CN); Wenwei Lin, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 0 days.

(21) Appl. No.: 18/955,583

(22) Filed: Nov. 21, 2024

Related U.S. Application Data

(63) Continuation of application No. 18/902,844, filed on Sep. 30, 2024.

(51) Int. Cl.

| | |
|---|---|
| ***C07D 417/14*** | (2006.01) |
| ***A61K 47/55*** | (2017.01) |
| ***C07F 5/02*** | (2006.01) |
| ***G01N 21/64*** | (2006.01) |
| ***G01N 33/53*** | (2006.01) |

(52) U.S. Cl.
CPC ............ *C07D 417/14* (2013.01); *A61K 47/55* (2017.08); *C07F 5/022* (2013.01); *G01N 21/6428* (2013.01); *G01N 33/5308* (2013.01); *G01N 2021/6439* (2013.01)

(58) Field of Classification Search
CPC .................................................... C07D 417/14
See application file for complete search history.

(56) References Cited

U.S. PATENT DOCUMENTS

| | | | | |
|---|---|---|---|---|
| 6,100,398 | A | 8/2000 | Hartwig et al. | |
| 11,179,373 | B2 * | 11/2021 | Ciulli | A61P 35/00 |
| 2013/0274298 | A1 | 10/2013 | Boechat et al. | |
| 2016/0279146 | A1 | 9/2016 | Tuiten et al. | |
| 2019/0077770 | A1 | 3/2019 | Chen et al. | |
| 2019/0367475 | A1 | 12/2019 | Mani et al. | |
| 2020/0071281 | A1 | 3/2020 | Chen et al. | |
| 2024/0252658 | A1 | 8/2024 | Pascussi et al. | |

FOREIGN PATENT DOCUMENTS

| | | | |
|---|---|---|---|
| WO | WO 2007/115058 | A2 | 10/2007 |
| WO | WO 2010/045188 | A1 | 4/2010 |
| WO | WO 2014/134232 | A1 | 9/2014 |
| WO | WO 2015/058160 | A1 | 4/2015 |
| WO | WO 2015/078949 | A1 | 6/2015 |
| WO | WO 2017/165139 | A1 | 9/2017 |

OTHER PUBLICATIONS

Aalten, H. L. et al., (1989) "The copper catalyzed reaction of sodium methoxide with aryl bromides. A mechanistic study leading to a facile synthesis of anisole derivatives" Tetrahedron 45, 5565-78.

Bai, B.; et al., (2020) "Deep Multilayer Brain Proteomics Identifies Molecular Networks in Alzheimer's Disease Progression" Neuron 105 (6), 975-991 e7.

Beattie, D. et al., (2012) "An investigation into the structure-activity relationships associated with the systematic modification of the β2-adrenoceptor agonist indacaterol" Bioorg. Med Chem. Lett. 22, 6280-6285.

Bertilsson, G.; et al., (1998) "Identification of a human nuclear receptor defines a new signaling pathway for CYP3A induction" Proc Natl Acad Sci U S A 95 (21), 12208-12213.

Blumberg, B.; et al., (1998) "SXR, a novel steroid and xenobiotic-sensing nuclear receptor" Genes Dev 12 (20), 3195-3205.

Bouhlel, A. et al., (2010) "Synthesis and evaluation of original amidoximes as antileishmanial agents" Bioorg. Med. Chem. 18, 7310-7320.

Burk, O.; et al., (2004) "The induction of cytochrome P450 3A5 (CYP3A5) in the human liver and intestine is mediated by the xenobiotic sensors pregnane X receptor (PXR) and constitutively activated receptor (CAR)" J Biol Chem 279 (37), 38379-85.

Carotti, A et al.(2014) "Beyond Bile Acids: Targeting Farnesoid X Receptor (FXR) with Natural and Synthetic Ligands" Current Topics in Medicinal Chemistry, vol. 14, pp. 2129-2142; p. 2131, col. 2, paragraph 2; p. 2137, figure 14.

Chai, S. C.; et al., (2020) "Strategies for developing pregnane X receptor antagonists: Implications from metabolism to cancer" Med Res Rev 40 (3), 1061-1083.

Chakrabarty, M. et al., (1996) "An expedient synthesis of 5,11-dimethylindolo[3,2-b]carbazole, a potent ligand and the receptor for TCDD" Synth. Commun. 26, 3015-3023.

Chamberlain, P. P.; et al., (2019) "Development of targeted protein degradation therapeutics" Nat Chem Biol 15 (10), 937-944.

Chan et al., (2018) "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds" J Med Chem 61(2) 504-513.

Chen, C.; et al., (2003) "Nuclear receptor, pregname X receptor, is required for induction of UDP-glucuronosyltranferases in mouse liver by pregnenolone-16 alpha-carbonitrile" Drug Metab Dispos 2003, 31 (7), 908-15.

Chen, D.; et al., (2020) "E3 ligase ZFP91 inhibits Hepatocellular Carcinoma Metabolism Reprogramming by regulating PKM splicing" Theranostics 10 (19), 8558-8572.

Chen, J.; et al., (1985) "Synthesis and crystal structure of isomerized butadiene (dicarbonyl)(ethoxyarylcarbene)iron complexes" J. Organomet. Chem. 286, 55-67.

(Continued)

*Primary Examiner* — Golam M Shameem
(74) *Attorney, Agent, or Firm* — Ballard Spahr LLP

(57) ABSTRACT

The present disclosure in one aspect, relates to compounds, compositions, and methods for degrading pregnane X receptor (PXR) protein. The invention further relates to the use of the disclosed compounds in decreasing adverse drug reactions such as, for example, adverse drug reactions associated with administration of an anticancer agent, an antibacterial agent, a non-steroidal anti-inflammatory agent, or an anti-convulsant agent. The invention, in one aspect, further relates to compounds, compositions, and methods for identifying PXR ligands. This abstract is intended as a scanning tool for purposes of searching in the particular art and is not intended to be limiting of the present disclosure.

15 Claims, 41 Drawing Sheets

(56) References Cited

OTHER PUBLICATIONS

Cheng, Z.; et al., (2009) "Structural insights into eRF3 and stop codon recognition by eRF1" Genes Dev 23 (9), 1106-18.
Connelly, J. P.; et al., (2019) "CRIS.py: A Versatile and High-throughput Analysis Program for CRISPR-based Genome Editing" Sci Rep 9 (1), 4194.
DiMasi, J. A.; et al., (2016) "Innovation in the pharmaceutical industry: New estimates of R&D costs" J Health Econ 47, 20-33.
Dixon, A. S.; et al., (2016) "NanoLuc Complementation Reporter Optimized for Accurate Measurement of Protein Interactions in Cells" ACS Chem Biol 11 (2), 400-8.
Donovan, K. A.; et al., (2020) "Mapping the Degradable Kinome Provides a Resource for Expedited Degrader Development" Cell 2020, 183 (6), 1714-1731 e10.
Dowden, H.; et al., (2019) "Trends in clinical success rates and therapeutic focus" Nat Rev Drug Discov 18 (7), 495-496.
Doyle, M. P. et al., (1977) "Alkyl nitrite-metal halide deamination reactions. 2. Substitutive deamination of arylamines by alkyl nitrites and copper(II) halides. A direct and remarkably efficient conversion of arylamines to aryl halides" J. Org. Chem. 42, 2426-31.
El-Ayache, N. C. et al., (2010) "Novel bis-arylsulfonamides and aryl sulfonimides as inactivators of plasminogen activator inhibitor-1 (PAI-1)" Bioorg. Med. Chem. Lett. 2010, 20, 966-970.
Florke Gee, R. R.; et al., (2023) "The F-box-only protein 44 regulates pregnane X receptor protein level by ubiquitination and degradation" Acta Pharm Sin B 13 (11), 4523-4534.
Furuya, T. et al., (2008) "Palladium-mediated fluorination of arylboronic acids" Angew. Chem., Int. Ed. 47, 5993-5996, S5993/1-S5993/78.
Galdeano, C.; et al., (2014) "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities" J Med Chem 57 (20), 8657-8663.
Garcia-Maldonado, E.; et al., (2024) "Chemical manipulation of an activation/inhibition switch in the nuclear receptor PXR" Nat Commun 15 (1), 4054.
Geick, A.; et al., (2001) "Nuclear receptor response elements mediate induction of intestinal MDR1 by rifampin" J Biol Chem 276 (18), 14581-7.
Goodwin, B.; et al., (2001) "Regulation of the human CYP2B6 gene by the nuclear pregnane X receptor" Mol Pharmacol 60 (3), 427-31.
Goodwin, B.; et al., (1999) "The orphan human pregnane X receptor mediates the transcriptional activation of CYP3A4 by rifampicin through a distal enhancer module" Mol Pharmacol 56 (6), 1329-1339.
Harmsen, S.; et al., (2009) "Nuclear receptor mediated induction of cytochrome P450 3A4 by anticancer drugs: a key role for the pregnane X receptor" Cancer Chemother Pharmacol 64 (1), 35-43.
High, A. A.; et al., (2017) "Deep Proteome Profiling by Isobaric Labeling, Extensive Liquid Chromatography, Mass Spectrometry, and Software-assisted Quantification" J Vis Exp (129).
Honig, P. K.; et al. (1992) "Changes in the pharmacokinetics and electrocardiographic pharmacodynamics of terfenadine with concomitant administration of erythromycin" Clin Pharmacol Ther 52 (3), 231-238.
Honig, P. K.; et al., (1993) "Terfenadine-ketoconazole interaction. Pharmacokinetic and electrocardiographic consequences" JAMA 269 (12), 1513-1518.
Huber, A. D.; et al., (2022) "SJPYT-195: A Designed Nuclear Receptor Degrader That Functions as a Molecular Glue Degrader of GSPT1" ACS Med Chem Lett 13 (8), 1311-1320.
Huber, A. D.; et al., (2024) A bromodomain-independent mechanism of gene regulation by the BET inhibitor JQ1: direct activation of nuclear receptor PXR. Nucleic Acids Res 52 (4), 1661-1676.
Huber, A. D.; et al., (2021) "Mutation of a single amino acid of pregnane X receptor switches an antagonist to agonist by altering AF-2 helix positioning" Cell Mol Life Sci 78 (1), 317-335.
Huber, A.D.; et al., (2024) "PROTAC-mediated activation, rather than degradation, of a nuclear receptor reveals complex ligand-receptor interaction network" Structure 32 1-12.
Ikemoto, N. et al., (2003) "Practical routes to the triarylsulfonyl chloride intermediate of a 133 adrenergic receptor agonist" Tetrahedron 59, 1317-1325.
Ishoey, M.; et al., (2018) "Translation Termination Factor GSPT1 Is a Phenotypically Relevant Off-Target of Heterobifunctional Phthalimide Degraders" ACS Chem Biol 13 (3), 553-560.
Ito, T.; et al., (2010) "Identification of a primary target of thalidomide teratogenicity" Science 327 (5971), 1345-50.
Ito, Y. et al., (2004) "The absolute stereochemistry of anachelins, siderophores from the cyanobacterium Anabaena cylindrica" Tetrahedron 60, 9075-9080.
Jin, X.; et al., (2010) "An atypical E3 ligase zinc finger protein 91 stabilizes and activates NF-kappaB-inducing kinase via Lys63-linked ubiquitination" J Biol Chem 285 (40), 30539-47.
Kliewer, S. A.; et al., (1998) "An orphan nuclear receptor activated by pregnanes defines a novel steroid signaling pathway" Cell 92 (1), 73-82.
Korwar, S. et al., (2014) Preparation and evaluation of deconstruction analogues of 7-deoxykalafungin as AKT kinase inhibitors. Bioorg. Med Chem. Lett. 24, 271-274.
Kronke, J.; et al., (2014) "Lenalidomide causes selective degradation of IKZF1 and IKZF3 in multiple myeloma cells" Science 343 (6168), 301-5.
Kruse, L. I. (1981) "Synthesis of 4-Substituted Indoles from o-Nitrotoluenes" "Heterocycles16(7): 1119-24".
Lehmann, J. M.; et al., (1998) "The human orphan nuclear receptor PXR is activated by compounds that regulate CYP3A4 gene expression and cause drug interactions" J Clin Invest 102 (5), 1016-1023.
Li, Y.; et al., (2021) "Building a Chemical Toolbox for Human Pregnane X Receptor Research: Discovery of Agonists, Inverse Agonists, and Antagonists Among Analogs Based on the Unique Chemical Scaffold of SPA70" J Med Chem 64 (3), 1733-1761.
Li, Y.; et al., (2022) "Design and Optimization of 1H-1,2,3-Triazole-4-carboxamides as Novel, Potent, and Selective Inverse Agonists and Antagonists of PXR" J Med Chem 65 (24), 16829-16859.
Lin, W.; et al., (2020) "Development of BODIPY FL Thalidomide As a High-Affinity Fluorescent Probe for Cereblon in a Time-Resolved Fluorescence Resonance Energy Transfer Assay" Bioconjug Chem 31 (11), 2564-2575.
Lin, W.; et al., (2008) "Cyclin-dependent kinase 2 negatively regulates human pregnane X receptor-mediated CYP3A4 gene expression in HepG2 liver carcinoma cells" J Biol Chem 283 (45), 30650-30657.
Lin, W.; et al., (2017) "SPA70 is a potent antagonist of human pregnane X receptor" Nat Commun 8 (1), 741.
Lin, W.; et al., (2020) "CITCO Directly Binds to and Activates Human Pregnane X Receptor" Mol Pharmacol 97 (3), 180-190.
Lin, W.; et al., (2021) "Development of BODIPY FL VH032 as a High-Affinity and Selective von Hippel-Lindau E3 Ligase Fluorescent Probe and Its Application in a Time-Resolved Fluorescence Resonance Energy-Transfer Assay" ACS Omega 6 (1), 680-695.
Lin, W.; et al., (2023) "Structure-guided approach to modulate small molecule binding to a promiscuous ligand-activated protein" Proc Natl Acad Sci U S A 120 (10), e2217804120.
Livak, K. J.; et al., (2001) "Analysis of relative gene expression data using real-time quantitative PCR and the 2(-Delta Delta C(T)) Method" Methods 25 (4), 402-408.
Lu, G.; et al., (2014) "The myeloma drug lenalidomide promotes the cereblon-dependent destruction of Ikaros proteins" Science 343 (6168), 305-9.
Mahase, E. (2021) "Covid-19: Pfizer's paxlovid is 89% effective in patients at risk of serious illness company reports" BMJ 375, n2713.
Maligres, P. E. et al., (1999) "A highly catalytic robust palladium catalyzed cyanation of aryl bromides" Tetrahedron Lett. 40, 8193-8195.
Malta-Vacas, J.; et al., (2009) "Differential expression of GSPT1 GGCn alleles in cancer" Cancer Genet Cytogenet 195 (2), 132-42.
Martinez, C.; et al., (2002) "Expression of paclitaxel-inactivating CYP3A activity in human colorectal cancer: implications for drug therapy" Br J Cancer 87 (6), 681-686.

(56) References Cited

OTHER PUBLICATIONS

Masuyama, H.; et al., (2016) "Inhibition of pregnane X receptor pathway contributes to the cell growth inhibition and apoptosis of anticancer agents in ovarian cancer cells" Int J Oncol 49 (3), 1211-1220.
Matyskiela, M. E.; et al., (2016) "A novel cereblon modulator recruits GSPT1 to the CRL4(CRBN) ubiquitin ligase" Nature 535 (7611), 252-7.
McKean, D. R. et al., (1987) "Synthesis of functionalized styrenes via palladium-catalyzed coupling of aryl bromides with vinyl tin reagents" J. Org. Chem. 52, 422-4.
Melchert, M.; et al., (2007) "The thalidomide saga" Int J Biochem Cell Biol 39 (7-8), 1489-99.
Mo, J. et al., (2006) "Ionic liquid-promoted regioselective catalysis by palladium" Proc.—Electrochem. Soc. 2004-24, 564-571.
Nabet, B.; et al., (2018) "The dTAG system for immediate and target-specific protein degradation" Nat Chem Biol 2018, 14 (5), 431-441.
Nahm, S. et al., (1981) "N-Methoxy-N-methylamides as effective acylating agents" Tetrahedron Lett. 22, 3815-18.
Nishiguchi, G.; et al., (2021) "Identification of Potent, Selective, and Orally Bioavailable Small-Molecule GSPT1/2 Degraders from a Focused Library of Cereblon Modulators" J Med Chem 64 (11), 7296-7311.
Niu, M.; et al., (2017) "Extensive Peptide Fractionation and y1 Ion-Based Interference Detection Method for Enabling Accurate Quantification by Isobaric Labeling and Mass Spectrometry" Anal Chem 89 (5), 2956-2963.
Niu, X.; et al., (2022) "Combination of Paclitaxel and PXR Antagonist SPA70 Reverses Paclitaxel-Resistant Non-Small Cell Lung Cancer" Cells 11 (19).
O'Connell, J. F. et al.,(1988) "Convenient synthesis of methyl 1-methy1-2,4-dibromo-5-imidazolecarboxylate" Synthesis 767-71.
Ortiz-Marciales, M. et al., (1998) "N-tert-Butyldimethylsilyl imines as intermediates for the synthesis of amines and ketones" Synth. Commun. 28, 4067-4075.
Pascussi, JM et al. (2000) "Interleukin-6 Negatively Regulates the Expression of Pregnane X Receptor and Constitutively Activated Receptor in Primary Human Hepatocytes" Biochemical and Biophysical Research Communications, vol. 274, pp. 707-713; abstract.
Peng, J.; et al., (2003) "Evaluation of multidimensional chromatography coupled with tandem mass spectrometry (LC/LC-MS/MS) for large-scale protein analysis: the yeast proteome" J Proteome Res 2 (1), 43-50.
Peng, Y. (2014) "Cu(I)-catalyzed coupling of arylsulfinic salts with aryl bromides" J. Chem. Res. 38, 447-449.
Pokhodylo, N. T et al., (2009) "(Arylsulfonyl)acetones and—acetonitriles: new activated methylenic building blocks for synthesis of 1,2,3-triazoles" Synthesis 2321-2323.
Preis, A.; et al., (2014) "Cryoelectron microscopic structures of eukaryotic translation termination complexes containing eRF1-eRF3 or eRF1-ABCE1" Cell Rep 8 (1), 59-65.
PUBCHEM 20865737, Modify Date Apr. 22, 2017.
PUBCHEM AKOS001822451, Modify Date Apr. 22, 2017.
PUBCHEM MolPort-005-282-644, Modify Date Apr. 22, 2017.
PUBCHEM MolPort-007-647-768, Modify Date Apr. 22, 2017.
Rao, B. N. et al., (1989) "PdCl2(PPh3)2 catalysed carboalkoxylation of aryl bromides" Journal of Molecular Catalysis 50(3), L27-L29.
Recnik, L.-M. et al., (2013) "Selective sequential cross-coupling reactions on imidazole towards neurodazine and analogues" Synthesis 45, 1387-1405.
Rosenmund, K. W. et al., (1919,) "Halogen attached to a ring carbon atom and its replacement by other substituents. I. Replacement of the halogen by the carboxyl group" Ber. Dtsch. Chem. Ges. B 52B, 1749-56.
Sentmanat, M. F.; et al., (2018) "A Survey of Validation Strategies for CRISPR-Cas9 Editing" Sci Rep 8 (1), 888.
Shaginian, A. et al., (2009) "Design, Synthesis, and Evaluation of an a-Helix Mimetic Library Targeting Protein-Protein Interactions" J. Am. Chem. Soc. 2009, 131, 5564-5572.
Shrestha, J. P. et al., (2014) "Synthesis and anticancer structure activity relationship investigation of cationic anthraquinone analogs" Eur. J. Med. Chem. 2014, 77, 96-102.
Slocum, D. et al., (2009) "Metalations utilizing aryllithiums; ortho-functionalization of p-bromoanisole (pBrA)" Tetrahedron Lett. 50, 1593-1595.
Surka, C.; et al., (2021) "CC-90009, a novel cereblon E3 ligase modulator, targets acute myeloid leukemia blasts and leukemia stem cells" Blood 137 (5), 661-677.
Sutherland, H. S. et al. , (2010) "Synthesis and Structure-activity Relationships of Antitubercular 2-Nitroimidazooxazines Bearing Heterocyclic Side Chains" J. Med. Chem. 53, 855-866.
Synold, T. W.; et al., (2001) "The orphan nuclear receptor SXR coordinately regulates drug metabolism and efflux" Nat Med 7 (5), 584-90.
Tang, D. E.; et al., (2020) "The ubiquitinase ZFP91 promotes tumor cell survival and confers chemoresistance through FOXA1 destabilization" Carcinogenesis 41 (1), 56-66.
Tseng, A.; et al., (2017) "Cobicistat Versus Ritonavir: Similar Pharmacokinetic Enhancers But Some Important Differences" Ann Pharmacother 51 (11), 1008-1022.
Wang, A.; et al., (2021) "ZFP91 is required for the maintenance of regulatory T cell homeostasis and function" J Exp Med 218 (2).
Wang, X.; et al., (2014) "Jump: a tag-based database search tool for peptide identification with high sensitivity and accuracy" Mol Cell Proteomics 13 (12), 3663-73.
Wang, Y. M.; et al. , (2015) "Serine 350 of human pregnane X receptor is crucial for its heterodimerization with retinoid X receptor alpha and transactivation of target genes in vitro and in vivo" Biochem Pharmacol 96 (4), 357-368.
Wienkers, L. C.; et al., (2005) "Predicting in vivo drug interactions from in vitro drug discovery data" Nat Rev Drug Discov 4 (10), 825-833.
Winter, G. E.; et al., (2015) "Drug Development. Phthalimide conjugation as a strategy for in vivo target protein degradation" Science 348 (6241), 1376-81.
Wouters, O. J., et al. (2020) "Estimated Research and Development Investment Needed to Bring a New Medicine to Market" JAMA 323 (9), 844-853.
Xie, W.; et al., (2000) "Humanized xenobiotic response in mice expressing nuclear receptor SXR" Nature 406 (6794), 435-9.
Xie, Y.; et al., (2019) "Activation of Pregnane X Receptor Sensitizes Mice to Hemorrhagic Shock-Induced Liver Injury" Hepatology 70 (3), 995-1010.
Xu, S. H.; et al., (2018) "ECD promotes gastric cancer metastasis by blocking E3 ligase ZFP91-mediated hnRNP F ubiquitination and degradation" Cell Death Dis 9 (5), 479.
Xue, Y.; et al., (2007) "Crystal structure of the PXR-T1317 complex provides a scaffold to examine the potential for receptor antagonism" Bioorg Med Chem 15 (5), 2156-2166.
Yang, J.; et al., (2019) "Simple Structural Modifications Converting a Bona fide MDM2 PROTAC Degrader into a Molecular Glue Molecule: A Cautionary Tale in the Design of PROTAC Degraders" J Med Chem 62 (21), 9471-9487.
Yun, C. H.; et al., (1993,) "Oxidation of the antihistaminic drug terfenadine in human liver microsomes. Role of cytochrome P-450 3A(4) in N-dealkylation and C-hydroxylation" Drug Metab Dispos 21 (3), 403-409.
Zeldin, R. K.; et al., (2004) "Pharmacological and therapeutic properties of ritonavir-boosted protease inhibitor therapy in HIV-infected patients" J Antimicrob Chemother 53 (1), 4-9.
Zhou, B.; et al., (2018) "Discovery of a Small-Molecule Degrader of Bromodomain and Extra-Terminal (BET) Proteins with Picomolar Cellular Potencies and Capable of Achieving Tumor Regression" J. Med Chem 61(2) 462-481.
Zhouravleva, G.; et al., (1995) "Termination of translation in eukaryotes is governed by two interacting polypeptide chain release factors, eRF1 and eRF3" EMBO J 14 (16), 4065-72.

* cited by examiner

Rifampicin (1)

Dexamethasone (2)

T0901317 (3)

SJB7 (4)

SPA70 (5)
Antagonist

SJPYT-328 (6)

SJPYT-312 (7)
Antagonist

SJPYT-331 (8)
Antagonist

Thalidomide (9)
CRBN Ligand

Pomalidomide (10)
CRBN Ligand

SJPYT-195 (11)
GSPT1 Degrader

VH032 (12)
VHL Ligand

13
$K_d$ = 38.7 ± 3.0 nM

14
$K_d$ = 22.3 ± 1.3 nM

Compound 8 (SJPYT-331)

12 (VH032)

38

39

40

SMALL MOLECULE DEGRADERS AND FLUORESCENT PROBES OF PXR

CROSS-REFERENCE TO RELATED APPLICATIONS

This Application is a continuation of U.S. application Ser. No. 18/902,844, filed on Sep. 30, 2024, the contents of which are incorporated herein by reference in their entirety

STATEMENT REGARDING FEDERALLY SPONSORED RESEARCH

This invention was made with government support under grant number GM118041 awarded by The National Institute of Health. The government has certain rights in the invention.

BACKGROUND

Development of new therapeutics is a multibillion-dollar enterprise, with the average single-drug research and development investment estimated at 1.6 billion US dollars (Wouters, O. J.; et al., (2020) *JAMA* 323 (9), 844-853). Less than 10% of drugs that enter phase I clinical testing are eventually commercially launched (Dowden, H.; et al., (2019) *Nat Rev Drug Discov,* 18 (7), 495-496), and the time between initiation of a drug discovery program and resulting clinical approval is roughly a decade (DiMasi, J. A.; et al., (2016) *J Health Econ,* 47, 20-33). Although there are various reasons for clinical trial failure, ~80% of failures are attributable to safety or efficacy (Dowden, H.; et al., (2019) *Nat Rev Drug Discov,* 18 (7), 495-496), and safety concerns also lead to approved drugs being withdrawn from the market (Wienkers, L. C.; et al., (2005) *Nat Rev Drug Discov* 4 (10), 825-833). A common cause for such concerns is the occurrence of pharmacokinetic drug-drug interactions in which one drug alters the absorption, distribution, metabolism, or excretion of a co-administered drug. For example, the antihistamine terfenadine was withdrawn by the United States Food and Drug Administration (FDA) in 1997 after a series of reports showed metabolism-mediated cardiac dysfunction in patients cotreated with terfenadine [a substrate of the metabolic enzyme cytochrome P450 3A4 (CYP3A4)] and potent CYP3A4 inhibitors such as the antifungal ketoconazole (Honig, P. K.; et al., (1993) *JAMA* 269 (12), 1513-1518; Yun, C. H.; et al., (1993) *Drug Metab Dispos* 21 (3), 403-409; Honig, P. K.; et al., (1992) *Clin Pharmacol Ther* 52 (3), 231-238). To prevent adverse effects caused by metabolic events, the FDA has established guidelines to evaluate the drug-drug interaction potential of preclinical drug candidates by determining if compounds are substrates, inhibitors, or inducers of drug metabolizing enzymes and drug transporters (https://www.fda.gov/regulatory-information/search-fda-guidance-documents/in-vitro-drug-interaction-studies-cytochrome-p450-enzyme-and-transporter-mediated-drug- interactions).

In addition to enhanced safety, knowledge of molecules' metabolic profiles allows drug regimens to be designed that leverage the metabolic effects. Ritonavir, for example, was approved in 1996 as an anti-HIV treatment but is now commonly used as a "booster" for co-administered drugs due to its potent inhibition of CYP3A enzymes (Zeldin, R. K.; et al., (2004) *J Antimicrob Chemother* 53 (1), 4-9). This booster strategy has been successful in many cases, including the combination of ritonavir with nirmatrelvir in the SARS-CoV-2 drug Paxlovid (Mahase, E. (2021) *BMJ* 375, n2713). However, the approach is accompanied by its own set of potential adverse events, particularly in patients receiving multiple medications that may include inducers of CYP enzymes and drug transporters (Tseng, A.; et al., (2017) *Ann Pharmacother* 51 (11), 1008-1022). Drug-mediated activation of pregnane X receptor (PXR) is the main source of CYP3A induction and may increase the expression of enzymes and transporters beyond the levels that can be inhibited by booster drugs (Tseng, A.; et al., (2017) *Ann Pharmacother* 51 (11), 1008-1022; Bertilsson, G.; et al., (1998) *Proc Natl Acad Sci USA* 95 (21), 12208-12213; Blumberg, B.; et al., (1998) *Genes Dev* 1998, 12 (20), 3195-3205; Lehmann, J. M.; et al., (1998) *J Clin Invest* 102 (5), 1016-1023; Kliewer, S. A.; et al., (1998) *Cell* 19 92 (1), 73-82). In these cases, blocking the activity of the transcription factor PXR would prove advantageous over inhibition of the downstream gene products, such as CYP3A enzymes. However, even discovery-stage PXR antagonists are rare due to PXR's evolved function as a chemical-activated sensor.

A selective and nontoxic PXR antagonist was previously reported (Lin, W.; et al., (2017) *Nat Commun* 8 (1), 74), subsequent derivatization to yield high potency analogs (Li, Y.; et al., (2021) *J Med Chem* 64 (3), 1733-1761; Li, Y.; et al., (2022) *J Med Chem* 65 (24), 16829-16859), and structural characterization of such analogs (Garcia-Maldonado, E.; et al., (2024) *Nat Commun* 15 (1), 4054. DOI: 10.1038/s41467-024-48472-1). These molecules have been shown to ameliorate PXR-induced metabolism and enhance the effectiveness of co-administered drugs by blocking the binding of agonists to the PXR ligand binding domain (LBD)(Lin, W.; et al., (2017) *Nat Commun* 8 (1), 741; Xie, Y.; et al., (2019) *Hepatology* 70 (3), 995-1010; Niu, X.; et al., (2022) *Cells* 11 (19):3094). Interestingly, slight chemical changes to the compounds as well as mutations around the PXR ligand binding pocket can switch the biological activities of the ligands from antagonists to agonists (Garcia-Maldonado, E.; et al., (2024) *Nat Commun* 15 (1), 4054); Huber, A. D.; et al., (2021) *Cell Mol Life Sci* 78 (1), 317-335).

PXR degradation may be an attractive alternative to traditional antagonism. For example, the degradation tag system with PXR fused to the synthetic FKBP12$^{F36V}$ mutant protein was previously used to show that PXR degraders may potentially be superior to antagonists in reducing PXR-mediated gene expression (Huber, A. D., et al, (2024) *Structure* 32 DOI: 10.1016/j.str.2024.09.016). However, a previous set of PXR ligands conjugated to ligands of the E3 cullin-RING ligase 4 (CRL4) substrate receptor cereblon (CRBN) resulted in indirect reduction of PXR protein through unintended degradation of the translation termination factor G1 To S phase transition protein 1 homologue (GSPT1)(Huber, A. D.; et al., (2022) *ACS Med Chem Lett* 13 (8), 1311-1320).

Fluorescent probes are critical tools for evaluating compound binding to protein targets. Currently there is no fluorescent PXR probe designed from PXR ligands that have been co-crystalized with PXR (without a co-crystal structure, it is unclear how a probe binds to the protein).

Accordingly, there remains a need for compounds that induce protein degradation such as, for example, degradation of PXR, to prevent therapy-related toxicities, drug-drug interactions, and drug resistance, and improve therapeutic efficacy and safety and methods of making and using same. In addition, despite the significance of identifying PXR ligands, sensitive and selective assays to identify such ligands have remained elusive. Thus, there remains a need for methods and probes to identify, develop, and evaluate PXR ligands. These needs and others are met by the instant invention.

SUMMARY

In accordance with the purpose(s) of the invention, as embodied and broadly described herein, the invention, in one aspect, relates to compounds, compositions, and methods for degrading pregnane X receptor (PXR) protein. The invention further relates to the use of the disclosed compounds in decreasing adverse drug reactions such as, for example, adverse drug reactions associated with administration of an anticancer agent, an antibacterial agent, a non-steroidal anti-inflammatory agent, or an anticonvulsant agent. The invention, in one aspect, further relates to compounds, compositions, and methods for identifying PXR agonists.

Thus, disclosed are compounds having a structure represented by a formula:

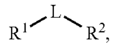

wherein L is a linker; wherein $R^1$ is a residue of a pregnane X receptor (PXR) ligand; and wherein $R^2$ is a residue of a von Hippel-Lindau protein (pVHL) ligand, or a pharmaceutically acceptable salt thereof.

Also disclosed are pharmaceutical compositions comprising an effective amount of a disclosed compound, or a pharmaceutically acceptable salt thereof and a pharmaceutically acceptable carrier.

Also disclosed are methods of degrading a target protein in a cell in need thereof, the method comprising contacting the cell with an effective amount of a disclosed compound, or a pharmaceutically acceptable salt thereof.

Also disclosed are methods of degrading a target protein in a subject, the method comprising administering to the subject an effective amount of a disclosed compound, or a pharmaceutically acceptable salt thereof.

Also disclosed are methods of treating a disease or disorder in a subject in need thereof, the method comprising administering to the subject an effective amount of a disclosed compound, or a pharmaceutically acceptable salt thereof.

Also disclosed are kits comprising a disclosed compound or a pharmaceutically acceptable salt thereof, and one or more of: (a) an agent known to cause a PXR-mediated metabolism event; (b) an agent known to treat a cancer; (c) instructions for administering the compound in connection with preventing a PXR-mediated metabolism event; (d) instructions for preventing a PXR-mediated metabolism event; (e)instructions for administering the compound in connection with treating a cancer; and (f) instructions for treating a cancer.

Also disclosed are compounds having a structure represented by a formula:

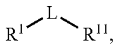

wherein L is a linker; wherein $R^1$ is a residue of a pregnane X receptor (PXR) ligand; and wherein $R^{11}$ is a residue of a residue of a fluorophore, a residue of biotin, or a residue of a biotin derivative, or a pharmaceutically acceptable salt thereof.

Also disclosed are methods of modulating PXR protein in a sample, the method comprising contacting the sample with an effective amount of a disclosed compound, thereby modulating PXR protein in the sample.

Also disclosed are methods of identifying a PXR ligand in a library, the method comprising: (a) providing a library that contains a plurality of ligands; (b) combining a disclosed compound and a sample having PXR protein, thereby forming a mixture; (c) exposing each ligand to the mixture; and (d) detecting a fluorescence emission of the mixture after exposure to each ligand, wherein a decrease in fluorescence emission indicates that the ligand is a PXR ligand, and wherein a lack of decrease in fluorescence emission indicates that the ligand is a non-PXR ligand.

Also disclosed are kits comprising a disclosed compound or a pharmaceutically acceptable salt thereof, and one or more of: (a) a sample that contains PXR protein; (b) a library that contains a plurality of ligands; (c) instructions for modulating PXR; (d) instructions for identifying a PXR ligand and/or a non-PXR ligand; and (e) instructions for performing a fluorescence-based assay.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

Figure 1A:
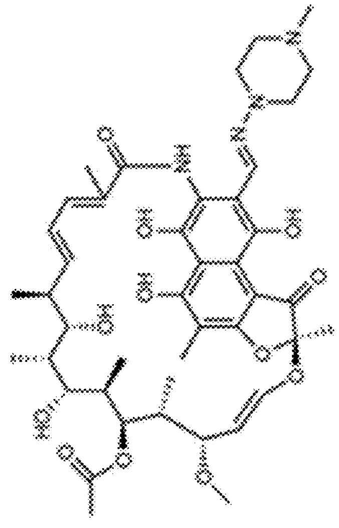
FIG. 1A and FIG. 1B show representative structures of PXR ligands and E3 binding ligands.
Figure 1A:
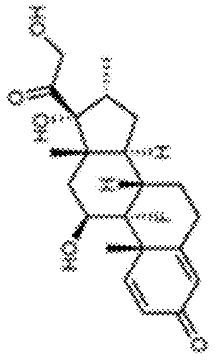
Figure 1A:
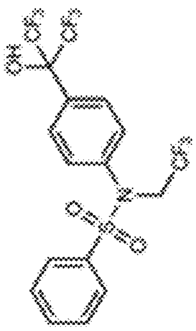
Figure 1A:
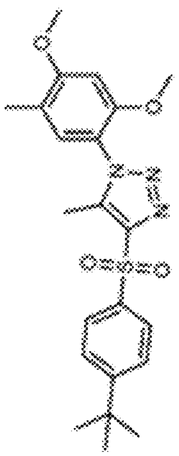
Figure 1A:
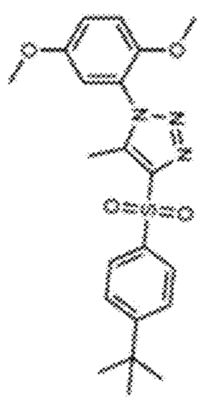
Figure 1A:
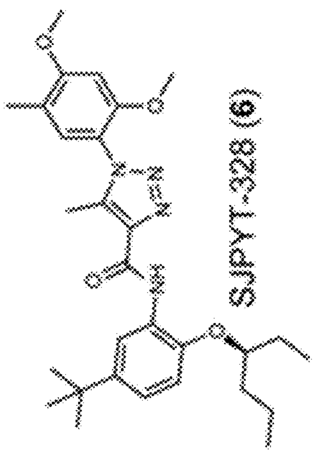
Figure 1A:
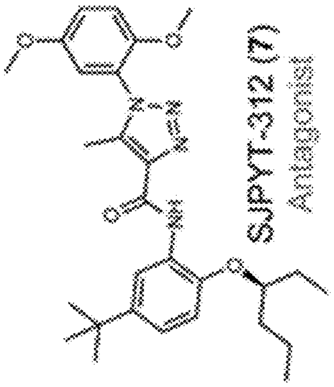
Figure 1A:
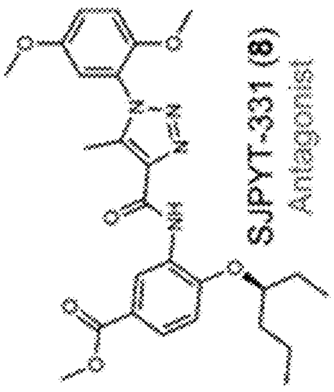

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of this disclosure can be described and claimed in a particular statutory class, such as the system statutory class, this is for convenience only and one of skill in the art will understand that each aspect of this disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present application is not entitled to antedate such publication by virtue of prior invention. Further, stated publication dates may be different from actual publication dates, which can require independent confirmation.

A. DEFINITIONS

As used in the specification and the appended claims, the singular forms "a," "an," and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of".

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage form can comprise a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the term, "PXR-mediated metabolism event" means any event in which the activation of PXR is undesired such as, for example, reduced drug efficacy and increased drug toxicity. The PXR-mediated metabolism event may be due to a drug-drug interaction, a drug-related toxicity, or drug resistance.

As used herein, the term "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more $—OCH_2CH_2O—$ units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein, which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be branched or unbranched. The alkyl group can also be substituted or unsubstituted. For example, the alkyl group can be substituted with one or more groups including, but not limited to, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl. For example, the term "C1-C4 alkyl" includes methyl, ethyl, n-propyl, isopropyl, n-butyl, isobutyl, s-butyl, and t-butyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. The term "cycloalkyl" includes monocyclic rings as well as ring systems including more than one cyclic ring, e.g. bicyclic rings. In ring systems including more than one cyclic ring, the rings of the "cycloalkyl" may be fused rings, bridged rings, or spirocyclic rings. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. For example, the cycloalkyl group and heterocycloalkyl group can be substituted with 0, 1, 2, 3, or 4 groups independently selected from C1-C4 alkyl, C3-C7 cycloalkyl, C1-C4 alkoxy, —$NH_2$, (C1-C4) alkylamino, (C1-C4)(C1-C4) dialkylamino, ether, halogen, —OH, C1-C4 hydroxyalkyl, —$NO_2$, silyl, sulfo-oxo, —SH, and C1-C4 thioalkyl, as described herein.

The term "polyalkylene group" as used herein is a group having two or more $CH_2$ groups linked to one another. The polyalkylene group can be represented by the formula $(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. For example, the cycloalkenyl group and heterocycloalkenyl group can be substituted with 0, 1, 2, 3, or 4 groups independently selected from C1-C4 alkyl, C3-C7 cycloalkyl, C1-C4 alkoxy, C2-C4 alkenyl, C3-C6 cycloalkenyl, C2-C4 alkynyl, aryl, heteroaryl, aldehyde, —$NH_2$, (C1-C4) alkylamino, (C1-C4)(C1-C4) dialkylamino, carboxylic acid, ester, ether, halogen, —OH, C1-C4 hydroxyalkyl, ketone, azide, —$NO_2$, silyl, sulfo-oxo, —SH, and C1-C4 thioalkyl, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl. Accordingly, the term "C6-C10 aryl" for example includes phenyl and naphthyl.

The term "aldehyde" as used herein is represented by the formula —C(O)H. Throughout this specification "C(O)" or "CO" is a short hand notation for a carbonyl group, i.e., C═O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula—($A^1$O(O)C-$A^2$—C(O)O)$_a$— or—($A^1$O(O)C-$A^2$—OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula—($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo" as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl" as used herein can be used interchangeably and refer to single and multicyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxy" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $—N_3$.

The term "nitro" as used herein is represented by the formula $—NO_2$.

The term "nitrile" or "cyano" as used herein is represented by the formula —CN or —C≡N.

The term "silyl" as used herein is represented by the formula $—SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $—(CH_2)_{0-4}R^o$; $—(CH_2)_{0-4}OR^o$; $—O(CH_2)_{0-4}R^o$, $—O—(CH_2)_{0-4}C(O)OR^o$; $—(CH_2)_{0-4}CH(OR^o)_2$; $—(CH_2)_{0-4}SR^o$; $—(CH_2)_{0-4}Ph$, which may be substituted with $R^o$; $—(CH_2)_{0-4}O(CH_2)_{0-1}Ph$ which may be substituted with $R^o$; —CH═CHPh, which may be substituted with $R^o$; $—(CH_2)_{0-4}O(CH_2)_{0-1}$-pyridyl which may be substituted with $R^o$; $—NO_2$; —CN; $—N_3$; $—(CH_2)_{0-4}N(R^o)_2$; $—(CH_2)_{0-4}N(R^o)C(O)R^o$; $—N(R^o)C(S)R^o$; $—(CH_2)_{0-4}N(R^o)C(O)NR^o_2$; $—N(R^o)C(S)NR^o_2$; $—(CH_2)_{0-4}N(R^o)C(O)OR^o$; $—N(R^o)N(R^o)C(O)R^o$; $—N(R^o)N(R^o)C(O)NR^o_2$; $—N(R^o)N(R^o)C(O)OR^o$; $—(CH_2)_{0-4}C(O)R^o$; $—C(S)R^o$; $—(CH_2)_{0-4}C(O)OR^o$; $—(CH_2)_{0-4}C(O)SR^o$; $—(CH_2)_{0-4}C(O)OSiR^o_3$; $—(CH_2)_{0-4}OC(O)R^o$; $—OC(O)(CH_2)_{0-4}SR—$, $SC(S)SR^o$; $—(CH_2)_{0-4}SC(O)R^o$; $—(CH_2)_{0-4}C(O)NR^o_2$; $—C(S)NR^o_2$; $—C(S)SR^o$; $—(CH_2)_{0-4}OC(O)NR^o_2$; $—C(O)N(OR^o)R^o$; $—C(O)C(O)R^o$; $—C(O)CH_2C(O)R^o$; $—C(NOR^o)R^o$; $—(CH_2)_{0-4}SSR^o$; $—(CH_2)_{0-4}S(O)_2R^o$; $—(CH_2)_{0-4}S(O)_2OR^o$; $—(CH_2)_{0-4}OS(O)_2R^o$; $—S(O)_2NR^o_2$; $—(CH_2)_{0-4}S(O)R^o$; $—N(R^o)S(O)_2NR^o_2$; $—N(R^o)S(O)_2R^o$; $—N(OR^o)R^o$; $—C(NH)NR^o_2$; $—P(O)_2R^o$; $—P(O)R^o_2$; $—OP(O)R^o_2$; $—OP(O)(OR^o)_2$; $SiR^o_3$; $—(C_{1-4}$ straight or branched alkylene$)O—N(R^o)_2$; or $—(C_{1-4}$ straight or branched alkylene$)C(O)O—N(R^o)_2$, wherein each $R^o$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, $—(CH_2)_{0-2}R^•$, -(halo$R^•$), $—(CH_2)_{0-2}OH$, $—(CH_2)_{0-2}OR^•$, $—(CH_2)_{0-2}CH(OR^•)_2$; —O(halo$R^•$), —CN, $—N_3$, $—(CH_2)_{0-2}C(O)R^•$, $—(CH_2)_{0-2}C(O)OH$, $—(CH_2)_{0-2}C(O)OR^•$, $—(CH_2)_{0-2}SR^•$, $—(CH_2)_{0-2}SH$, $—(CH_2)_{0-2}NH_2$, $—(CH_2)_{0-2}NHR^•$, $—(CH_2)_{0-2}NR^•_2$, $—NO_2$, $—SiR^•_3$, $—OSiR^•_3$, $—C(O)SR^•$, $—(C_{1-4}$ straight or branched alkylene$)C(O)OR^•$, or $—SSR^•$ wherein each $R^•$ is unsubstituted or where preceded by "halo" is substituted only with one or more halogens, and is independently selected from C1-4 aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, $=NNR^*_2$, =NNHC(O)R*, =NNHC(O)OR*, $=NNHS(O)_2R^*$, =NR*, =NOR*, $—O(C(R^*_2))_{2-3}O—$, or $—S(C(R^*_2))_{2-3}S—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $—R^{\bullet}$, $-(haloR^{\bullet})$, —OH, $—OR^{\bullet}$, $—O(haloR^{\bullet})$, —CN, —C(O)OH, $—C(O)OR^{\bullet}$, $—NH_2$, $—NHR^{\bullet}$, $—NR^{\bullet}_2$, or $—NO_2$, wherein each $R^{\bullet}$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^{\dagger}$, $—NR^{\dagger}_2$, $—C(O)R^{\dagger}$, $—C(O)OR^{\dagger}$, $—C(O)C(O)R^{\dagger}$, $—C(O)CH_2C(O)R^{\dagger}$, $—S(O)_2R^{\dagger}$, $—S(O)_2NR^{\dagger}_2$, $—C(S)NR^{\dagger}_2$, $—C(NH)NR^{\dagger}_2$, or $—N(R^{\dagger})S(O)_2R^{\dagger}$; wherein each Rt is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, $—R^{\bullet}$, $-(haloR^{\bullet})$, —OH, $—OR^{\bullet}$, $—O(haloR^{\bullet})$, —CN, —C(O)OH, $—C(O)OR^{\bullet}$, $—NH_2$, $—NHR^{\bullet}$, $—NR^{\bullet}_2$, or $—NO_2$, wherein each $R^{\bullet}$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

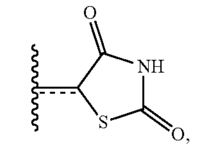

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and 1 or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}C_1$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

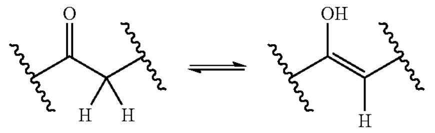

keto form enol form

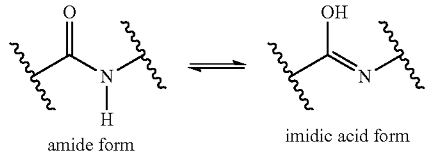

amide form imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

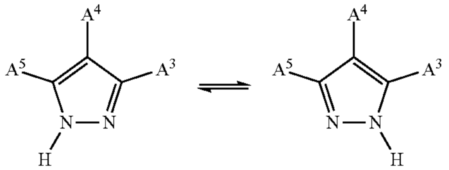

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

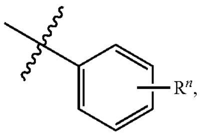

which is understood to be equivalent to a formula:

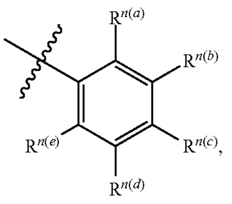

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

Generally, the invention relates to compounds having a structure represented by a formula:

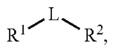

wherein L is a linker; wherein $R^1$ is a residue of a pregnane X receptor (PXR) ligand; and wherein $R^2$ is a residue of a von Hippel-Lindau protein (pVHL) ligand, or a pharmaceutically acceptable salt thereof.

Further, the invention relates to compounds having a structure represented by a formula:

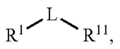

wherein L is a linker; wherein $R^1$ is a residue of a pregnane X receptor (PXR) ligand; and wherein $R^{11}$ is a residue of a residue of a fluorophore, a residue of biotin, or a residue of a biotin derivative, or a pharmaceutically acceptable salt thereof.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. STRUCTURE

In one aspect, disclosed are compounds having a structure represented by a formula:

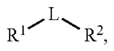

wherein L is a linker; wherein $R^1$ is a residue of a pregnane X receptor (PXR) ligand; and wherein $R^2$ is a residue of a von Hippel-Lindau protein (pVHL) ligand, or a pharmaceutically acceptable salt thereof.

In various aspects, the compound has a structure represented by a formula:

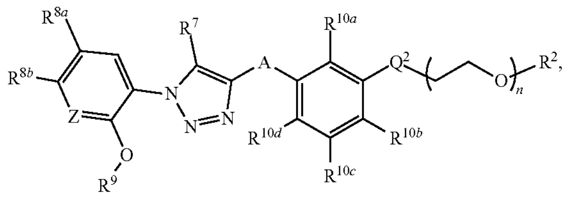

wherein n is selected from 2, 3, 4, 5, 6, 7, and 8, or a pharmaceutically acceptable salt thereof.

In various aspects, the compound has a structure represented by a formula:

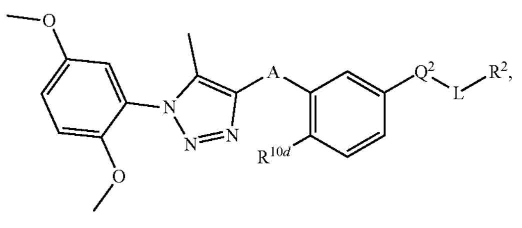

or a pharmaceutically acceptable salt thereof.

In various aspects, the compound has a structure represented by a formula:

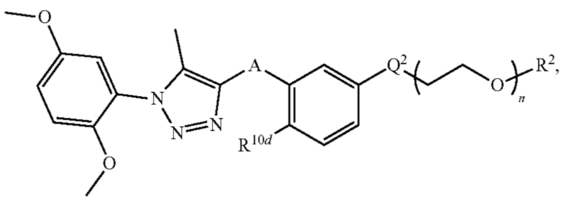

wherein n is selected from 2, 3, 4, 5, 6, 7, and 8, or a pharmaceutically acceptable salt thereof.

In various aspects, the compound has a structure represented by a formula:

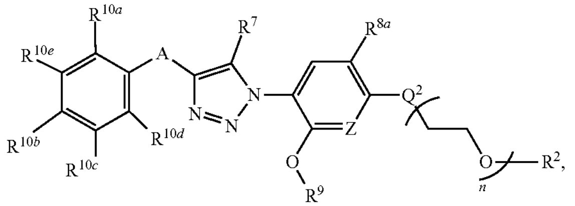

wherein n is selected from 2, 3, 4, 5, 6, 7, and 8, or a pharmaceutically acceptable salt thereof.

In various aspects, the compound has a structure represented by a formula:

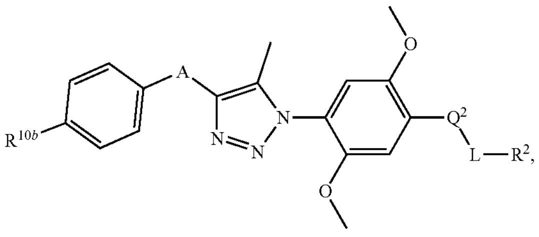

or a pharmaceutically acceptable salt thereof.

In various aspects, the compound has a structure represented by a formula:

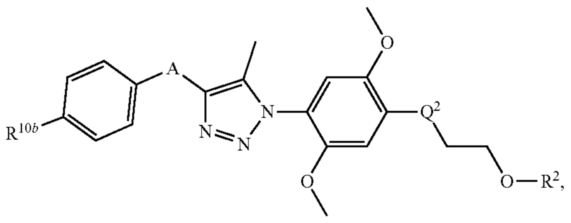

wherein n is selected from 2, 3, 4, 5, 6, 7, and 8, or a pharmaceutically acceptable salt thereof.

In various aspects, the compound has a structure represented by a formula:

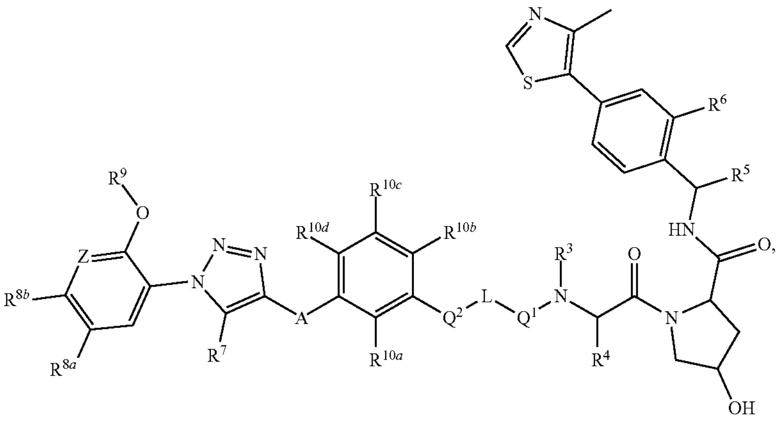

wherein A is selected from *—$SO_2$—**, *—$NR^{24}C(O)$—**, *—$N(R^{24})C(O)NR^{25}$—**, *—$C(O)NR^{24}$—**, *—$SO_2NR^{24}$—**, and *—$NR^{24}SO_2$—**, wherein * denotes a bond connected to the triazole and ** denotes a bond connected to the phenyl; wherein each of $R^{24}$ and $R^{25}$ is independently selected from hydrogen and C1-C4 alkyl; wherein $Q^1$ is selected from *—C(O)—**, *—OC(O)—**, *—$C(R^{20a})(R^{20b})C(O)$—**, *—$OC(R^{20a})(R^{20b})C(O)$—**, *—$C(R^{20a})(R^{20b})$C(O)C(cyclopropyl)C(O)—**, *—$C(R^{20a})(R^{20b})C(O)N(R^{21a})CH_2CH(R^{21b})C(O)$—**, *—C(C3-C4 cycloalkyl)C(O)—**, *—$NH(CH_2CH_2O)_qCH_2C(O)$—**, *—$NHCH_2$C(cyclopropyl)C(O)—**, and *—$CH_2C(O)N(R^{22})CH(R^{23})C(O)$—**, wherein * denotes a bond connected to -L- and ** denotes a bond connected to —$N(R^3)$—; wherein q is selected from 1, 2, 3, 4, 5, and 6; wherein each of $R^{20a}$ and $R^{20b}$ is independently selected from hydrogen and C1-C4 alkyl; or wherein each of $R^{20a}$ and $R^{20b}$ are covalently bound, and, together comprise a C3-C4 cycloalkyl or a C2-C3 heterocycloalkyl; or wherein $R^{20}$ is covalently bound to $R^3$, and, together with the intermediate atoms, comprises a 5-membered heterocycle; wherein each of $R^{21a}$ and $R^{21b}$ are covalently bound, and, together with the intermediate atoms, comprise a 4-membered heterocycle; wherein $R^{22}$ is hydrogen; and wherein $R^{23}$ is selected from C1-C4 alkyl, —$CH_2C_6H_5$, and —$C_6H_5$; or wherein each of $R^{22}$ and $R^{23}$ are covalently bound, and, together with the intermediate atoms, comprise an 10-membered heterocycloalkyl; wherein $Q^2$ is selected from *—O—**, *—O(C1-$C_8$ alkylene)-**, *—$OCH_2C(O)NH$—**, and *—C(O)NH—**, wherein * denotes a bond connected to the phenyl and ** denotes a bond connected to -L-; wherein Z is selected from N and CH; wherein $R^3$ is selected from hydrogen and C1-C4 alkyl; and wherein $R^4$ is selected from C1-C4 alkyl, C1-C4 hydroxyalkyl, and $C_6H_5$; or wherein each of $R^3$ and $R^4$ are covalently bound, and, together with the intermediate atoms, comprise a 5- or 6-membered heterocycle having 0 or 1 —OH group; or wherein each of $R^3$ and $R^{20a}$, when present, are covalently bound, and, together with the intermediate atoms, comprise a 5-membered heterocycle; wherein $R^5$ is selected from hydrogen and methyl; and wherein $R^6$ is selected from hydrogen, —OH, and C1-C4 alkyl halide; wherein $R^7$ is selected from hydrogen and C1-C4 alkyl; wherein each of $R^{8a}$ and $R^{8b}$ is independently selected from hydrogen, halogen, C1-C4 alkyl, C1-C4 haloalkyl, C1-C4 alkoxy, and C1-C4 haloalkoxy; wherein $R^9$ is C1-C4 alkyl; and wherein each of $R^{10a}$, $R^{10b}$, $R^{10c}$, and $R^{10d}$ is independently selected from hydrogen, halogen, —CN, —$NH_2$, —OH, —$NO_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, C1-C8 alkylamino, and —$CO_2$(C1-C4 alkyl), or a pharmaceutically acceptable salt thereof.

In various aspects, the compound has a structure represented by a formula:

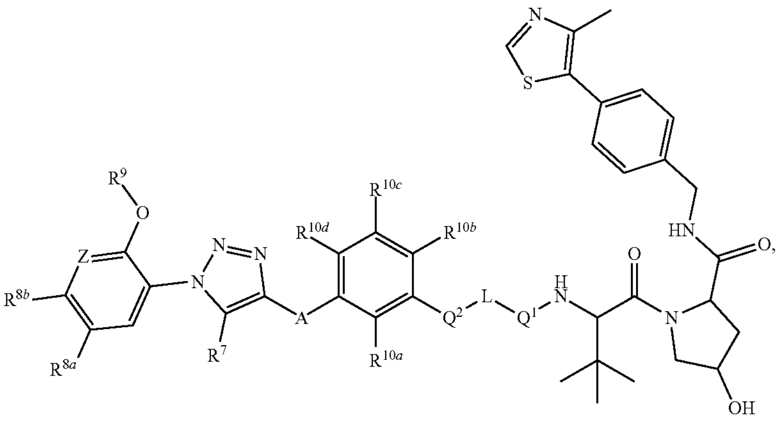

or a pharmaceutically acceptable salt thereof.

In various aspects, the compound has a structure represented by a formula:

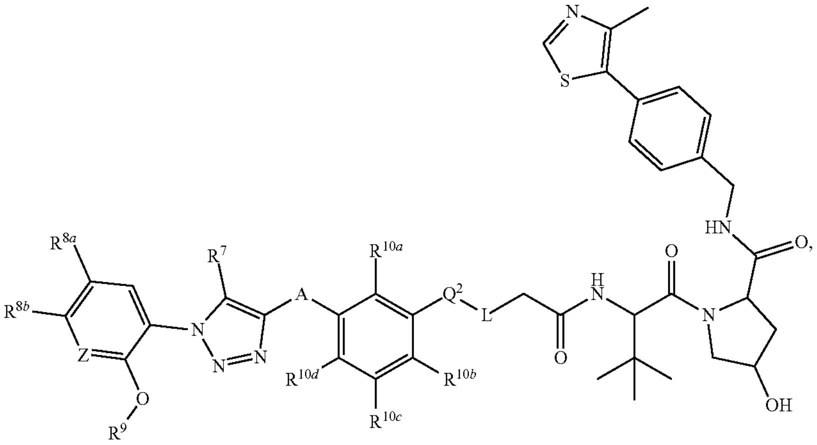

or a pharmaceutically acceptable salt thereof.

In various aspects, the compound has a structure represented by a formula:

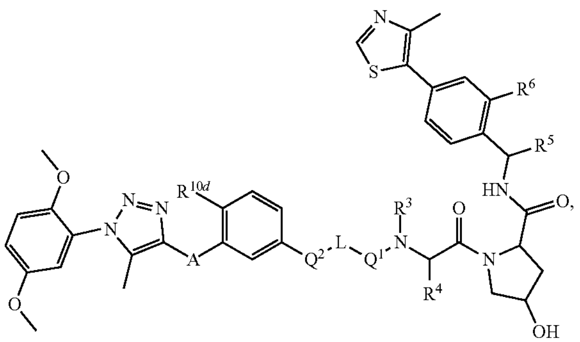

or a pharmaceutically acceptable salt thereof.

In various aspects, the compound has a structure represented by a formula:

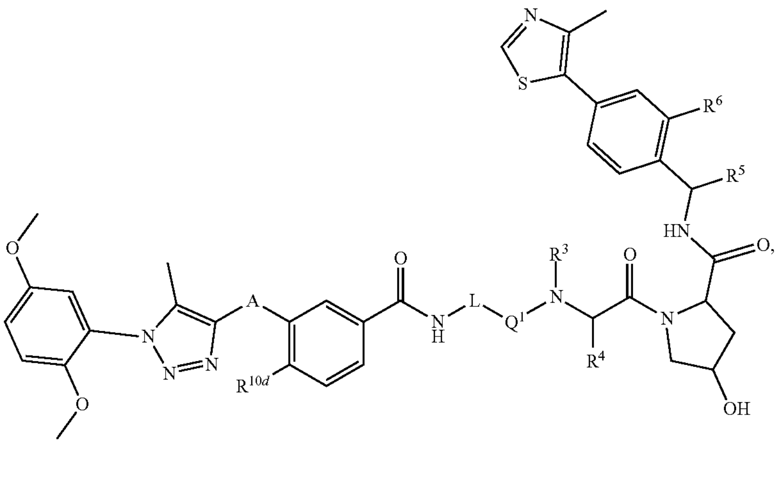

or a pharmaceutically acceptable salt thereof.

In various aspects, the compound has a structure represented by a formula:

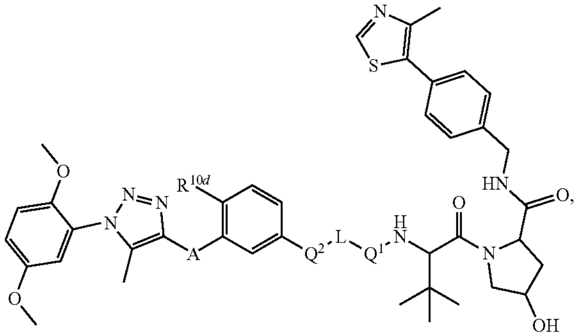

or a pharmaceutically acceptable salt thereof.

In various aspects, the compound has a structure represented by a formula:

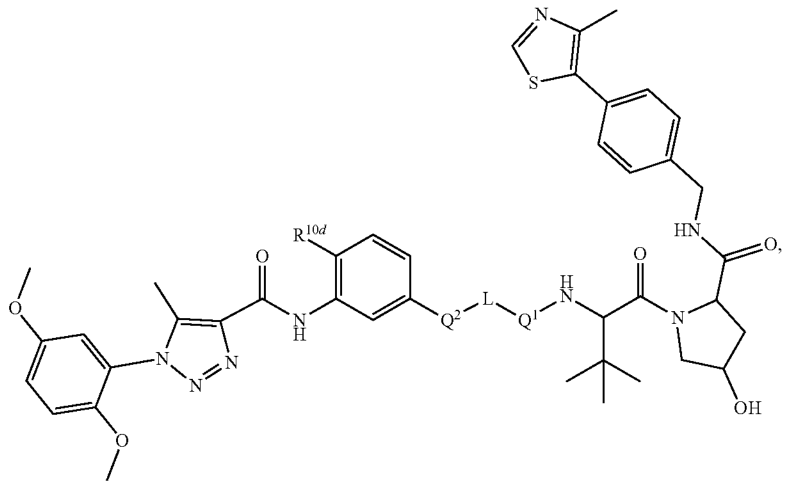

or a pharmaceutically acceptable salt thereof.

In various aspects, the compound has a structure represented by a formula:

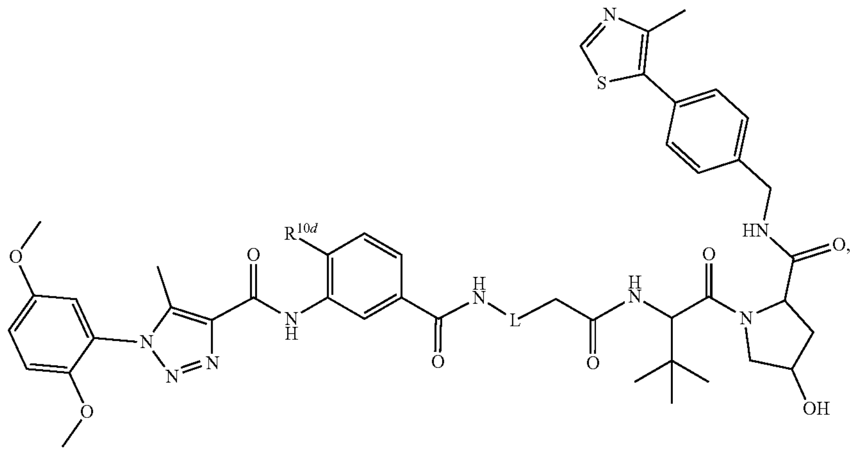

or a pharmaceutically acceptable salt thereof.

In various aspects, the compound has a structure represented by a formula:

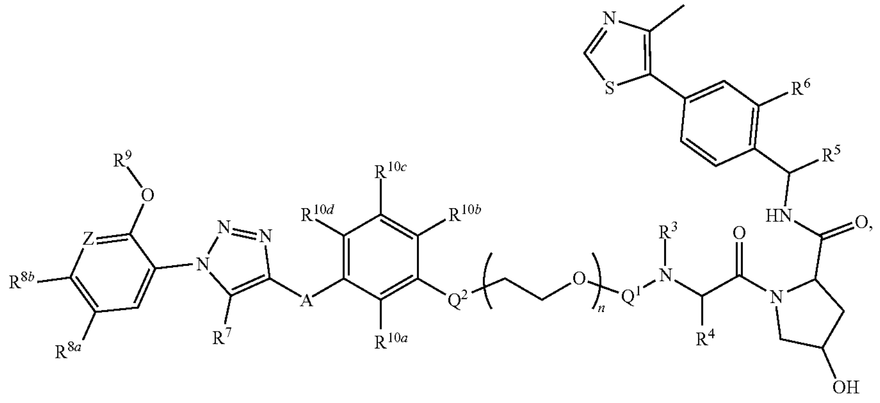

wherein n is selected from 2, 3, 4, 5, 6, 7, and 8, or a pharmaceutically acceptable salt thereof.

In various aspects, the compound has a structure represented by a formula:

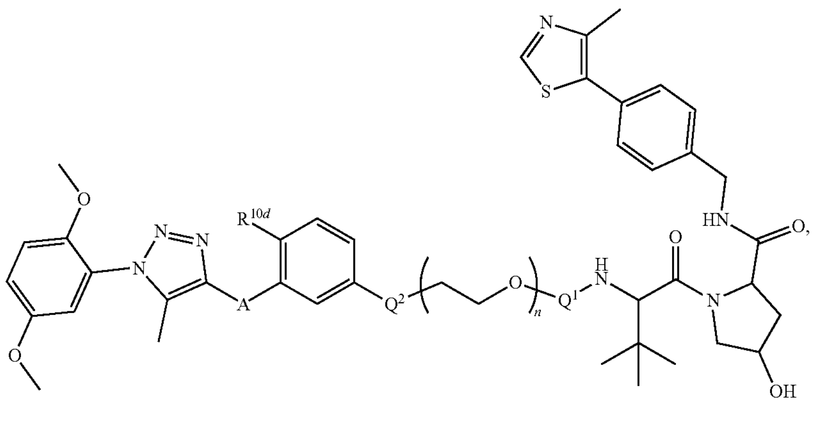

wherein n is selected from 2, 3, 4, 5, 6, 7, and 8, or a pharmaceutically acceptable salt thereof.

In various aspects, the compound is selected from:
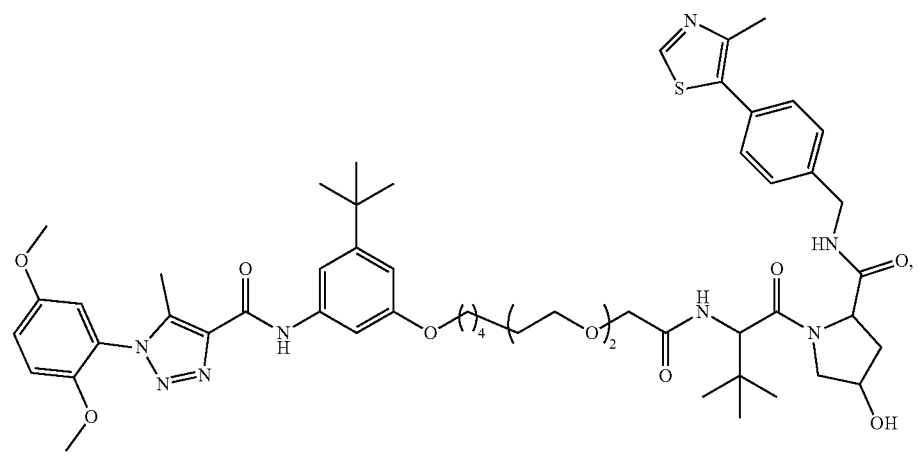
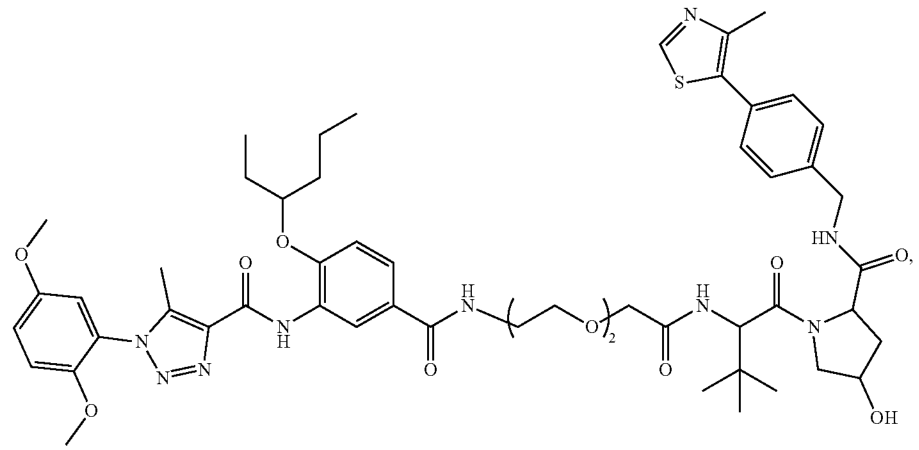
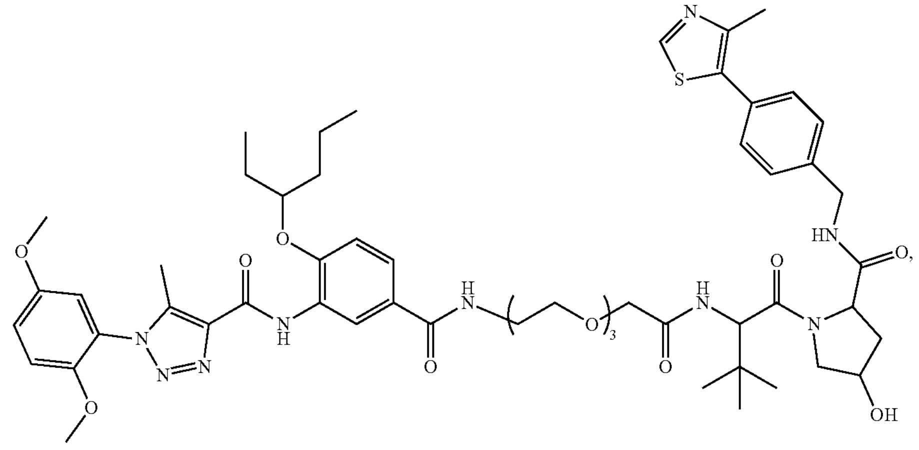

-continued
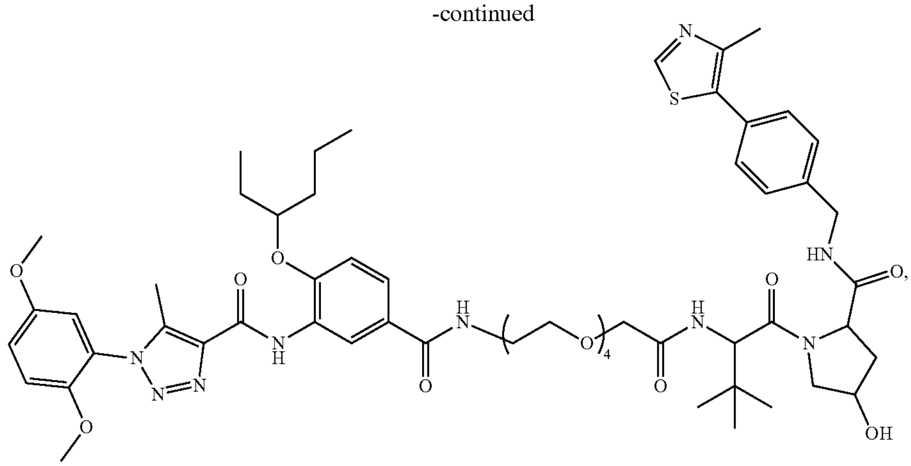
,
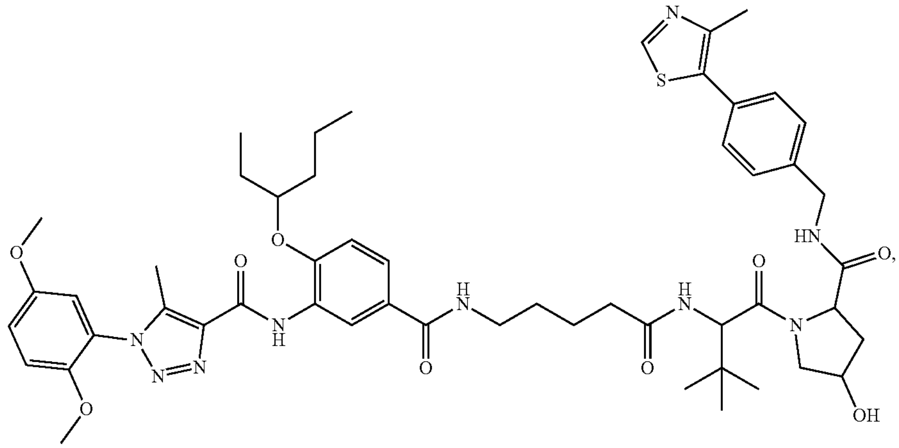
, and
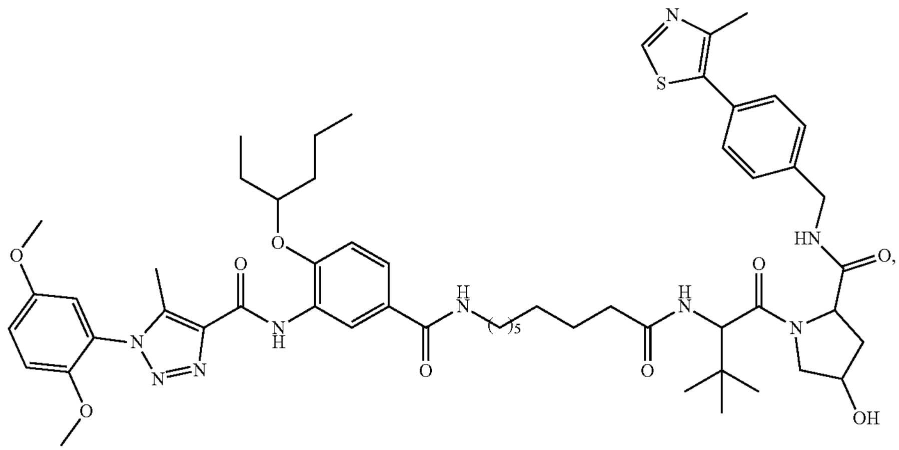
,
or a pharmaceutically acceptable salt thereof.

In various aspects, the compound is selected from:
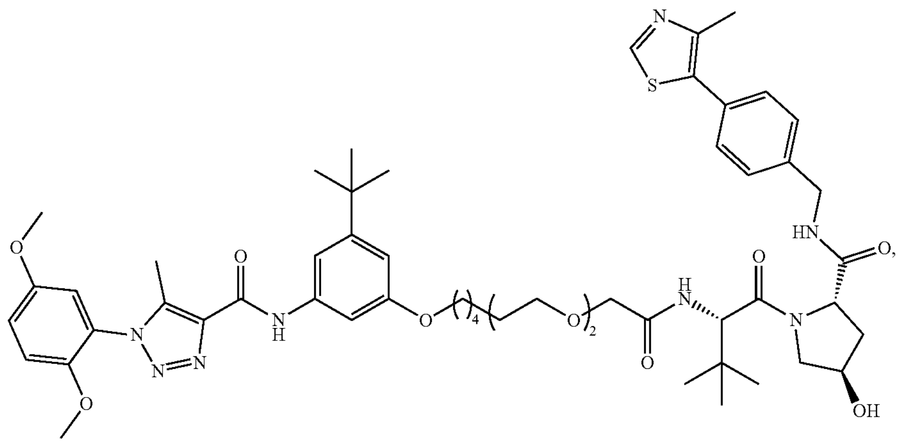
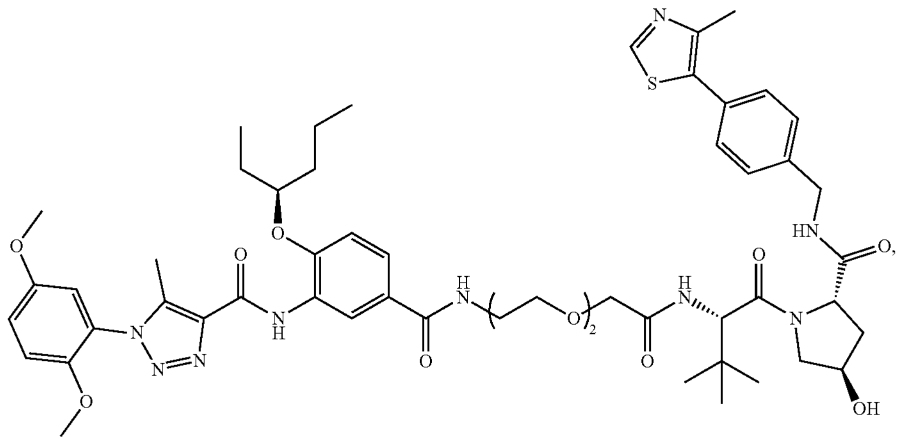
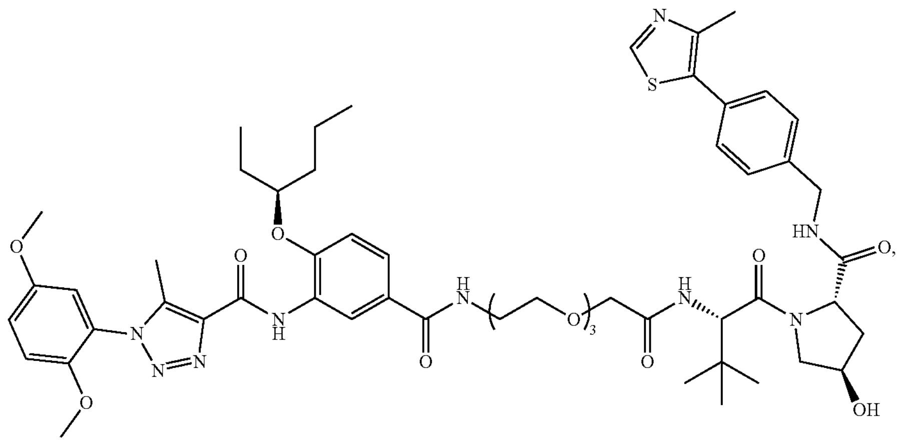

-continued
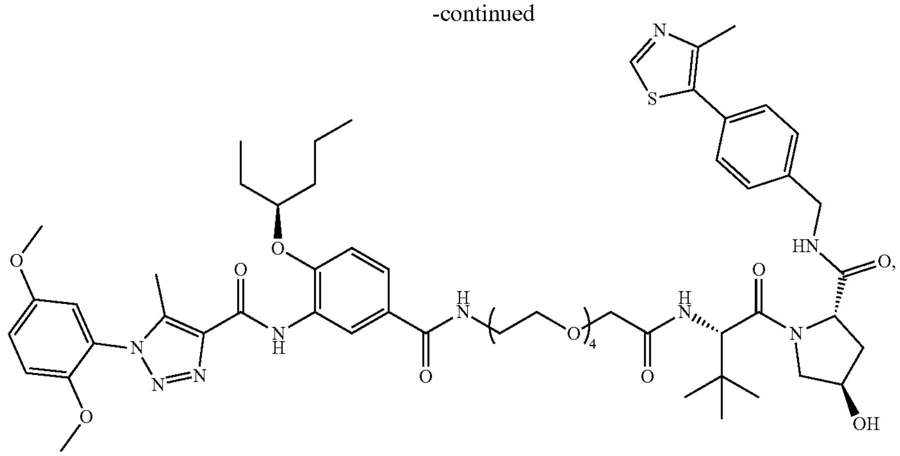
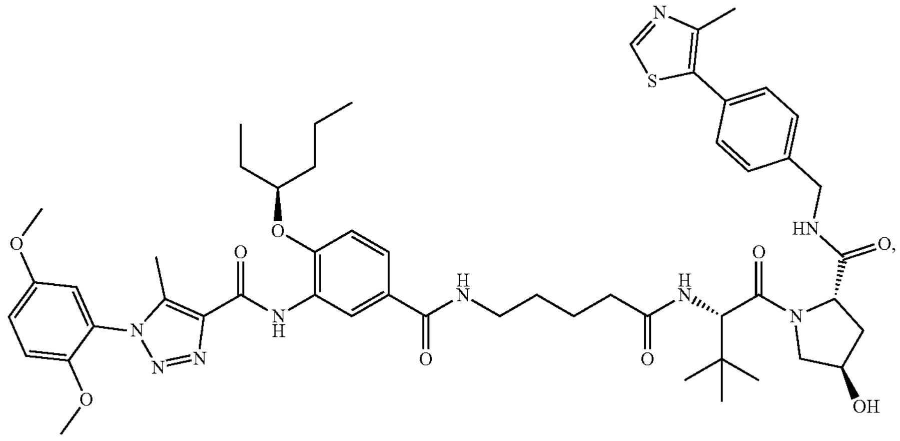
and
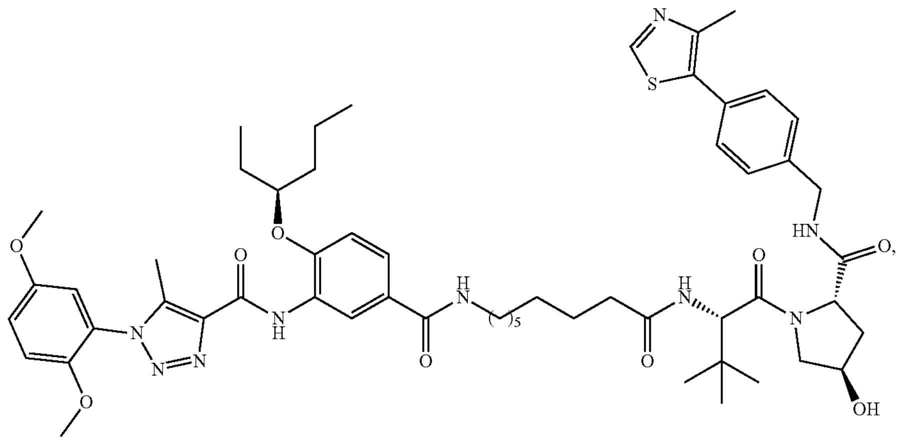
or a pharmaceutically acceptable salt thereof.

In various aspects, the compound has a structure represented by a formula:

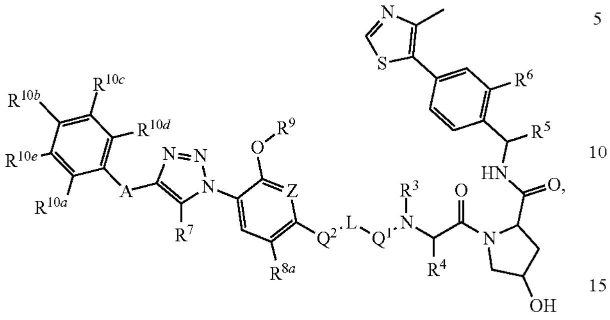

wherein A is selected from *—$SO_2$—**, *—$NR^{24}C(O)$—**, *—$N(R^{24})C(O)NR^{25}$—**, *—$C(O)NR^{24}$—**, *—$SO_2NR^2$—**, and *—$NR^{24}SO_2$—**, wherein * denotes a bond connected to the triazole and ** denotes a bond connected to the phenyl; wherein each of $R^{24}$ and $R^{25}$ is independently selected from hydrogen and C1-C4 alkyl; wherein $Q^1$ is selected from *—C(O)—**, *—OC(O)—**, *—$C(R^{20a})(R^{20b})C(O)$—**, *—$OC(R^{20a})(R^{20b})C(O)$—**, *—$C(R^{20a})(R^{20b})$C(O)C(cyclopropyl)C(O)—**, *—$C(R^{20a})(R^{20b})C(O)N(R^{21a})CH_2CH(R^{21b})C(O)$—**, *—C(C3-C4 cycloalkyl)C(O)—**, *—$NH(CH_2CH_2O)_qCH_2C(O)$—**, *—$NHCH_2C$(cyclopropyl)C(O)—**, and *—$CH_2C(O)N(R^{22})CH(R^{23})C(O)$—**, wherein * denotes a bond connected to -L- and ** denotes a bond connected to —$N(R^3)$—; wherein q is selected from 1, 2, 3, 4, 5, and 6; wherein each of $R^{20a}$ and $R^{20b}$ is independently selected from hydrogen and C1-C4 alkyl; or wherein each of $R^{20a}$ and $R^{20b}$ are covalently bound, and, together comprise a C3-C4 cycloalkyl or a C2-C3 heterocycloalkyl; or wherein $R^{20}$ is covalently bound to $R^3$, and, together with the intermediate atoms, comprises a 5-membered heterocycle; wherein each of $R^{21a}$ and $R^{21b}$ are covalently bound, and, together with the intermediate atoms, comprise a 4-membered heterocycle; wherein $R^{22}$ is hydrogen; and wherein $R^{23}$ is selected from C1-C4 alkyl, —$CH_2C_6H_5$, and —$C_6H_5$; or wherein each of $R^{22}$ and $R^{23}$ are covalently bound, and, together with the intermediate atoms, comprise an 10-membered heterocycloalkyl; wherein $Q^2$ is selected from *—O—**, *—O(C1-C8 alkylene)-**, *—$OCH_2C(O)NH$—**, and *—C(O)NH—**, wherein * denotes a bond connected to the phenyl and ** denotes a bond connected to -L-; wherein Z is selected from N and CH; wherein $R^3$ is selected from hydrogen and C1-C4 alkyl; and wherein $R^4$ is selected from C1-C4 alkyl, C1-C4 hydroxyalkyl, and $C_6H_5$; or wherein each of $R^3$ and $R^4$ are covalently bound, and, together with the intermediate atoms, comprise a 5- or 6-membered heterocycle having 0 or 1 —OH group; or wherein each of $R^3$ and $R^{20a}$, when present, are covalently bound, and, together with the intermediate atoms, comprise a 5-membered heterocycle; wherein $R^5$ is hydrogen or methyl; and wherein $R^6$ is hydrogen, —OH, or C1-C4 alkyl halide; wherein $R^7$ is selected from hydrogen and C1-C4 alkyl; wherein each of $R^{8a}$ and $R^{8b}$ is independently selected from hydrogen, halogen, C1-C4 alkyl, C1-C4 haloalkyl, C1-C4 alkoxy, and C1-C4 haloalkoxy; wherein $R^9$ is C1-C4 alkyl; and wherein each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, C1-C8 alkylamino, and —$CO_2$(C1-C4 alkyl), or a pharmaceutically acceptable salt thereof.

In various aspects, the compound has a structure represented by a formula:

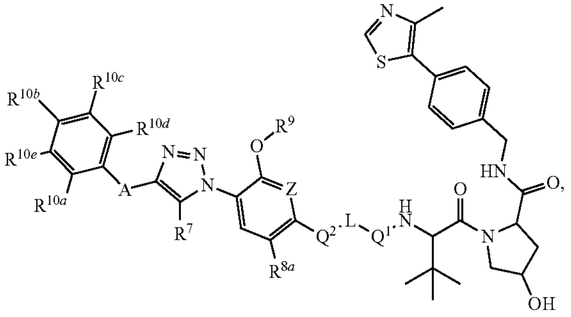

or a pharmaceutically acceptable salt thereof.

In various aspects, the compound has a structure represented by a formula:

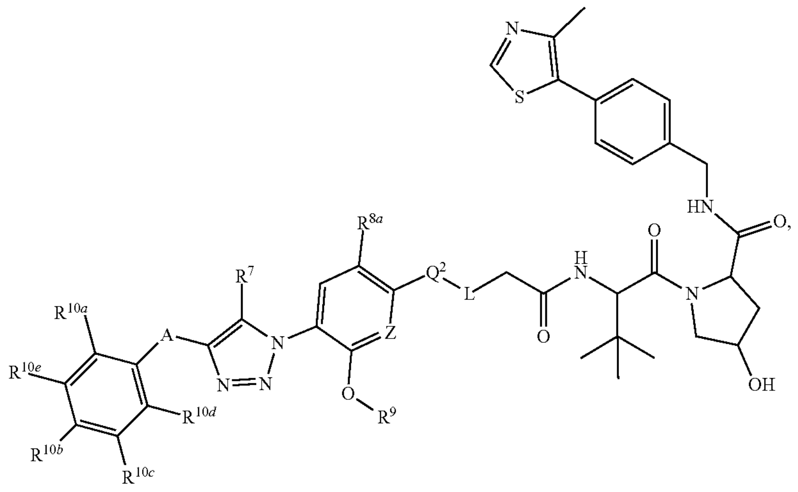

or a pharmaceutically acceptable salt thereof.

In various aspects, the compound has a structure represented by a formula:

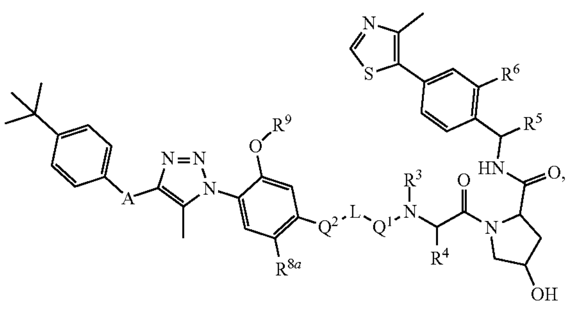

or a pharmaceutically acceptable salt thereof.

In various aspects, the compound has a structure represented by a formula:

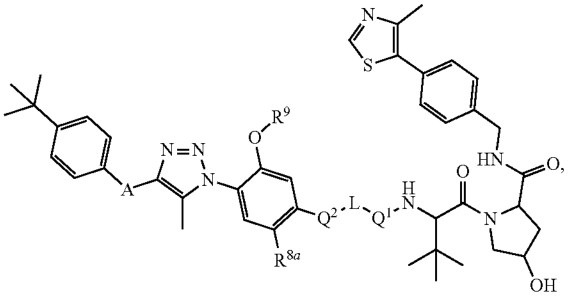

or a pharmaceutically acceptable salt thereof.

In various aspects, the compound has a structure represented by a formula:

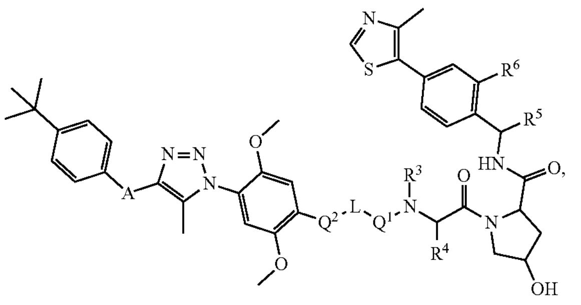

or a pharmaceutically acceptable salt thereof.

In various aspects, the compound has a structure represented by a formula:

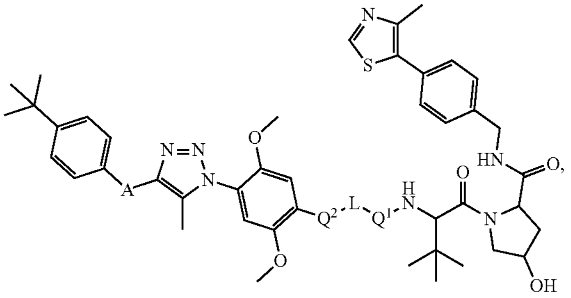

or a pharmaceutically acceptable salt thereof.

In various aspects, the compound has a structure represented by a formula:

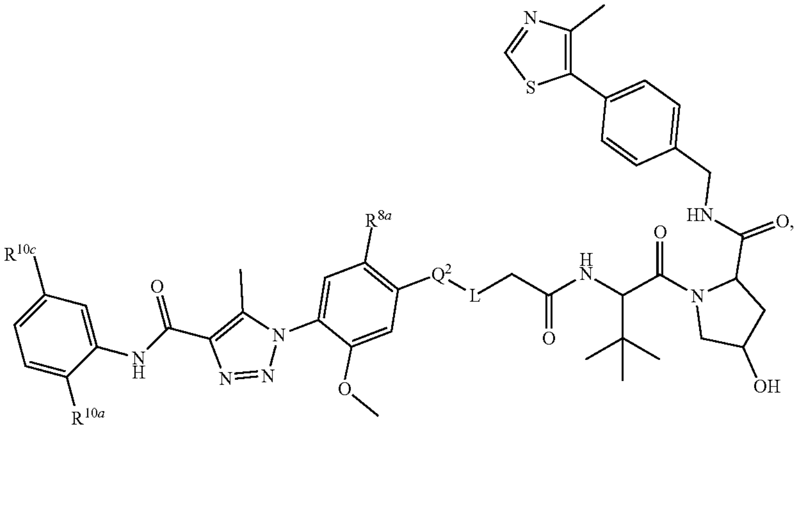

or a pharmaceutically acceptable salt thereof.

In various aspects, the compound has a structure represented by a formula:
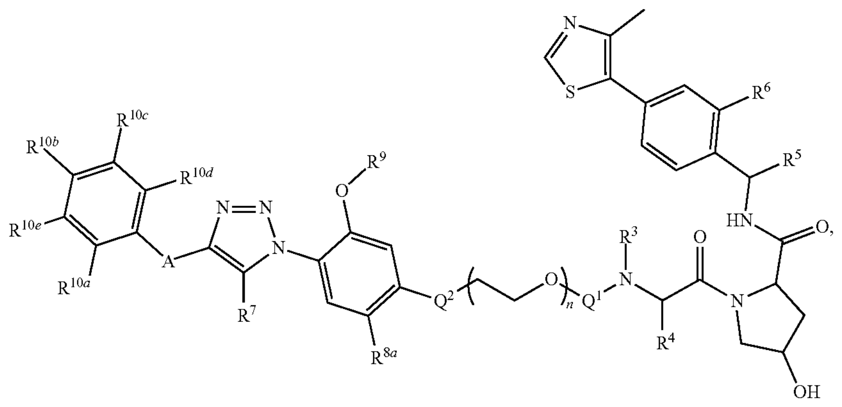
wherein n is selected from 2, 3, 4, 5, 6, 7, and 8, or a pharmaceutically acceptable salt thereof.
In various aspects, the compound has a structure represented by a formula:
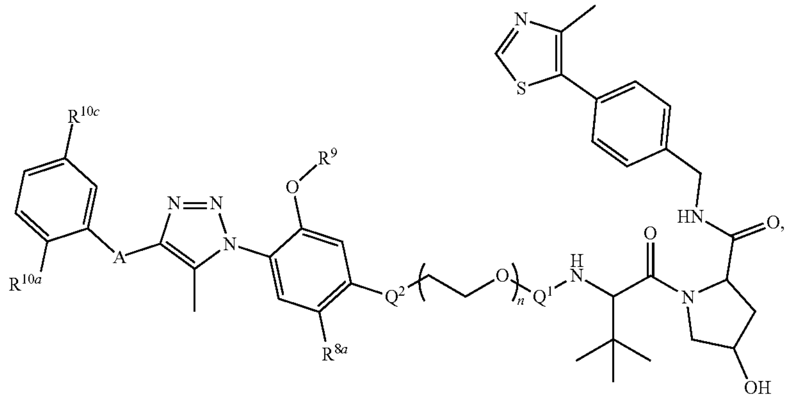
wherein n is selected from 2, 3, 4, 5, 6, 7, and 8, or a pharmaceutically acceptable salt thereof.
In various aspects, the compound is selected from:
ke
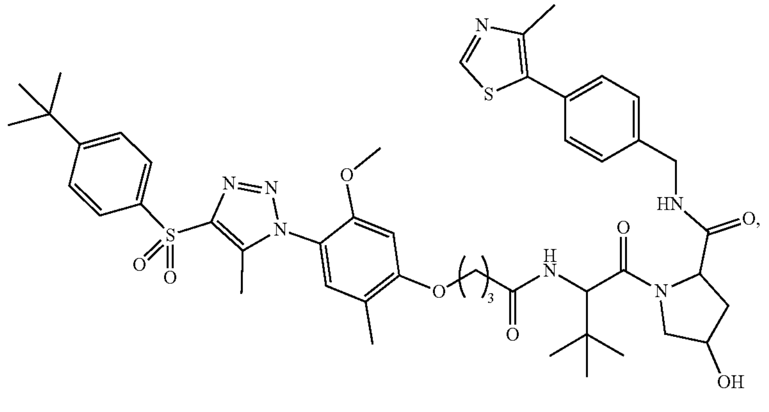

-continued
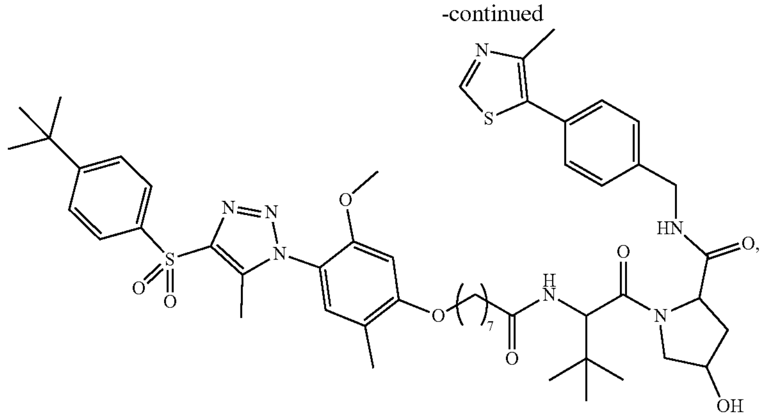
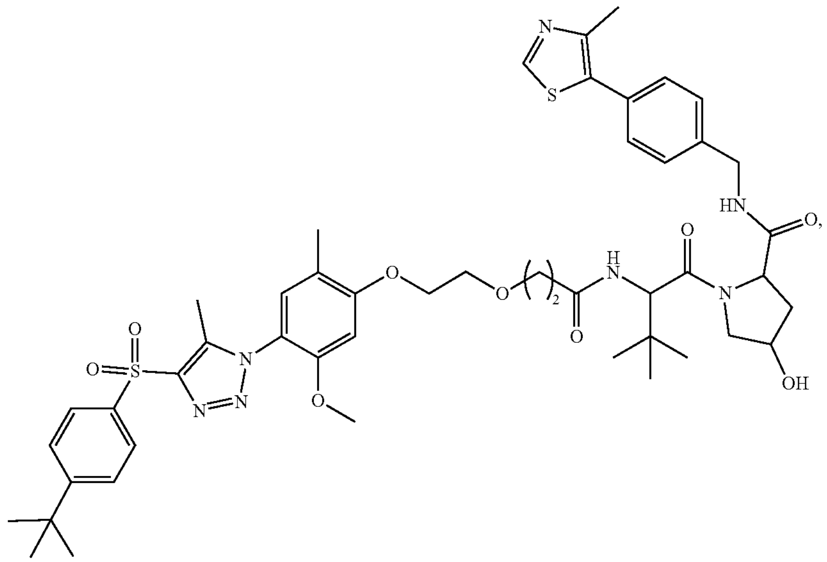
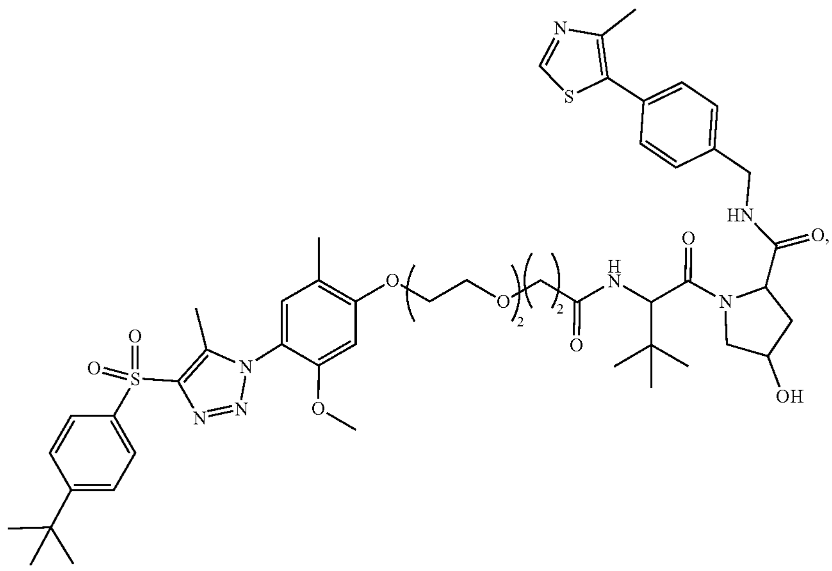

-continued
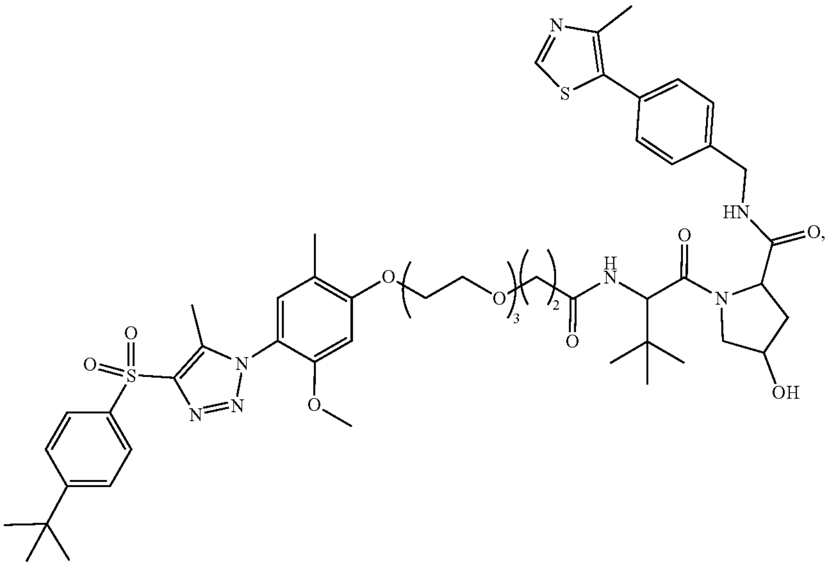
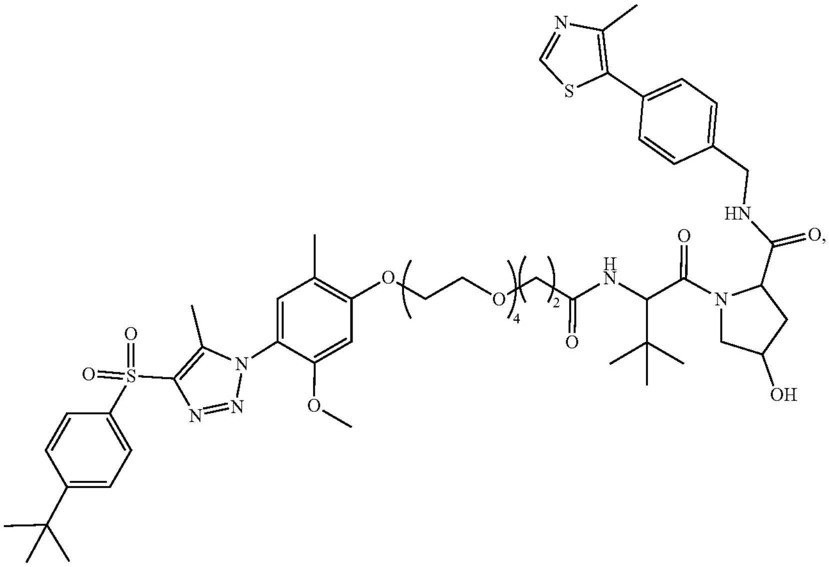
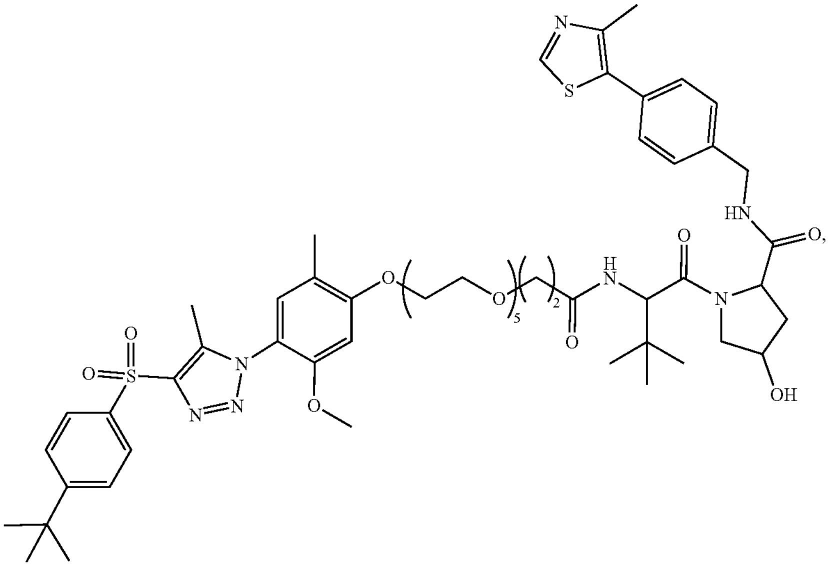

-continued
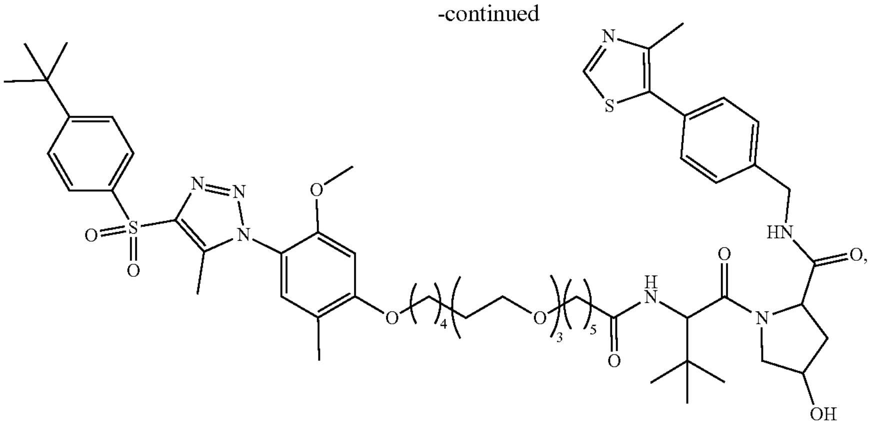
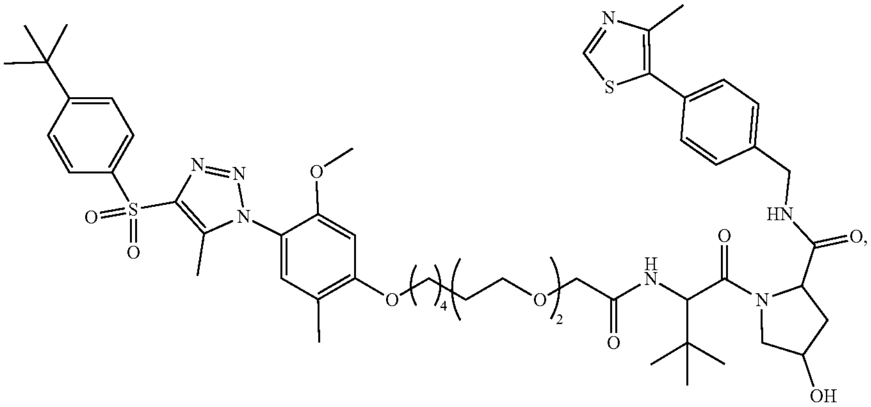
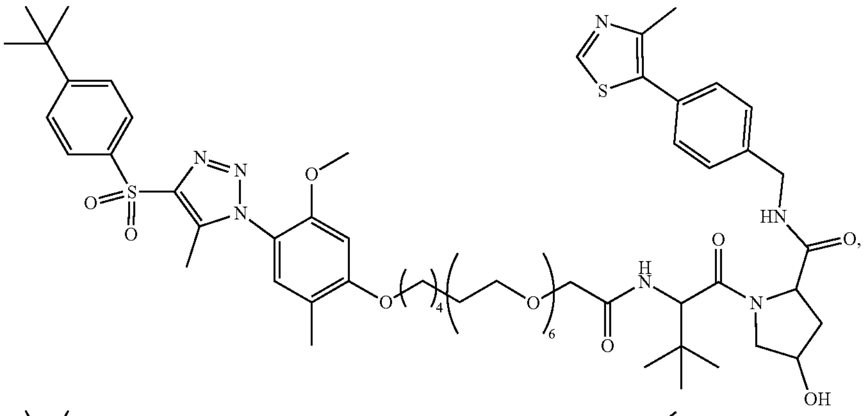
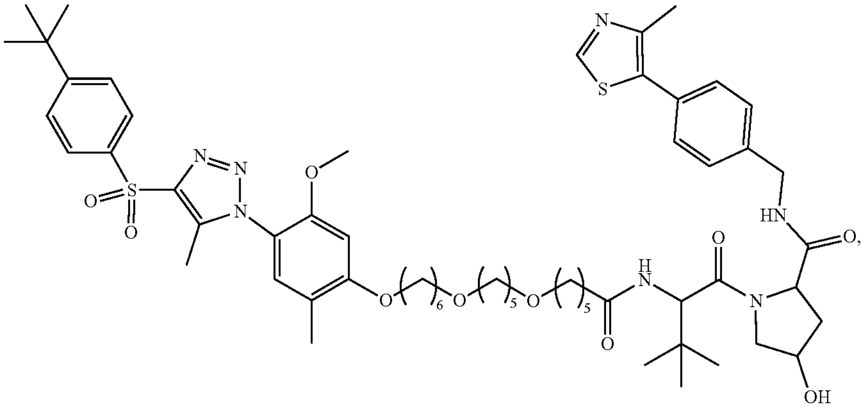

-continued
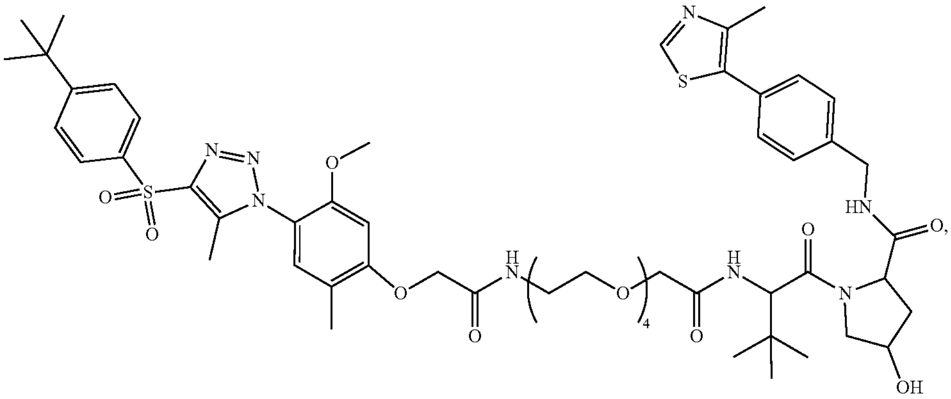
,
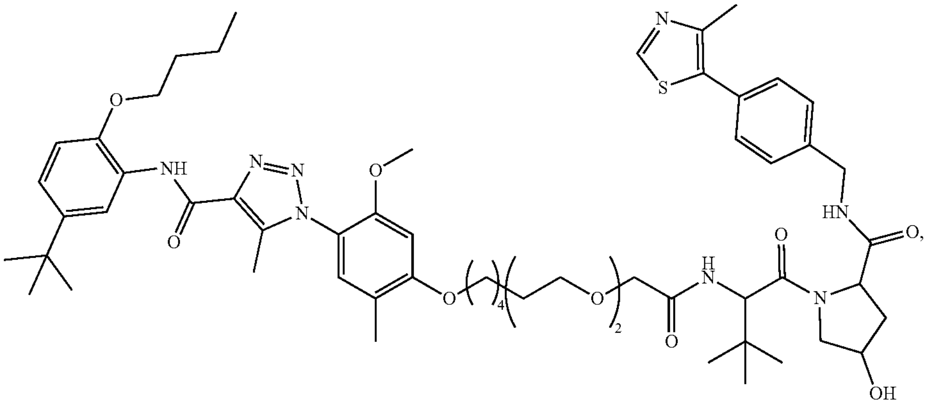
,
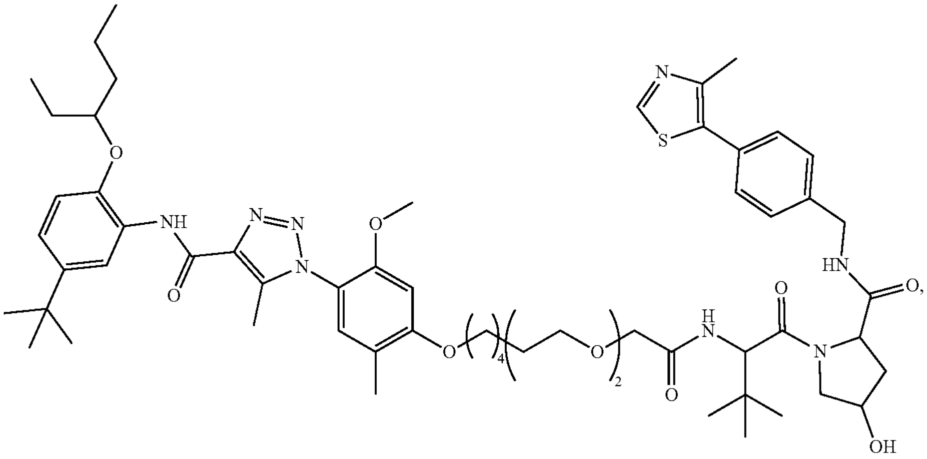
,
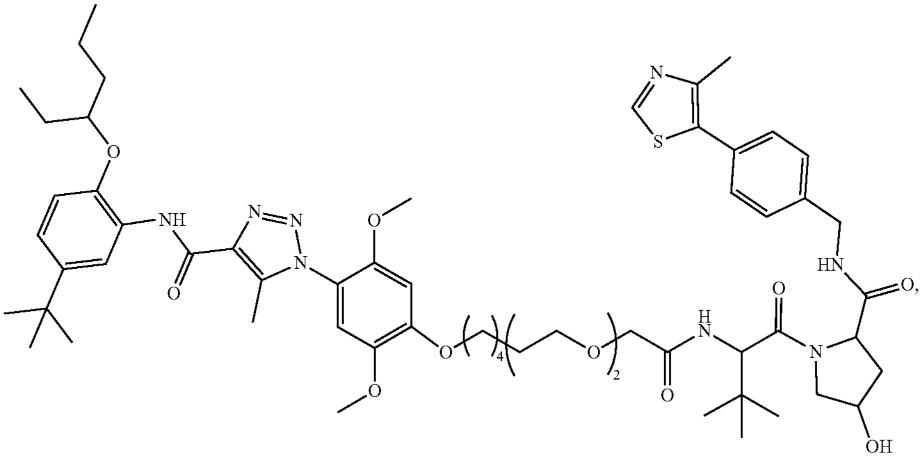
, and

-continued
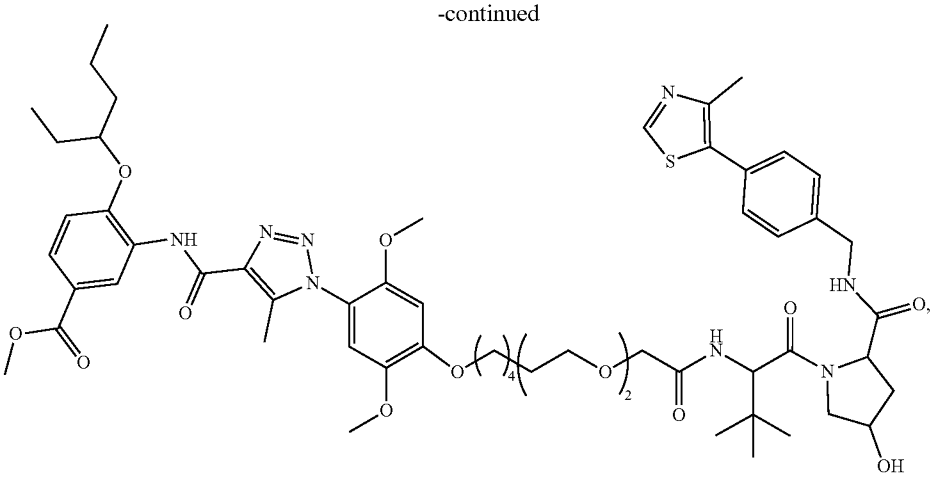
or a pharmaceutically acceptable salt thereof.
In various aspects, the compound is selected from:
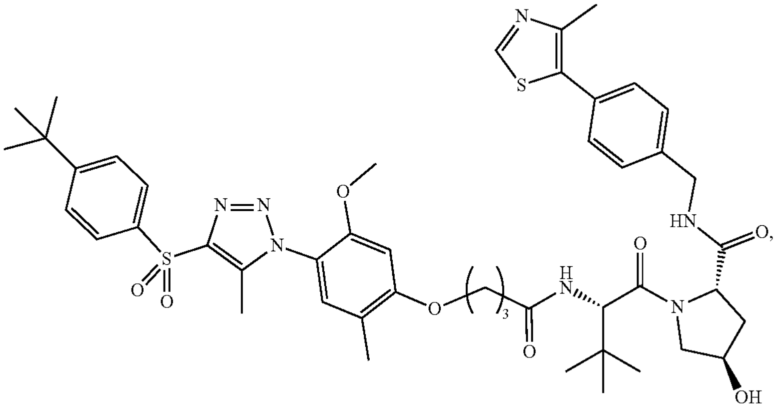
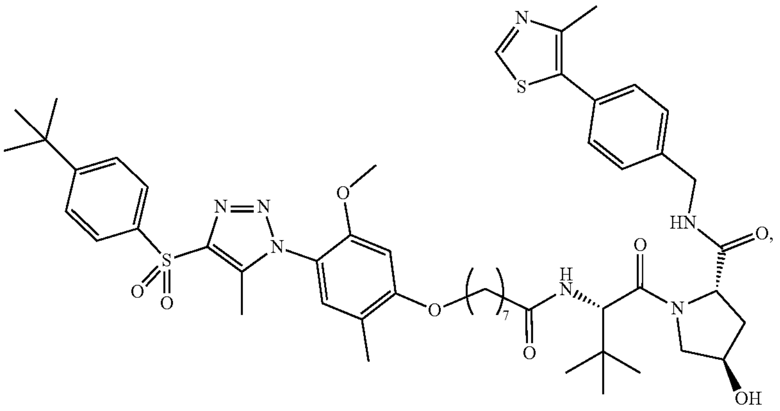

-continued
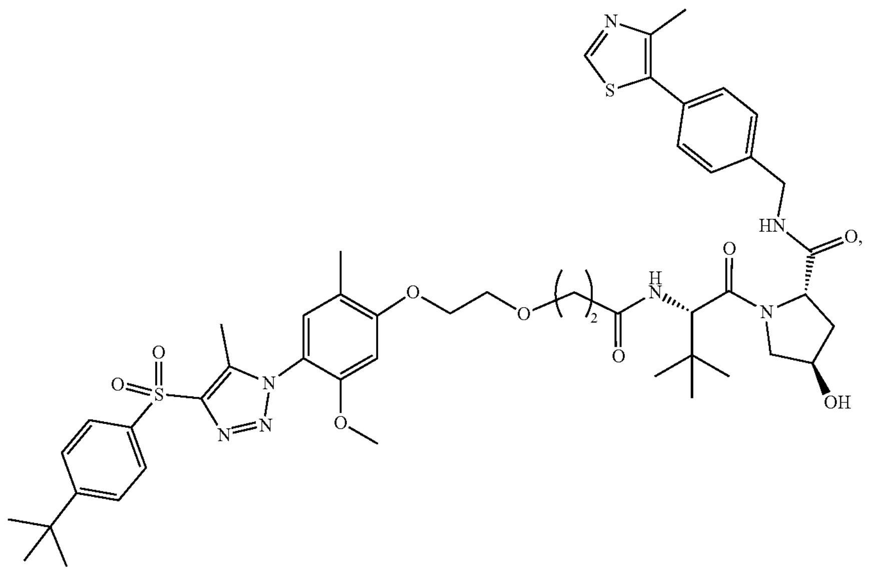
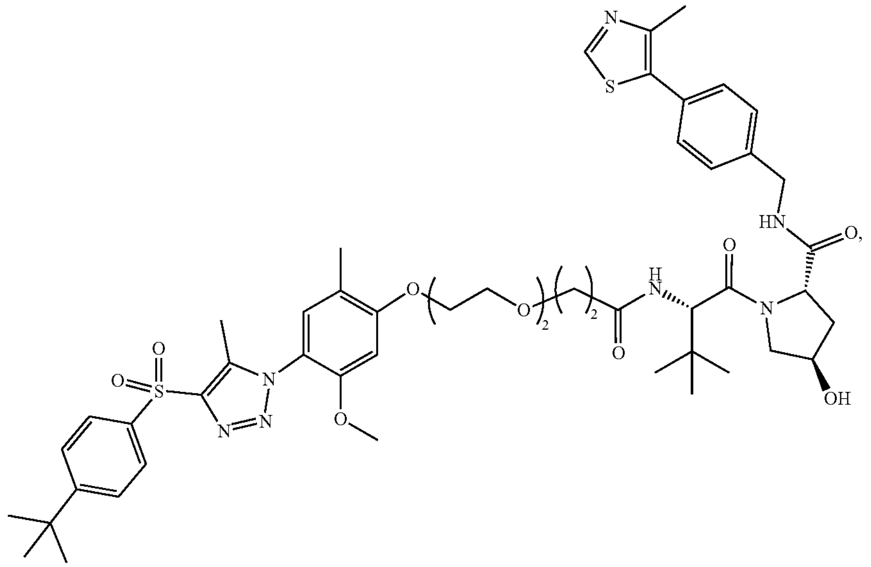
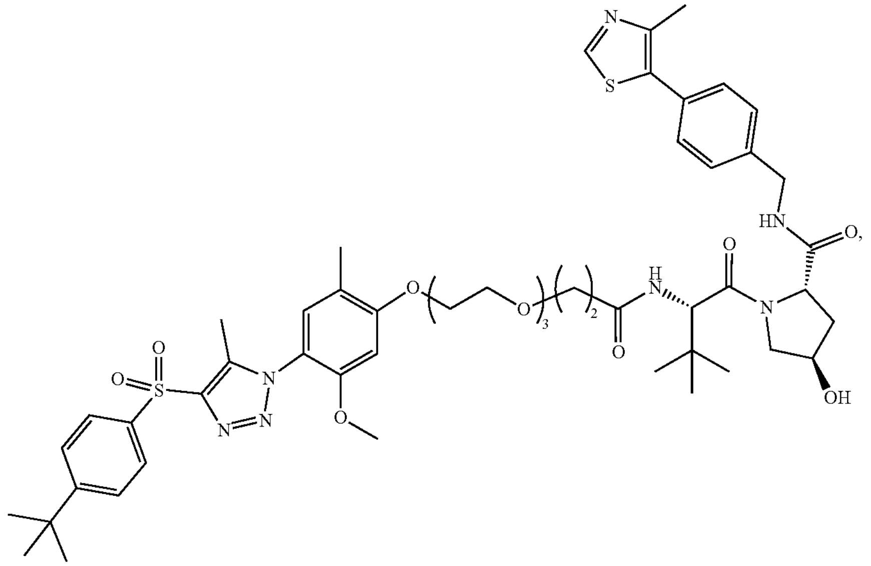

-continued
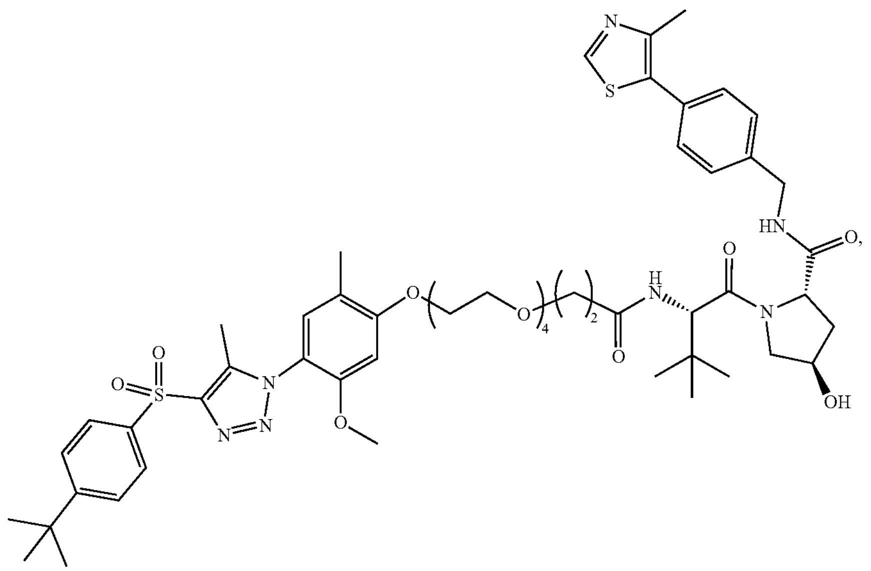
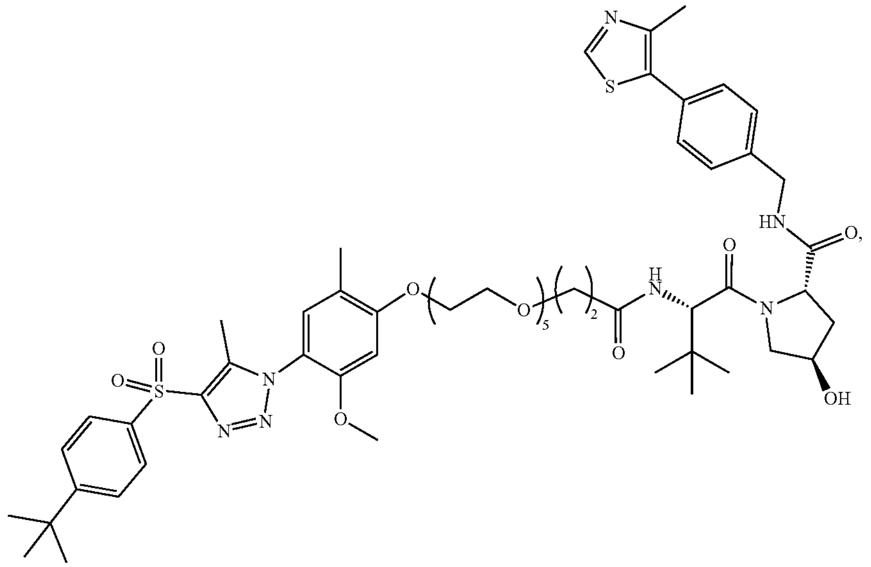
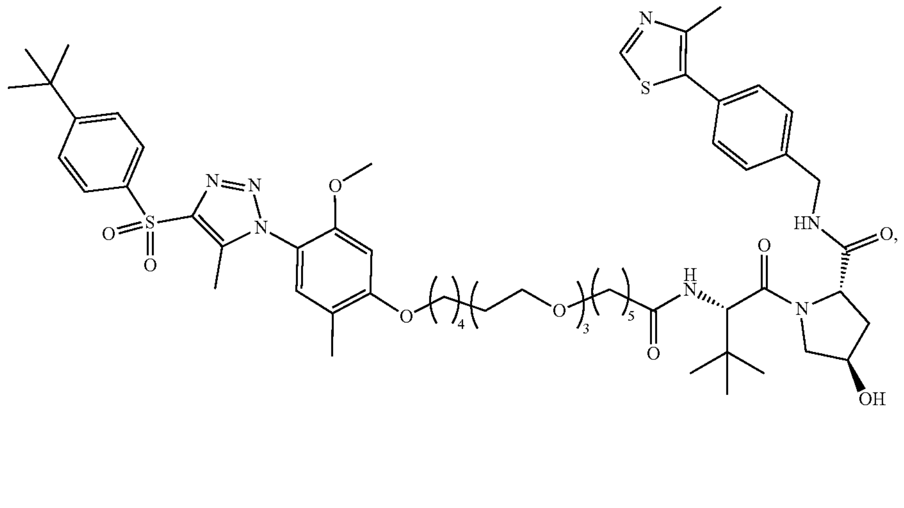

-continued
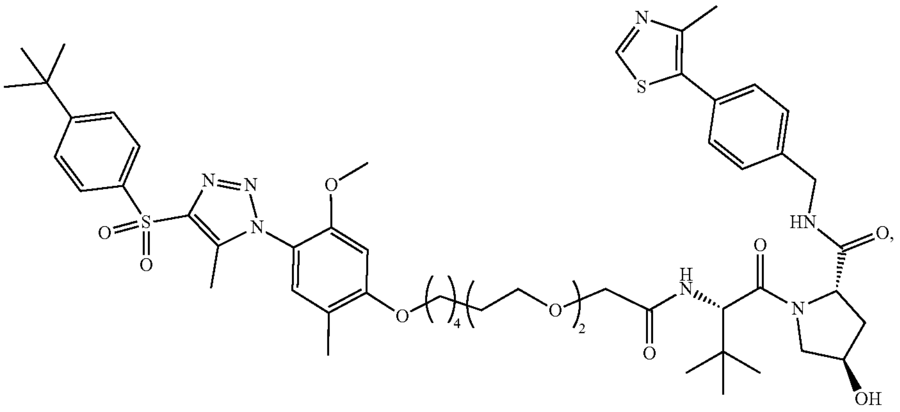
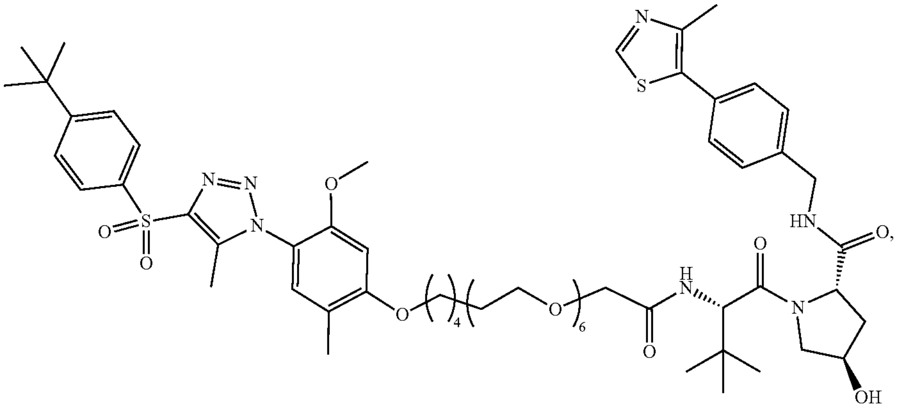
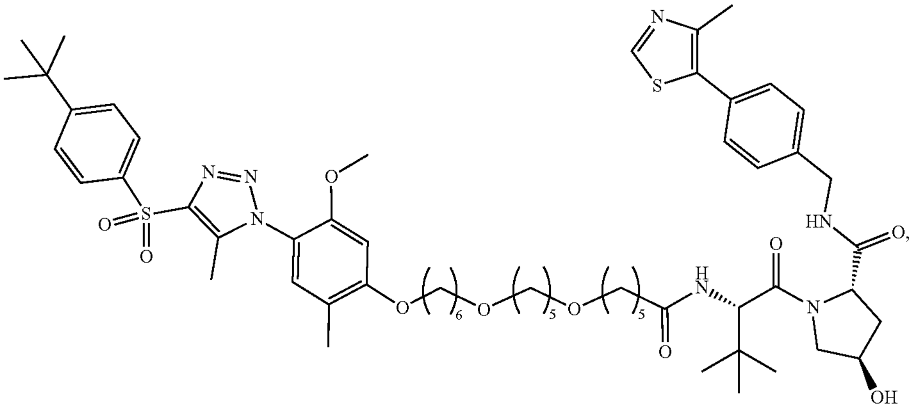
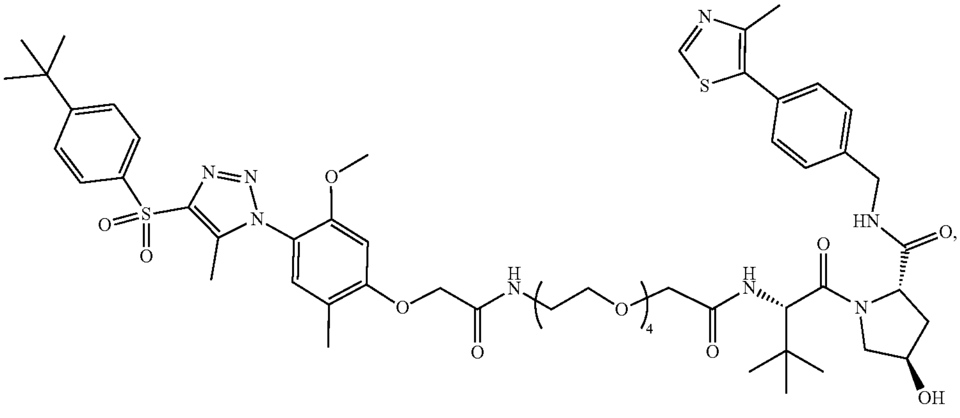

-continued
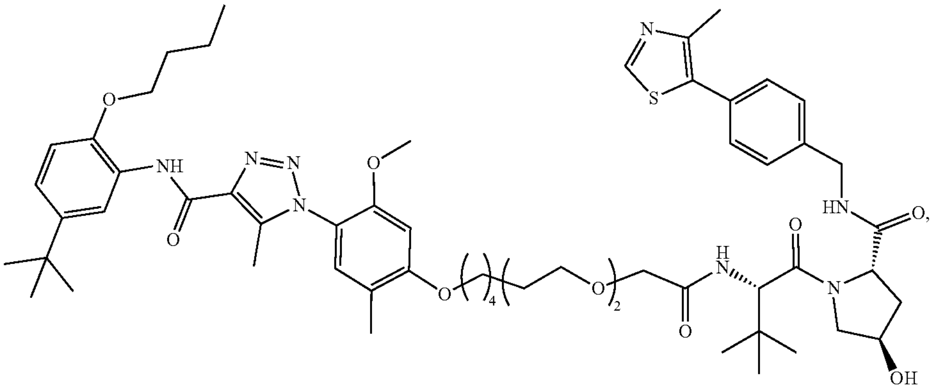
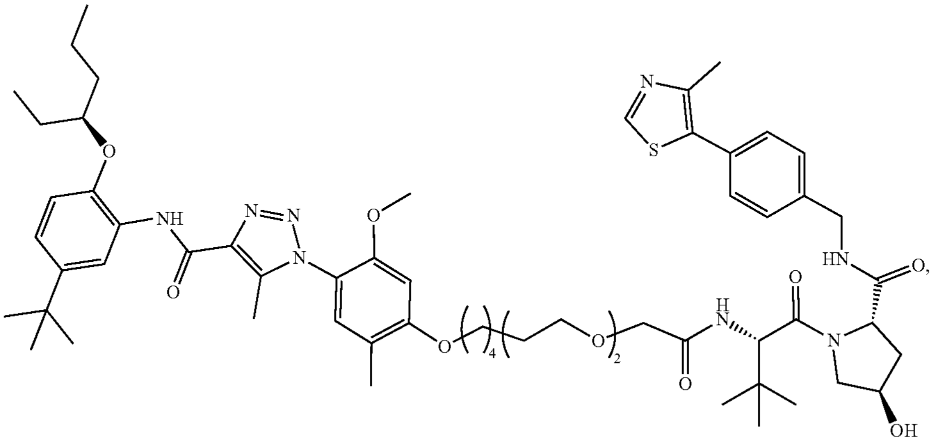
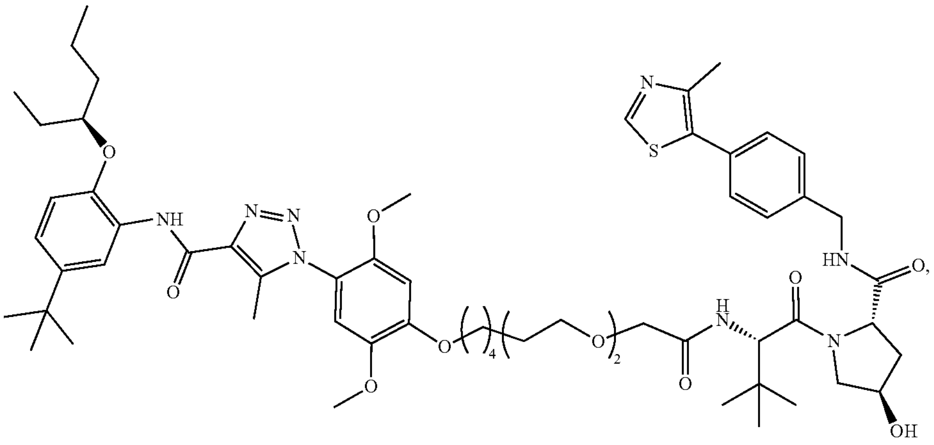
and

-continued
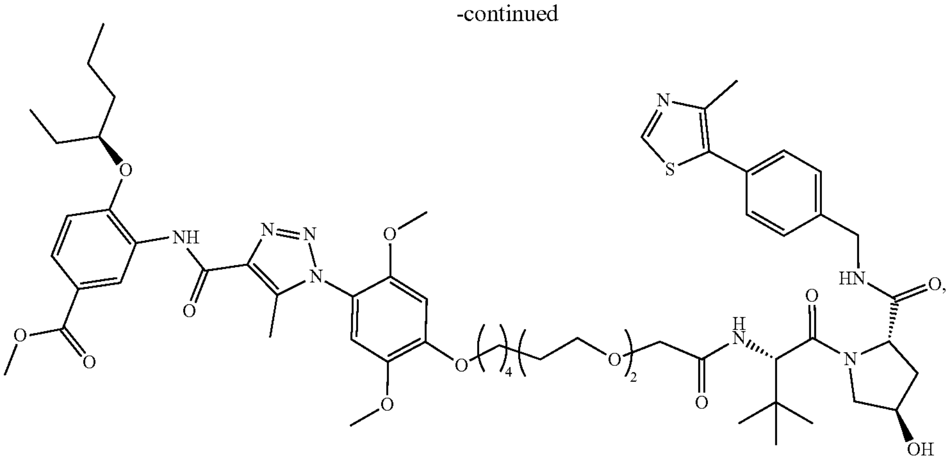
or a pharmaceutically acceptable salt thereof.
In various aspects, the compound is selected from:
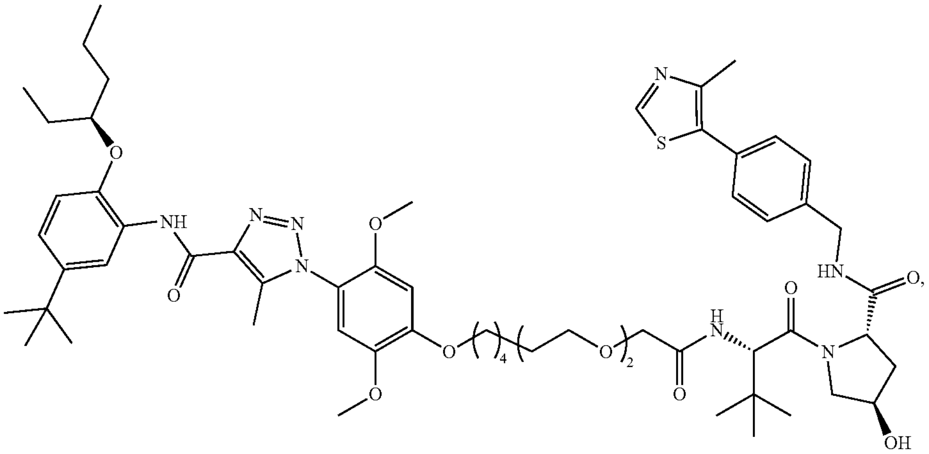
and
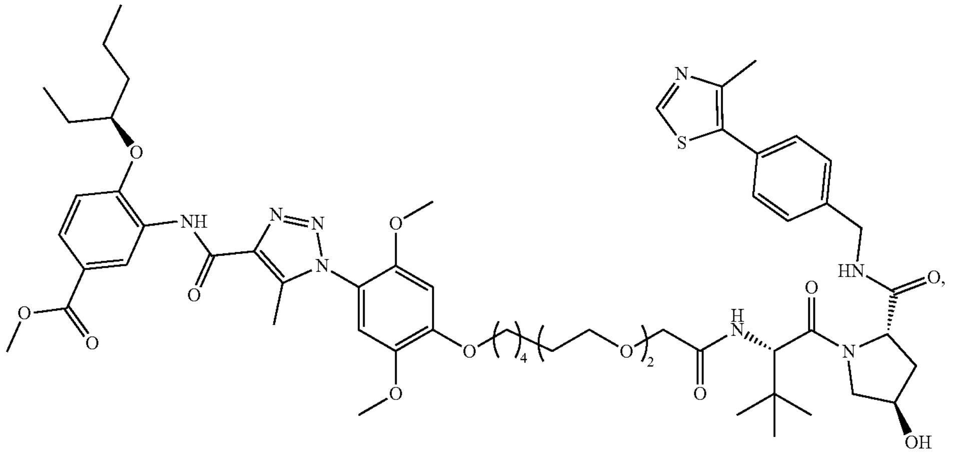
or a pharmaceutically acceptable salt thereof.

In one aspect, disclosed are compounds having a structure represented by a formula:

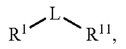

wherein L is a linker; wherein $R^1$ is a residue of a pregnane X receptor (PXR) ligand; and wherein $R^{11}$ is a residue of a residue of a fluorophore, a residue of biotin, or a residue of a biotin derivative, or a pharmaceutically acceptable salt thereof.

In various aspect, the compound has a structure represented by a formula:

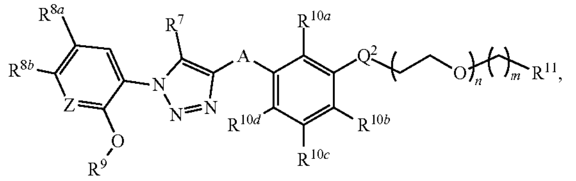

wherein m is selected from 1, 2, 3, 4, and 5; and wherein n is selected from 2, 3, 4, 5, 6, 7, and 8, or a pharmaceutically acceptable salt thereof.

In various aspect, the compound has a structure represented by a formula:

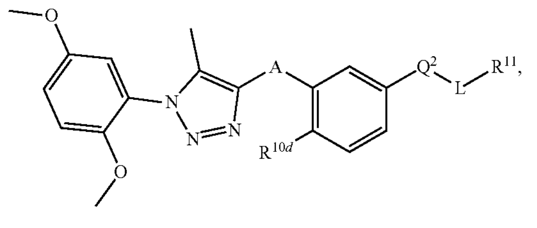

or a pharmaceutically acceptable salt thereof.

In various aspect, the compound has a structure represented by a formula:

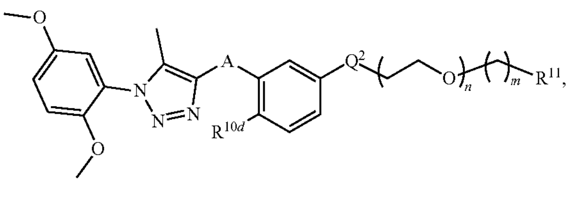

wherein m is selected from 1, 2, 3, 4, and 5; and wherein n is selected from 2, 3, 4, 5, 6, 7, and 8, or a pharmaceutically acceptable salt thereof.

In various aspect, the compound has a structure represented by a formula:

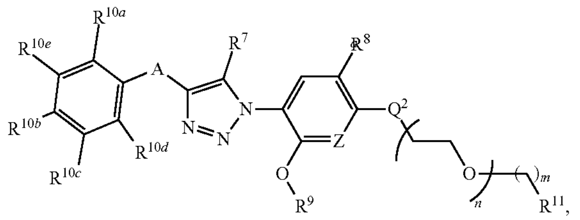

wherein m is selected from 1, 2, 3, 4, and 5; and wherein n is selected from 2, 3, 4, 5, 6, 7, and 8, or a pharmaceutically acceptable salt thereof.

In various aspect, the compound has a structure represented by a formula:

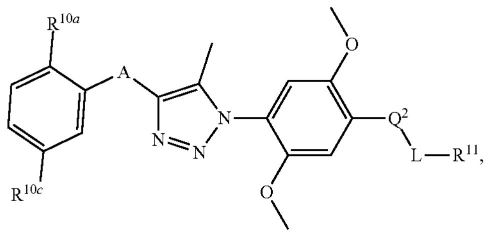

or a pharmaceutically acceptable salt thereof.

In various aspect, the compound has a structure represented by a formula:

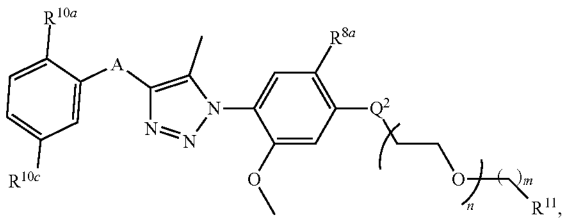

or a pharmaceutically acceptable salt thereof.

In various aspects, the compound is selected from:

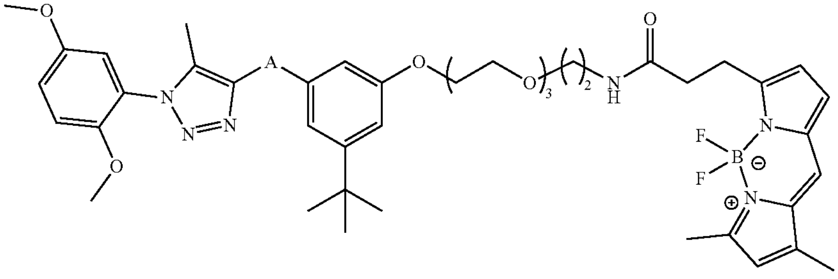

-continued

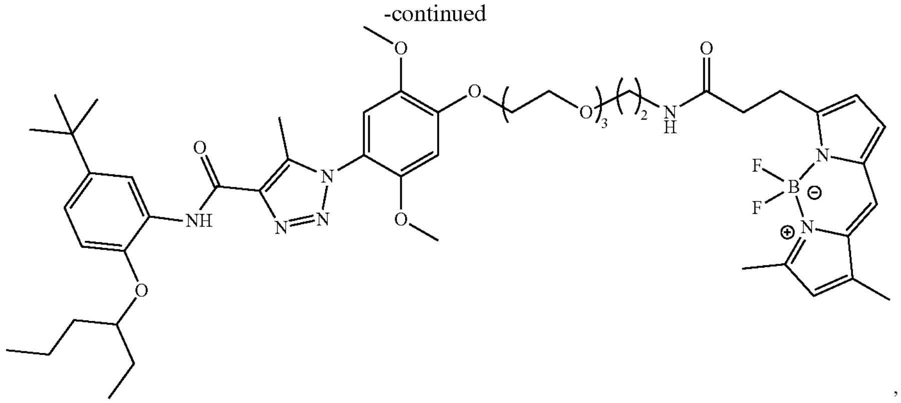

and , or a pharmaceutically acceptable salt thereof.

In various aspects, the compound is selected from:

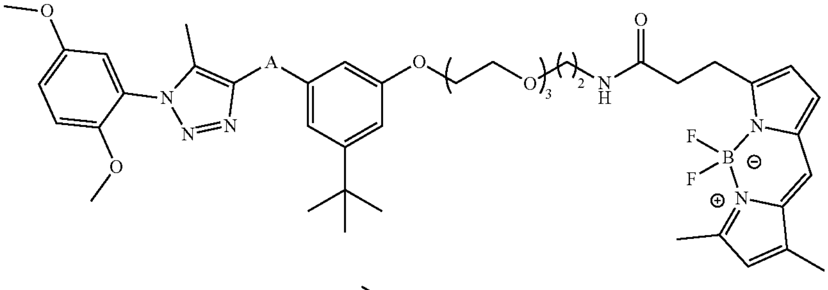

and

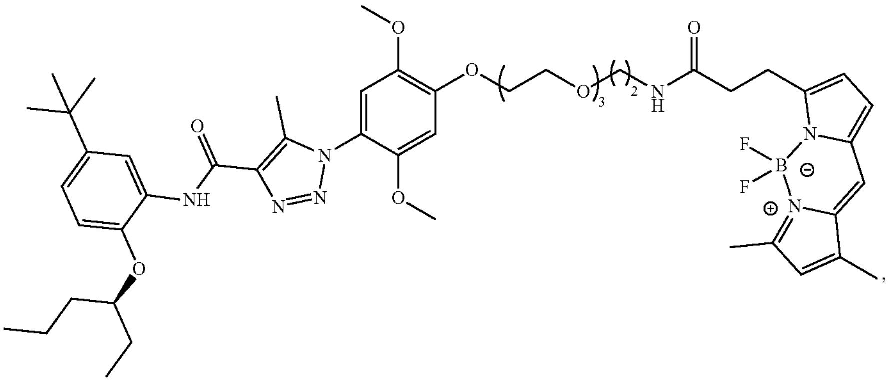

, or a pharmaceutically acceptable salt thereof.

In one aspect, m is selected from 1, 2, 3, 4, and 5. In a further aspect, m is selected from 1, 2, 3, and 4. In a still further aspect, m is selected from 1, 2, and 3. In yet a further aspect, m is selected from 1 and 2. In an even further aspect, m is selected from 2, 3, 4, and 5. In an even still further aspect, m is selected from 3, 4, and 5. In yet an even further aspect, m is selected from 4 and 5.

In one aspect, n is selected from 1, 2, 3, 4, 5, 6, 7, and 8. In a further aspect, n is selected from 1, 2, 3, 4, 5, 6, and 7. In a still further aspect, n is selected from 1, 2, 3, 4, 5, and 6. In yet a further aspect, n is selected from 1, 2, 3, 4, and 5. In an even further aspect, n is selected from 1, 2, 3, and 4. In a still further aspect, n is selected from 1, 2, and 3. In yet a further aspect, n is selected from 1 and 2. In an even further aspect, n is selected from 2, 3, 4, 5, 6, 7, and 8. In a still further aspect, n is selected from 3, 4, 5, 6, 7, and 8. In yet a further aspect, n is selected from 4, 5, 6, 7, and 8. In an even further aspect, n is selected from 5, 6, 7, and 8. In a still further aspect, n is selected from 6, 7, and 8. In yet a further aspect, n is selected from 7 and 8.

In one aspect, q is selected from 1, 2, 3, 4, 5, and 6. In a further aspect, q is selected from 1, 2, 3, 4, and 5. In a still further aspect, q is selected from 1, 2, 3, and 4. In yet a further aspect, q is selected from 1, 2, and 3. In an even further aspect, q is selected from 1 and 2. In a still further aspect, q is selected from 2, 3, 4, 5, and 6. In yet a further aspect, q is selected from 3, 4, 5, and 6. In an even further aspect, q is selected from 4, 5, and 6. In a still further aspect, q is selected from 5 and 6.

In one aspect, t is selected from 1, 2, 3, 4, 5, and 6. In a further aspect, t is selected from 1, 2, 3, 4, and 5. In a still further aspect, t is selected from 1, 2, 3, and 4. In yet a further aspect, t is selected from 1, 2, and 3. In an even further aspect, t is selected from 1 and 2. In a still further aspect, t is selected from 2, 3, 4, 5, and 6. In yet a further aspect, t is selected from 3, 4, 5, and 6. In an even further aspect, t is selected from 4, 5, and 6. In a still further aspect, t is selected from 5 and 6.

a. A Group

In one aspect, A is selected from *—$SO_2$—**, *—$NR^{24}C$(O)—**, *—$N(R^{24})C(O)NR^{25}$—**, *—$C(O)NR^{24}$—**, *—$SO_2NR^{24}$—**, and *—$NR^{24}SO_2$—**, wherein * denotes a bond connected to the triazole and ** denotes a bond connected to the phenyl. In a further aspect, A is selected from *—$SO_2$—**, *—$NR^{24}C(O)$—**, *—$N(R^{24})C(O)NR^{25}$—**, *—$C(O)NR^{24}$—**. In a still further aspect, A is selected from *—$SO_2$—**, *—$NR^{24}C(O)$—**, *—$C(O)NR^{24}$—**.

In various aspects, A is *—$SO_2$—**.

In various aspects, A is selected from *—$C(O)NR^{24}$—** and *—$SO_2NR^{24}$—**. In a further aspect, A is *—$C(O)NR^{24}$—**. In a still further aspect, A is *—$SO_2NR^{24}$**.

In various aspects, A is *—$C(O)NR^2$—**.

b. L Groups

In one aspect, L is a linker. Examples of linkers include, but are not limited to, *-(C3-C24 alkylene)-**, *-(C3-C24 alkoxy)-**, *—$(CH_2CH_2O)_n$—**, *—$(CH_2CH_2O)_n$(C1-C4 alkyl)-**, and a structure selected from:

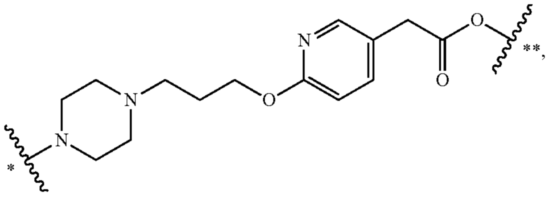

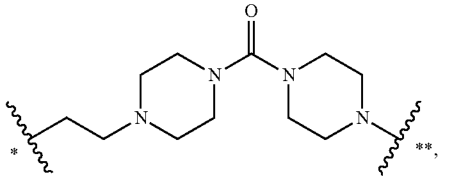

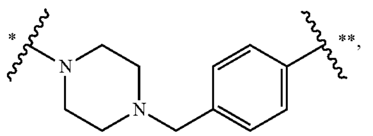

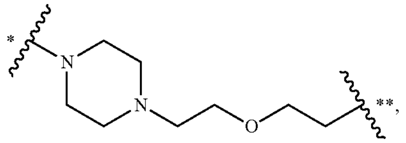

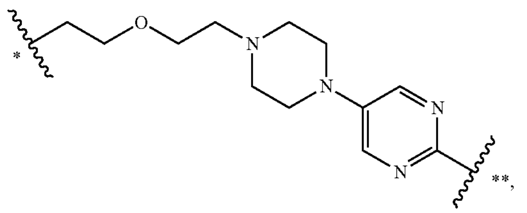

-continued

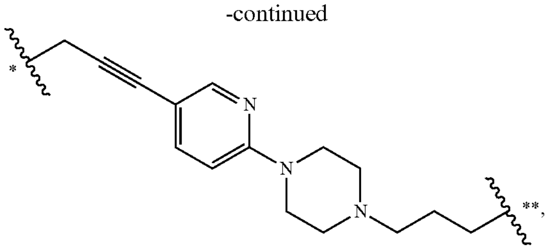

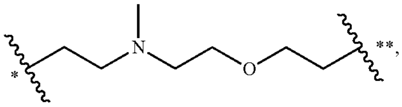

and

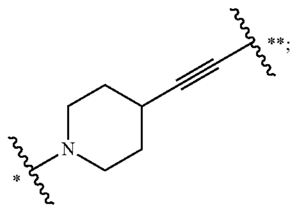

wherein * denotes a bond connected to $R^1$ and ** denotes a bond connected to $R^2$.

In various aspects, L is selected from *-(C3-C24 alkylene)-**, *-(C3-C24 alkoxy)-**, *—$(CH_2CH_2O)_n$—**, *—$(CH_2CH_2O)_n$(C1-C4 alkyl)-**, wherein * denotes a bond connected to $R^1$ and ** denotes a bond connected to $R^2$, and wherein n is selected from 2, 3, 4, 5, 6, 7, and 8.

In various aspects, L is *-(C3-C24 alkylene)-**. In a further aspect, L is *—(C8-C24 alkylene)-**. In a still further aspect, L is *-(C3-C8 alkylene)-**. In yet a further aspect, L is *-(C3-C4 alkylene)-**.

In various aspects, L is *—$(CH_2CH_2O)_n$—**. In a further aspect, L is *—$(CH_2CH_2O)_4$—**.

c. $Q^1$ Groups

In one aspect, $Q^1$ is selected from *—C(O)—**, *—OC(O)—**, *—$C(R^{20a})(R^{20b})C(O)$—**, *—$OC(R^{20a})(R^{20b})C(O)$—**, *—$C(R^{20a})(R^{20b})C(O)C$(cyclopropyl)C(O)—**, *—$C(R^{20a})(R^{20b})C(O)N(R^{21a})CH_2CH(R^{21b})C(O)$—**, *—C(C3-C4 cycloalkyl)C(O)—**, *—$NH(CH_2CH_2O)_qCH_2C(O)$—**, *—$NHCH_2C$(cyclopropyl)C(O)—**, and *—$CH_2C(O)N(R^{22})CH(R^{23})C(O)$—**, wherein * denotes a bond connected to -L- and ** denotes a bond connected to —$N(R^3)$—; wherein q is selected from 1, 2, 3, 4, 5, and 6.

In various aspects, $Q^1$ is selected from *—C(O)—** and *—$C(R^{20a})(R^{20b})C(O)$—**. In a further aspect, $Q^1$ is *—C(O)—**. In a still further aspect, $Q^1$ is *—$C(R^{20a})(R^{20b})C(O)$—**.

In various aspects, $Q^1$ is *—$C(R^{20a})(R^{20b})C(O)$—**. In a further aspect, $Q^1$ is *—$CH_2C(O)$—**.

In a further aspect, $Q^1$, when present, is —$C(R^{20a})(R^{20b})C(O)$—, —$C(R^{20a})(R^{20b})C(O)C$(cyclopropyl)C(O)—, —$C(R^{20a})(R^{20b})C(O)N(R^{21a})CH_2CH(R^{21b})C(O)$—, —C(C3-C4 cycloalkyl)C(O)—, or —$CH_2C(O)N(R^{22})CH(R^{23})C(O)$—. In a still further aspect, $Q^1$, when present, is —$C((R^{20a})(R^{20b})C(O)$—, —$C((R^{20a})(R^{20b})C(O)C$(cyclopropyl)C(O)—, or —C(C3-C4 cycloalkyl)C(O)—. In yet a further aspect, $Q^1$, when present, is —$C(R^{20a})(R^{20b})C(O)$— or —$C(R^{20a})(R^{20b})C(O)C$(cyclopropyl)C(O)—. In an even further aspect, Q, when present, is —$C(R^{20a})(R^{20b})C(O)C$(cyclopropyl)C(O)— or —C(C3-C4 cycloalkyl)C(O)—. In a still further aspect, Q, when present, is —$C(R^{20a})(R^{20b})$ C(O)— or —C(C3-C4 cycloalkyl)C(O)—. In yet a further aspect, Q, when present, is —C($R^{20a}$)($R^{20b}$)C(O)—. In an even further aspect, $Q^1$, when present, is —C($R^{20a}$)($R^{20b}$)C(O)C(cyclopropyl)C(O)—. In a still further aspect, $Q^1$, when present, is —C(C3-C4 cycloalkyl)C(O)—.

In a further aspect, $Q^1$, when present, is —C($R^{20a}$)($R^{20b}$)C(O)N($R^{21a}$)$CH_2$CH($R^{21b}$)C(O)— or —$CH_2$C(O)N($R^{22}$)CH($R^{23}$)C(O)—. In a still further aspect, Q, when present, is —C($R^{20a}$)($R^{20b}$)C(O)N($R^{21a}$)$CH_2$CH($R^{21b}$)C(O)—. In yet a further aspect, Q, when present, is —$CH_2$C(O)N($R^{22}$)CH($R^{23}$)C(O)—.

In a further aspect, $Q^1$, when present, is —NH($CH_2CH_2O$)$_q$$CH_2$C(O)— or —NH$CH_2$C(cyclopropyl)C(O)—. In a still further aspect, $Q^1$, when present, is —NH($CH_2CH_2O$)$_q$$CH_2$C(O)—. In yet a further aspect, $Q^1$, when present, is —NH$CH_2$C(cyclopropyl)C(O)—.

d. $Q^2$ Groups

In one aspect, $Q^2$ is selected from *—O—**, *—O(C1-C8 alkylene)-**, *—O$CH_2$C(O)NH—**, and *—C(O)NH—**, wherein * denotes a bond connected to the phenyl and ** denotes a bond connected to -L-. In a further aspect, $Q^2$ is selected from *—O—**, *—O(C1-C8 alkylene)-**, and *—O$CH_2$C(O)NH—**. In a still further aspect, $Q^2$ is selected from *—O—**, *—O(C1-C8 alkylene)-**, and *—C(O)NH—**. In yet a further aspect, $Q^2$ is selected from *—O—**, *—O$CH_2$C(O)NH—**, and *—C(O)NH—**. In an even further aspect, $Q^2$ is selected from *—O(C1-C8 alkylene)-**, *—O$CH_2$C(O)NH—**, and *—C(O)NH—**. In an even still further aspect, $Q^2$ is selected from *—O—** and *—O(C1-C8 alkylene)-**. In yet an even further aspect, $Q^2$ is selected from *—O—** and *—O$CH_2$C(O)NH—**. In a further aspect, $Q^2$ is selected from *—O—** and *—C(O)NH—**. In a still further aspect, $Q^2$ is selected from *—O(C1-C8 alkylene)-** and *—O$CH_2$C(O)NH—**. In yet a further aspect, $Q^2$ is selected from *—O(C1-C8 alkylene)-** and *—C(O)NH—**. In an even further aspect, $Q^2$ is selected from *—O$CH_2$C(O)NH—** and *—C(O)NH—**. In an even still further aspect, $Q^2$ is *—O—**. In yet an even further aspect, $Q^2$ is *—O(C1-C8 alkylene)-**. In a further aspect, $Q^2$ is *—O$CH_2$C(O)NH—**. In a still further aspect, $Q^2$ is *—C(O)NH—**.

a. $Q^3$ Groups

In one aspect, $Q^3$ is selected from *—C(O)—**, *—OC(O)—**, and *—C($R^{26a}$)($R^{26b}$)C(O)—**, wherein * denotes a bond connected to -L- and ** denotes a bond connected to —N(H)—. In a further aspect, $Q^3$ is selected from *—C(O)—** and *—OC(O)—**. In a still further aspect, $Q^3$ is selected from *—C(O)—** and *—C($R^{26a}$)($R^{26b}$)C(O)—**. In yet a further aspect, $Q^3$ is selected from *—OC(O)—** and *—C($R^{26a}$)($R^{26b}$)C(O)—**. In an even further aspect, $Q^3$ is *—C(O)—**. In an even still further aspect, $Q^3$ is *—OC(O)—**. In yet an even further aspect, $Q^3$ is *—C($R^{26a}$)($R^{26b}$)C(O)—**.

b. Z Groups

In one aspect, Z is selected from N and CH. In a further aspect, Z is N. In a still further aspect, Z is CH.

In various aspects, Z is CH.

c. $R^1$ Groups

In one aspect, $R^1$ is a residue of a pregnane X receptor (PXR) ligand.

In various aspects, the residue of the PXR ligand has a structure represented by a formula:

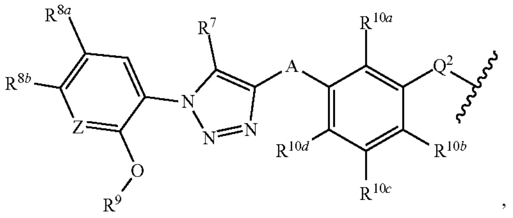

, wherein A is selected from *—$SO_2$—**, *—$NR^{24}$C(O)—**, *—N($R^{24}$)C(O)$NR^{25}$—**, *—C(O)$NR^{24}$—**, *—$SO_2NR^{24}$—**, and *—$NR^{24}SO_2$—**, wherein * denotes a bond connected to the triazole and ** denotes a bond connected to the phenyl; wherein each of $R^{24}$ and $R^{21}$ is independently selected from hydrogen and C1-C4 alkyl; wherein $Q^2$ is selected from *—O—**, *—O(C1-C8 alkylene)-**, *—O$CH_2$C(O)NH—**, and *—C(O)NH—**, wherein * denotes a bond connected to the phenyl and ** denotes a bond connected to -L-; wherein Z is selected from N and CH; wherein $R^7$ is selected from hydrogen and C1-C4 alkyl; wherein each of $R^{8a}$ and $R^{8b}$ is independently selected from hydrogen, halogen, C1-C4 alkyl, C1-C4 haloalkyl, C1-C4 alkoxy, and C1-C4 haloalkoxy; wherein $R^9$ is C1-C4 alkyl; and wherein each of $R^{10a}$, $R^{10b}$, $R^{10c}$, and $R^{10d}$ is independently selected from hydrogen, halogen, —CN, —$NH_2$, —OH, —$NO_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, C1-C8 alkylamino, and —$CO_2$(C1-C4 alkyl).

In various aspects, the residue of the PXR ligand has a structure represented by a formula:

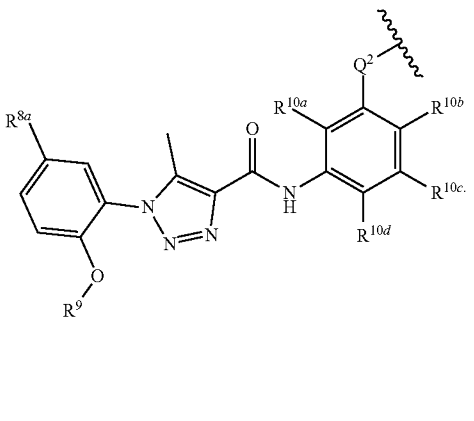

In various aspects, the residue of the PXR ligand has a structure represented by a formula:

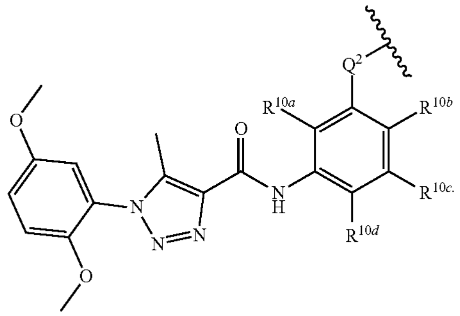

In various aspects, the residue of the PXR ligand has a structure represented by a formula:

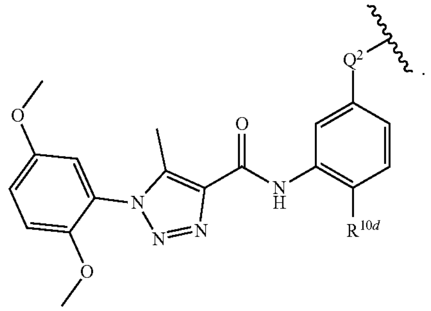

In various aspects, the residue of the PXR ligand has a structure represented by a formula:

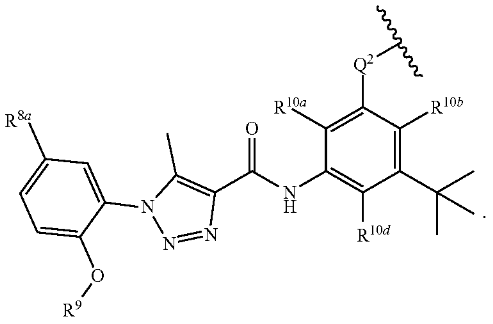

In various aspects, the residue of the PXR ligand has a structure represented by a formula:

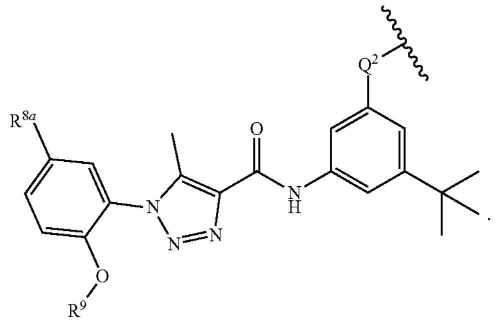

In various aspects, the residue of the PXR ligand has a structure represented by a formula:

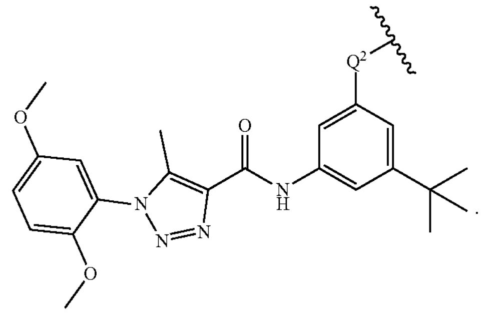

In various aspects, the residue of the PXR ligand has a structure represented by a formula:

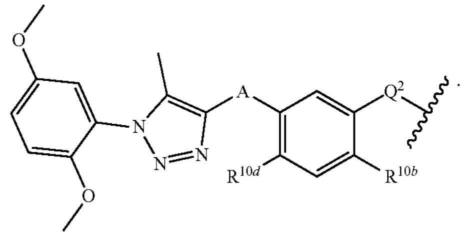

In various aspects, the residue of the PXR ligand has a structure represented by a formula:

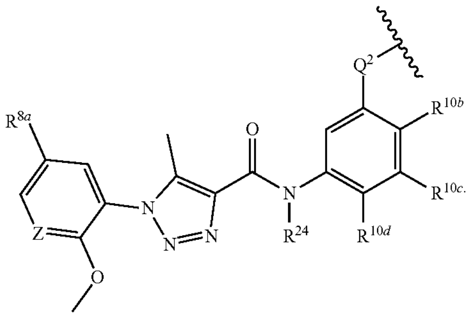

In various aspects, the compound has a structure represented by a formula:

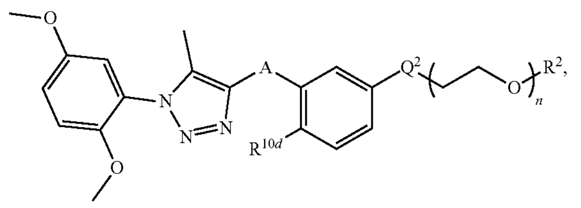

wherein n is selected from 2, 3, 4, 5, 6, 7, and 8, or a pharmaceutically acceptable salt thereof.

In various aspects, the residue of the PXR ligand has a structure represented by a formula:

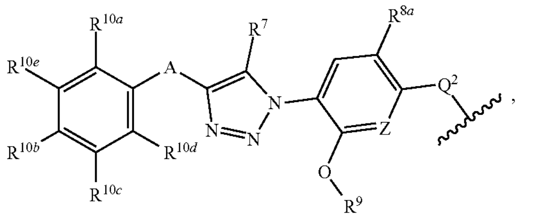

wherein A is selected from *—$SO_2$—**, *—$NR^{24}C(O)$—**, *—$N(R^{24})C(O)NR^{25}$—**, *—$C(O)NR^{24}$—**, *—$SO_2NR^2$—**, and *—$NR^{24}SO_2$—**, wherein * denotes a bond connected to the triazole and ** denotes a bond connected to the phenyl; wherein each of $R^{24}$ and $R^{25}$ is independently selected from hydrogen and C1-C4 alkyl; wherein $Q^2$ is selected from *—O—**, *—O(C1-C8 alkylene)-**, *—$OCH_2C(O)NH$—**, and *—C(O)NH—**, wherein * denotes a bond connected to the phenyl and ** denotes a bond connected to -L-; wherein Z is selected from N and CH; wherein $R^7$ is selected from hydrogen and C1-C4 alkyl; wherein each of $R^{8a}$ and $R^{8b}$ is independently selected from hydrogen, halogen, C1-C4 alkyl, C1-C4 haloalkyl, C1-C4 alkoxy, and C1-C4 haloalkoxy; wherein $R^9$ is C1-C4 alkyl; and wherein each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, C1-C8 alkylamino, and —$CO_2$(C1-C4 alkyl).

In various aspects, the residue of the PXR ligand has a structure represented by a formula:

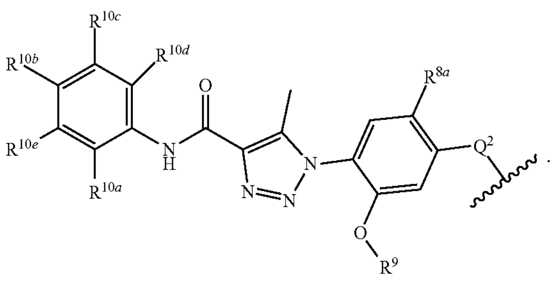

In various aspects, the residue of the PXR ligand has a structure represented by a formula:

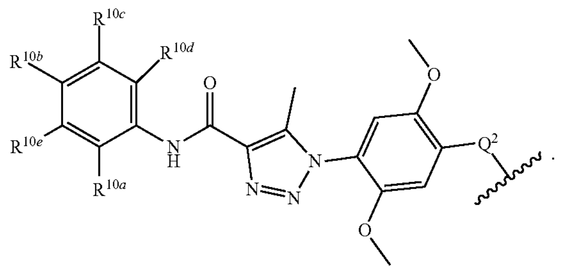

In various aspects, the residue of the PXR ligand has a structure represented by a formula:

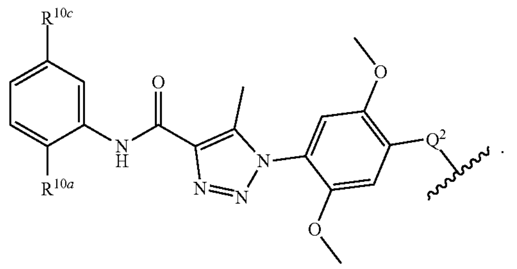

In various aspects, the residue of the PXR ligand has a structure represented by a formula:

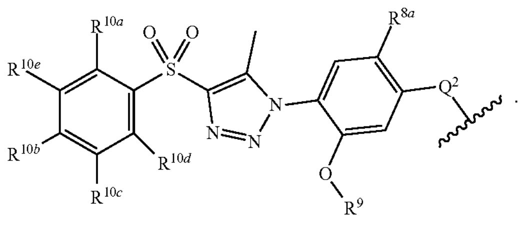

In various aspects, the residue of the PXR ligand has a structure represented by a formula:

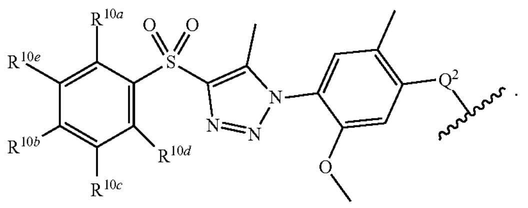

In various aspects, the residue of the PXR ligand has a structure represented by a formula:

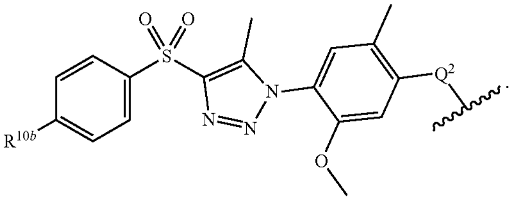

d. $R^2$ Groups

In one aspect, $R^2$ is a residue of a Cereblon (CRBN) ligand or a residue of a von Hippel-Lindau protein (pVHL) ligand. In a further aspect, $R^2$ is the residue of the CRBN ligand. In a still further aspect, $R^2$ is the residue of the pVHL ligand.

In various aspects, $R^2$ is a residue of a Cereblon (CRBN). Examples of CRBN ligands are In a further aspect, the CRBN ligand has a structure selected from:

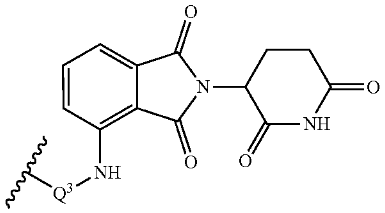

and

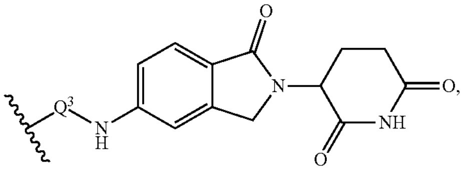

wherein, $Q^3$ is selected from *—C(O)—**, *—OC(O)—**, and *—C($R^{26a}$)($R^{26b}$)C(O)—**, wherein * denotes a bond connected to -L- and ** denotes a bond connected to —N(H)—.

In various aspects, $R^2$ is the residue of the pVHL ligand. Example of pVHL ligands are In various aspects, the residue of the pVHL ligand has a structure selected from:

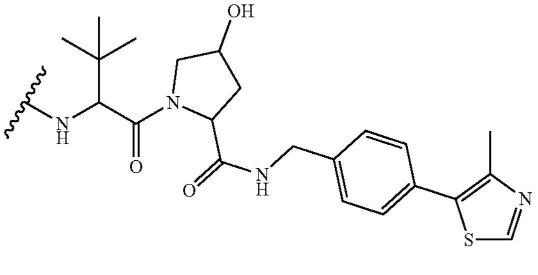

and

-continued

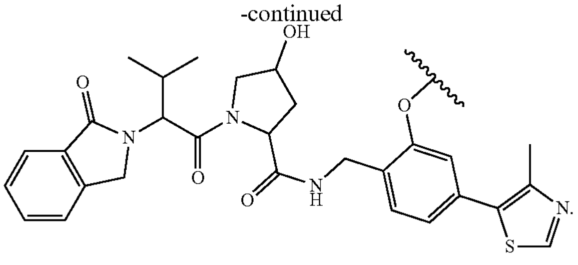

In a further aspect, the residue of the pVHL ligand has a structure selected from:

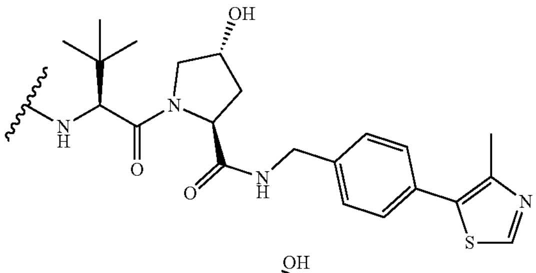

and

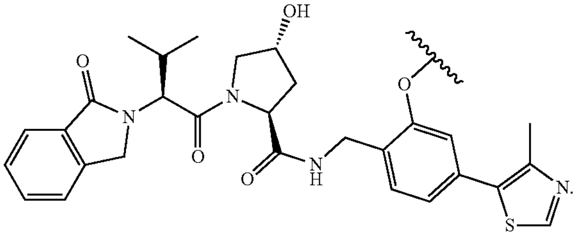

In a further aspect, the residue of the pVHL ligand has a structure represented by a formula:

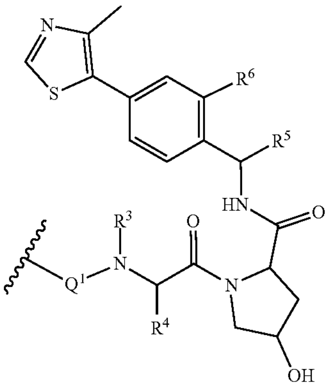

wherein $Q^1$ is selected from *—C(O)—**, *—OC(O)—**, *—C($R^{20a}$)($R^{20b}$)C(O)—**, *—OC($R^{20a}$)($R^{20b}$)C(O)—**, *—C($R^{20a}$)($R^{20b}$)C(O)C(cyclopropyl)C(O)—**, *—C($R^{20a}$)($R^{20b}$)C(O)N($R^{21a}$)$CH_2$CH($R^{21b}$)C(O)—**, *—C(C3-C4 cycloalkyl)C(O)—**, *—NH($CH_2CH_2O$)$_q$$CH_2$C(O)—**, *—NHCH$_2$C(cyclopropyl)C(O)—**, and *—$CH_2$C(O)N($R^{22}$)CH($R^{23}$)C(O)—**, wherein * denotes a bond connected to -L- and ** denotes a bond connected to —N($R^3$)—; wherein q is selected from 1, 2, 3, 4, 5, and 6; wherein each of $R^{20a}$ and $R^{20b}$ is independently selected from hydrogen and C1-C4 alkyl; or wherein each of $R^{20a}$ and $R^{20b}$ are covalently bound, and, together comprise a C3-C4 cycloalkyl or a C2-C3 heterocycloalkyl; or wherein $R^{20}$ is covalently bound to $R^3$, and, together with the intermediate atoms, comprises a 5-membered heterocycle; wherein each of $R^{21a}$ and $R^{21b}$ are covalently bound, and, together with the intermediate atoms, comprise a 4-membered heterocycle; wherein $R^{22}$ is hydrogen; and wherein $R^{23}$ is selected from C1-C4 alkyl, —$CH_2C_6H_5$, and —$C_6H_5$; or wherein each of $R^{22}$ and $R^{23}$ are covalently bound, and, together with the intermediate atoms, comprise an 10-membered heterocycloalkyl; wherein $R^3$ is selected from hydrogen and C1-C4 alkyl; and wherein $R^4$ is selected from C1-C4 alkyl, C1-C4 hydroxyalkyl, and $C_6H_5$; or wherein each of $R^3$ and $R^4$ are covalently bound, and, together with the intermediate atoms, comprise a 5- or 6-membered heterocycle having 0 or 1 —OH group; or wherein each of $R^3$ and $R^{20a}$, when present, are covalently bound, and, together with the intermediate atoms, comprise a 5-membered heterocycle; wherein $R^5$ is selected from hydrogen and methyl; and wherein $R^6$ is selected from hydrogen, —OH, and C1-C4 alkyl halide.

In a further aspect, the residue of the pVHL ligand has a structure represented by a formula:

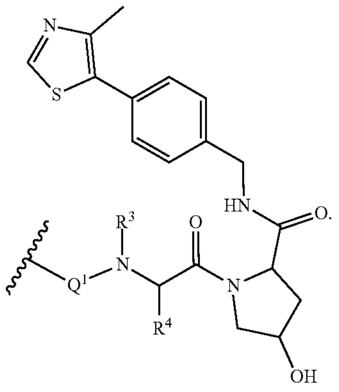

In a further aspect, the residue of the pVHL ligand has a structure represented by a formula:

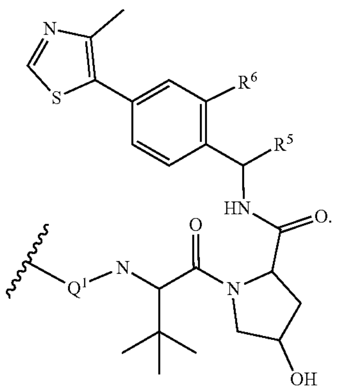

In a further aspect, the residue of the pVHL ligand has a structure represented by a formula:

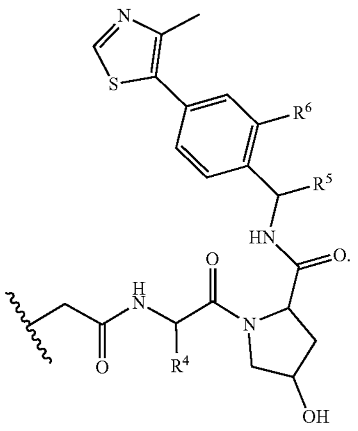

In a further aspect, the residue of the pVHL ligand has a structure represented by a formula:

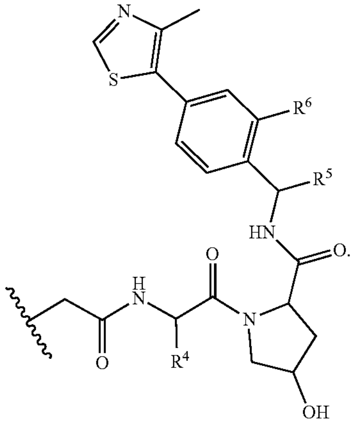

In a further aspect, the residue of the pVHL ligand has a structure selected from:

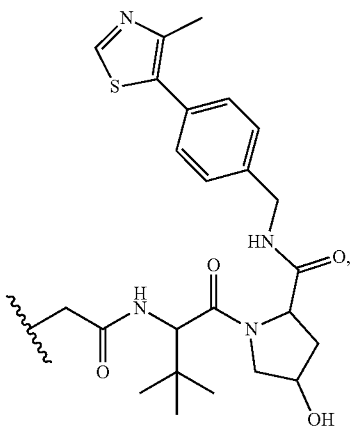

-continued
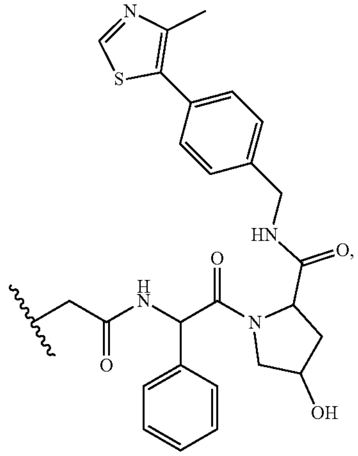
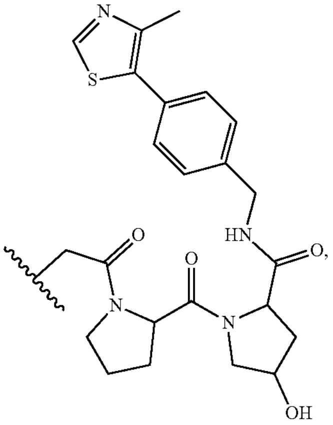
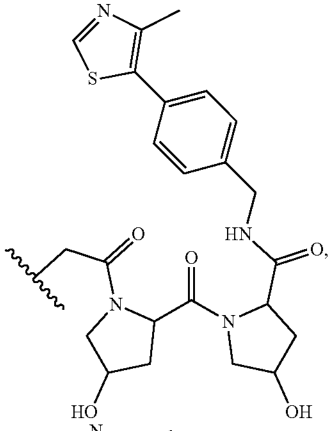
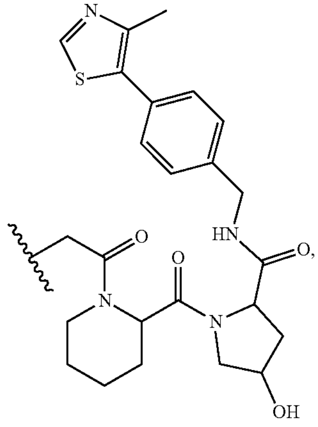
-continued
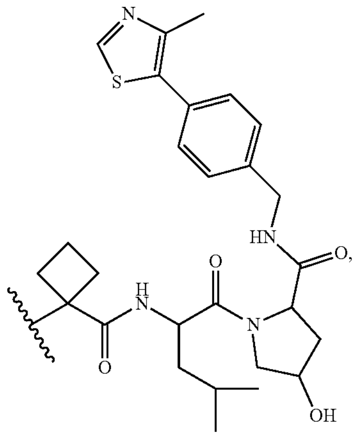
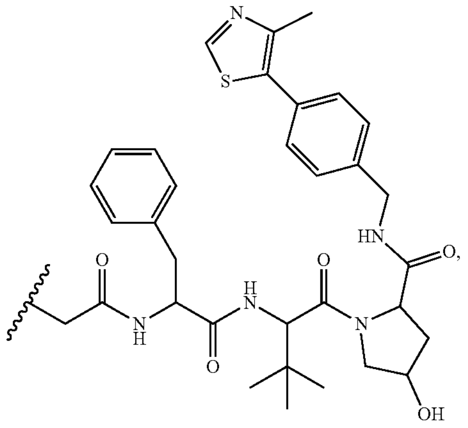
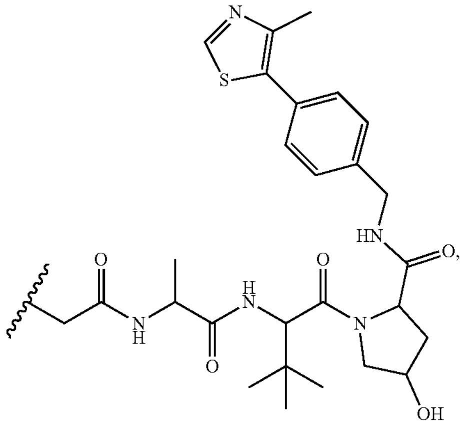
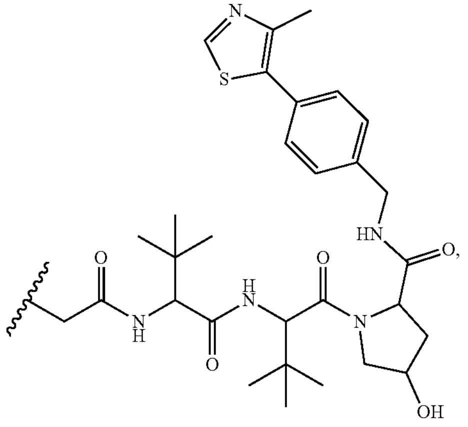

-continued
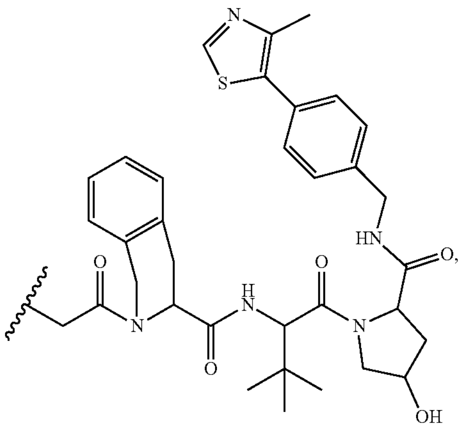
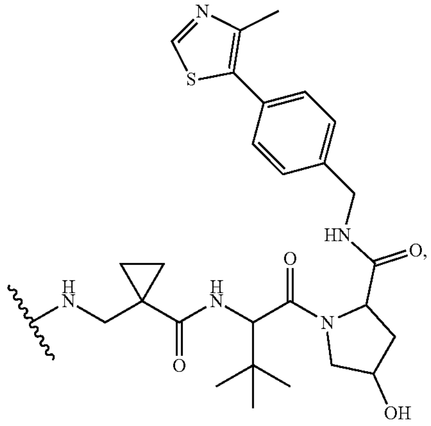
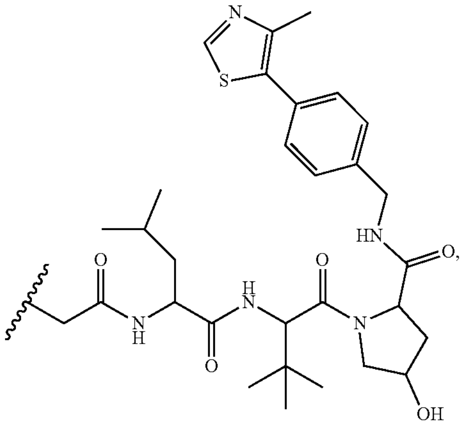
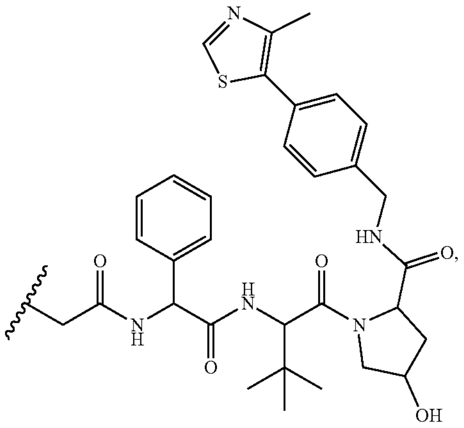
-continued
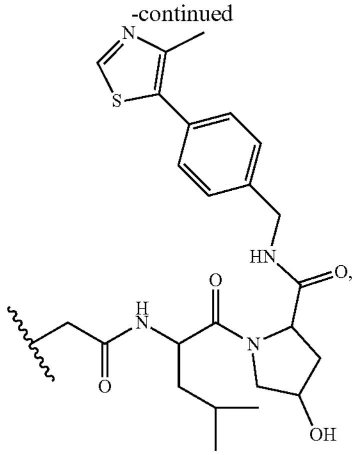
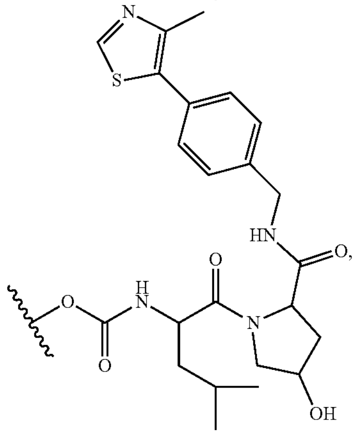
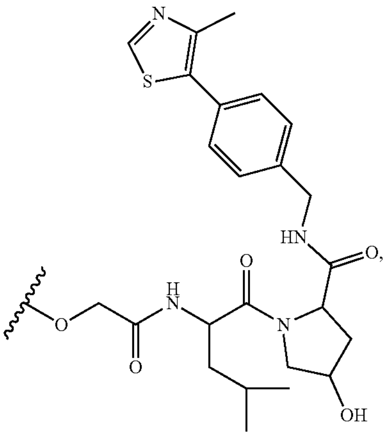
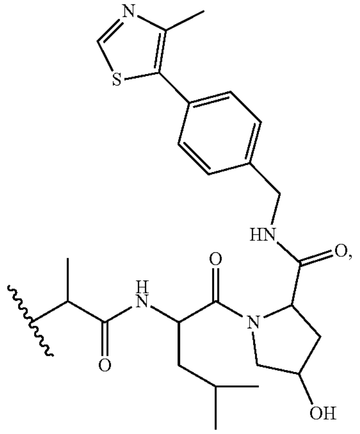

-continued
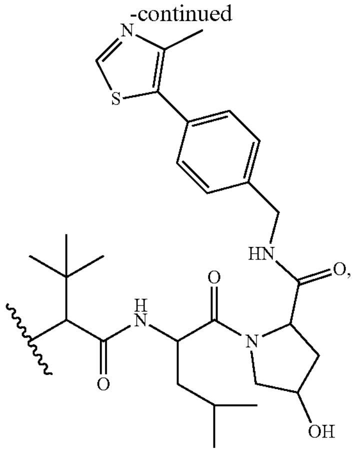
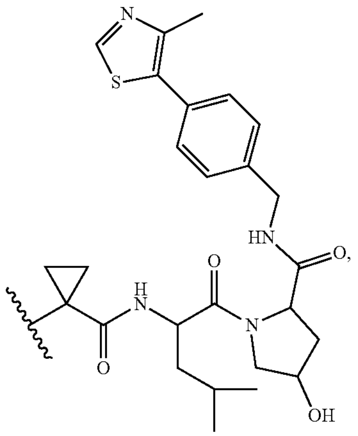
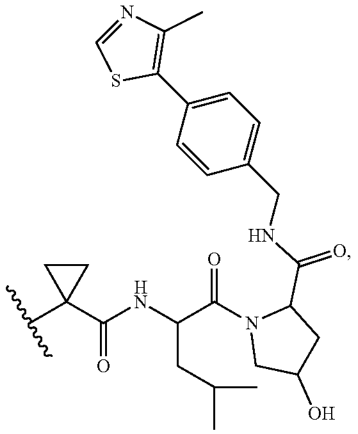
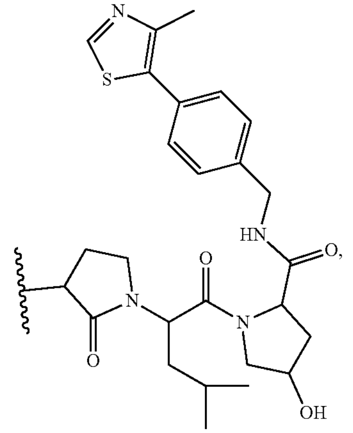
-continued
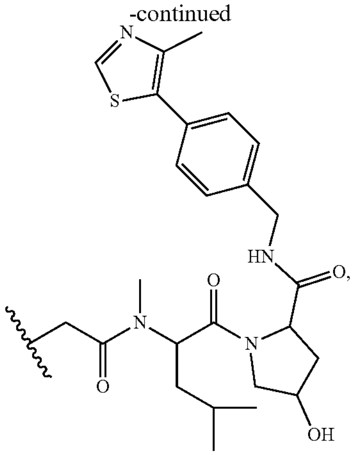
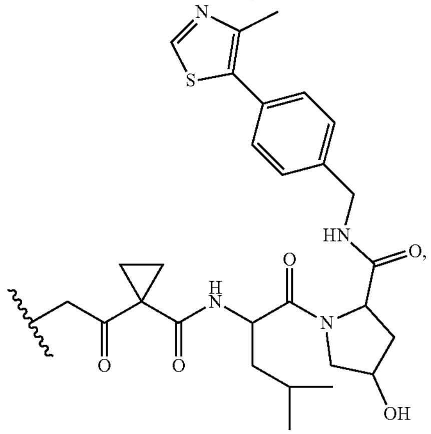
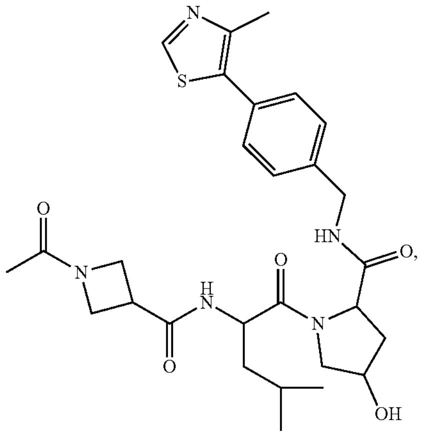
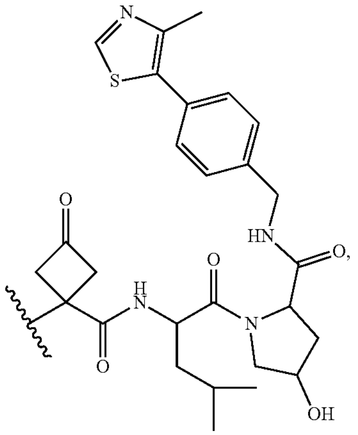

-continued
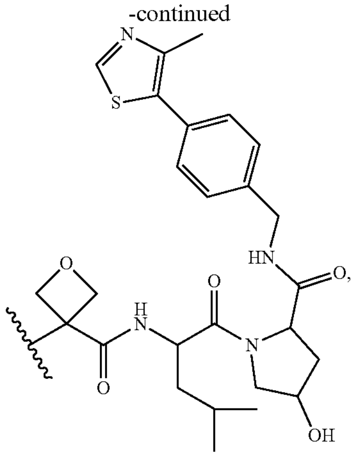
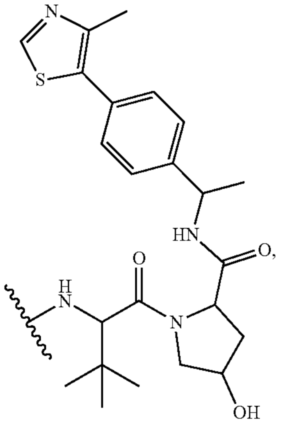
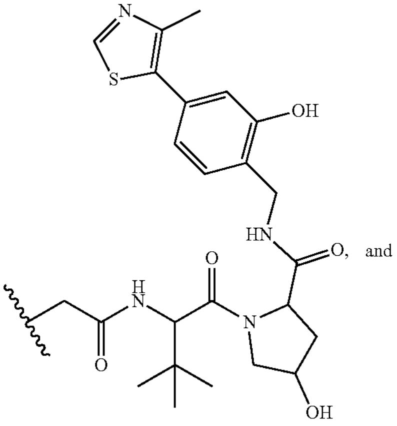
and
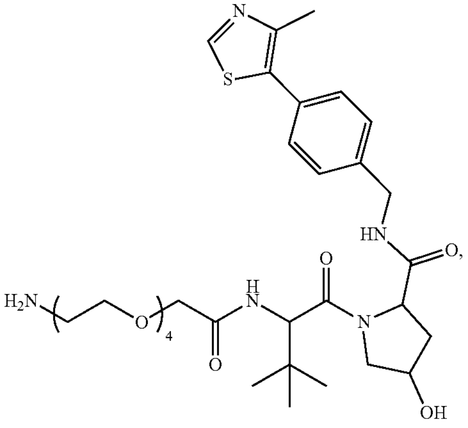
In a further aspect, the residue of the pVHL ligand has a structure:
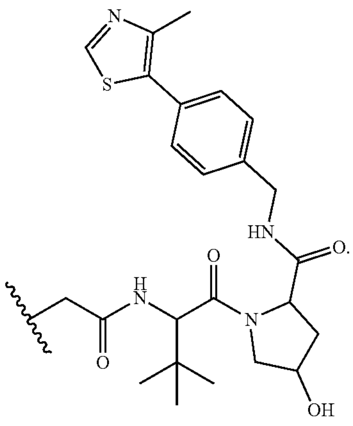 [SMILES: *CC(=O)NC(C(=O)N1CC(O)CC1C(=O)NCc1ccc(-c2scnc2C)cc1)C(C)(C)C]
In a further aspect, the residue of the pVHL ligand has a structure:
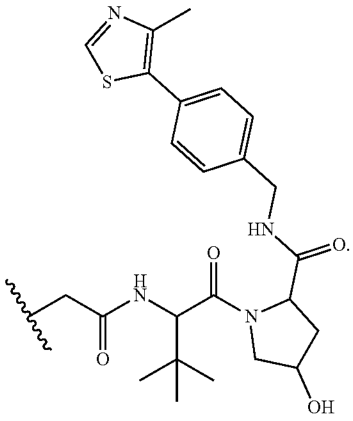 [SMILES: *CC(=O)NC(C(=O)N1CC(O)CC1C(=O)NCc1ccc(-c2scnc2C)cc1)C(C)(C)C]
In a further aspect, the residue of the pVHL ligand has a structure:
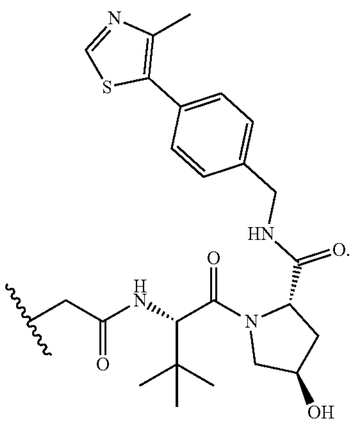 [SMILES: *CC(=O)N[C@H](C(=O)N1C[C@H](O)C[C@H]1C(=O)NCc1ccc(-c2scnc2C)cc1)C(C)(C)C]
e. $R^3$ AND $R^4$ Groups
In various aspects, $R^3$ is hydrogen or C1-C4 alkyl; and wherein $R^4$ is a C1-C4 alkyl, C1-C4 hydroxyalkyl, or $C_6H_5$;

or wherein each of $R^3$ and $R^4$ are covalently bound, and, together with the intermediate atoms, comprise a 5- or 6-membered heterocycle having 0 or 1 —OH group; or wherein each of $R^3$ and $R^{20a}$, when present, are covalently bound, and, together with the intermediate atoms, comprise a 5-membered heterocycle.

In a further aspect, $R^3$ is hydrogen or C1-C4 alkyl. In a still further aspect, $R^3$ is hydrogen, methyl, ethyl, n-propyl, or isopropyl. In yet a further aspect, $R^3$ is hydrogen, methyl, or ethyl. In an even further aspect, $R^3$ is hydrogen or ethyl. In a still further aspect, $R^3$ is hydrogen or methyl.

In a further aspect, $R^3$ is C1-C4 alkyl. In a still further aspect, $R^3$ is methyl, ethyl, n-propyl, or isopropyl. In yet a further aspect, $R^3$ is methyl or ethyl. In an even further aspect, $R^3$ is ethyl. In a still further aspect, $R^3$ is methyl.

In a further aspect, $R^3$ is hydrogen.

In a further aspect, $R^4$ is C1-C4 alkyl, C1-C4 hydroxyalkyl, or $C_6H_5$. In a still further aspect, $R^4$ is methyl, ethyl, n-propyl, isopropyl, $—CH_2OH$, $—CH_2CH_2OH$, $—CH_2CH_2CH_2OH$, $—CH(CH_3)CH_2OH$, or $C_6H_5$. In yet a further aspect, $R^4$ is methyl, ethyl, $—CH_2OH$, $—CH_2CH_2OH$, or $C_6H_5$. In an even further aspect, $R^4$ is methyl, $—CH_2OH$, or C6H.

In a further aspect, $R^4$ is a C1-C4 alkyl. In a still further aspect, $R^4$ is methyl, ethyl, n-propyl, or isopropyl. In yet a further aspect, $R^4$ is methyl or ethyl. In an even further aspect, $R^4$ is methyl. In a still further aspect, $R^4$ is a C4 alkyl. In yet a further aspect, $R^4$ is isobutyl, sec-butyl, or tert-butyl. In an even further aspect, $R^4$ is tert-butyl.

In a further aspect, $R^4$ is a C1-C4 hydroxyalkyl. In a still further aspect, $R^4$ is $—CH_2OH$, $—CH_2CH_2OH$, $—CH_2CH_2CH_2OH$, or $—CH(CH_3)CH_2OH$. In yet a further aspect, $R^4$ is $—CH_2OH$ or $—CH_2CH_2OH$. In an even further aspect, $R^4$ is $—CH_2OH$.

In a further aspect, $R^4$ is C6H.

In a further aspect, each of $R^3$ and $R^4$ are covalently bound, and, together with the intermediate atoms, comprise a 5- or 6-membered heterocycle having 0 or 1 —OH group. Examples of 5- and 6-membered heterocycles include, but are not limited to, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. In a still further aspect, each of $R^3$ and $R^4$ are covalently bound, and, together with the intermediate atoms, comprise a 5- or 6-membered heterocycle having 1 —OH group. In yet a further aspect, each of $R^3$ and $R^4$ are covalently bound, and, together with the intermediate atoms, comprise a 5- or 6-membered heterocycle having 0 —OH groups. In an even further aspect, each of $R^3$ and $R^4$ are covalently bound, and, together with the intermediate atoms, comprise an unsubstituted 5- or 6-membered heterocycle.

In a further aspect, each of $R^3$ and $R^4$ are covalently bound, and, together with the intermediate atoms, comprise a 5-membered heterocycle having 0 or 1 —OH group. In a still further aspect, each of $R^3$ and $R^4$ are covalently bound, and, together with the intermediate atoms, comprise a 5-membered heterocycle having 1 —OH group. In yet a further aspect, each of $R^3$ and $R^4$ are covalently bound, and, together with the intermediate atoms, comprise a 5-membered heterocycle having 0 —OH groups.

In a further aspect, each of $R^3$ and $R^4$ are covalently bound, and, together with the intermediate atoms, comprise a 6-membered heterocycle having 0 or 1 —OH group. In a still further aspect, each of $R^3$ and $R^4$ are covalently bound, and, together with the intermediate atoms, comprise a 6-membered heterocycle having 1 —OH group. In yet a further aspect, each of $R^3$ and $R^4$ are covalently bound, and, together with the intermediate atoms, comprise a 6-membered heterocycle having 0 —OH groups.

In a further aspect, each of $R^3$ and $R^{20a}$, when present, are covalently bound, and, together with the intermediate atoms, comprise a 5-membered heterocycle. Examples of 5-membered heterocycles include, but are not limited to, pyrrolidinyl, pyrrolidino, thiolanyl, and tetrahydrofuranyl. In a still further aspect, each of $R^3$ and $R^{20a}$, when present, are covalently bound, and, together with the intermediate atoms, comprise an unsubstituted 5-membered heterocycle.

f. $R^5$ Groups

In one aspect, $R^5$ is hydrogen or methyl. In a further aspect, $R^5$ is hydrogen. In a still further aspect, $R^5$ is methyl.

g. $R^6$ Groups

In various aspects, $R^6$ is selected from hydrogen, —OH, and C1-C4 alkyl halide. In a further aspect, $R^6$ is selected from hydrogen, —OH, $—CH_2F$, $—CH_2Cl$, $—CH_2Br$, $—CH_2CH_2F$, $—CH_2CH_2Cl$, $—CH_2CH_2Br$, $—CH_2CH_2CH_2F$, $—CH_2CH_2CH_2Cl$, $—CH_2CH_2CH_2Br$, $—CH(CH_3)CH_2F$, $—CH(CH_3)CH_2Cl$ and $—CH(CH_3)CH_2Br$. In a still further aspect, $R^6$ is selected from hydrogen, —OH, $—CH_2F$, $—CH_2Cl$, $—CH_2CH_2F$, and $—CH_2CH_2Cl$. In yet a further aspect, $R^6$ is selected from hydrogen, —OH, $—CH_2F$, $—CH_2Cl$, and $—CH_2Br$.

In a further aspect, $R^6$ is —OH.

In a various aspects, $R^6$ is C1-C4 alkyl halide. In a further aspect, $R^6$ is selected from $—CH_2F$, $—CH_2Cl$, $—CH_2Br$, $—CH_2CH_2F$, $—CH_2CH_2Cl$, $—CH_2CH_2Br$, $—CH_2CH_2CH_2F$, $—CH_2CH_2CH_2Cl$, $—CH_2CH_2CH_2Br$, $—CH(CH_3)CH_2F$, $—CH(CH_3)CH_2Cl$, and $—CH(CH_3)CH_2Br$. In a still further aspect, $R^6$ is selected from $—CH_2F$, $—CH_2Cl$, $—CH_2Br$, $—CH_2CH_2F$, $—CH_2CH_2Cl$, and $—CH_2CH_2Br$. In yes a further aspect, $R^6$ is selected from $—CH_2F$, $—CH_2Cl$, or $—CH_2Br$. In an even further aspect, $R^6$ is selected from $—CH_2Cl$ and $—CH_2Br$.

In a further aspect, $R^6$ is hydrogen.

h. $R^7$ Groups

In one aspect, $R^7$ is selected from hydrogen and C1-C4 alkyl. In a further aspect, $R^7$ is selected from hydrogen, methyl, ethyl, n-propyl, and isopropyl. In a still further aspect, $R^7$ is selected from hydrogen, methyl, and ethyl. In a still further aspect, $R^7$ is selected from hydrogen and methyl.

In various aspects, $R^7$ is C1-C4 alkyl. In a further aspect, $R^7$ is selected from methyl, ethyl, n-propyl, and isopropyl. In a still further aspect, $R^7$ is selected from methyl and ethyl. In yet a further aspect, $R^7$ is ethyl. In an even further aspect, $R^7$ is methyl.

In various aspects, $R^7$ is hydrogen.

i. $R^{8A}$ AND $R^{8B}$ Groups

In various aspects, each of $R^{8a}$ and $R^{8b}$ is independently selected from hydrogen, halogen, C1-C4 alkyl, C1-C4 haloalkyl, C1-C4 alkoxy, and C1-C4 haloalkoxy. In a further aspect, each of $R^{8a}$ and $R^{8b}$ is independently selected from hydrogen, —F, —Cl, methyl, ethyl, n-propyl, i-propyl, $—CH_2F$, $—CH_2Cl$, $—CH_2CH_2F$, $—CH_2CH_2Cl$, $—CH_2CH_2CH_2F$, $—CH_2CH_2CH_2Cl$, $—CH(CH_3)CH_2F$, $—CH(CH_3)CH_2Cl$, $—OCH_3$, $—OCH_2CH_3$, —$OCH_2CH_2CH_3$, —$OCH(CH_3)CH_3$, —$OCF_3$, —$OCH_2CF_3$, —$OCH_2CH_2CF_3$, and —$OCH(CH_3)CF_3$. In a still further aspect, each of $R^{8a}$ and $R^{8b}$ is independently selected from hydrogen, —F, —Cl, methyl, ethyl, —$CH_2F$, —$CH_2Cl$, —$CH_2CH_2F$, —$CH_2CH_2Cl$, —$CH_2CN$, —$CH_2CH_2CN$, —$OCH_3$, —$OCH_2CH_3$, —$OCF_3$, —$OCH_2CF_3$, and —$OCH_2CH_2CF_3$. In yet a further aspect, each of $R^{8a}$ and $R^{8b}$ is independently selected from hydrogen, —F, —Cl, methyl, —$CH_2F$, —$CH_2Cl$, —$OCH_3$, —$OCF_3$, —$OCH_2CF_3$.

In various aspects, each of $R^{8a}$ and $R^{8b}$ is independently selected from hydrogen, halogen, and C1-C4 alkyl. In a further aspect, each of $R^{8a}$ and $R^{8b}$ is independently selected from hydrogen, —F, —Cl, methyl, ethyl, n-propyl, and i-propyl. In a still further aspect, each of $R^{8a}$ and $R^{8b}$ is independently selected from hydrogen, —F, —Cl, methyl, and ethyl. In yet a further aspect, each of $R^{8a}$ and $R^{8b}$ is independently selected from hydrogen, —F, —Cl, and methyl.

In various aspects, each of $R^{8a}$ and $R^{8b}$ is independently selected from hydrogen, halogen, C1-C4 alkyl, and C1-C4 alkoxy. In a further aspect, each of $R^{8a}$ and $R^{8b}$ is independently selected from hydrogen, —F, —Cl, methyl, ethyl, n-propyl, i-propyl, —$OCH_3$, —$OCH_2CH_3$, —$OCH_2CH_2CH_3$, and —$OCH(CH_3)CH_3$. In a still further aspect, each of $R^{8a}$ and $R^{8b}$ is independently selected from hydrogen, —F, —Cl, methyl, ethyl, —$OCH_3$, and —$OCH_2CH_3$. In yet a further aspect, each of $R^{8a}$ and $R^{8b}$ is independently selected from hydrogen, —F, —Cl, methyl, and —$OCH_3$.

In various aspects, each of $R^{8a}$ and $R^{8b}$ is independently selected from hydrogen, halogen, C1-C4 haloalkyl and C1-C4 haloalkoxy. In a further aspect, each of $R^{8a}$ and $R^{8b}$ is independently selected from hydrogen, —F, —Cl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, and —$CH(CH_3)CH_2Cl$, —$OCF_3$, —$OCH_2CF_3$, —$OCH_2CH_2CF_3$, and —$OCH(CH_3)CF_3$. In a still further aspect, each of $R^{8a}$ and $R^{8b}$ is independently selected from hydrogen, —F, —Cl, —$CH_2F$, —$CH_2Cl$, —$CH_2CH_2F$, and —$CH_2CH_2Cl$. In yet a further aspect, each of $R^{8a}$ and $R^{8b}$ is independently selected from hydrogen, —F, —Cl, —$CH_2F$, and —$CH_2Cl$.

In various aspects, each of $R^{8a}$ and $R^{8b}$ is independently selected from hydrogen and C1-C4 alkyl. In a further aspect, each of $R^{8a}$ and $R^{8b}$ is independently selected from hydrogen, methyl, ethyl, n-propyl, and i-propyl. In a further aspect, each of $R^{8a}$ and $R^{8b}$ is independently selected from hydrogen, methyl, and ethyl. In a still further aspect, each of $R^{8a}$ and $R^{8b}$ is independently selected from hydrogen and methyl.

In various aspects, each of $R^{8a}$ and $R^{8b}$ is independently selected from hydrogen and C1-C4 alkoxy. In a further aspect, each of $R^{8a}$ and $R^{8b}$ is independently selected from hydrogen, —$OCH_3$, —$OCH_2CH_3$, —$OCH_2CH_2CH_3$, and —$OCH(CH_3)CH_3$. In a further aspect, each of $R^{8a}$ and $R^{8b}$ is independently selected from hydrogen, —$OCH_3$, and —$OCH_2CH_3$. In a still further aspect, each of $R^{8a}$ and $R^{8b}$ is independently selected from hydrogen and —$OCH_3$.

In various aspects, each of $R^{8a}$ and $R^{8b}$ is hydrogen.

In various aspects, $R^{8a}$ is selected from hydrogen, halogen, C1-C4 alkyl, C1-C4 haloalkyl, C1-C4 alkoxy, and C1-C4 haloalkoxy. In a further aspect, $R^{8a}$ is selected from hydrogen, —F, —Cl, methyl, ethyl, n-propyl, i-propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$OCH_3$, —$OCH_2CH_3$, —$OCH_2CH_2CH_3$, —$OCH(CH_3)CH_3$, —$OCF_3$, —$OCH_2CF_3$, —$OCH_2CH_2CF_3$, and —$OCH(CH_3)CF_3$. In a still further aspect, $R^{8a}$ is selected from hydrogen, —F, —Cl, methyl, ethyl, —$CH_2F$, —$CH_2Cl$, —$CH_2CH_2F$, —$CH_2CH_2Cl$, —$CH_2CN$, —$CH_2CH_2CN$, —$OCH_3$, —$OCH_2CH_3$, —$OCF_3$, —$OCH_2CF_3$, and —$OCH_2CH_2CF_3$. In yet a further aspect, $R^{8a}$ is selected from hydrogen, —F, —Cl, methyl, —$CH_2F$, —$CH_2Cl$, —$OCH_3$, —$OCF_3$, —$OCH_2CF_3$.

In various aspects, $R^{8a}$ is selected from hydrogen, C1-C4 alkyl, and C1-C4 alkoxy. In a further aspect, $R^{8a}$ is selected from hydrogen, methyl, ethyl, n-propyl, i-propyl, —$OCH_3$, —$OCH_2CH_3$, —$OCH_2CH_2CH_3$, and —$OCH(CH_3)CH_3$. In a still further aspect, $R^{8a}$ is selected from hydrogen, methyl, ethyl, —$OCH_3$, and —$OCH_2CH_3$. In yet a further aspect, $R^{8a}$ is selected from hydrogen, methyl, and —$OCH_3$.

In various aspects, $R^{8a}$ is selected from hydrogen, halogen, C1-C4 haloalkyl and C1-C4 haloalkoxy. In a further aspect, $R^{8a}$ is selected from hydrogen, —F, —Cl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, and —$CH(CH_3)CH_2Cl$, —$OCF_3$, —$OCH_2CF_3$, —$OCH_2CH_2CF_3$, and —$OCH(CH_3)CF_3$. In a still further aspect, $R^{8a}$ is selected from hydrogen, —F, —Cl, —$CH_2F$, —$CH_2Cl$, —$CH_2CH_2F$, and —$CH_2CH_2Cl$. In yet a further aspect, $R^{8a}$ is selected from hydrogen, —F, —Cl, —$CH_2F$, and —$CH_2Cl$.

In various aspects, $R^{8a}$ is C1-C4 alkoxy. In a further aspect, $R^{8a}$ is selected from —$OCH_3$, —$OCH_2CH_3$, —$OCH_2CH_2CH_3$, and —$OCH(CH_3)CH_3$. In a still further aspect, $R^{8a}$ is selected from —$OCH_3$, and —$OCH_2CH_3$. In yet a further aspect, $R^{8a}$ is —$OCH_3$.

In various aspects, $R^{8b}$ is hydrogen j. $R^9$ Groups

In one aspect, $R^9$ is C1-C4 alkyl. In a further aspect, $R^9$ is selected from methyl, ethyl, n-propyl, and isopropyl. In a still further aspect, $R^9$ is selected from methyl and ethyl. In yet a further aspect, $R^9$ is methyl.

k. $R^{10A}$, $R^{10B}$, $R^{10C}$, $R^{10D}$, AND $R^{10E}$ Groups

In various aspects, each of $R^{10a}$, $R^{10b}$, $R^{10c}$, and $R^{10d}$ is independently selected from hydrogen, halogen, —CN, —$NH_2$, —OH, —$NO_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, C1-C8 alkylamino, and —$CO_2$(C1-C4 alkyl). In a further aspect, each of $R^{10a}$, $R^{10b}$, $R^{10c}$, and $R^{10d}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 alkylamino, and —$CO_2$(C1-C4 alkyl). In a still further aspect, each of $R^{10a}$, $R^{10b}$, $R^{10c}$, and $R^{10d}$ is independently selected from hydrogen, —F, —Cl, —$NH_2$, —CN, —OH, —$NO_2$, methyl, ethyl, n-propyl, i-propyl, ethenyl, propenyl, isopropenyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$CH_2CN$, —$CH_2CH_2CN$, —$CH_2CH_2CH_2CN$, —$CH(CH_3)CH_2CN$, —$CH_2OH$, —$CH_2CH_2OH$, —$CH_2CH_2CH_2OH$, —$CH(CH_3)CH_2OH$, —$OCF_3$, —$OCH_2CF_3$, —$OCH_2CH_2CF_3$, —$OCH(CH_3)CF_3$, —$OCH_3$, —$OCH_2CH_3$, —$OCH_2CH_2CH_3$, —$OCH(CH_3)CH_3$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, —$CH(CH_3)CH_2NH_2$, —$CO_2CH_3$, —$CO_2CH_2CH_3$, and —$CO_2CH_2CH_2CH_3$. In yet a further aspect, each of $R^{10a}$, $R^{10b}$, $R^{10c}$ and $R^{10d}$ independently selected from hydrogen, —F, —Cl, —$NH_2$, —CN, —OH, —$NO_2$, methyl, ethyl, ethenyl, —$CH_2F$, —$CH_2Cl$, —$CH_2CH_2F$, —$CH_2CH_2Cl$, —$CH_2CN$, —$CH_2CH_2CN$, —$CH_2OH$, —$CH_2CH_2OH$, —$OCF_3$, —$OCH_2CF_3$, —$OCH_3$, —$OCH_2CH_3$, —$NHCH_3$, —$NHCH_2CH_3$, —$N(CH_3)_2$, —$N(CH_2CH_3)_2$, —$N(CH_3)(CH_2CH_3)$, —$CH_2NH_2$, —$CH_2CH_2NH_2$, —$CO_2CH_3$, and —$CO_2CH_2CH_3$. In an even further aspect, each of $R^{10a}$, $R^{10b}$, $R^{10c}$, and $R^{10d}$ is independently selected from hydrogen, —F, —Cl, —$NH_2$, —CN, —OH, —$NO_2$, methyl, —$CH_2F$, —$CH_2Cl$, —$CH_2CN$, —$CH_2OH$, —$OCF_3$, —$OCH_2CF_3$, —$OCH_3$, —$NHCH_3$, —$N(CH_3)_2$, —$CH_2NH_2$, and —$CO_2CH_3$.

In various aspects, each of $R^{10a}$, $R^{10b}$, $R^{10c}$, and $R^{10d}$ is independently selected from hydrogen, halogen, —CN, —$NH_2$, —OH, —$NO_2$, C1-C8 alkyl, and C2-C8 alkenyl. In a further aspect, each of $R^{10a}$, $R^{10b}$, $R^{10c}$, and $R^{10d}$ is independently selected from hydrogen, halogen, —CN, —$NH_2$, —OH, —$NO_2$, C1-C4 alkyl, and C2-C4 alkenyl. In a still further aspect, each of $R^{10a}$, $R^{10b}$, $R^{10c}$, and $R^{10d}$ is independently selected from hydrogen, —F, —Cl, —$NH_2$, —CN, —OH, —$NO_2$, methyl, ethyl, n-propyl, i-propyl, ethenyl, propenyl, and isopropenyl. In yet a further aspect, each of $R^{10a}$, $R^{10b}$, $R^{10c}$, and $R^{10d}$ is independently selected from hydrogen, —F, —Cl, —$NH_2$, —CN, —OH, —$NO_2$, methyl, ethyl, and ethenyl. In an even further aspect, each of $R^{10a}$, $R^{10b}$, $R^{10c}$, and $R^{10d}$ is independently selected from hydrogen, —F, —Cl, —$NH_2$, —CN, —OH, —$NO_2$, and methyl.

In various aspects, each of $R^{10a}$, $R^{10b}$, $R^{10c}$c, and $R^{10d}$ is independently selected from hydrogen, halogen, —CN, C1-C8 alkyl, C1-C8 alkoxy, and —$CO_2$(C1-C4 alkyl). In a further aspect, each of $R^{10a}$, $R^{10b}$, $R^{10c}$, and $R^{10d}$ is independently selected from hydrogen, halogen, —CN, C1-C4 alkyl, C1-C4 alkoxy, and —$CO_2$(C1-C4 alkyl). In a further aspect, each of $R^{10a}$, $R^{10b}$, $R^{10c}$, and $R^{10d}$ is independently selected from hydrogen, —F, —Cl, —CN, methyl, ethyl, n-propyl, i-propyl, —$OCH_3$, —$OCH_2CH_3$, —$OCH_2CH_2CH_3$, —$OCH(CH_3)CH_3$, —$CO_2CH_3$, —$CO_2CH_2CH_3$, and —$CO_2CH_2CH_2CH_3$. In a still further aspect, each of $R^{10a}$, $R^{10b}$, $R^{10c}$, and $R^{10d}$ is independently selected from hydrogen, —F, —Cl, —CN, methyl, ethyl, —$OCH_3$, —$OCH_2CH_3$, —$CO_2CH_3$, and —$CO_2CH_2CH_3$. In yet a further aspect, each of $R^{10a}$, $R^{10b}$, $R^{10c}$, and $R^{10d}$ is independently selected from hydrogen, —F, —Cl, —CN, methyl, and —$OCH_3$, and —$CO_2CH_3$.

In various aspects, each of $R^{10a}$, $R^{10b}$, $R^{10c}$, and $R^{10d}$ is independently selected from hydrogen, halogen, —CN, —$NH_2$, —OH, —$NO_2$, C1-C8 haloalkyl, C1-C8 cyanoalkyl. In a further aspect, each of $R^{10a}$, $R^{10b}$, $R^{10c}$, and $R^{10d}$ is independently selected from hydrogen, halogen, —CN, —$NH_2$, —OH, —$NO_2$, C1-C4 haloalkyl, and C1-C4 cyanoalkyl. In a further aspect, each of $R^{10a}$, $R^{10b}$, $R^{10c}$, and $R^{10d}$ is independently selected from hydrogen, —F, —Cl, —$NH_2$, —CN, —OH, —$NO_2$, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$CH_2CN$, —$CH_2CH_2CN$, —$CH_2CH_2CH_2CN$, and —$CH(CH_3)CH_2CN$. In a further aspect, each of $R^{10a}$, $R^{10b}$, $R^{10c}$, and $R^{10d}$ is independently selected from hydrogen, —F, —Cl, —$NH_2$, —CN, —OH, —$NO_2$, —$CH_2F$, —$CH_2Cl$, —$CH_2CH_2F$, —$CH_2CH_2Cl$, —$CH_2CN$, and —$CH_2CH_2CN$. In a still further aspect, each of $R^{10a}$, $R^{10b}$, $R^{10c}$, and $R^{10d}$ is independently selected from hydrogen, —F, —Cl, —$NH_2$, —CN, —OH, —$NO_2$, —$CH_2F$, —$CH_2Cl$, and —$CH_2CN$.

In various aspects, each of $R^{10a}$, $R^{10b}$, $R^{10c}$, and $R^{10d}$ is independently selected from hydrogen, halogen, —CN, —$NH_2$, —OH, —$NO_2$, C1-C8 alkylamino, (C1-C8)(C1-C8) dialkylamino, and C1-C8 alkylamino. In a further aspect, each of $R^{10a}$, $R^{10b}$, $R^{10c}$, and $R^{10d}$ is independently selected from hydrogen, halogen, —CN, —$NH_2$, —OH, —$NO_2$, C1-C4 alkylamino, (C1-C4)(C1-C4) dialkylamino, and C1-C4 aminoalkyl. In a still further aspect, each of $R^{10a}$, $R^{10b}$, $R^{10c}$, and $R^{10d}$ is independently selected from hydrogen, —F, —Cl, —$NH_2$, —CN, —OH, —$NO_2$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, and —$CH(CH_3)CH_2NH_2$. In yet a further aspect, each of $R^{10a}$, $R^{10b}$, $R^{10c}$, and $R^{10d}$ is independently selected from hydrogen, —F, —Cl, —$NH_2$, —CN, —OH, —$NO_2$, —$NHCH_3$, —$NHCH_2CH_3$, —$N(CH_3)_2$, —$N(CH_2CH_3)_2$, —$N(CH_3)(CH_2CH_3)$, —$CH_2NH_2$, and —$CH_2CH_2NH_2$. In an even further aspect, each of $R^{10a}$, $R^{10b}$, $R^{10c}$, and $R^{10d}$ is independently selected from hydrogen, —F, —Cl, —$NH_2$, —CN, —OH, —$NO_2$, —$NHCH_3$, —$N(CH_3)_2$, and —$CH_2NH_2$.

In various aspects, each of $R^{10a}$, $R^{10b}$, $R^{10c}$c, and $R^{10d}$ is independently selected from hydrogen, C1-C8 alkyl, and —$CO_2$(C1-C4 alkyl). In a further aspect, each of $R^{10a}$, $R^{10b}$, $R^{10c}$, and $R^{10d}$ is independently selected from hydrogen, C1-C4 alkyl, and —$CO_2$(C1-C4 alkyl). In a still further aspect, each of $R^{10a}$, $R^{10b}$, $R^{10c}$, and $R^{10d}$ is independently selected from hydrogen, methyl, ethyl, n-propyl, and i-propyl, —$CO_2CH_3$, —$CO_2CH_2CH_3$, and —$CO_2CH_2CH_2CH_3$. In a further aspect, each of $R^{10a}$, $R^{10b}$, $R^{10c}$, and $R^{10d}$ is independently selected from hydrogen, methyl, and ethyl, —$CO_2CH_3$, and —$CO_2CH_2CH_3$. In a still further aspect, each of $R^{10a}$, $R^{10b}$, $R^{10c}$, and $R^{10d}$ is independently selected from hydrogen and methyl, and —$CO_2CH_3$.

In various aspects, at least one of $R^{10a}$, $R^{10b}$, $R^{10c}$, and $R^{10d}$ is hydrogen. In a further aspect, at least two of $R^{10a}$, $R^{10b}$, $R^{10c}$, and $R^{10d}$ is hydrogen. In a still further aspect, at least three of $R^{10a}$, $R^{10b}$, $R^{10c}$, and $R^{10d}$ is hydrogen.

In various aspects, each of $R^{10a}$, $R^{10b}$, and $R^{10c}$ is hydrogen.

In various aspects, each of $R^{10b}$ and $R^{10c}$ is hydrogen.

In various aspects, each of $R^{10b}$ and $R^{10d}$ is hydrogen

In various aspect, $R^{10d}$ is selected from halogen, —CN, —$NH_2$, —OH, —$NO_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, and C1-C8 alkylamino. In a further aspect, $R^{10d}$ is selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 alkylamino. In a still further aspect, $R^{10d}$ is selected from hydrogen, —F, —Cl, —$NH_2$, —CN, —OH, —$NO_2$, methyl, ethyl, n-propyl, i-propyl, ethenyl, propenyl, isopropenyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$CH_2CN$, —$CH_2CH_2CN$, —$CH_2CH_2CH_2CN$, —$CH(CH_3)CH_2CN$, —$CH_2OH$, —$CH_2CH_2OH$, —$CH_2CH_2CH_2OH$, —$CH(CH_3)CH_2OH$, —$OCF_3$, —$OCH_2CF_3$, —$OCH_2CH_2CF_3$, —$OCH(CH_3)CF_3$, —$OCH_3$, —$OCH_2CH_3$, —$OCH_2CH_2CH_3$, —$OCH(CH_3)CH_3$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, and —$CH(CH_3)CH_2NH_2$. In yet a further aspect, $R^{10d}$ selected from —F, —Cl, —$NH_2$, —CN, —OH, —$NO_2$, methyl, ethyl, ethenyl, —$CH_2F$, —$CH_2Cl$, —$CH_2CH_2F$, —$CH_2CH_2Cl$, —$CH_2CN$, —$CH_2CH_2CN$, —$CH_2OH$, —$CH_2CH_2OH$, —$OCF_3$, —$OCH_2CF_3$, —$OCH_3$, —$OCH_2CH_3$, —$NHCH_3$, —$NHCH_2CH_3$, —$N(CH_3)_2$, —$N(CH_2CH_3)_2$, —$N(CH_3)(CH_2CH_3)$, —$CH_2NH_2$, and —$CH_2CH_2NH_2$. In an even further aspect, $R^{10d}$ is selected from —F, —Cl, —$NH_2$, —CN, —OH, —$NO_2$, methyl, —$CH_2F$, —$CH_2Cl$, —$CH_2CN$, —$CH_2OH$, —$OCF_3$, —$OCH_2CF_3$, —$OCH_3$, —$NHCH_3$, —$N(CH_3)_2$, and —$CH_2NH_2$.

In various aspects, $R^{10d}$ is selected from —$NH_2$, C1-C8 alkoxy, C1-C8 alkylamino, and (C1-C8)(C1-C8) dialkylamino. In a further aspect, $R^{10d}$ is selected from —$NH_2$, C1-C4 alkoxy, C1-C4 alkylamino, and (C1-C4)(C1-C4) dialkylamino. In a still further aspect, $R^{10d}$ is selected from —$NH_2$, —$OCH_3$, —$OCH_2CH_3$, —$OCH_2CH_2CH_3$, —$OCH(CH_3)CH_3$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, and —$N(CH_3)(CH_2CH_3)$. In yet a further aspect, $R^{10d}$ selected from —$NH_2$, —$OCH_3$, —$OCH_2CH_3$, —$NHCH_3$, —$NHCH_2CH_3$, —$N(CH_3)_2$, —$N(CH_2CH_3)_2$, and —$N(CH_3)(CH_2CH_3$. In an even further aspect, $R^{10d}$ is selected from —$NH_2$, —$OCH_3$, —$NHCH_3$, and —$N(CH_3)_2$.

In various aspects, $R^{10d}$ is selected from C1-C8 alkoxy, C1-C8 alkylamino, and (C1-C8)(C1-C8) dialkylamino. In a further aspect, $R^{10d}$ is selected from C1-C4 alkoxy, C1-C4 alkylamino, and (C1-C4)(C1-C4) dialkylamino. In a still further aspect, $R^{10d}$ is selected from —$OCH_3$, —$OCH_2CH_3$, —$OCH_2CH_2CH_3$, —$OCH(CH_3)CH_3$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, and —$N(CH_3)(CH_2CH_3)$. In yet a further aspect, $R^{10d}$ selected from —$OCH_3$, —$OCH_2CH_3$, —$NHCH_3$, —$NHCH_2CH_3$, —$N(CH_3)_2$, —$N(CH_2CH_3)_2$, and —$N(CH_3)(CH_2CH_3$. In an even further aspect, $R^{10d}$ is selected from —$OCH_3$, —$NHCH_3$, and —$N(CH_3)_2$.

In various aspects, $R^{10d}$ is C1-C8 alkoxy. Examples of C1-C8-alkoxy include but are not limited to methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 2,2-dimethylpropoxy, 1-ethylpropoxy, 1,1-dimethylpropoxy, 1,2-dimethylpropoxy, n-hexyloxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. In a further aspect, $R^{10d}$ is selected from n-butoxy and 1-ethylbutoxy.

In various aspects, each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, C1-C8 alkylamino, and —$CO_2$(C1-C4 alkyl). In a further aspect, each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 alkylamino, and —$CO_2$(C1-C4 alkyl). In a still further aspect, each of $R^{10a}$, $R^{10b}$, $R^{10c}$, $R^{10d}$, and $R^{10e}$ is independently selected from hydrogen, —F, —Cl, —$NH_2$, —CN, —OH, —$NO_2$, methyl, ethyl, n-propyl, i-propyl, ethenyl, propenyl, isopropenyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$CH_2CN$, —$CH_2CH_2CN$, —$CH_2CH_2CH_2CN$, —$CH(CH_3)CH_2CN$, —$CH_2OH$, —$CH_2CH_2OH$, —$CH_2CH_2CH_2OH$, —$CH(CH_3)CH_2OH$, —$OCF_3$, —$OCH_2CF_3$, —$OCH_2CH_2CF_3$, —$OCH(CH_3)CF_3$, —$OCH_3$, —$OCH_2CH_3$, —$OCH_2CH_2CH_3$, —$OCH(CH_3)CH_3$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, —$CH(CH_3)CH_2NH_2$, —$CO_2CH_3$, —$CO_2CH_2CH_3$, and —$CO_2CH_2CH_2CH_3$. In yet a further aspect, each of $R^{10a}$, $R^{10b}$, $R^{10c}$, $R^{10d}$, and $R^{10e}$ independently selected from hydrogen, —F, —Cl, —$NH_2$, —CN, —OH, —$NO_2$, methyl, ethyl, ethenyl, —$CH_2F$, —$CH_2Cl$, —$CH_2CH_2F$, —$CH_2CH_2Cl$, —$CH_2CN$, —$CH_2CH_2CN$, —$CH_2OH$, —$CH_2CH_2OH$, —$OCF_3$, —$OCH_2CF_3$, —$OCH_3$, —$OCH_2CH_3$, —$NHCH_3$, —$NHCH_2CH_3$, —$N(CH_3)_2$, —$N(CH_2CH_3)_2$, —$N(CH_3)(CH_2CH_3)$, —$CH_2NH_2$, —$CH_2CH_2NH_2$, —$CO_2CH_3$, and —$CO_2CH_2CH_3$. In an even further aspect, each of $R^{10a}$, $R^{10b}$, $R^{10c}$, $R^{10d}$, and $R^{10e}$ is independently selected from hydrogen, —F, —Cl, —$NH_2$, —CN, —OH, —$NO_2$, methyl, —$CH_2F$, —$CH_2Cl$, —$CH_2CN$, —$CH_2OH$, —$OCF_3$, —$OCH_2CF_3$, —$OCH_3$, —$NHCH_3$, —$N(CH_3)_2$, —$CH_2NH_2$, and —$CO_2CH_3$.

In various aspects, each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C8 alkyl, and C2-C8 alkenyl. In a further aspect, each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C4 alkyl, and C2-C4 alkenyl. In a still further aspect, each of $R^{10a}$, $R^{10b}$, $R^{10c}$, $R^{10d}$, and $R^{10e}$ is independently selected from hydrogen, —F, —Cl, —$NH_2$, —CN, —OH, —$NO_2$, methyl, ethyl, n-propyl, i-propyl, ethenyl, propenyl, and isopropenyl. In yet a further aspect, each of $R^{10a}$, $R^{10b}$, $R^{10c}$, and $R^{10d}$ is independently selected from hydrogen, —F, —Cl, —$NH_2$, —CN, —OH, —$NO_2$, methyl, ethyl, and ethenyl. In an even further aspect, each of $R^{10a}$, $R^{10b}$, $R^{10c}$, $R^{10d}$, and $R^{10e}$ is independently selected from hydrogen, —F, —Cl, —$NH_2$, —CN, —OH, —$NO_2$, and methyl.

In various aspects, each of $R^{10a}$, $R^{10b}$, $R^{10c}$, $R^{10d}$, and $R^{10e}$ is independently selected from hydrogen, halogen, —CN, C1-C8 alkyl, C1-C8 alkoxy, and —$CO_2$(C1-C4 alkyl). In a further aspect, each of $R^{10a}$, $R^{10b}$, $R^{10c}$, $R^{10d}$, and $R^{10e}$ is independently selected from hydrogen, halogen, —CN, C1-C4 alkyl, C1-C4 alkoxy, and —$CO_2$(C1-C4 alkyl). In a further aspect, each of $R^{10a}$, $R^{10b}$, $R^{10c}$, $R^{10d}$, and $R^{10e}$ is independently selected from hydrogen, —F, —Cl, —CN, methyl, ethyl, n-propyl, i-propyl, —$OCH_3$, —$OCH_2CH_3$, —$OCH_2CH_2CH_3$, —$OCH(CH_3)CH_3$, —$CO_2CH_3$, —$CO_2CH_2CH_3$, and —$CO_2CH_2CH_2CH_3$. In a still further aspect, each of $R^{10a}$, $R^{10b}$, $R^{10a}$, $R^{10d}$, and $R^{10e}$ is independently selected from hydrogen, —F, —Cl, —CN, methyl, ethyl, —$OCH_3$, —$OCH_2CH_3$, —$CO_2CH_3$, and —$CO_2CH_2CH_3$. In yet a further aspect, each of $R^{10a}$, $R^{10b}$, $R^{10c}$, $R^{10d}$, and $R^{10e}$ is independently selected from hydrogen, —F, —Cl, —CN, methyl, and —$OCH_3$, and —$CO_2CH_3$.

In various aspects, each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C8 haloalkyl, C1-C8 cyanoalkyl. In a further aspect, each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C4 haloalkyl, and C1-C4 cyanoalkyl. In a further aspect, each of $R^{10a}$, $R^{10b}$, $R^{10c}$, $R^{10d}$, and $R^{10e}$ is independently selected from hydrogen, —F, —Cl, —$NH_2$, —CN, —OH, —$NO_2$, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$CH_2CN$, —$CH_2CH_2CN$, —$CH_2CH_2CH_2CN$, and —$CH(CH_3)CH_2CN$. In a further aspect, each of $R^{10a}$, $R^{10b}$, $R^{10c}$, $R^{10d}$, and $R^{10e}$ is independently selected from hydrogen, —F, —Cl, —$NH_2$, —CN, —OH, —$NO_2$, —$CH_2F$, —$CH_2Cl$, —$CH_2CH_2F$, —$CH_2CH_2Cl$, —$CH_2CN$, and —$CH_2CH_2CN$. In a still further aspect, each of $R^{10a}$, $R^{10b}$, $R^{10c}$, $R^{10d}$, and $R^{10e}$ is independently selected from hydrogen, —F, —Cl, —$NH_2$, —CN, —OH, —$NO_2$, —$CH_2F$, —$CH_2Cl$, and —$CH_2CN$.

In various aspects, each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C8 alkylamino, (C1-C8)(C1-C8) dialkylamino, and C1-C8 alkylamino. In a further aspect, each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C4 alkylamino, (C1-C4)(C1-C4) dialkylamino, and C1-C4 aminoalkyl. In a still further aspect, each of $R^{10a}$, $R^{10b}$, $R^{10c}$, $R^{10d}$, and $R^{10e}$ is independently selected from hydrogen, —F, —Cl, —$NH_2$, —CN, —OH, —$NO_2$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, and —$CH(CH_3)CH_2NH_2$. In yet a further aspect, each of $R^{10a}$, $R^{10b}$, $R^{10c}$, $R^{10d}$, and $R^{10e}$ is independently selected from hydrogen, —F, —Cl, —$NH_2$, —CN, —OH, —$NO_2$, —$NHCH_3$, —$NHCH_2CH_3$, —$N(CH_3)_2$, —$N(CH_2CH_3)_2$, —$N(CH_3)(CH_2CH_3)$, —$CH_2NH_2$, and —$CH_2CH_2NH_2$. In an even further aspect, each of $R^{10a}$, $R^{10b}$, $R^{10c}$, $R^{10d}$, and $R^{10e}$ is independently selected from hydrogen, —F, —Cl, —$NH_2$, —CN, —OH, —$NO_2$, —$NHCH_3$, —$N(CH_3)_2$, and —$CH_2NH_2$.

In various aspects, each of $R^{10a}$, $R^{10b}$, $R^{10c}$, $R^{10d}$, and $R^{10e}$ is independently selected from hydrogen, C1-C8 alkyl, and —$CO_2$(C1-C4 alkyl). In a further aspect, each of $R^{10a}$, $R^{10b}$, $R^{10c}$, $R^{10d}$, and $R^{10e}$ is independently selected from hydrogen, C1-C4 alkyl, and —$CO_2$(C1-C4 alkyl). In a still further aspect, each of $R^{10a}$, $R^{10b}$, $R^{10c}$, $R^{10d}$, and $R^{10e}$ is independently selected from hydrogen, methyl, ethyl, n-propyl, and i-propyl, —$CO_2CH_3$, —$CO_2CH_2CH_3$, and —$CO_2CH_2CH_2CH_3$. In a further aspect, each of $R^{10a}$, $R^{10b}$, $R^{10c}$, $R^{10d}$, and $R^{10e}$ is independently selected from hydrogen, methyl, and ethyl, —$CO_2CH_3$, and —$CO_2CH_2CH_3$. In a still further aspect, each of $R^{10a}$, $R^{10b}$, $R^{10c}$, $R^{10d}$, and $R^{10e}$ is independently selected from hydrogen and methyl, and —$CO_2CH_3$.

In various aspects, at least one of $R^{10a}$, $R^{10b}$, $R^{10c}$, $R^{10d}$, and $R^{10e}$ is hydrogen. In a further aspect, at least two of $R^{10a}$, $R^{10b}$, $R^{10c}$, $R^{10d}$, and $R^{10e}$ is hydrogen. In a still further aspect, at least three of $R^{10a}$, $R^{10b}$, $R^{10c}$, $R^{10d}$, and $R^{10e}$ is hydrogen.

In various aspects, each of $R^{10a}$, $R^{10b}$, $R^{10c}$, and $R^{10e}$ is hydrogen.

1. $R^{11}$ Groups

In one aspect, $R^{11}$ is a residue of a fluorophore, a residue of biotin, or a residue of a biotin derivative. In one aspect, $R^{11}$ is a residue of a fluorophore, a residue of biotin, or a residue of a biotin derivative.

In a further aspect, $R^{11}$ is a residue of biotin or a residue of a biotin derivative. In a still further aspect, $R^{11}$ is a residue of biotin. In yet a further aspect, $R^1$ is a residue of a biotin derivative. Examples of biotin derivatives include, but are not limited to, biocytin and desthiobiotin. In an even further aspect, the biotin derivative is biocytin or desthiobiotin.

In a further aspect, $R^{11}$ is a residue of a fluorophore. Examples of fluorophores include, but are not limited to, fluorescein, Oregon green, rhodamine (e.g., TAMRA dye), eosin, Texas red, indocarbocyanine, oxacarbocyanine, thiacarbocyanine, merocyanine, a squaraine derivative, a naphthalene derivative (e.g., a dansyl or prodan derivative), a coumarin derivative, an oxadiazole derivative (e.g., pyridyloxazole, nitrobenzoxadiazole, benzoxadiazole), an anthracene derivative (e.g., an anthraquinone such as DRAQ5, DRAQ7, and CyTRAK Orange), cascade blue, Nile red, Nile blue, cresyl violate, oxazine 170, proflavin, acridine orange, acridine yellow, auramine, crystal violet, malachite green, prophin, phthalocyanine, an alexa fluor series dye, bilirubin, and 4,4-difluoro-4-bora-3a,4a-diaza-s-indacene (BODIPY) fluorophores.

In a further aspect, the fluorophore is a 4,4-difluoro-4-bora-3a,4a-diaza-s-indacene (BODIPY) fluorophore. In a still further aspect, the BODIPY fluorophore is selected from:

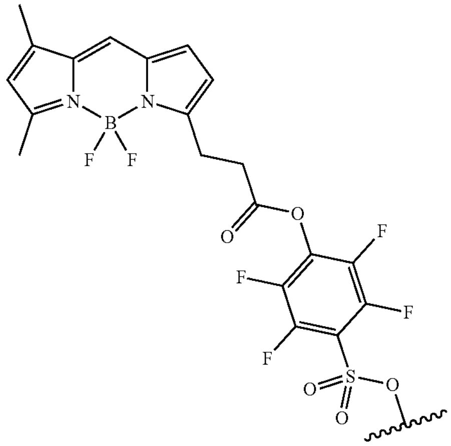

,

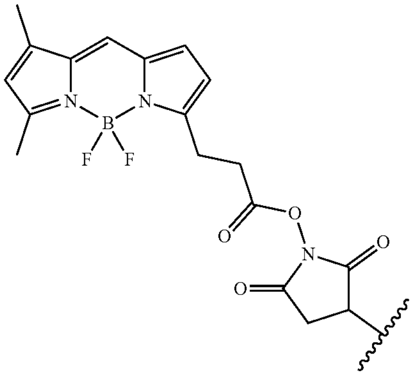

,

-continued
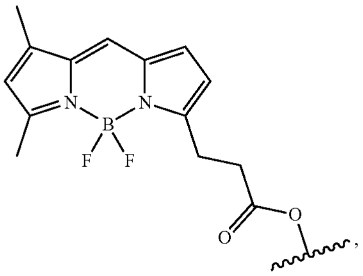
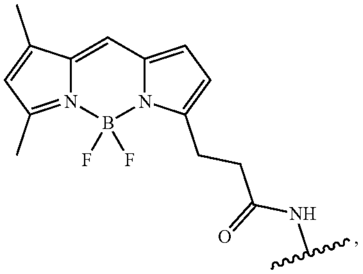
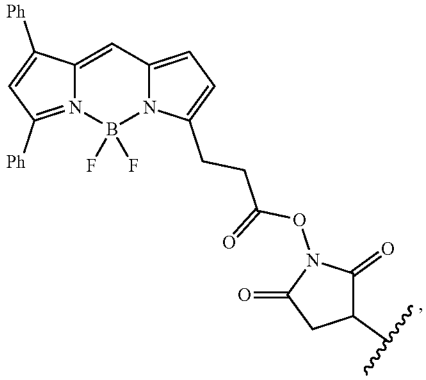
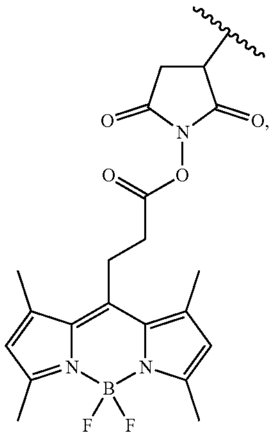
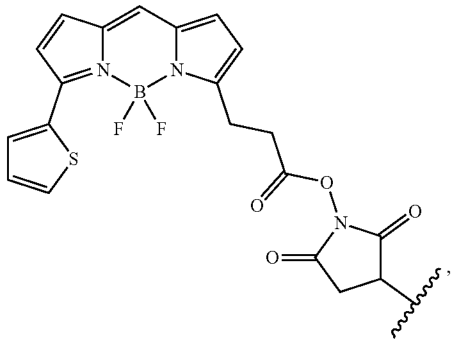
-continued
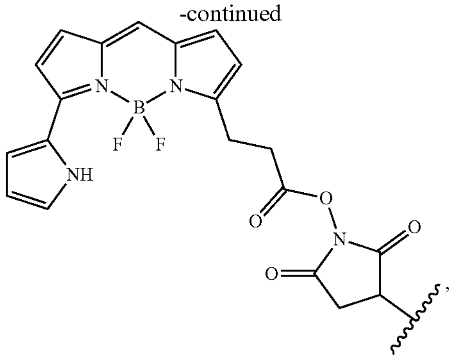
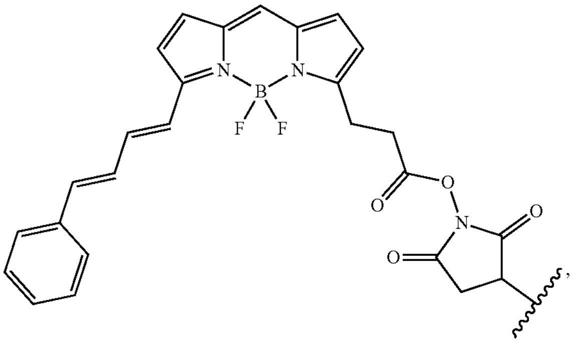
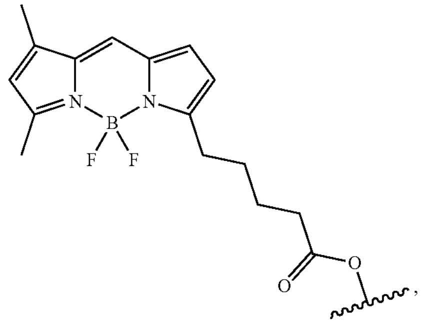
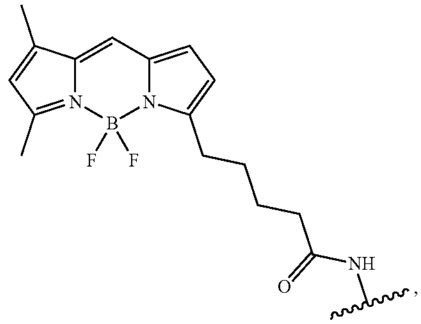
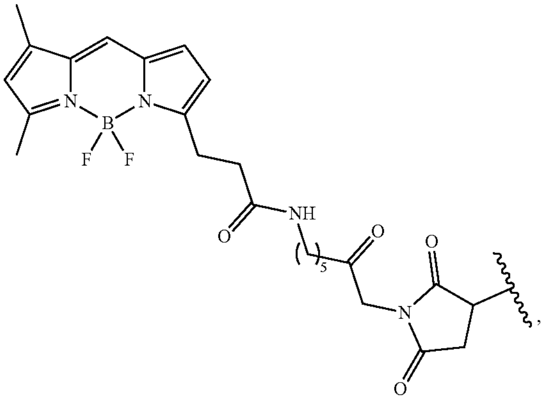

-continued

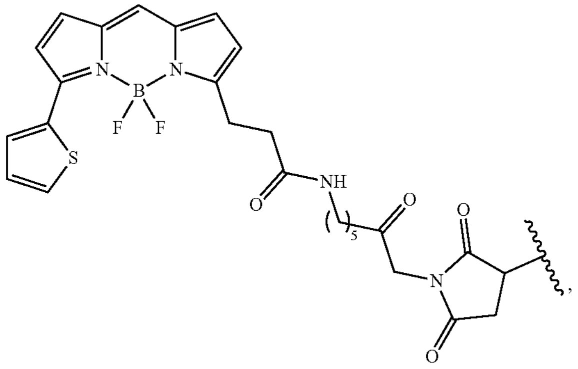

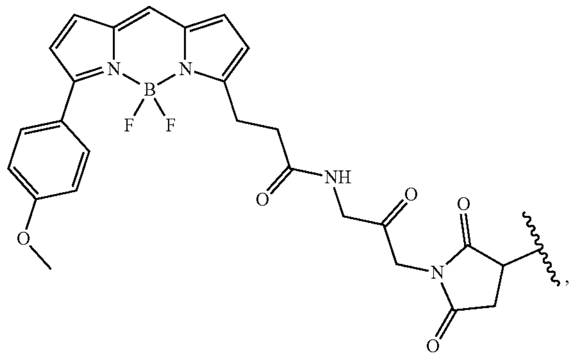

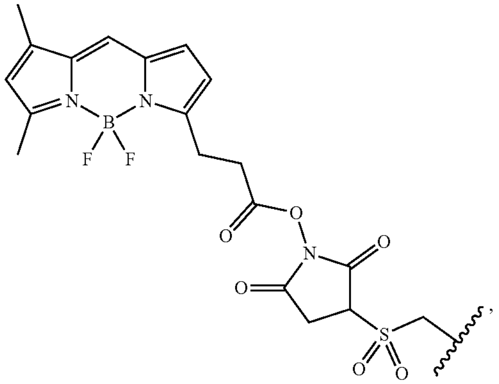

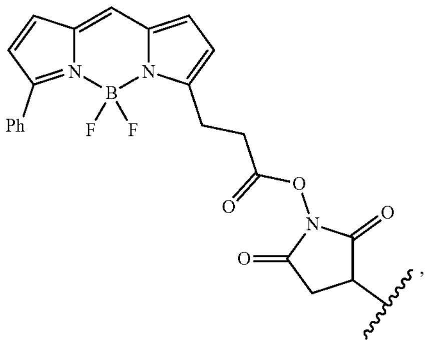

-continued

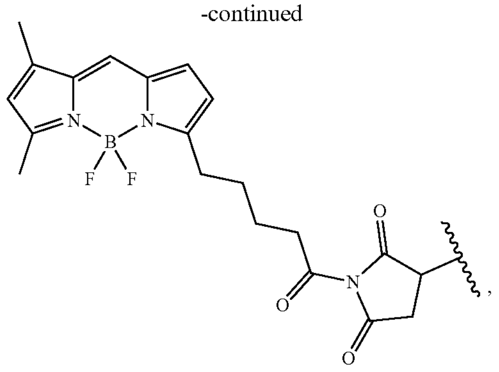

In various aspects, the BODIPY fluorophore is:

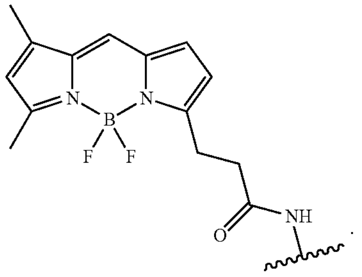

m. $R^{20A}$ AND $R^{20b}$ Groups

In one aspect, each of $R^{20a}$ and $R^{20b}$ is independently selected from hydrogen and C1-C4 alkyl, or wherein each of $R^{20a}$ and $R^{20b}$ are covalently bound, and, together comprise a C3-C4 cycloalkyl or a C2-C3 heterocycloalkyl, wherein $R^{20a}$ is covalently bound to $R^3$, and, together with the intermediate atoms, comprises a 5-membered heterocycle.

In a further aspect, each of $R^{20a}$ and $R^{20b}$, when present, is independently hydrogen or C1-C4 alkyl. In a still further aspect, each of $R^{20a}$ and $R^{20b}$, when present, is independently hydrogen, methyl, ethyl, n-propyl, or isopropyl. In yet a further aspect, each of $R^{20a}$ and $R^{20b}$, when present, is independently hydrogen, methyl, or ethyl. In an even further aspect, each of $R^{20a}$ and $R^{20b}$, when present, is independently hydrogen or methyl.

In a further aspect, each of $R^{20a}$ and $R^{20b}$, when present, is independently C1-C4 alkyl. In a still further aspect, each of $R^{20a}$ and $R^{20b}$, when present, is independently methyl, ethyl, n-propyl, or isopropyl. In yet a further aspect, each of $R^{20a}$ and $R^{20b}$, when present, is independently methyl or ethyl. In an even further aspect, each of $R^{20a}$ and $R^{20b}$, when present, is methyl.

In a further aspect, each of $R^{20a}$ and $R^{20b}$, when present, is hydrogen.

In a further aspect, each of $R^{20a}$ and $R^{20b}$, when present, are covalently bound, and, together comprise a C3-C4 cycloalkyl or a C2-C3 heterocycloalkyl. In a still further aspect, each of $R^{20a}$ and $R^{20b}$, when present, are covalently bound, and, together comprise a C3-C4 cycloalkyl or a C2-C3 heterocycloalkyl, and are unsubstituted.

In a further aspect, each of $R^{20a}$ and $R^{20b}$, when present, are covalently bound, and, together comprise a C3-C4 cycloalkyl. In a still further aspect, each of $R^{20a}$ and $R^{20b}$, when present, are covalently bound, and, together comprise a cyclopropyl. In yet a further aspect, each of $R^{20a}$ and $R^{20b}$, when present, are covalently bound, and, together comprise a cyclobutyl. In an even further aspect, each of $R^{20a}$ and $R^{20b}$, when present, are covalently bound, and, together comprise an unsubstituted C3-C4 cycloalkyl.

In a further aspect, each of $R^{20a}$ and $R^{20b}$, when present, are covalently bound, and, together comprise a C2-C3 heterocycloalkyl. Examples of C2-C3 heterocycloalkyls include, but are not limited to, oxirane, aziridine, and thiirane. In a still further aspect, each of $R^{20a}$ and $R^{20b}$, when present, are covalently bound, and, together comprise an unsubstituted C2-C3 heterocycloalkyl.

In a further aspect, $R^{20a}$, when present, is covalently bound to $R^3$, and, together with the intermediate atoms, comprises a 5-membered heterocycle. Examples of 5-membered heterocycles include, but are not limited to, pyrrolidinyl, pyrrolidino, thiolanyl, and tetrahydrofuranyl. In a still further aspect, $R^{20a}$, when present, is covalently bound to $R^3$, and, together with the intermediate atoms, comprises an unsubstituted 5-membered heterocycle.

n. $R^{21A}$ AND $R^{21B}$ Groups

In one aspect, each of $R^{21a}$ and $R^{21b}$ are covalently bound, and, together with the intermediate atoms, comprise a 4-membered heterocycle. Examples of 4-membered heterocycles include, but are not limited to, trimethylene oxide, thietane, 1,3-diazetidine, and azetidine. In a further aspect, each of $R^{21a}$ and $R^{21b}$, when present, are covalently bound, and, together with the intermediate atoms, comprise an unsubstituted 4-membered heterocycle o. $R^{22}$ AND $R^{23}$ Groups

In one aspect, $R^{22}$, when present, is hydrogen; and wherein $R^{23}$, when present, is C1-C4 alkyl, $—CH_2C_6H_5$, or $—C_6H_5$; or wherein each of $R^{22}$ and $R^{23}$, when present, are covalently bound, and, together with the intermediate atoms, comprise a 10-membered heterocycloalkyl.

In a further aspect, $R^{22}$, when present, is hydrogen.

In a further aspect, $R^{23}$, when present, is C1-C4 alkyl, $—CH_2C_6H_5$, or $—C_6H_5$. In a still further aspect, $R^{23}$, when present, is methyl, ethyl, n-propyl, isopropyl, $—CH_2C_6H_5$, or $—C_6H_5$. In yet a further aspect, $R^{23}$, when present, is methyl, ethyl, $—CH_2C_6H_5$, or $—C_6H_5$. In an even further aspect, $R^{23}$, when present, is methyl, $—CH_2C_6H_5$, or $—C_6H_5$.

In a further aspect, $R^{23}$, when present, is C1-C4 alkyl. In a still further aspect, $R^{23}$, when present, is methyl, ethyl, n-propyl, or isopropyl. In yet a further aspect, $R^{13}$, when present, is methyl or ethyl. In an even further aspect, $R^{23}$, when present, is methyl.

In a further aspect, $R^{23}$, when present, is $—CH_2C_6H_5$ or $—C_6H_5$. In a still further aspect, $R^{23}$, when present, is $—CH_2C_6H_5$. In yet a further aspect, $R^{23}$, when present, is $—C_6H_5$.

In a further aspect, each of $R^{22}$ and $R^{23}$, when present, are covalently bound, and, together with the intermediate atoms, comprise a 10-membered heterocycloalkyl. Examples of 10-membered heterocycloalkyls include, but are not limited to, tetrahydroisoquinolinyl and decahydroisoquinolinyl.

p. $R^{24}$ AND $R^{25}$ Groups

In one aspect, each of $R^{24}$ and $R^{25}$ is independently selected from hydrogen and C1-C4 alkyl. In a further aspect, each of $R^{24}$ and $R^{25}$ is independently selected from hydrogen, methyl, ethyl, propyl, and isopropyl. In a further aspect, each of $R^{24}$ and $R^{25}$ is independently selected from hydrogen, methyl, and ethyl. In a still further aspect, each of $R^{24}$ and $R^{25}$ is independently selected from hydrogen and ethyl. In yet a further aspect, $R^2$ is selected from hydrogen and methyl.

In various aspects, each of $R^{24}$ and $R^{25}$ is independently C1-C4 alkyl. In a further aspect, each of $R^{24}$ and $R^{25}$ is independently selected from methyl, ethyl, propyl, and isopropyl. In a further aspect, each of $R^{24}$ and $R^{25}$ is independently selected from methyl and ethyl. In a still further aspect, each of $R^{24}$ and $R^{25}$ is ethyl. In yet a further aspect, each of $R^{24}$ and $R^{25}$ is methyl.

In various aspects, each of $R^{24}$ and $R^{21}$ is hydrogen.

In various aspects, $R^{24}$ hydrogen.

q. $R^{26A}$ AND $R^{26B}$ Groups

In one aspect, each of $R^{26a}$ and $R^{26b}$, when present, is independently hydrogen or C1-C4 alkyl. In a still further aspect, each of $R^{26a}$ and $R^{26b}$, when present, is independently hydrogen, methyl, ethyl, n-propyl, or isopropyl. In yet a further aspect, each of $R^{26a}$ and $R^{26b}$, when present, is independently hydrogen, methyl, or ethyl. In an even further aspect, each of $R^{26a}$ and $R^{26b}$, when present, is independently hydrogen or methyl.

In a further aspect, each of $R^{26a}$ and $R^{26b}$, when present, is independently C1-C4 alkyl. In a still further aspect, each of $R^{26a}$ and $R^{26b}$, when present, is independently methyl, ethyl, n-propyl, or isopropyl. In yet a further aspect, each of $R^{26a}$ and $R^{26b}$, when present, is independently methyl or ethyl. In an even further aspect, each of $R^{26a}$ and $R^{26b}$, when present, is methyl.

In a further aspect, each of $R^{26a}$ and $R^{26b}$, when present, is hydrogen.

2. EXEMPLARY COMPOUNDS

In one aspect, a compound can be present as one or more of the following structures:

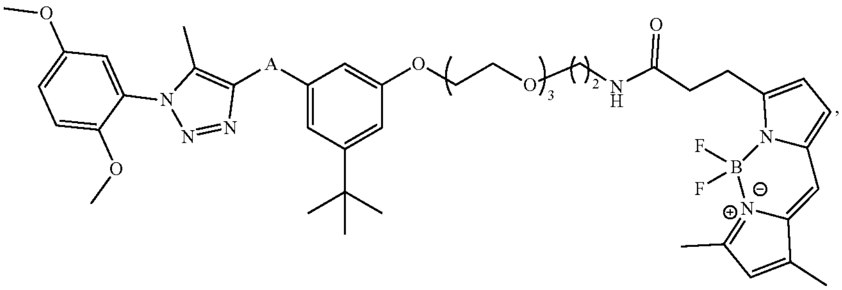

,

-continued
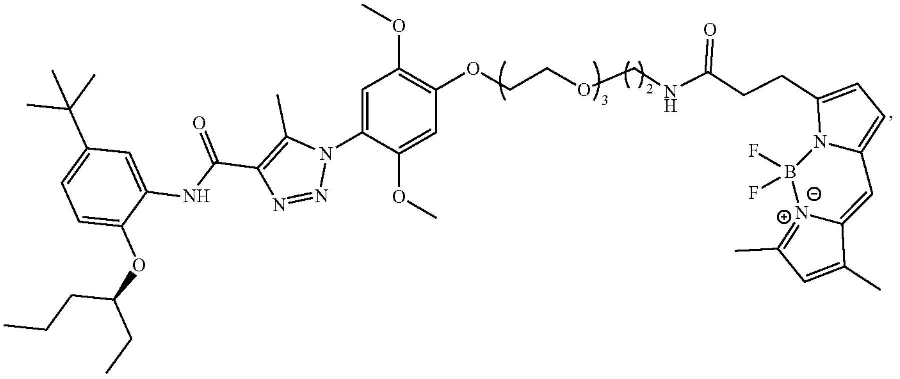
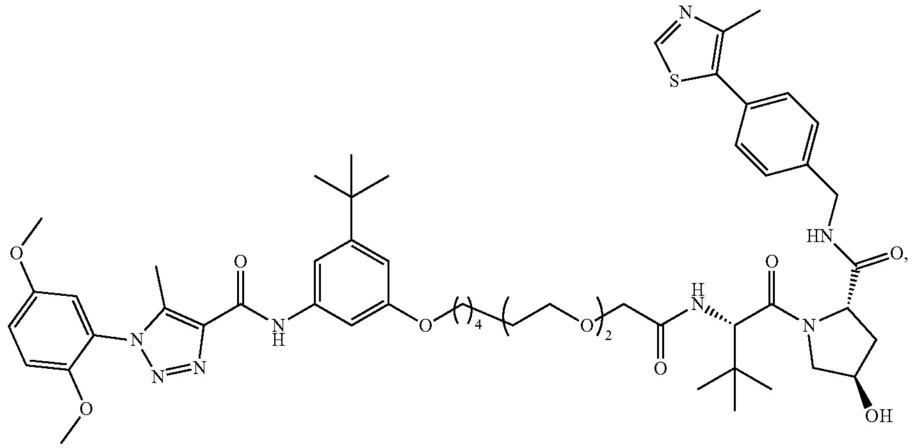
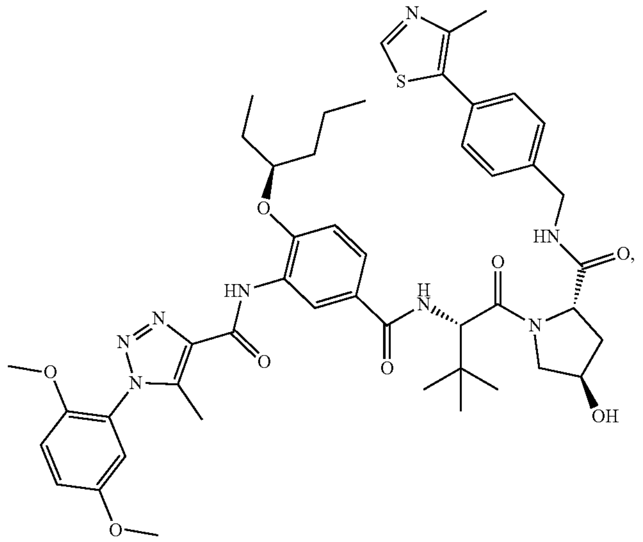

-continued
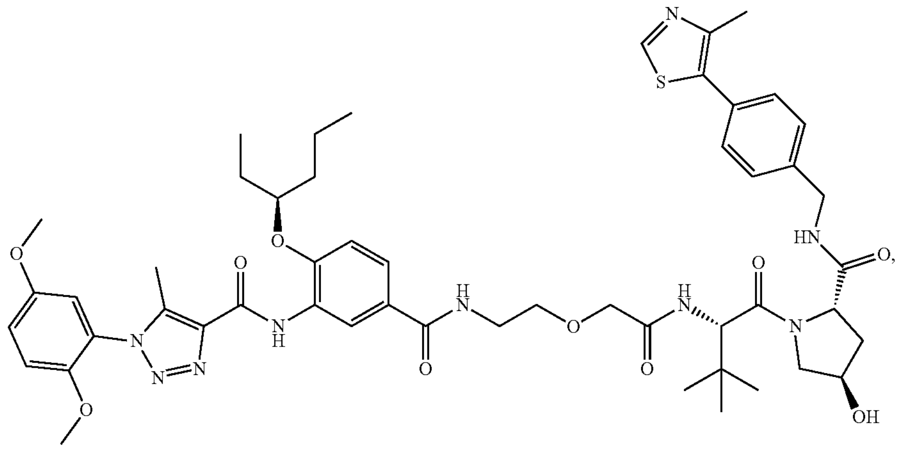
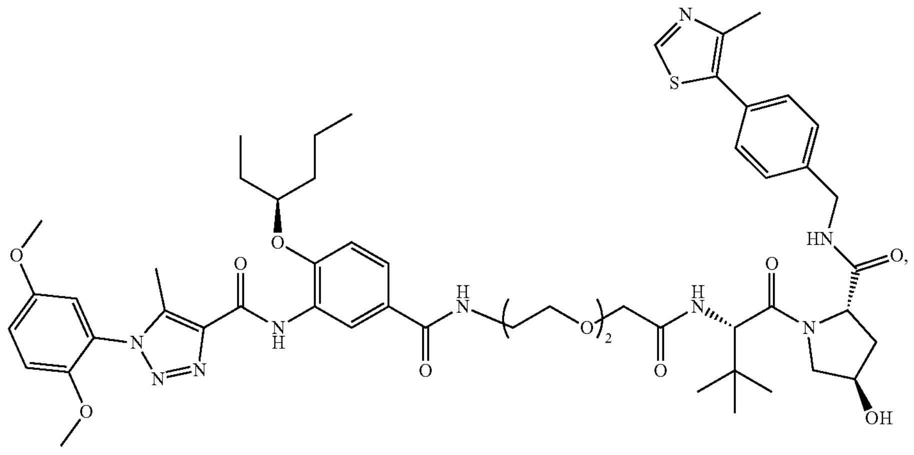
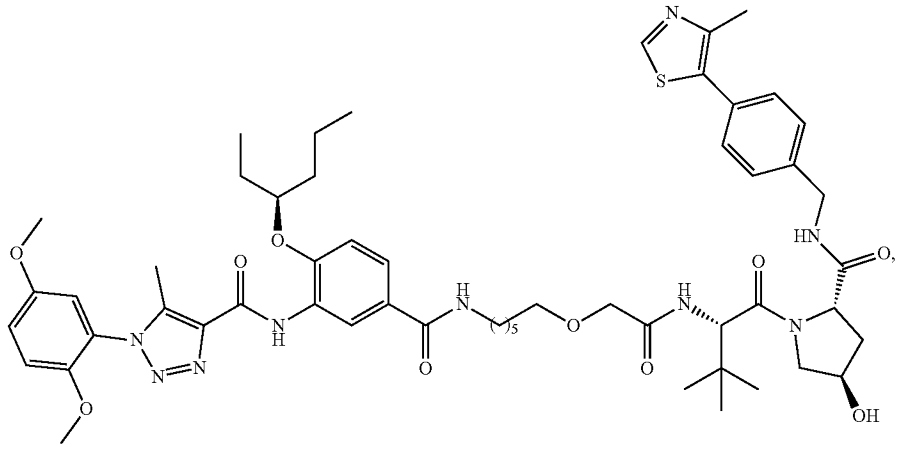

-continued
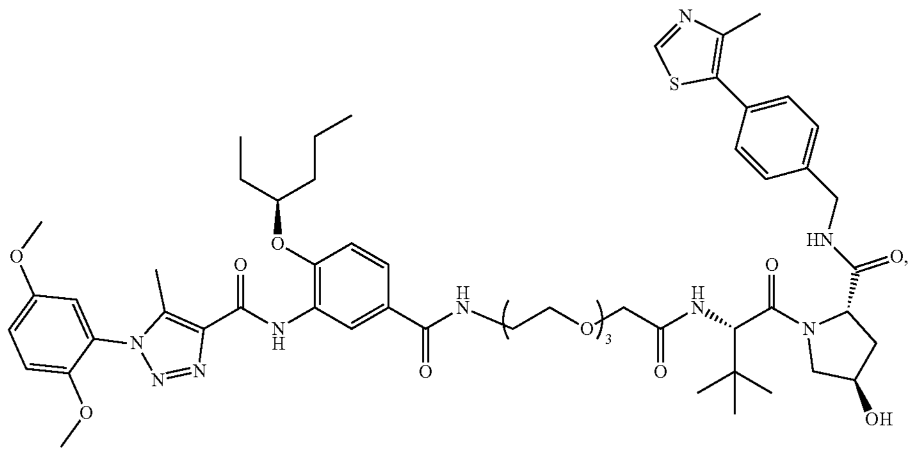
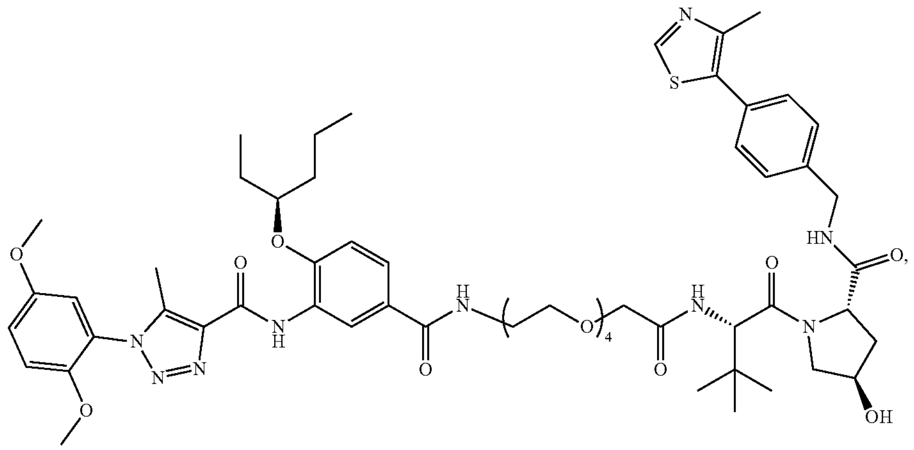
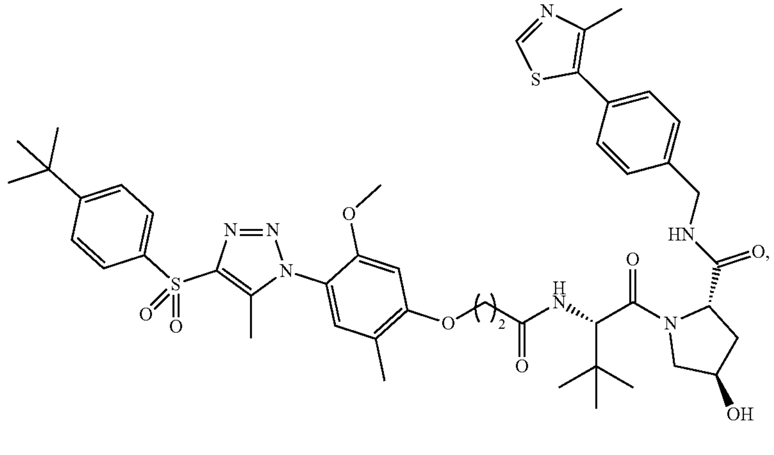

-continued
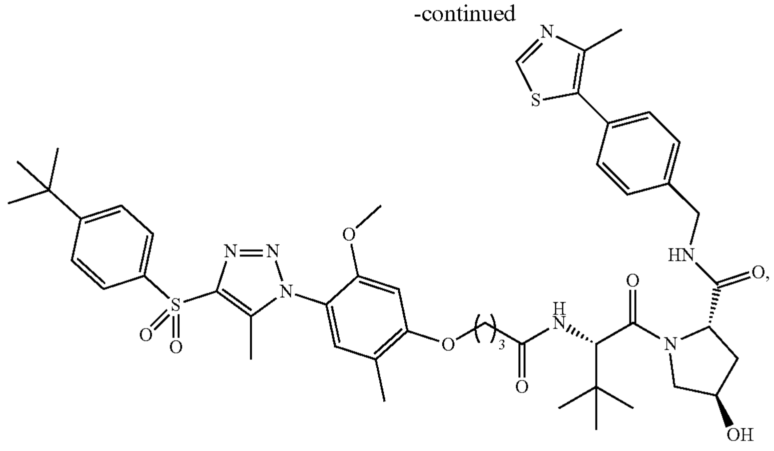
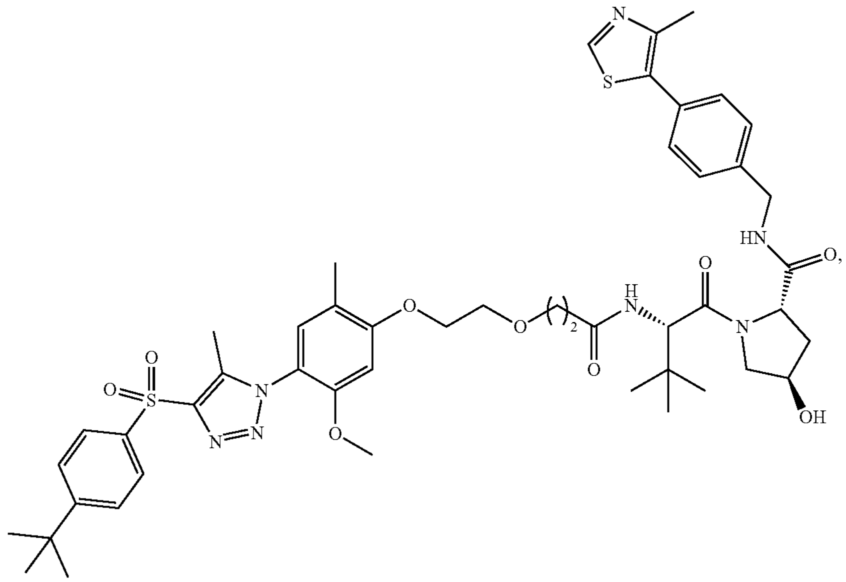
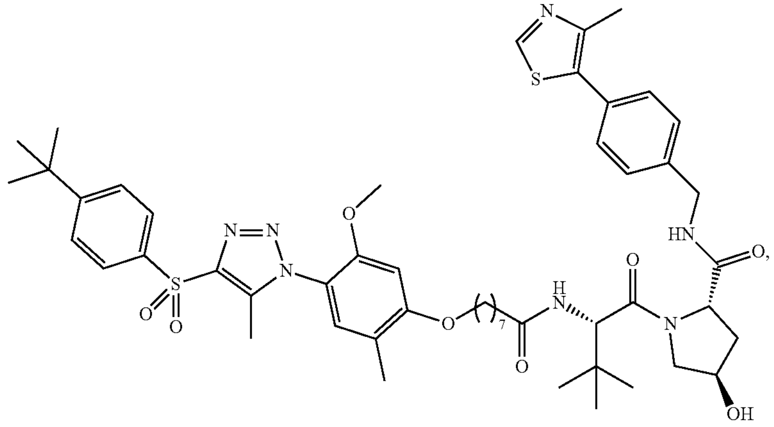

-continued
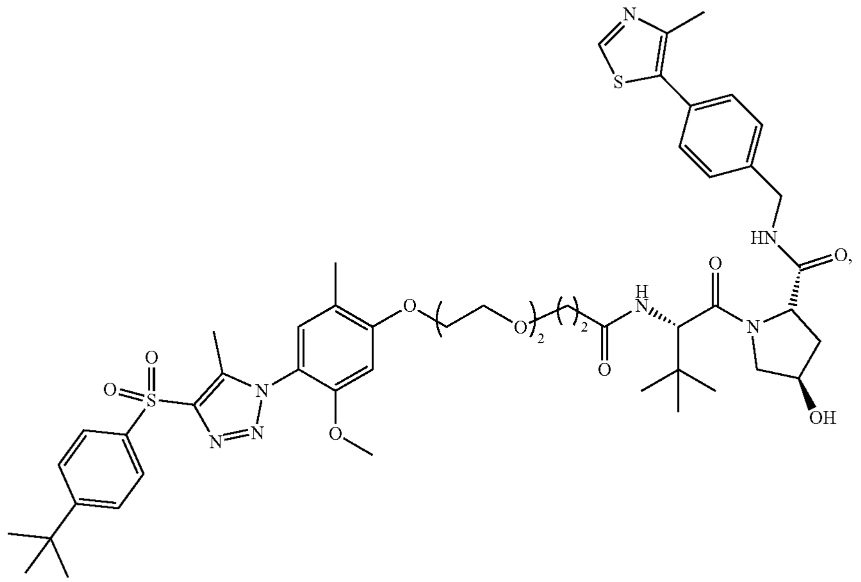
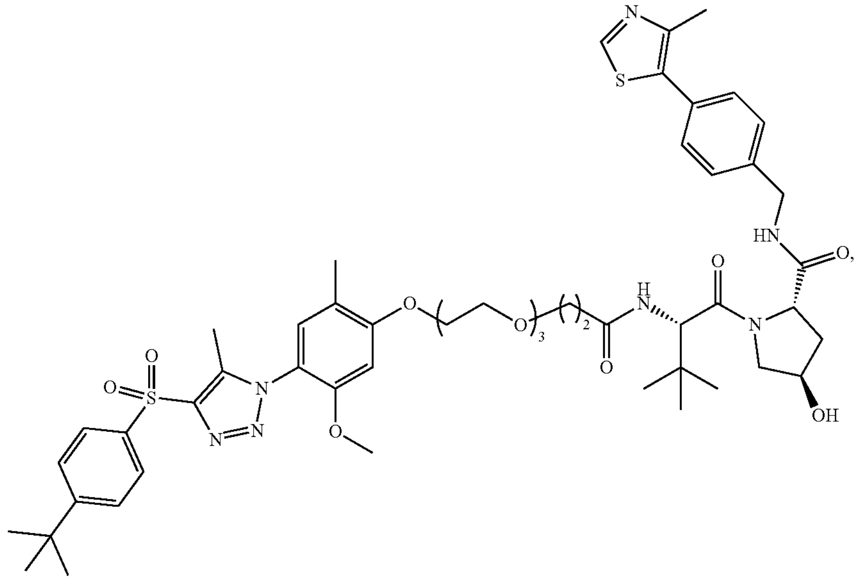
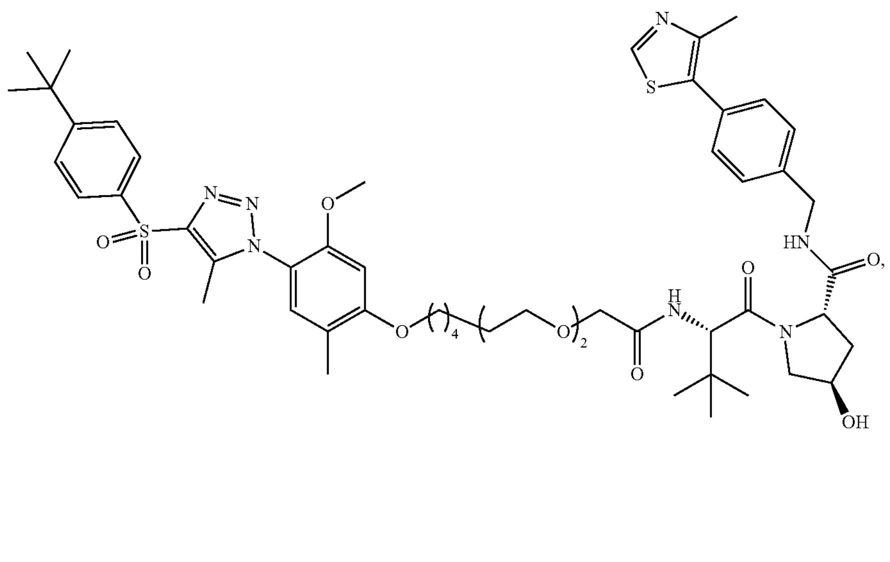

-continued
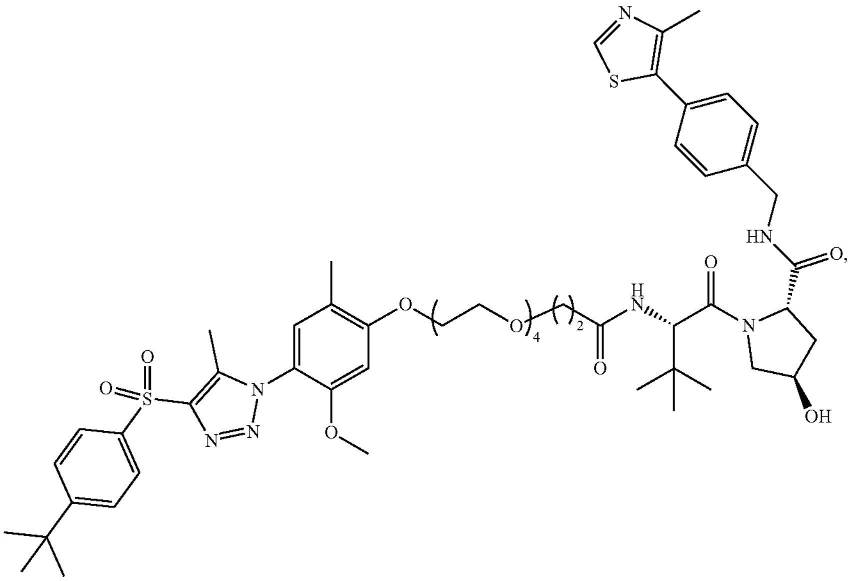
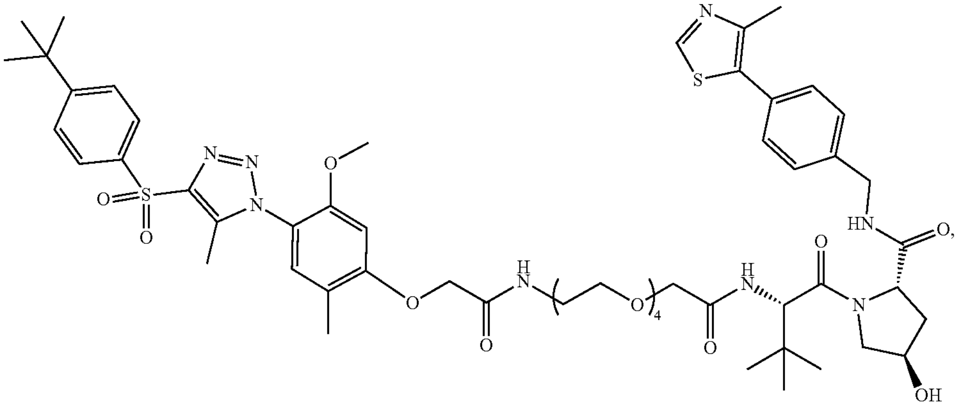
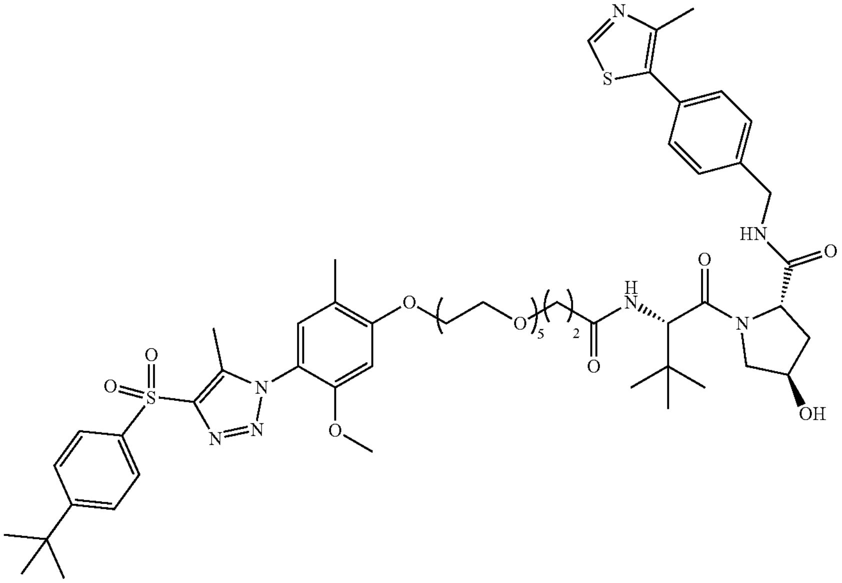

-continued
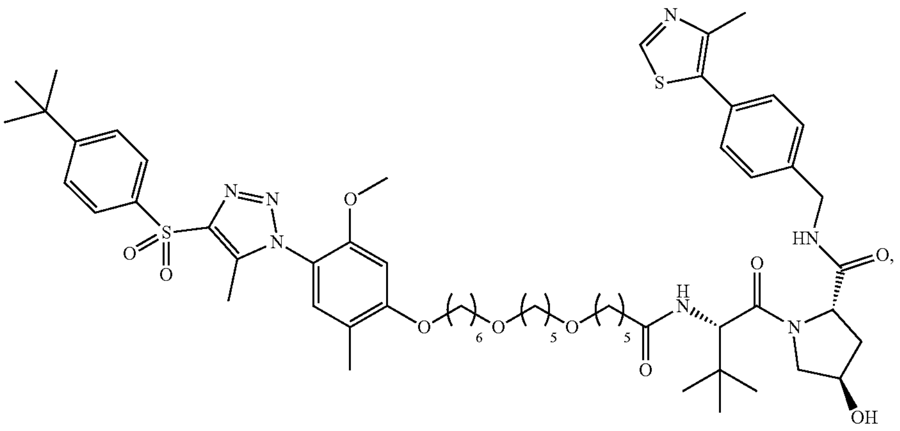
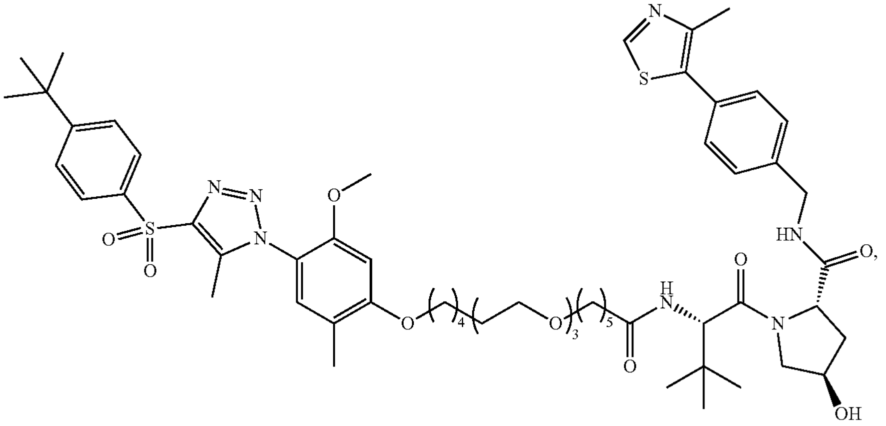
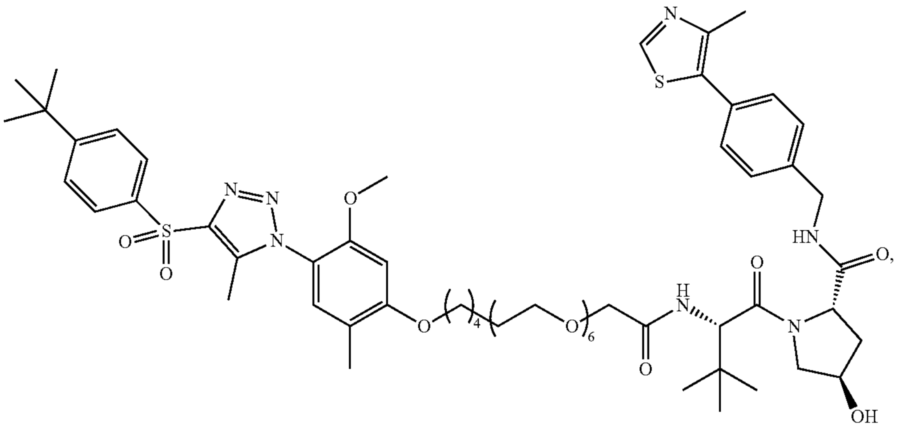
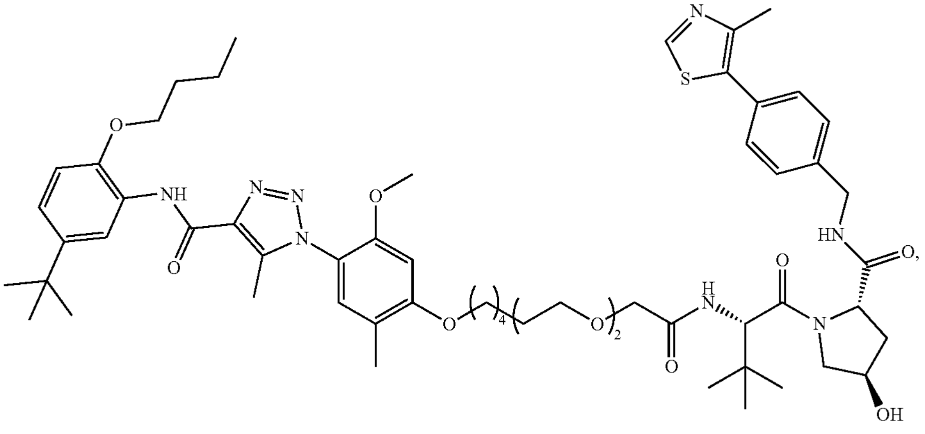

-continued
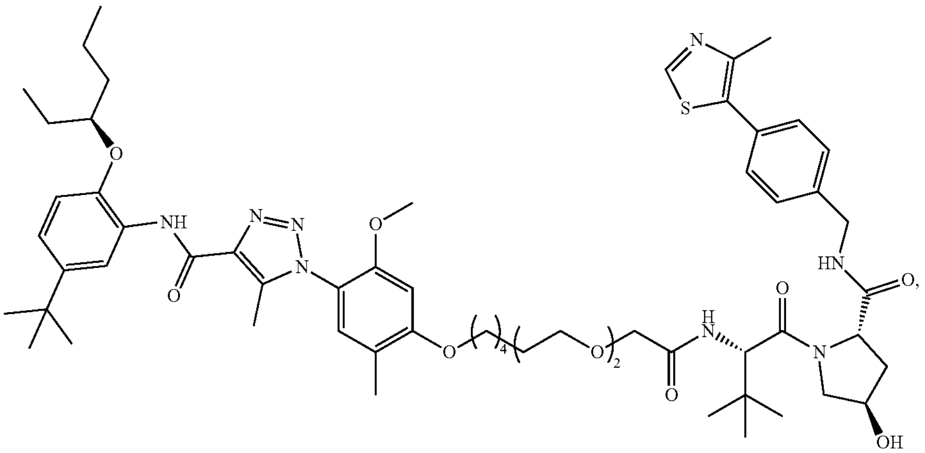
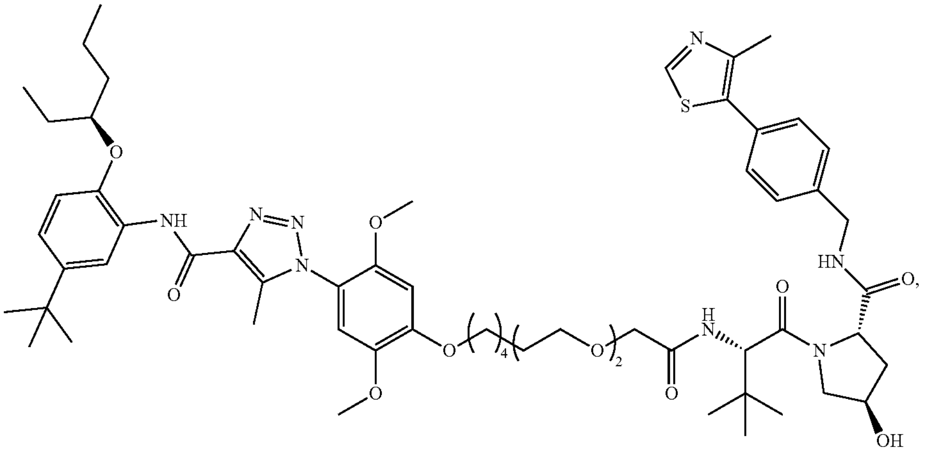
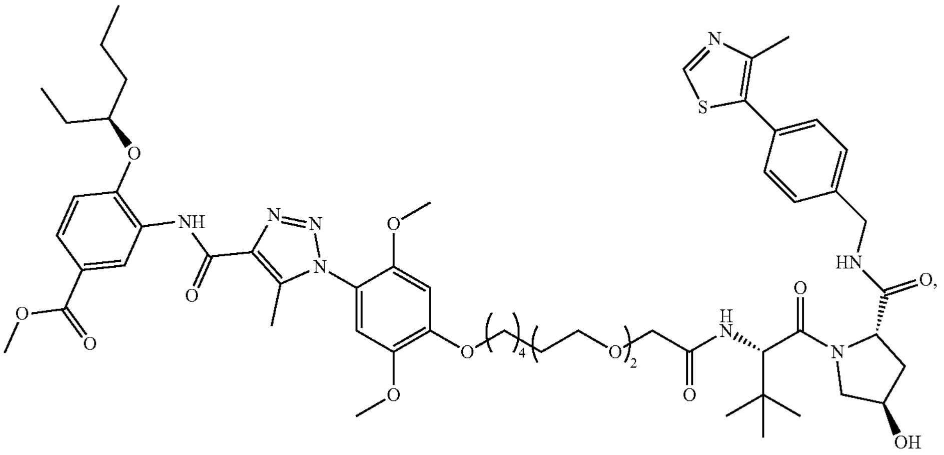
or

-continued

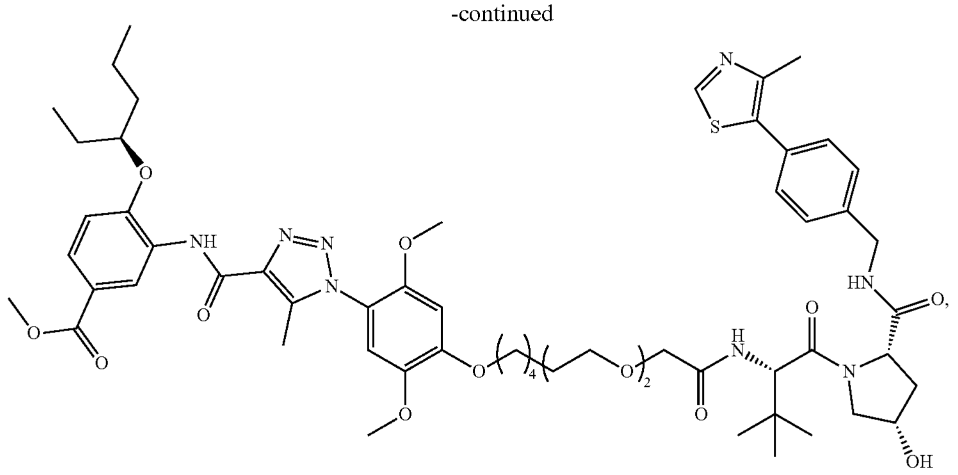

or a pharmaceutically acceptable salt thereof.

In one aspect, a compound can be present as one or more of the following structures:

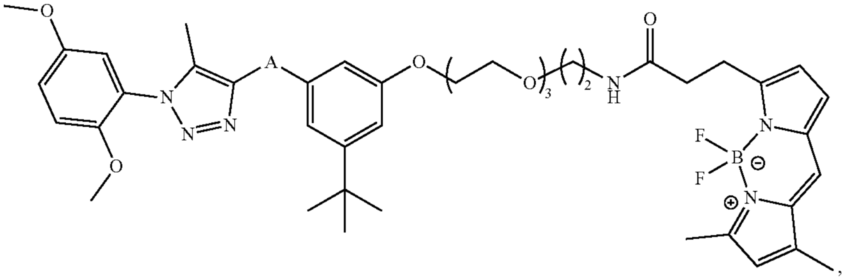

, or

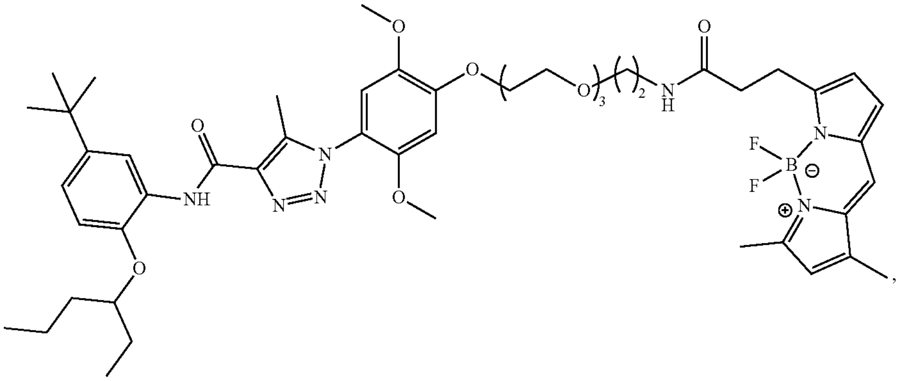

, or a pharmaceutically acceptable salt thereof.

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-III, as described and exemplified below. The following examples are provided so that the invention might be more fully understood, are illustrative only, and should not be construed as limiting.

1. ROUTE I

In one aspect, the compounds disclosed herein can be prepared as shown below.

SCHEME 1A

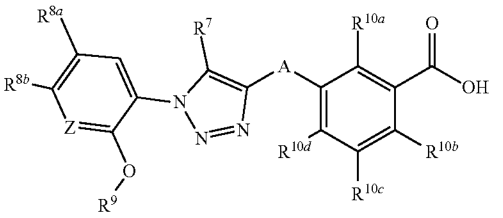

1.1

+

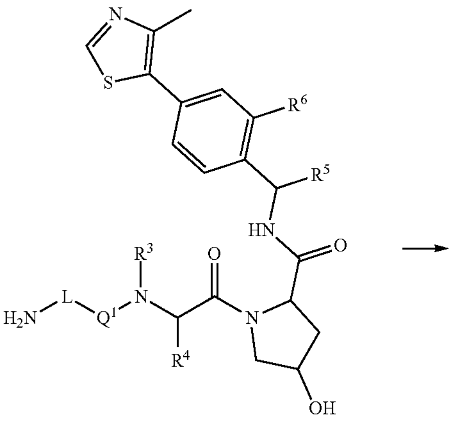

1.2

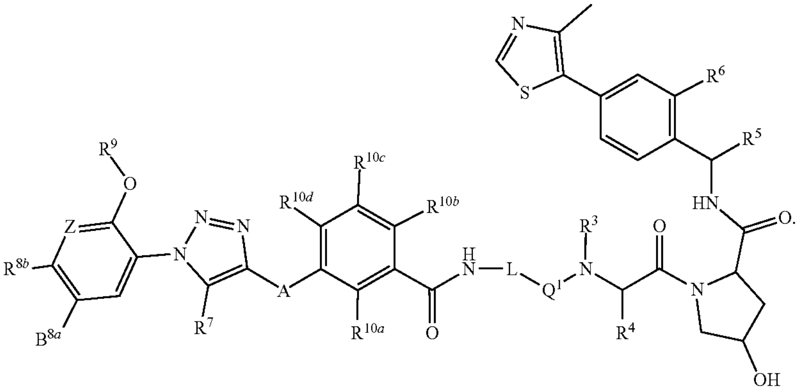

1.3

Compounds are represented in generic form, with substituents as noted in compound descriptions elsewhere herein. A more specific example is set forth below.

SCHEME 1B

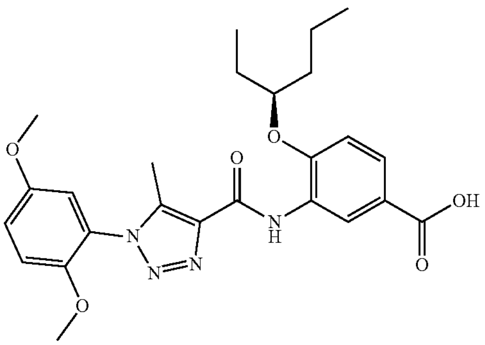

1.4

+

-continued

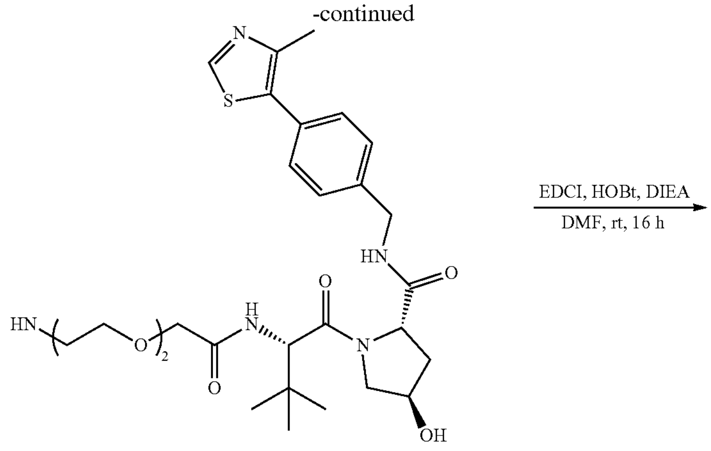

1.5

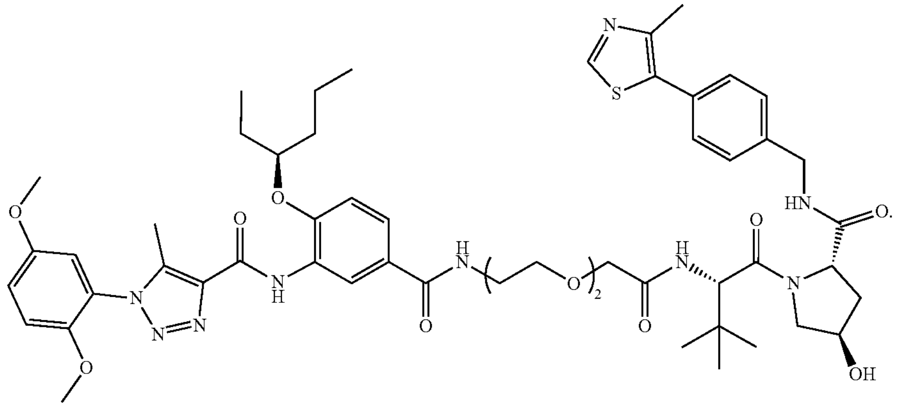

1.6

In one aspect, compounds of type 1.6, and similar compounds, can be prepared according to reaction Scheme 1B above. Thus, compounds of type 1.6 can be prepared by a coupling reaction between a carboxylic acid, e.g., 1.4 as shown above, and an appropriate amine, e.g., 1.5 as shown above. Appropriate carboxylic acids and appropriate amines are commercially available or prepared by methods known to one skilled in the art. The coupling reaction is carried out in the presence of an appropriate coupling agent, e.g., hydroxybenzotriazole (HOBt), an appropriate activating agent, e.g., 1-ethyl-3-(3-dimethylaminopropyl)carbodiimide (EDCI), and an appropriate base, e.g., diisopropylethylamine (DIPEA), at an appropriate temperature, e.g., room temperature, for an appropriate amount of time, e.g., 16 h. As can be appreciated by one skilled in the art, the above reactions provide an example of a generalized approach wherein compounds similar in structure to the specific reactants above (compounds similar to compounds of type 1.1 and 1.2), can be substituted in the reaction to provide compounds similar to Formula 1.3.

2. ROUTE 2

In one aspect, the compounds disclosed herein can be prepared as shown below.

SCHEME 2A

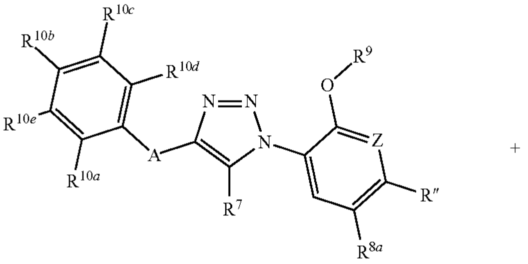

2.1

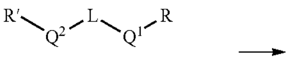

2.2

-continued

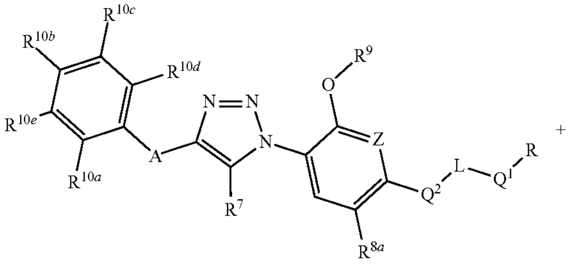

2.3

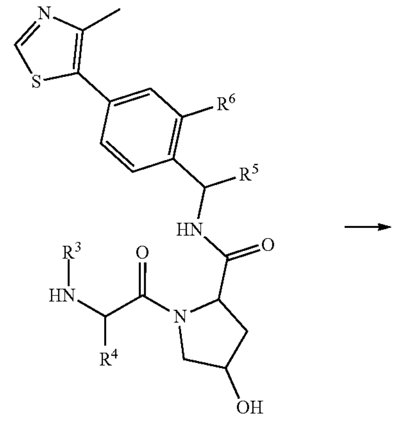

2.4

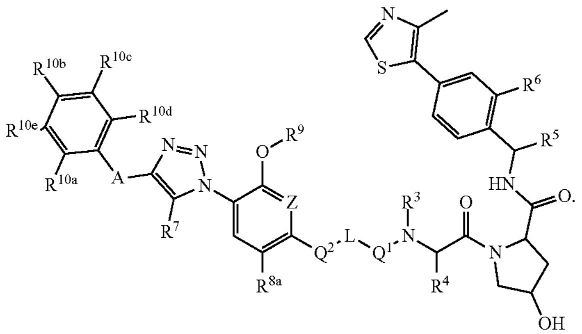

2.5

Compounds are represented in generic form, where R' and R" are independently groups capable of coupling with one another such as, for example, carboxylic acids, amines, alcohols and halides, and with other substituents as noted in compound descriptions elsewhere herein. A more specific example is set forth below.

SCHEME 2B

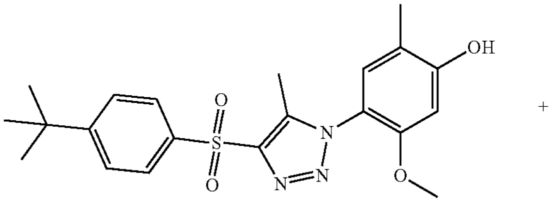

2.6

-continued

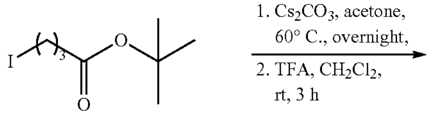

2.7

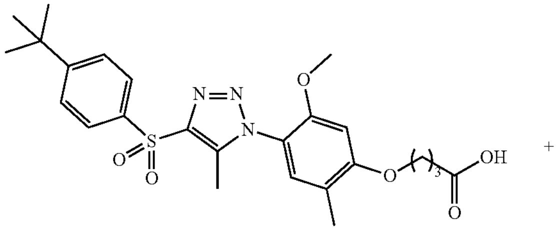

2.8

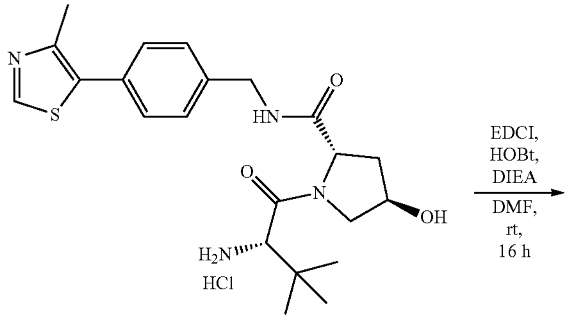

2.9

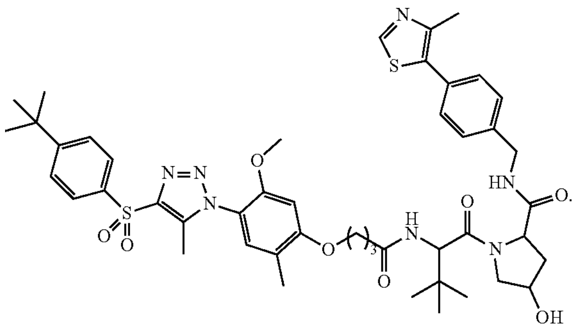

2.10

In one aspect, compounds of type 2.10, and similar compounds, can be prepared according to reaction Scheme 2B above. Thus, compounds of type 2.8 can be prepared by alkylating an appropriate alcohol, e.g., 2.6 as shown above, with an appropriate alkyl halide, e.g., 2.7 as shown above. Appropriate alcohols and appropriate alkyl halides are commercially available or prepared by methods known to one skilled in the art. The alkylation reaction is carried out in the presence of an appropriate base, e.g., cesium carbonate, in an appropriate solvent, e.g., acetone, at an appropriate temperature, e.g., 60° C., for an appropriate period of time, e.g., 18 hours, followed by deprotection with appropriate cleavage agent, e.g., trifluoroacetic acid, in an appropriate solvent, e.g., dichloromethane, at an appropriate temperature, e.g., room temperature, for an appropriate period of time, e.g., 3 hours. Compounds of type 2.10 can be prepared by a coupling reaction between a carboxylic acid, e.g., 2.8 as shown above, and an appropriate amine, e.g., 2.9 as shown above. Appropriate amines are commercially available or prepared by methods known to one skilled in the art. The coupling reaction is carried out in the presence of an appropriate coupling agent, e.g., hydroxybenzotriazole (HOBt), an appropriate activating agent, e.g., 1-ethyl-3-(3-dimethylaminopropyl)carbodiimide (EDCI), and an appropriate base, e.g., diisopropylethylamine (DIPEA), at an appropriate temperature, e.g., room temperature, for an appropriate amount of time, e.g., 16h. As can be appreciated by one skilled in the art, the above reactions provide an example of a generalized approach wherein compounds similar in structure to the specific reactants above (compounds similar to compounds of type 2.1, 2.2, 2.3, and 2.2), can be substituted in the reaction to provide compounds similar to Formula 2.5.

3. ROUTE III

In one aspect, the compounds disclosed herein can be prepared as shown below.

Scheme 3A

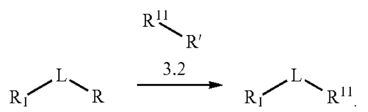

3.2

3.1

3.3

Compounds are represented in generic form, where R and R' are independently groups capable of coupling with one another such as, for example, carboxylic acids and amines, and with other substituents as noted in compound descriptions elsewhere herein. A more specific example is set forth below.

SCHEME 3B

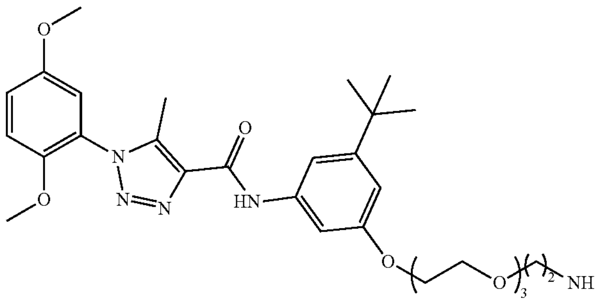

+

3.4

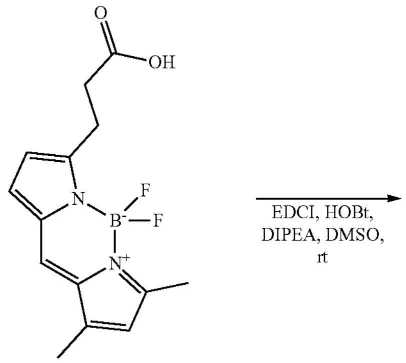

3.5

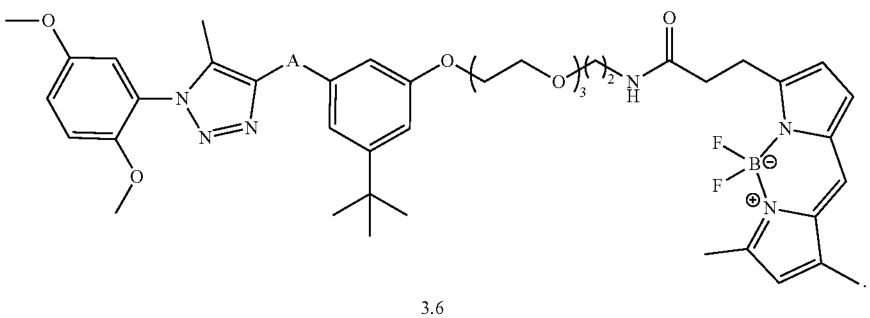

3.6

In one aspect, compounds of type 3.6, and similar compounds, can be prepared according to reaction Scheme 3B above. Thus, compounds of type 3.6 can be prepared by a coupling reaction between an appropriate alcohol or amine analog, e.g., 3.4 as shown above, and an appropriate carboxylic acid, e.g., 3.5 as shown above. Appropriate carboxylic acids are commercially available or prepared by methods known to one skilled in the art. The coupling reaction is carried out in the presence of an appropriate coupling agent, e.g., hydroxybenzotriazole (HOBt), an appropriate activating agent, e.g., 1-ethyl-3-(3-dimethylaminopropyl)carbodiimide (EDCI), and an appropriate base, e.g., diisopropylethylamine (DIPEA), in an appropriate solvent, e.g., dimethylsulfoxide, at an appropriate temperature, e.g., room temperature. As can be appreciated by one skilled in the art, the above reaction provides an example of a generalized approach wherein compounds similar in structure to the specific reactants above (compounds similar to compounds of type 3.1 and 3.2), can be substituted in the reaction to provide compounds similar to Formula 3.6.

D. PHARMACEUTICAL COMPOSITIONS

In one aspect, disclosed are pharmaceutical compositions comprising an effective amount of a disclosed compound, or a pharmaceutically acceptable salt thereof, and a pharmaceutically acceptable carrier.

Thus, in one aspect, disclosed are pharmaceutical compositions comprising an effective amount of a compound having a structure represented by a formula:

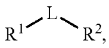, wherein L is a linker; wherein $R^1$ is a residue of a pregnane X receptor (PXR) ligand; and wherein $R^2$ is a residue of a Cereblon (CRBN) ligand or a residue of a von Hippel-Lindau protein (pVHL) ligand, or a pharmaceutically acceptable salt thereof and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used for inducing the degradation of proteins (e.g., PXR) that are relevant to conditions that results from activation of the target protein. The disclosed compounds and compositions can be useful in the treatment of a variety of different conditions due to a PXR-mediated metabolism event (e.g., drug-drug interaction, a drug-related toxicity, or drug resistance).

It is understood that the disclosed compositions can be prepared from the disclosed compounds. It is also understood that the disclosed compositions can be employed in the disclosed methods of using.

E. METHODS OF DEGRADING A TARGET PROTEIN IN A CELL

In one aspect, disclosed are methods of degrading a target protein (e.g., PXR) in a cell, the method comprising contacting the cell with an effective amount of a disclosed compound or a pharmaceutically acceptable salt thereof. Thus, in one aspect, disclosed are methods of degrading a target protein in a cell, the method comprising contacting the cell with an effective amount of a compound having a structure represented by a formula:

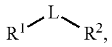

wherein L is a linker; wherein $R^1$ is a residue of a pregnane X receptor (PXR) ligand; and wherein $R^2$ is a residue of a Cereblon (CRBN) ligand or a residue of a von Hippel-Lindau protein (pVHL) ligand, or a pharmaceutically acceptable salt thereof and a pharmaceutically acceptable carrier.

In various aspects, the target protein is PXR.

In various aspects, the cell is mammalian. In a further aspect, the cell is human.

In various aspects, the cell has been isolated from a mammal prior to the contacting step.

In various aspects, the contacting is ex vivo.

In various aspects, the contacting is in vitro.

In various aspects, contacting is via administration to a mammal. In a further aspect, the mammal has been diagnosed with a need for degrading the target protein prior to the administering step.

F. METHODS OF DEGRADING A TARGET PROTEIN IN A SUBJECT

In one aspect, disclosed are methods of degrading a target protein (e.g., PXR) in a subject, the method comprising administering to the subject an effective amount of a disclosed compound or a pharmaceutically acceptable salt thereof. Thus, in one aspect, disclosed are methods of degrading a target protein in a subject in need thereof, the method comprising administering to the subject an effective amount of a compound having a structure represented by a formula:

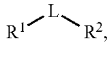

wherein L is a linker; wherein $R^1$ is a residue of a pregnane X receptor (PXR) ligand; and wherein $R^2$ is a residue of a Cereblon (CRBN) ligand or a residue of a von Hippel-Lindau protein (pVHL) ligand, or a pharmaceutically acceptable salt thereof and a pharmaceutically acceptable carrier.

In various aspects, the subject is a mammal. In a further aspect, the subject is a human.

In various aspects, the subject has been diagnosed with a need for degrading the target protein prior to the administering step.

In various aspects, the method further comprising identifying a subject in need of degradation of the target protein.

In various aspects, the subject has been diagnosed as having a condition that results from activation of the target protein. In a further aspect, the condition is due to a PXR-mediated metabolism event. In a still further aspect, the PXR-mediated metabolism event is due to a drug-drug interaction, a drug-related toxicity, or drug resistance.

G. METHODS OF TREATING A DISEASE OR DISORDER IN A SUBJECT

In one aspect, disclosed are methods of treating a disease in a subject, the method comprising administering to the subject an effective amount of a disclosed compound or a pharmaceutically acceptable salt thereof. Thus, in one aspect, disclosed are methods of treating a cancer in a subject, the method comprising administering to the subject an effective amount of a compound having a structure represented by a formula:

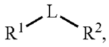, wherein L is a linker; wherein $R^1$ is a residue of a pregnane X receptor (PXR) ligand; and wherein $R^2$ is a residue of a Cereblon (CRBN) ligand or a residue of a von Hippel-Lindau protein (pVHL) ligand, or a pharmaceutically acceptable salt thereof and a pharmaceutically acceptable carrier.

In various aspects, treatment of the disease or disorder is associated with PXR activation. In a further aspect, treatment of the disease or disorder is associated with a PXR-mediated metabolism event.

In various aspects, the subject is a mammal. In a further aspect, the subject is a human.

In various aspects, the subject has been diagnosed with a need for treatment of the cancer prior to the administering step.

In various aspects, the subject has been diagnosed with a need for prevention of a PXR-mediated metabolism event prior to the administering step.

In various aspects, the method further comprising the step of identifying a subject in need of treatment of the disease or disorder.

In a further aspect, the effective amount is a therapeutically effective amount.

In a further aspect, the effective amount is a prophylactically effective amount.

In a further aspect, the disease or disorder is cancer.

In a further aspect, the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma).

H. METHODS OF MODULATING PXR PROTEIN IN A SAMPLE

In one aspect, disclosed are methods of modulating PXR protein in a sample, the method comprising contacting the sample with an effective amount of a disclosed compound, thereby modulating PXR protein in the sample. Thus, in one aspect, disclosed are methods of modulating PXR protein in a sample, the method comprising administering to the subject an effective amount of a compound having a structure represented by a formula:

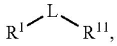, wherein L is a linker; wherein $R^1$ is a residue of a pregnane X receptor (PXR) ligand; and wherein $R^{11}$ is a residue of a fluorophore, a residue of biotin, or a residue of a biotin derivative, or a pharmaceutically acceptable salt thereof, thereby modulating PXR protein in the sample.

In various aspects, modulating is decreasing.

In various aspects, modulating is inhibiting.

In various aspects, contacting is in the presence of a PXR ligand.

In various aspects, contacting is in the presence of a non-PXR ligand.

In various aspects, the sample is a buffer.

In various aspects, the sample is a cell.

In various aspects, the cell is mammalian.

I. METHODS OF IDENTIFYING A PXR LIGAND IN A LIBRARY

In one aspect, disclosed are methods of identifying a PXR ligand in a library, the method comprising: (a) providing a library that contains a plurality of ligands; (b) combining a disclosed compound and a sample having PXR protein, thereby forming a mixture; (c) exposing each ligand to the mixture; and (d) detecting a fluorescence emission of the mixture after exposure to each ligand, wherein a decrease in fluorescence emission indicates that the ligand is a PXR ligand, and wherein a lack of decrease in fluorescence emission indicates that the ligand is a non-PXR ligand. Examples of fluorescence-based assays included, but are limited to, time-resolved fluorescence energy transfer (TR-FRET) assay, a fluorescence polarization (FP) assay, an enzyme-linked immunosorbent assay (ELISA), western blot analysis, an immunohistochemistry (IHC) assay, an immunoprecipitation (IP) assay, or a fluorescence-activated cell sorting (FACS) assay.

Thus, in one aspect, disclosed are methods of identifying a PXR ligand in a library, the method comprising: (a) providing a library that contains a plurality of ligands; (b) combining a compound having a structure represented by a formula:

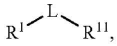, wherein L is a linker; wherein $R^1$ is a residue of a pregnane X receptor (PXR) ligand; and wherein $R^{11}$ is a residue of a fluorophore, a residue of biotin, or a residue of a biotin derivative, or a pharmaceutically acceptable salt thereof, and a sample having PXR protein, thereby forming a mixture; (c) exposing each ligand to the mixture; and (d) detecting a fluorescence emission of the mixture after exposure to each ligand, wherein a decrease in fluorescence emission indicates that the ligand is a PXR ligand, and wherein a lack of decrease in fluorescence emission indicates that the ligand is a non-PXR ligand.

In a further aspect, the fluorescence-based assay is a time-resolved fluorescence energy transfer (TR-FRET) assay, a fluorescence polarization (FP) assay, an enzyme-linked immunosorbent assay (ELISA), western blot analysis, an immunohistochemistry (IHC) assay, an immunoprecipitation (IP) assay, or a fluorescence-activated cell sorting (FACS) assay

J. ADDITIONAL METHODS OF USING THE COMPOUNDS

The compounds and pharmaceutical compositions of the invention are useful in inducing the degradation of proteins (e.g., PXR) relevant to a PXR-mediated metabolism event (e.g., a drug-drug interaction, a drug-related toxicity, or drug resistance).

To treat or control the condition, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a PXR-mediated metabolism event (e.g., a drug-drug interaction, a drug-related toxicity, or drug resistance).

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of cancer.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. MANUFACTURE OF A MEDICAMENT

In one aspect, the invention relates to a method for the manufacture of a medicament for inducing the degradation of proteins (e.g., PXR) relevant to a PXR-mediated metabolism event (e.g., a drug-drug interaction, a drug-related toxicity, or drug resistance) in a subject in need thereof, the method comprising combining a therapeutically effective amount of a disclosed compound or product of a disclosed method with a pharmaceutically acceptable carrier or diluent.

Also disclosed herein is the use of the disclosed compounds or a pharmaceutically acceptable salt thereof, together with a compound or agent known for inducing the degradation of proteins (e.g., PXR) relevant to a PXR-mediated metabolism event (e.g., a drug-drug interaction, a drug-related toxicity, or drug resistance), in the manufacture of a medicament. In one aspect, for example, when the subject has a cancer, disclosed is the use of the disclosed compounds or a pharmaceutically acceptable salt thereof along with a compound known for treating cancer.

In one aspect, the manufacture of the medicament can comprise co-formulating or co-packaging the disclosed compounds, or a pharmaceutically acceptable salt thereof, together with a chemotherapeutic agent. Non-limiting of chemotherapeutic agents include, but are not limited to, alkylating agents, antimetabolite agents, antineoplastic antibiotic agents, mitotic inhibitor agents, and mTor inhibitor agents.

In various aspects, the method for the manufacture of a medicament comprises combining a therapeutically effective amount of the disclosed compounds, or a pharmaceutically acceptable salt thereof, with a pharmaceutically acceptable carrier or diluent and/or with a compound known for treating cancer. In a further aspect, disclosed is a method for the manufacture of a medicament for treating cancer, the method comprising combining a therapeutically effective amount of a disclosed compounds or a pharmaceutically acceptable salt thereof with a therapeutically effective amount of a compound known for treating cancer, together with a pharmaceutically acceptable carrier or diluent.

2. USE OF COMPOUNDS AND COMPOSITIONS

In one aspect, the invention relates to the use of a disclosed compound, a disclosed composition, or a product of a disclosed method. In a further aspect, a use relates to the manufacture of a medicament for inducing the degradation of proteins (e.g., PXR) relevant to a PXR-mediated metabolism event (e.g., a drug-drug interaction, a drug-related toxicity, or drug resistance).

The compounds and pharmaceutical compositions of the invention are useful in treating or controlling disorders associated with overexpression of PXR.

Also provided are the uses of the disclosed compounds and products. In one aspect, the invention relates to use of at least one disclosed compound, or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a disorder associated with overexpression of PXR.

3. KITS

In one aspect, disclosed are kits comprising a disclosed compound or a pharmaceutically acceptable salt thereof, and one or more of: (a) an agent known to cause a PXR-mediated metabolism event; (b) an agent known to treat a cancer; (c) instructions for administering the compound in connection with preventing a PXR-mediated metabolism event; (d) instructions for preventing a PXR-mediated metabolism event; (e)instructions for administering the compound in connection with treating a cancer; and (f) instructions for treating a cancer.

Thus, in one aspect, also disclosed are kits comprising a compound having a structure represented by a formula:

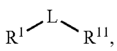, wherein L is a linker; wherein $R^1$ is a residue of a pregnane X receptor (PXR) ligand; and wherein $R^{11}$ is a residue of a fluorophore, a residue of biotin, or a residue of a biotin derivative, or a pharmaceutically acceptable salt thereof, and one or more of: (a) a sample that contains PXR protein; (b) a library that contains a plurality of ligands; (c) instructions for modulating PXR; (d) instructions for identifying a PXR ligand and/or a non-PXR ligand; and (e) instructions for performing a fluorescence-based assay.

In various aspects, the agent known to cause a PXR-mediated metabolism event is rifampicin, a corticosteroids (e.g., dexamethasone), mifepristone, or an estrogen-related contraceptive.

In various aspects, the compound and the agent known to cause a PXR-mediated metabolism event are co-packaged.

In various aspects, the compound and the agent known to cause a PXR-mediated metabolism event are co-formulated.

In various aspects, the agent is a chemotherapeutic agent.

In various aspects, the compound and the agent known to treat cancer are co-packaged.

In various aspects, the compound and the agent known to treat cancer are co-formulated.

In various further aspects, a disclosed compound or a pharmaceutically-acceptable salt thereof, the instructions for the use thereof (when present) and/or a combination therapy including a compound known for treating the target condition can be co-packaged and/or co-formulated. In a still further aspect, the compound or pharmaceutically-acceptable salt thereof, the instructions (when present), and/or the compound known for treating the target condition are not co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds and pharmaceutical formulations. It is also understood that the disclosed kits can be employed in connection with the disclosed methods of using the compounds and pharmaceutical formulations.

In a further aspect, the kit further comprises a plurality of dosage forms, the plurality comprising one or more doses; wherein each dose comprises an effective amount of the compound and the agent. In an even further aspect, each dose of the compound and the agent are co-packaged. In a still further aspect, each dose of the compound and the agent are co-formulated.

In one aspect, disclosed are kits comprising a disclosed compound or a pharmaceutically acceptable salt thereof, and one or more of: (a) a sample that contains PXR protein; (b) a library that contains a plurality of ligands; (c) instructions for modulating PXR; (d) instructions for identifying a PXR ligand and/or a non-PXR ligand; and (e) instructions for performing a fluorescence-based assay.

Thus in one aspect, disclosed are kits comprising a compound having a structure represented by a formula:

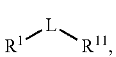, wherein L is a linker; wherein $R^1$ is a residue of a pregnane X receptor (PXR) ligand; and wherein $R^{11}$ is a residue of a fluorophore, a residue of biotin, or a residue of a biotin derivative, or a pharmaceutically acceptable salt thereof, and one or more of: (a) a sample that contains PXR protein; (b) a library that contains a plurality of ligands; (c) instructions for modulating PXR; (d) instructions for identifying a PXR ligand and/or a non-PXR ligand; and (e) instructions for performing a fluorescence-based assay.

In various aspects, the fluorescence-based assay is a time-resolved fluorescence energy transfer (TR-FRET) assay, a fluorescence polarization (FP) assay, an enzyme-linked immunosorbent assay (ELISA), western blot analysis, an immunohistochemistry (IHC) assay, an immunoprecipitation (IP) assay, or a fluorescence-activated cell sorting (FACS) assay.

4. SUBJECTS

In various aspects, the subject of the herein disclosed methods is a vertebrate, e.g., a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder of uncontrolled cellular proliferation prior to the administering step. In some aspects of the disclosed methods, the subject has been identified with a need for treatment prior to the administering step. In one aspect, a subject can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18th Ed., Gennaro, ed., Mack Publishing Co., Easton, PA). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, NY).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

In various aspects, the modes of administration described above may be combined in any order.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

K. EXAMPLES

The following examples are put forth so as to provide those of ordinary skill in the art with a complete disclosure and description of how the methods and products claimed herein are made and evaluated, and are intended to be purely exemplary and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way.

1. CHEMISTRY METHODS a. General Methods

All chemicals and anhydrous solvents were obtained directly from commercial sources. All NMR spectra were recorded on a Bruker 400 MHz or 500 MHz spectrometer, and spectra were processed using MestReNova (14.1.1). Chemical shifts are given in ppm (δ), calibrated to the residual solvent signal peaks of $CDCl_3$ (7.26 ppm), $CD_3OD$ (3.31 ppm), or DMSO-$d_6$ (2.50 ppm) for $^1H$ NMR and $^{13}C$ NMR with coupling constant (J) values reported in Hz. Flash column chromatography was performed using Biotage Isolera Flash Systems with Biotage Sfär Silica or Biotage Sfär C18 columns. All compounds used for biological assays have >95% purity as determined by using a Waters Acquity UPLC-MS system with a C18 column in a 2 min gradient ($H_2O$+0.1% formic acid (FA)→acetonitrile (ACN)+0.1% formic acid) and detectors of PDA (215-400 nm), ELSD, and Acquity SQD ESI-positive mass spectrometer (Waters Corporation, Milford, MA). High-resolution mass spectra were determined by using a Waters Acquity UPLC system with a C18 column ($H_2O$+0.1% FA→ACN+0.1% FA gradient over 2.5 min) and a Xevo G2Q-TOF ESI-positive mass spectrometer in resolution mode. Compounds were internally normalized to leucine-enkephalin lock solution, with a calculated error of <3 ppm.

b. Preparation of Compound 13

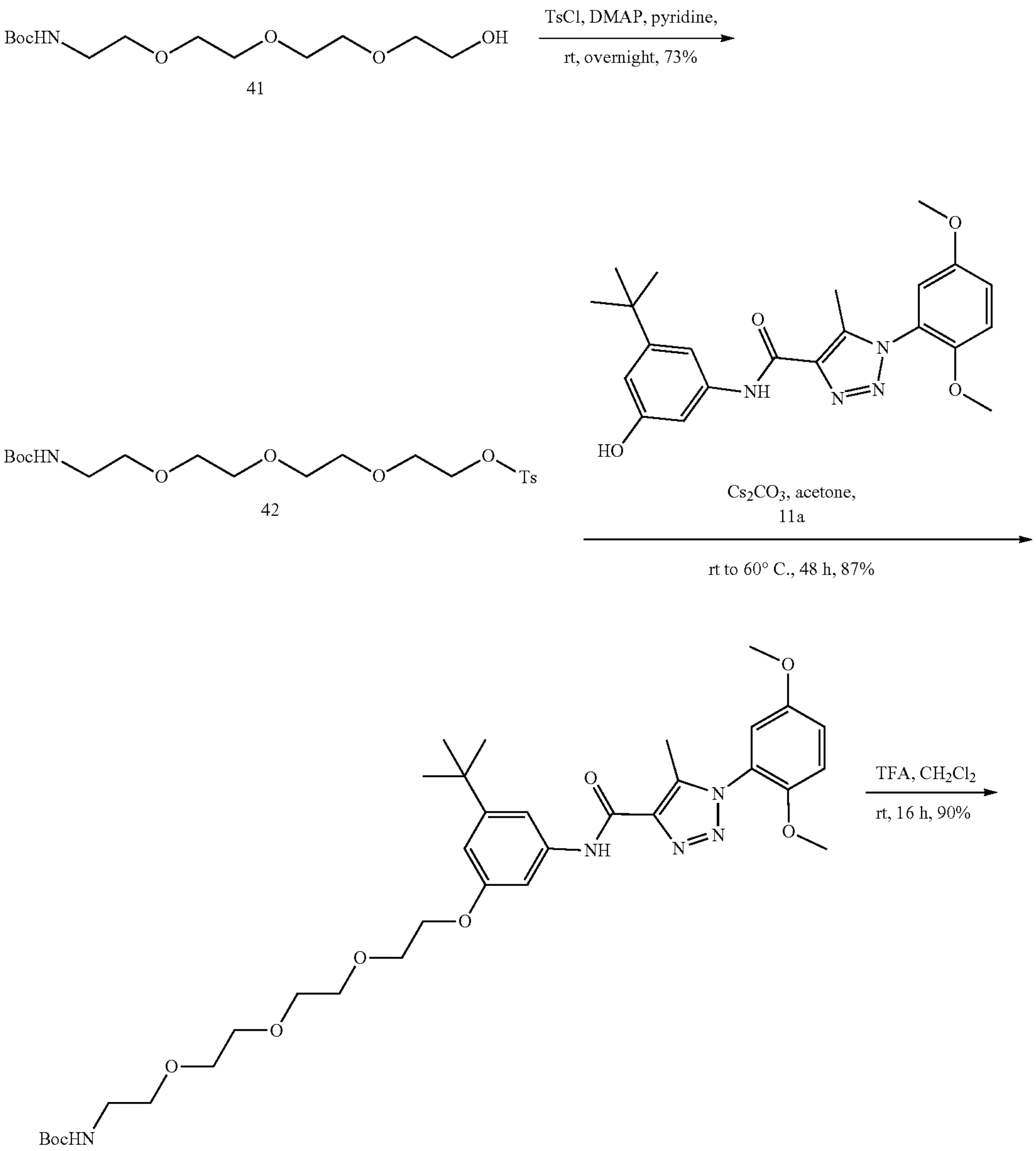

41

42

43

-continued
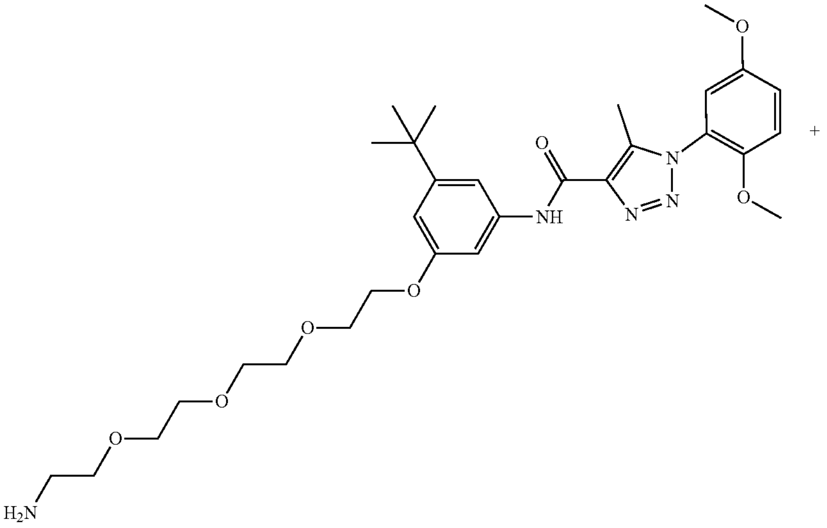
44
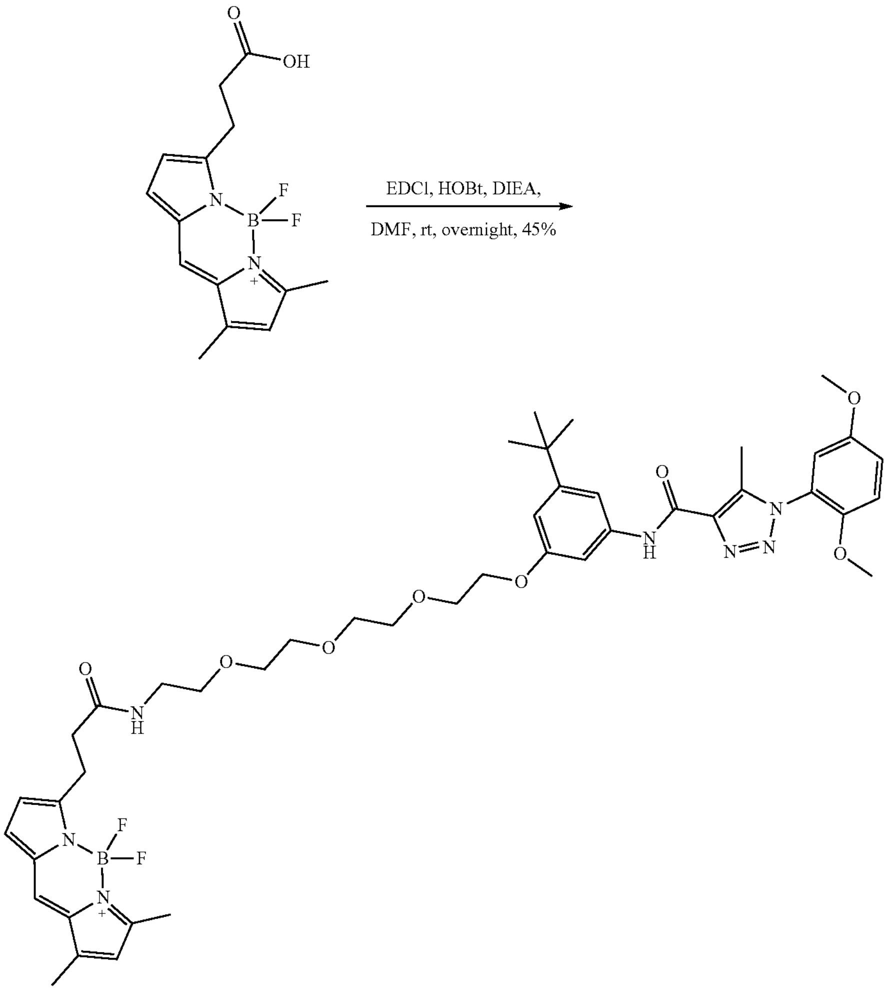
13 i. 2,2-DIMETHYL-4-oxo-3,8,11,14-TETRAOXA-5-AZAHEXADECAN-16-YL 4-METHYLBENZENESULFONATE (42)

To a solution of tert-butyl (2-(2-(2-(2-hydroxyethoxy)ethoxy)ethoxy)ethyl)carbamate (41, 0.7 g, 2.386 mmol) in pyridine (3 mL) at room temperature was added 4-methylbenzenesulfonyl chloride (0.500 g, 2.62 mmol) and N,N-dimethylpyridin-4-amine (0.292 g, 2.386 mmol). The suspension was stirred overnight. The reaction mixture was poured into water (50 mL) and extracted with EtOAc (50 mL×2). The EtOAc layer was washed with water, dried with anhydrous $Na_2SO_4$, and concentrated with a Rotavapor. The residue was purified by silica gel chromatography (0%-100% EtOAc in hexane) to give product as a colorless solid (782.3 mg, 73% yield, 97% purity). $^1$H NMR (400 MHz, $CDCl_3$) δ 7.78 (dq, J=8.5, 2.1 Hz, 2H), 7.34-7.30 (m, 2H), 4.19-4.11 (m, 2H), 3.70-3.66 (m, 2H), 3.60-3.55 (m, 8H), 3.51 (dd, J=5.6, 4.9 Hz, 2H), 3.28 (q, J=5.2 Hz, 2H), 2.43 (s, 3H), 1.43 (s, 9H). $^{13}$C NMR (101 MHz, $CDCl_3$) δ 155.93, 144.67, 133.35, 129.75, 127.91, 79.12, 70.78, 70.57, 70.52, 70.26, 70.19, 69.14, 68.72, 40.52, 28.39, 21.50.

ii. TERT-BUTYL (2-(2-(2-(2-(3-(TERT-BUTYL)-5-(1-(2,5-DIMETHOXYPHENYL)-5-METHYL-1H-1,2,3-TRIAZOLE-4-CARBOXAMIDO)PHENOXY)ETHOXY)ETHOXY)ETHOXY)ETHYL) CARBA MATE (43)

A mixture of compound 11a (1.5 g, 3.65 mmol, synthesized according to literature procedures reported)(Huber, A. D.; et al., (2022) *ACS Med Chem Lett* 13 (8), 1311-1320), $Cs_2CO_3$ (1.191 g, 3.65 mmol), and 2,2-dimethyl-4-oxo-3,8,11,14-tetraoxa-5-azahexadecan-16-yl 4-methylbenzenesulfonate (1.635 g, 3.65 mmol) was stirred in acetone (30 mL) at room temperature overnight. The mixture was then stirred at 60° C. overnight. The mixture was filtered, concentrated, and purified by silica gel chromatography (0%-100% EtOAc in hexane) to give compound 43 as a colorless oil (2.19 g, 87% yield, 100% purity). $^1$H NMR (400 MHz, DMSO-$d_6$) δ 10.20 (s, 1H), 7.51 (t, J=1.7 Hz, 1H), 7.44 (t, J=2.1 Hz, 1H), 7.28 (d, J=9.2 Hz, 1H), 7.22 (dd, J=9.1, 3.0 Hz, 1H), 7.12 (d, J=3.0 Hz, 1H), 6.68 (dd, J=2.3, 1.7 Hz, 1H), 6.59 (s, 1H), 4.11-4.07 (m, 2H), 3.79 (s, 3H), 3.78-3.76 (m, 2H), 3.76 (s, 3H), 3.62 (ddd, J=5.9, 3.8, 1.1 Hz, 2H), 3.58-3.48 (m, 6H), 3.39 (t, J=6.1 Hz, 2H), 2.39 (s, 3H), 1.37 (s, 9H), 1.29 (s, 9H). $^{13}$C NMR (101 MHz, DMSO-$d_6$) δ 159.38, 158.37, 155.49, 153.15, 152.37, 147.76, 139.26, 138.85, 137.58, 123.85, 117.42, 114.01, 110.04, 107.52, 103.60, 77.51, 69.93, 69.80, 69.74, 69.49, 69.17, 68.98, 67.07, 56.38, 55.89, 34.54, 31.01, 28.15, 13.99, 8.70. ESI-TOF HRMS: m/z 686.3766 ($C_{35}H_{51}N_5O_9$+$H^+$ requires 686.3760).

iii. N-(3-(2-(2-(2-(2-AMINOETHOXY)ETHOXY)ETHOXY)ETHOXY)-5-(TERT-BUTYL)PHENYL)-1-(2,5-DIMETHOXYPHENYL)-5-METHYL-1H-1,2,3-TRIAZOLE-4-CARBOXAMIDE (44)

A mixture of 43 (100 mg, 0.146 mmol) was stirred in DCM (15 mL) and $CF_3COOH$ (5 mL) at room temperature overnight. The reaction mixture was concentrated, added with $NaHCO_3$ saturated aq. solution (50 mL), and extracted with EtOAc (50 mL×2). The EtOAc layer was washed with water, dried with anhydrous $Na_2SO_4$, and concentrated with a Rotavapor. The residue was purified by silica gel chromatography (0%-100% acetonitrile in water) to give compound 44 as a white solid (76.5 mg, 90% yield, 97.08% purity). $^1$H NMR (400 MHz, $CDCl_3$) δ 9.04 (s, 1H), 7.39 (t, J=2.1 Hz, 1H), 7.16 (t, J=1.8 Hz, 1H), 7.08 (dd, J=9.1, 3.0 Hz, 1H), 7.02 (d, J=9.1 Hz, 1H), 6.94 (d, J=2.9 Hz, 1H), 6.77 (dd, J=2.4, 1.6 Hz, 1H), 4.17 (dd, J=5.8, 4.2 Hz, 2H), 3.86 (dd, J=5.5, 4.3 Hz, 2H), 3.81 (s, 3H), 3.75 (s, 3H), 3.74-3.71 (m, 2H), 3.70-3.62 (m, 8H), 3.55-3.51 (m, 2H), 3.36 (s, 3H), 2.51 (s, 3H), 1.32 (s, 9H). $^{13}$C NMR (101 MHz, $CDCl_3$) δ 159.32, 159.25, 153.86, 153.46, 148.15, 139.29, 138.56, 137.99, 124.60, 117.49, 113.98, 113.57, 109.60, 109.15, 102.88, 71.98, 70.84, 70.67, 70.64, 70.51, 69.81, 67.60, 58.89, 56.42, 56.00, 34.86, 31.23, 9.12. ESI-TOF HRMS: m/z 586.3245 ($C_{30}H_{44}N_5O_7$+$H^+$ requires 586.3235).

iv. N-(3-(TERT-BUTYL)-5-((15-(5,5-DIFLUORO-7,9-DIMETHYL-5H-5L$^4$,6L$^4$-DIPYRROLO[1,2-C:2',1'-F][1,3,2]DIAZABORININ-3-YL)-13-OXO-3,6,9-TRIOXA-12-AZAPENTADECYL)OXY)PHENYL)-1-(2,5-DIMETHOXYPHENYL)-5-METHYL-1H-1,2,3-TRIAZOLE-4-CARBOXAMIDE (13)

To a solution of N-(3-(2-(2-(2-(2-aminoethoxy)ethoxy)ethoxy)ethoxy)-5-(tert-butyl)phenyl)-1-(2,5-dimethoxyphenyl)-5-methyl-1H-1,2,3-triazole-4-carboxamide (100 mg, 0.171 mmol) in dimethyl formamide 5 mL was added 3-bodipy-propanoic Acid (BDP FL acid) (49.9 mg, 0.171 mmol), HOBt, 80% (34.6 mg, 0.205 mmol) and EDCI (49.1 mg, 0.256 mmol), followed by N-ethyl-N-isopropylpropan-2-amine (44.1 mg, 0.341 mmol). The suspension was stirred at room temperature overnight. The reaction mixture was then diluted with water (50 mL) and extracted with EtOAc (50 mL×2). The EtOAc layer was washed with water, dried with anhydrous $Na_2SO_4$, and concentrated with a Rotavapor. The residue was purified by silica gel chromatography (0%-100% acetonitrile in water) to give product as a brown solid (66.5 mg, 45% yield, 100% purity). $^1$H NMR (400 MHz, $CDCl_3$) δ 9.05 (s, 1H), 7.37 (s, 1H), 7.16 (s, 1H), 7.12-6.99 (m, 3H), 6.94 (s, 1H), 6.85 (s, 1H), 6.75 (s, 1H), 6.33-6.22 (m, 1H), 6.12 (m, 2H), 4.22-4.08 (m, 2H), 3.89-3.78 (m, 5H), 3.75 (s, 3H), 3.71 (s, 2H), 3.67-3.54 (m, 6H), 3.51 (d, J=5.2 Hz, 2H), 3.42 (t, J=5.3 Hz, 2H), 3.27 (t, J=7.6 Hz, 2H), 2.61 (t, J=7.6 Hz, 2H), 2.54 (s, 2H), 2.51 (s, 3H), 2.22 (s, 3H), 2.15 (s, 3H), 1.31 (s, 9H). $^{13}$C NMR (101 MHz, $CDCl_3$) δ 171.65, 159.95, 159.33, 159.20, 157.98, 153.86, 153.49, 148.15, 143.53, 139.31, 138.57, 137.98, 135.03, 133.46, 128.25, 124.58, 123.68, 120.22, 117.50, 117.45, 113.99, 113.56, 109.65, 109.10, 102.92, 70.84, 70.60, 70.54, 70.31, 69.80, 69.79, 67.58, 56.42, 56.01, 39.32, 35.81, 34.87, 31.23, 30.73, 24.79, 14.80, 11.14, 9.13. ESI-TOF HRMS: m/z 860.4332 ($C_{44}H_{57}BF_2N_7O_8$+$H^+$ requires 860.4324).

c. Compound 14
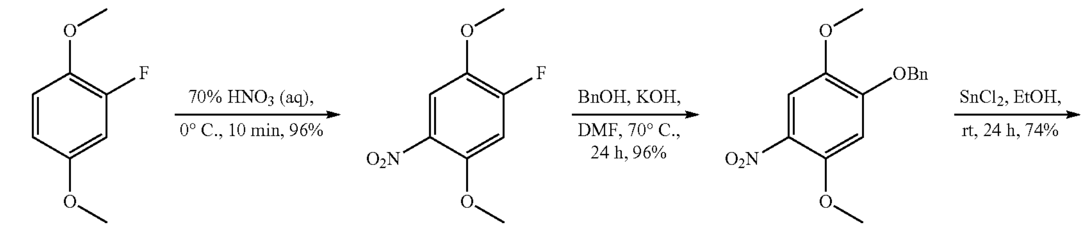
45 46 47
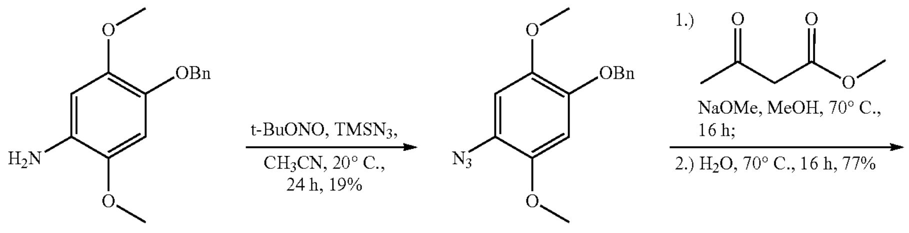
48 49
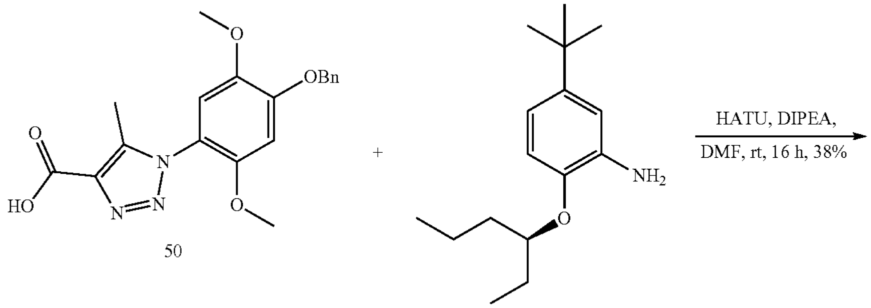
50
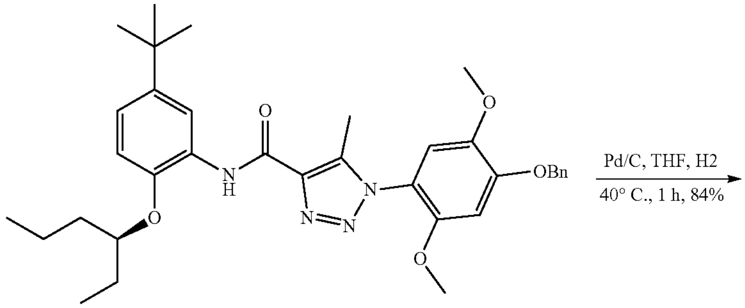
51
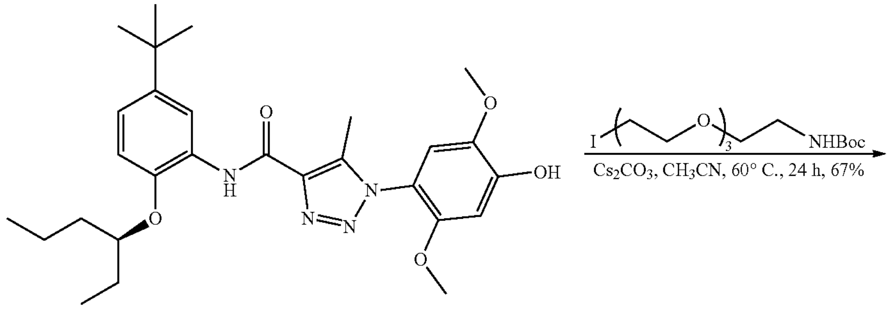
52

-continued
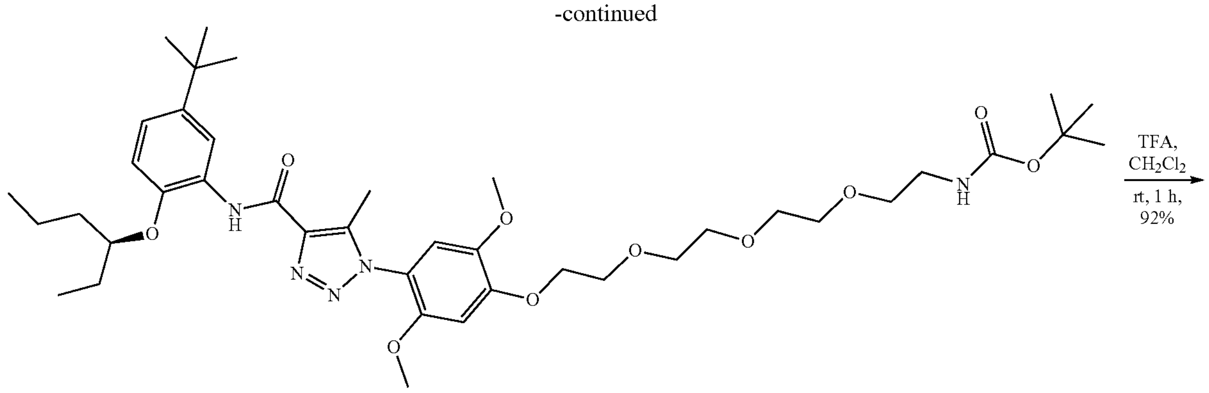
53
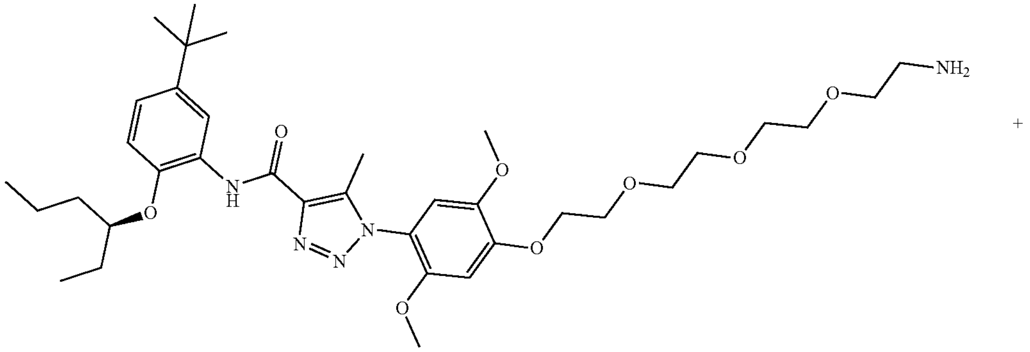
54
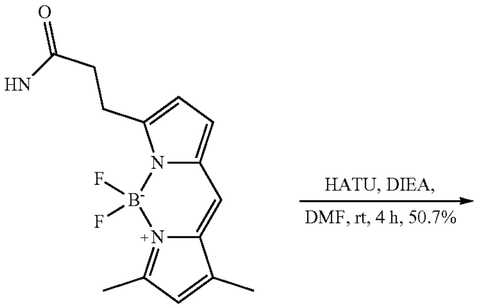
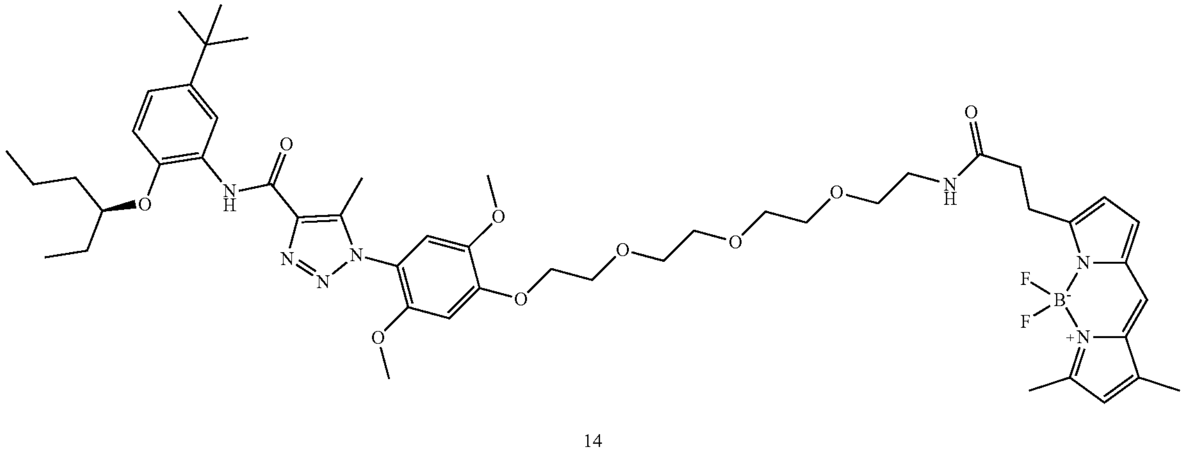
14 i. 1-FLUORO-2,5-DIMETHOXY-4-NITROBENZENE (46)

2-fluoro-1,4-dimethoxybenzene (45, 1 g, 6.40 mmol) was slowly added to a stirred solution of nitric acid (7 mL, 6.40 mmol) at 0° C. The solution was stirred for 10 min, poured onto ice water (50 mL), and stirred for 30 min. The precipitate was collected, washed with water, and dried to give compound 46 (1.24 g, 96% yield). $^1$H NMR (500 MHz, $CD_3OD$): δ 7.68 (d, J=8.80 Hz, 1H), 7.16 (d, J=12.5 Hz, 1H), 3.93 (s, 3H), 3.91 (s, 3H). $^{13}$C NMR ($CD_3OD$, 126 MHz) δ 156.86, 149.81, 142.2, 135.66, 112.18, 104.19, 57.87, 57.55. LCMS: m/z=202.38 $[M+H]^+$.

ii. 1-(BENZYLOXY)-2,5-DIMETHOXY-4-NITROBENZENE (47)

To a solution of 46 (1.092 g, 5.43 mmol) in DMF (10 mL) were added benzyl alcohol (1.124 ml, 10.86 mmol) and potassium hydroxide (0.914 g, 16.29 mmol). The mixture was stirred at 70° C. for 20 h under $N_2$ atmosphere. The mixture was poured into water (200 mL) under stirring, then the solid was collected by filtration. The crude product was triturated with MeOH (100 mL) at 25° C. and filtered, and the cake was collected to give the compound 47 (1.5 g, 96% yield). $^1$H NMR (500 MHz, $CDCl_3$): δ 7.59 (s, 1H), 7.44-7.34 (m, 5H), 6.57 (s, 1H), 5.25 (s, 2H), 3.90 (s, 3H), 3.84 (s, 3H). $^{13}$C NMR (126 MHz, $CDCl_3$) δ 153.88, 150.14, 143.01, 135.64, 131.27, 129.02, 128.67, 127.42 109.51, 99.99, 71.58, 57.20, 56.75. LCMS: m/z=290.47 $[M+H]^+$.

iii. 4-(BENZYLOXY)-2,5-DIMETHOXYANILINE (48)

To a solution of 47 (860 mg, 2.97 mmol) was added tin(II) chloride (5637 mg, 29.7 mmol) in EtOH (10 mL) at 0° C., and the mixture was stirred at room temperature for 20 h. LCMS showed the starting material was consumed completely and desired compound was formed. The solvent was evaporated under reduced pressure, and the residue was purified by reversed-phase flash chromatography (running a gradient of 3%-10% methanol in dichloromethane) to give compound 48 (574 mg, 74.4% yield). $^1$H NMR (500 MHz, DMSO-$d_6$): δ 7.43 (d, J=7.00 Hz, 2H), 7.38 (t, J=7.45 Hz, 2H), 7.32 (t, J=7.15 Hz, 1H), 6.91 (s, 1H), 6.81 (s, 1H), 5.10 (s, 2H), 3.80 (s, 3H), 3.69 (s, 3H). $^{13}$C NMR (126 MHz, DMSO-$d_6$) δ 145.98, 144.84, 143.24, 136.96, 128.49, 128.00, 127.80, 107.03, 101.39, 70.93, 56.68, 56.48. LCMS: m/z=260.19 $[M+H]^+$.

iv. 1-AZIDO-4-(BENZYLOXY)-2,5-DIMETHOXYBENZENE (49)

To a solution of 48 (2.32 g, 8.95 mmol) in acetonitrile (10 mL) was added tert-butyl nitrite (2.365 mL, 17.89 mmol) at 0° C. Then, azidotrimethylsilane (1.875 mL, 13.42 mmol) in acetonitrile (5 mL) was added dropwise at 0° C., and the mixture was stirred at 20° C. for 3 h. LCMS showed the starting material was consumed completely and desired compound was formed. The reaction mixture was poured into ice water (10 mL) and extracted with EtOAc (10 mL×3), and then the combined organic layer was dried ($Na_2SO_4$), filtered, and evaporated under reduced pressure. The residue was purified by reversed-phase flash chromatography (running a gradient of 0%-100% EtOAc in hexane over 16 min) to give compound 49 (500 mg, 19.6% yield). $^1$H NMR (500 MHz, $CDCl_3$) δ 7.43-7.41 (m, 2H), 7.38-7.36 (m, 2H), 7.33-7.29 (m, 1H), 6.56 (s, 1H), 6.53 (s, 1H), 5.12 (s, 2H), 3.83 (s, 3H), 3.74 (s, 3H). $^{13}$C NMR (126 MHz, $CDCl_3$) δ 146.10, 145.85, 144.74, 137.02, 128.75, 128.20, 127.62, 105.81, 102.93, 72.28, 57.11, 56.94.

v. 1-(4-(BENZYLOXY)-2,5-DIMETHOXYPHENYL)-5-METHYL-1H-1,2,3-TRIAZOLE-4-CARBOXYLIC ACID (50)

To a solution of 49 (50 mg, 0.175 mmol) and methyl 3-oxobutanoate (76 μL, 0.701 mmol) in MeOH (5 mL) was added $CH_3ONa$ (95 mg, 1.753 mmol) and the mixture was stirred at 70° C. for 16 h. Water (3 mL) was added, and the mixture was stirred at 70° C. for 3 h. LCMS showed the starting material was consumed completely and desired compound was formed. The reaction mixture was concentrated under reduced pressure. The residue was purified by reversed-phase flash chromatography (running a gradient of 0%-10% methanol in dichloromethane over 16 min) to give compound 50 (50 mg, 77% yield). $^1$H NMR (500 MHz, CD3OD) δ 7.49-7.48 (m, 2H), 7.40-7.37 (m, 2H), 7.34-7.32 (m, 1H), 7.05 (s, 1H), 6.93 (s, 1H), 5.22 (s, 2H), 3.80 (s, 3H), 3.73 (s, 3H), 2.37 (s, 3H). $^{13}$C NMR (126 MHz, CD3OD) δ 163.08, 151.20, 148.71, 143.76, 141.01, 136.68, 128.23, 127.54, 127.51, 112.38, 104.18, 99.92, 70.99, 56.07, 55.68, 8.16. LCMS: m/z=370.34 $[M+H]^+$.

vi. (S)-1-(4-(BENZYLOXY)-2,5-DIMETHOXYPHENYL)-N-(5-(TERT-BUTYL)-2-(HEXAN-3-YLOXY)PHENYL)-5-METHYL-1H-1,2,3-TRIAZOLE-4-CARBOXAMIDE (51)

To a solution of 50 (55 mg, 0.156 mmol) in DMF (5 mL) was added HATU (89 mg, 0.233 mmol), and the mixture was stirred at 25° C. for 30 min. (S)-(5-(tert-butyl)-2-(hexan-3-yloxy)phenyl)-12-azane (58.0 mg, 0.233 mmol) and DIPEA (40.7 μL, 0.233 mmol) were added to the reaction mixture and stirred at 25° C. for 4 h. LCMS showed the starting material was consumed completely and desired compound was formed. The reaction mixture was poured into brine (10 mL) and extracted with EtOAc (10 mL×3), and the combined organic layer was dried ($Na_2SO_4$), filtered, and evaporated under reduced pressure. The residue was purified by reversed-phase flash chromatography (running a gradient of 0%-100% EtOAc in hexane over 16 min) to give compound 51 (35 mg, 38.5% yield). $^1$H NMR (500 MHz, $CDCl_3$) δ 8.65 (d, J=2.35 Hz, 1H), 7.47 (d, J=6.70 Hz, 2H), 7.42 (t, J=7.85 Hz, 2H), 7.38-7.35 (m, 1H), 7.16 (s, 1H), 7.04 (dd, J=8.55, 2.45 Hz, 1H), 6.84 (d, J=8.55 Hz, 1H), 6.60 (s, 1H), 5.17 (s, 2H), 4.26 (p, J=5.8 Hz, 1H), 3.73 (s, 3H), 2.50 (s, 3H), 2.26 (s, 3H), 1.81-1.64 (m, 4H), 1.53-1.44 (m, 2H), 1.35 (s, 9H), 1.00 (t, J=7.40 Hz, 3H), 0.94 (t, J=7.35 Hz, 3H). $^{13}$C NMR (126 MHz, $CDCl_3$) δ 160.34, 159.23, 152.13, 145.17, 143.70, 139.17, 138.51, 136.64, 129.86, 128.86, 128.56, 128.31, 127.29, 120.09, 119.83, 117.13, 116.58, 112.17, 97.06, 80.41, 70.58, 56.13, 35.63, 34.57, 31.73, 26.69, 18.82, 15.55, 14.36, 9.70, 9.42. LCMS: m/z=601.71 $[M+H]^+$.

vii. (S)—N-(5-(TERT-BUTYL)-2-(HEXAN-3-YLOXY)PHENYL)-1-(4-HYDROXY-2,5-DIMETHOXYPHENYL)-5-METHYL-1H-1,2,3-TRIAZOLE-4-CARBOXAMIDE (52)

To a solution of 51 (7 mg, 0.012 mmol) in THF (5 mL) was added Pd/C (12.40 mg, 0.117 mmol). The suspension was degassed under vacuum and purged with $H_2$ three times. The mixture was stirred under $H_2$ at 40° C. for 1 h, filtrated from a pad of the celite, and the cake was washed with THF (50 mL). The filtrate was evaporated under reduced pressure, and the residue was purified by reversed-phase flash chromatography (running a gradient of 0%-5% methanol in dichloromethane) to give compound 52 (5 mg, 84% yield). $^1$H NMR (500 MHz, CD3OD) δ 8.53 (d, J=2.45 Hz, 1H), 7.11 (dd, J=8.65, 2.40 Hz, 1H), 7.02 (s, 1H), 6.98 (d, J=8.65 Hz, 1H), 6.76 (s, 1H), 4.37 (p, J=5.8 Hz, 1H), 3.85 (s, 3H), 3.76 (s, 3H), 2.47 (s, 3H), 1.81-1.66 (m, 4H), 1.56-1.45 (m, 2H), 1.35 (s, 9H), 1.02 (t, J=7.45 Hz, 3H), 0.96 (t, J=7.4 Hz, 3H). $^{13}$C NMR (126 MHz, $CD_3OD$) δ 160.95, 151.51, 150.53, 146.59, 144.86, 143.10, 140.89, 138.97, 129.02, 121.92, 118.20, 115.32, 113.91, 113.22, 101.73, 81.62, 57.33, 56.79, 36.79, 35.29, 31.98, 27.68, 19.66, 14.54, 9.80, 9.29; ESI-TOF HRMS: m/z 511.2906 ($C_{28}H_{39}N_4O_5$+$H^+$ requires 511.2920).

viii. TERT-BUTYL (S)-(2-(2-(2-(2-(4-(4-((5-(TERT-BUTYL)-2-(HEXAN-3-YLOXY)PHENYL)CARBAMOYL)-5-METHYL-1H-1,2,3-TRIAZOL-1-YL)-2,5-DIMETHOXYPHENOXY)ETHOXY)ETHOXY)ETHOXY)ETHYL)CARBAMAT E (53)

To a mixture of 52 (24 mg, 0.047 mmol) and cesium carbonate (18 mg, 0.056 mmol) in acetone (5 mL) was added tert-butyl (2-(2-(2-(2-iodoethoxy)ethoxy)ethoxy)-ethyl)carbamate (38 mg, 0.094 mmol) at room temperature under $N_2$ atmosphere. The reaction mixture was stirred at 60° C. overnight. The mixture was poured into water (10 mL) and extracted with EtOAc (10 mL×3), and the combined organic layer was dried ($Na_2SO_4$), filtered, and evaporated under reduced pressure. The residue was purified by reversed-phase flash chromatography (running a gradient of 0%-100% EtOAc in hexane over 16 min) to give compound 53 (25 mg, 67.7% yield). $^1$H NMR (500 MHz, $CDCl_3$): δ 8.64 (d, J=2.40 Hz, 1H), 7.03 (dd, J=8.55, 2.40 Hz, 1H), 6.91 (s, 1H), 6.82 (d, J=8.55 Hz, 1H), 6.75 (s, 1H), 4.29-4.24 (m, 2H), 3.92 (t, J=4.95 Hz, 2H), 3.82 (s, 3H), 3.76-3.73 (m, 4H), 3.69-3.67 (m, 2H), 3.65-3.59 (m, 4H), 3.52 (t, J=5.20 Hz, 2H), 3.31-3.28 (m, 2H), 2.50 (s, 3H), 1.80-1.72 (m, 3H), 1.69-1.62 (m, 1H), 1.50-1.44 (m, 2H), 1.42 (s, 9H), 1.34 (s, 9H), 1.25-1.22 (m, 2H), 0.99 (t, J=7.40 Hz, 3H), 0.93 (t, J=7.35 Hz, 3H). $^{13}$C NMR (126 MHz, $CDCl_3$) δ 159.44, 156.01, 150.90, 148.34, 145.00, 143.72, 143.59, 139.19, 138.47, 128.37, 120.02, 116.97, 116.31, 112.12, 112.04, 100.00, 80.24, 79.19, 70.90, 70.64, 70.57, 70.25, 70.24, 69.72, 69.23, 56.69, 56.49, 40.36, 35.50, 34.44, 31.59, 30.94, 29.71, 28.43, 26.56, 21.06, 18.68, 14.23, 14.21, 9.56, 9.31. LCMS: m/z=786.80 [M+H]$^+$.

ix. (S)-1-(4-(2-(2-(2-(2-AMINOETHOXY)ETHOXY)ETHOXY)ETHOXY)-2,5-DIMETHOXYPHENYL)-N-(5-(TERT-BUTYL)-2-(HEXAN-3-YLOXY)PHENYL)-5-METHYL-1H-1,2,3-TRIAZOLE-4-CARBOXAMIDE (54)

A solution of 53 (20 mg, 0.025 mmol) in trifluoroacetic acid/tetrahydrofuran (3 mL, 2:1) was stirred at room temperature. The solvent was evaporated with toluene under reduced pressure. The residue was purified by reversed-phase flash chromatography (running a gradient of 0%-100% acetonitrile in water over 16 min) to yield compound 54 (16.0 mg, 92% yield). $^1$H NMR (500 MHz, CD3OD): δ 8.49 (s, 1H), 7.00-6.98 (m, 1H), 6.87 (s, 1H), 6.78 (d, J=8.55 Hz, 1H), 6.70 (s, 1H), 4.22 (s, 3H), 3.86 (s, 2H), 3.77 (s, 3H), 3.73-3.69 (m, 4H), 3.66-3.63 (m, 4H), 3.62-3.59 (m, 3H), 3.30-3.26 (m, 2H), 3.04 (s, 2H), 2.42 (s, 3H), 1.72-1.55 (m, 4H), 1.43-1.35 (m, 2H), 1.27 (s, 9H), 0.92 (t, J=7.55 Hz, 3H), 0.86 (t, J=7.50 Hz, 3H). $^{13}$C NMR (126 MHz, $CDCl_3$) δ 163.48, 154.58, 152.57, 149.06, 147.54, 147.16, 143.36, 142.22, 131.80, 124.43, 121.48, 120.01, 119.17, 116.17, 116.11, 103.44, 84.25, 74.25, 74.15, 74.06, 73.71, 73.28, 72.94, 70.55, 60.62, 60.31, 57.35, 43.40, 39.38, 38.26, 35.30, 30.41, 22.51, 17.94, 13.29, 12.97. LCMS: m/z=686.79 [M+H]$^+$.

x. (S)—N-(5-(TERT-BUTYL)-2-(HEXAN-3-YLOXY)PHENYL)-1-(4-((15-(5,5-DIFLUORO-7,9-DIMETHYL-5H-4L$^4$,5 L$^4$-DIPYRROLO[1,2-C:2',1'-A][1,3,2]DIAZABORININ-3-YL)-13-OXO-3,6,9-TRIOXA-12-AZAPENTADECYL)OXY)-2,5-DIMETHOXYPHENYL)-5-METHYL-1H-1,2,3-TRIAZOLE-4-CARBOXAMIDE (14)

To a solution of 3-bodipy-propanoic acid (BDP FL acid) (15 mg, 0.051 mmol) in DMF (5 mL) was added HATU (23 mg, 0.062 mmol), then the mixture was stirred at 25° C. for 30 min. 54 (42 mg, 0.062 mmol) and DIPEA (10.7 μl, 0.062 mmol) were added to the reaction mixture and stirred at 25° C. for 4 h. LCMS showed the starting material was consumed completely and desired compound was formed. The reaction mixture was poured into brine (10 mL) and extracted with EtOAc (10 mL×3), and then the combined organic layer was dried ($Na_2SO_4$), filtered, and evaporated under reduced pressure. The residue was purified by reversed-phase flash chromatography (running a gradient of 0%-100% acetonitrile in water over 16 min) to yield compound 14 (25 mg, 50.7% yield, 100% purity). $^1$H NMR (500 MHz, $CD_3OD$): δ 8.53 (d, J=2.40 Hz, 1H), 7.40 (s, 1H), 7.11 (dd, J=8.65, 2.40 Hz, 1H), 7.05 (s, 1H), 6.97-6.96 (s, 1H), 6.92 (s, 1H), 6.31 (d, J=4.00 Hz, 1H), 6.18 (s, 1H), 5.49 (s, 1H), 4.37 (p, J=5.80 Hz, 1H), 4.28-4.26 (m, 2H), 3.89-3.88 (m, 2H), 3.80 (s, 3H), 3.78 (s, 3H), 3.74-3.72 (m, 2H), 3.68-3.63 (m, 4H), 3.60-3.58 (m, 2H), 3.52 (t, J=5.40 Hz, 2H), 3.37-3.34 (m, 2H), 3.21 (t, J=7.65 Hz, 2H), 2.61 (t, J=7.65 Hz, 2H), 2.49 (s, 3H), 2.45 (s, 3H), 2.25 (s, 3H), 1.81-1.66 (m, 4H), 1.55-1.43 (m, 2H), 1.35 (s, 9H), 1.02 (t, J=7.45 Hz, 3H), 0.95 (t, J=7.35 Hz, 3H). $^{13}$C NMR (126 MHz, $CD_3OD$) δ 174.70, 161.25, 160.88, 158.55, 152.89, 150.23, 146.58, 144.98, 144.87, 140.85, 139.03, 129.64, 129.03, 125.79, 121.93, 121.34, 118.18, 117.70, 116.83, 113.92, 113.82, 100.92, 81.62, 71.80, 71.64, 71.61, 71.30, 70.81, 70.53, 70.33, 57.45, 57.10, 40.49, 36.79, 35.93, 35.30, 31.98, 30.67, 27.69, 25.62, 19.66, 14.88, 14.55, 14.46, 11.21, 9.81, 9.31. ESI-TOF HRMS: m/z 960.5236 ($C_{50}H_{69}BF_2N_7O_9$+$H^+$ requires 960.5218).

d. Compound 15
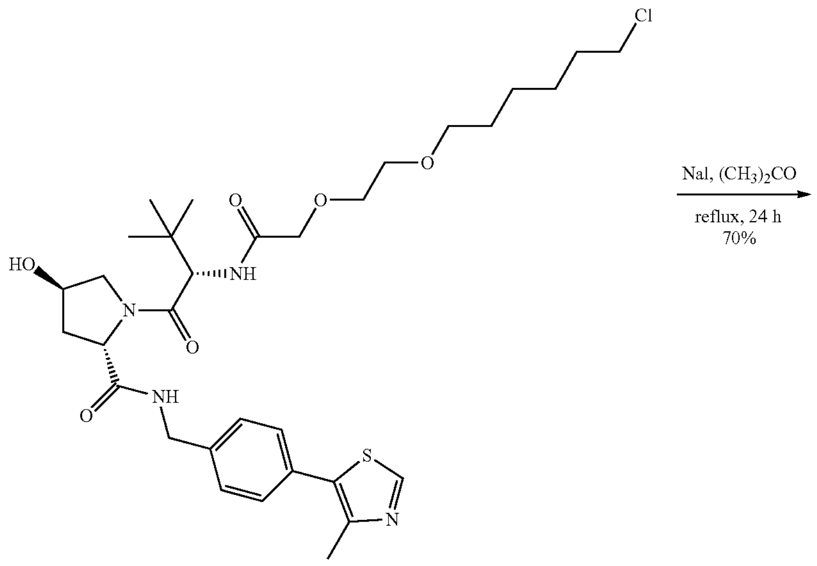
59
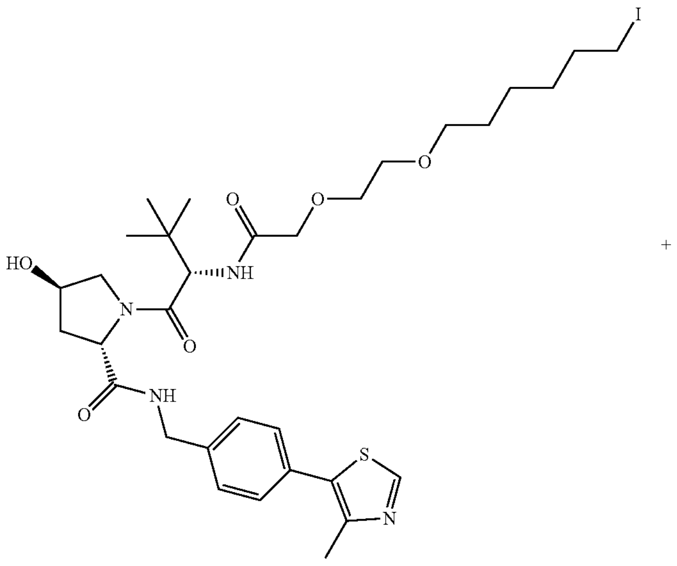
60
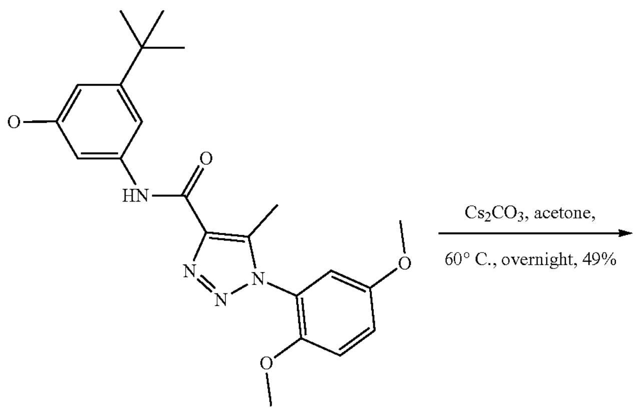
11a

-continued

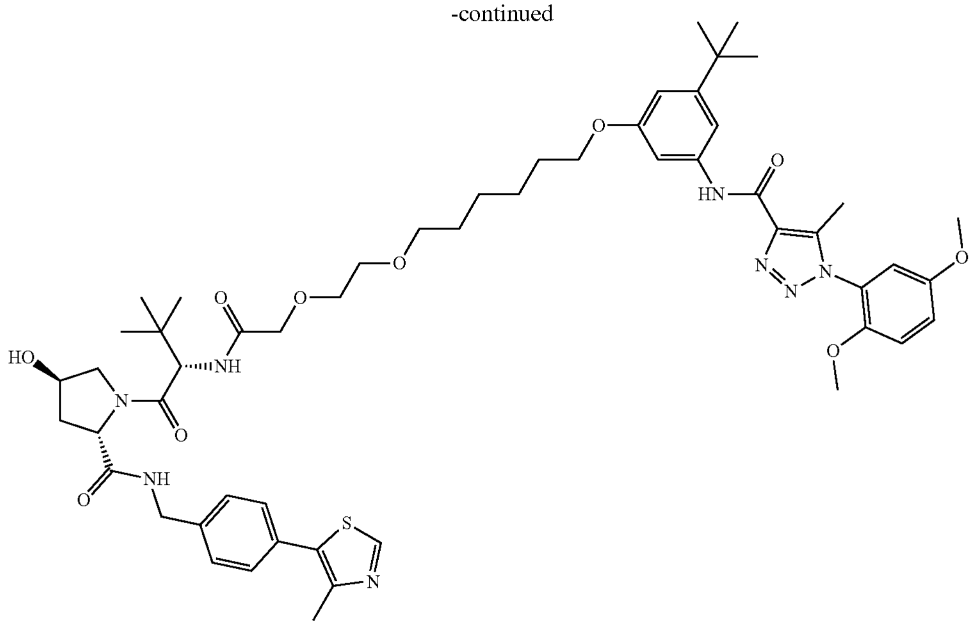

15 i. (2S,4R)-4-HYDROXY-1-((S)-2-(2-(2-((6-IODOHEXYL)OXY)ETHOXY)ACETAMIDO)-3,3-DIMETHYLBUTANOYL)-N-(4-(4-METHYLTHIAZOL-5-YL)BENZYL)PYRROLIDINE-2-CARBOXAMIDE (60)

To a solution of compound 59 (100 mg, 0.154 mmol) in acetone (10 mL) was added NaI (115 mg, 0.768 mmol). The reaction mixture was stirred at 80° C. for 48 h. The solvent was evaporated under reduced pressure, and the residue was purified by reversed-phase flash chromatography (running a gradient of 0%-10% methanol in dichloromethane) to give compound 60 (80 mg, 70% yield). $^{1}$H NMR (500 MHz, $CDCl_3$): δ 8.68 (s, 1H), 7.37-7.32 (m, 4H), 4.75 (t, J=7.85 Hz, 1H), 4.58-4.52 (m, 2H), 4.43 (d, J=8.25 Hz, 1H), 4.33 (dd, J=14.95, 5.30 Hz, 1H), 4.14-4.12 (m, 1H), 3.99 (d, J=8.80 Hz, 1H), 3.73-3.65 (m, 3H), 3.59-3.57 (m, 3H), 3.45 (td, J=6.60, 2.15 Hz, 2H), 3.16 (t, J=7.00 Hz, 2H), 2.61-2.56 (m, 1H), 2.51 (s, 3H), 2.13-2.09 (m, 1H), 1.83-1.77 (m, 2H), 1.61-1.55 (m, 2H), 1.41-1.33 (m, 4H), 0.95 (s, 9H). $^{13}$C NMR (126 MHz, CDCl3) δ 171.71, 170.64, 150.48, 148.57, 138.24, 131.77, 131.09, 129.69, 128.31, 71.52, 71.38, 70.41, 70.32, 69.91, 58.34, 57.49, 56.68, 55.82, 53.57, 43.41, 35.71, 34.67, 33.52, 30.42, 29.45, 26.55, 25.18, 18.79, 17.41, 16.19, 7.24. LCMS: m/z=743.57 $[M+H]^+$.

ii. N-(3-(TERT-BUTYL)-5-((6-(2-(2-(((S)-1-((2S,4R)-4-HYDROXY-2-((4-(4-METHYLTHIAZOL-5 YL)BENZYL)CARBAMOYL)PYRROLIDIN-1-YL)-3,3-DIMETHYL-1-OXOBUTAN-2-YL) AMINO)-2-OXOETHOXY)ETHOXY)HEXYL) OXY)PHENYL)-1-(2,5-DIMETHOXYPHENYL)-5-METHYL-1H-1,2,3-TRIAZOLE-4-CARBOXAMIDE (15)

To a solution of compound 59 (100 mg, 0.154 mmol) in acetone (10 mL) was added NaI (230 mg, 1.54 mmol). The reaction mixture was stirred under reflux for 24 h, the solvent was removed under vacuum, crude product was dissolved in EtOAc (15 mL) and an aqueous solution of $Na_2SO_3$ (10%, 10 mL), and the organic layer was separated, washed with water (10 mL), dried ($Na_2SO_4$), and evaporated under vacuum. It was used in the next step without any further purification. To the residue was added acetone (5 mL), cesium carbonate (0.100 g, 0.308 mmol), and 11a (0.063 g, 0.154 mmol, synthesized according to literature procedures reported)(Huber, A. D.; et al., (2022) *ACS Med Chem Lett* 13 (8), 1311-1320). The suspension was stirred at 60° C. overnight. The reaction mixture was diluted with water (20 mL) and extracted with EtOAc (20 mL×3). The EtOAc layers were washed with water (50 mL) and brine (50 mL), dried with anhydrous $Na_2SO_4$, and concentrated. The residue was purified by $C_{18}$ silica gel chromatography (0%-100% acetonitrile in water) to give compound 15 [78.2 mg, 49% yield (two steps), 100% purity]. $^{1}$H NMR (500 MHz, DMSO-$d_6$) δ 10.30 (s, 1H), 8.97 (s, 1H), 8.59 (t, J=6.1 Hz, 1H), 7.51 (t, J=1.7 Hz, 1H), 7.44 (t, J=2.1 Hz, 1H), 7.43-7.35 (m, 5H), 7.28 (d, J=9.2 Hz, 1H), 7.22 (dd, J=9.2, 3.1 Hz, 1H), 7.14 (d, J=3.0 Hz, 1H), 6.63 (t, J=2.0 Hz, 1H), 5.15 (d, J=3.6 Hz, 1H), 4.56 (d, J=9.6 Hz, 1H), 4.48-4.36 (m, 2H), 4.38-4.32 (m, 1H), 4.24 (dd, J=15.8, 5.6 Hz, 1H), 3.96 (s, 2H), 3.91 (t, J=6.5 Hz, 2H), 3.78 (s, 3H), 3.75 (s, 3H), 3.67 (dd, J=10.7, 4.0 Hz, 1H), 3.61 (q, J=5.5, 4.9 Hz, 3H), 3.56-3.50 (m, 2H), 3.48-3.39 (m, 2H), 2.43 (s, 3H), 2.38 (s, 3H), 2.09-2.01 (m, 1H), 1.90 (td, J=9.0, 8.5, 4.4 Hz, 1H), 1.73-1.64 (m, 2H), 1.54 (p, J=6.8 Hz, 2H), 1.37 (ddt, J=22.6, 8.8, 5.8 Hz, 4H), 1.26 (s, 9H), 0.94 (s, 9H). $^{13}$C NMR (126 MHz, DMSO-$d_6$) δ 172.24, 169.58, 169.04, 159.90, 159.05, 153.55, 152.74, 151.89, 148.19, 148.17, 139.91, 139.82, 139.44, 138.08, 131.61, 130.14, 129.14, 127.91, 124.19, 117.89, 114.47, 114.35, 110.26, 107.95, 103.77, 70.99, 70.90, 70.06, 69.70, 69.35, 67.70, 59.21, 57.03, 56.80, 56.35, 56.12, 42.13, 38.37, 36.16, 35.06, 31.55, 29.59, 29.22, 26.62, 25.93, 25.91, 16.38, 9.30. ESI-TOF HRMS: m/z 1025.5197 ($C_{54}H_{73}N_8O_{10}S+H^+$ requires 1025.517).

e. Synthesis of PXR Protac Compounds 16-21
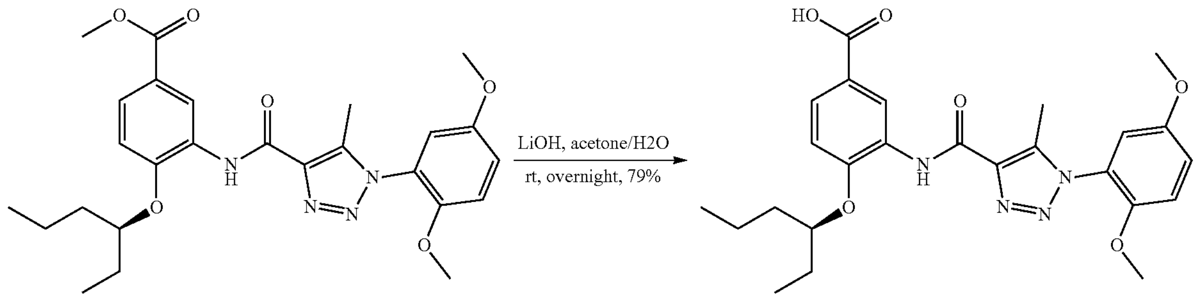
8 61
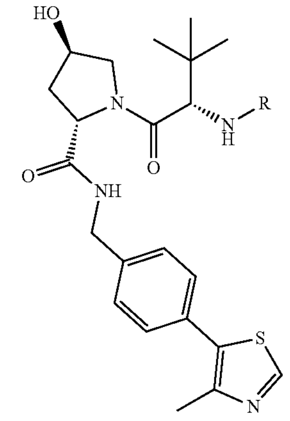
62-67
R =
62 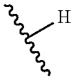
63 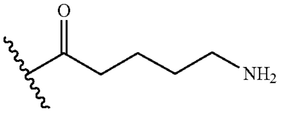
64 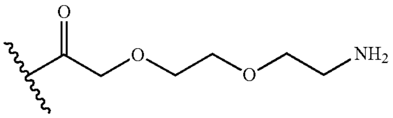
65 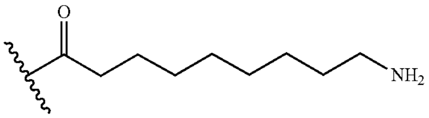
66 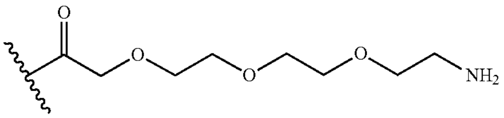
67 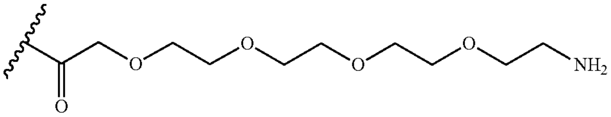
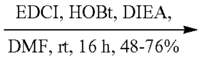
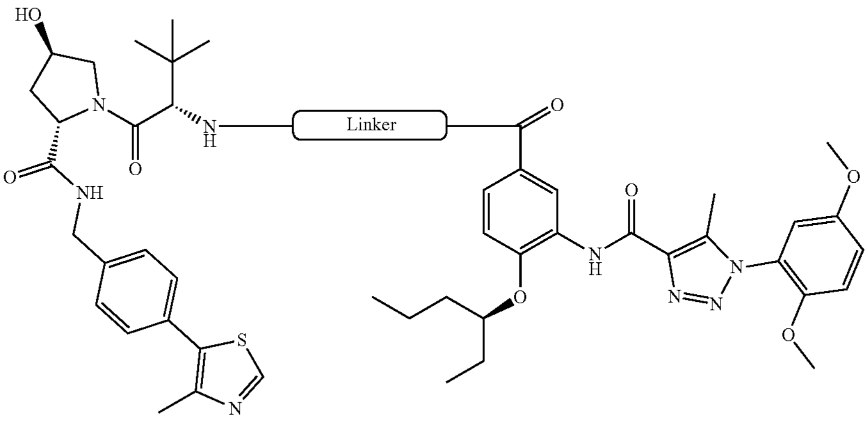

-continued

| | Linker |
|---|---|
| 16 | Bond |
| 17 | 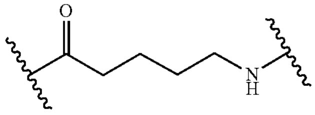 |
| 18 | 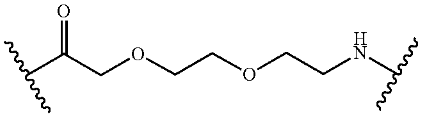 |
| 19 | 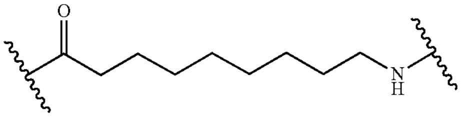 |
| 20 | 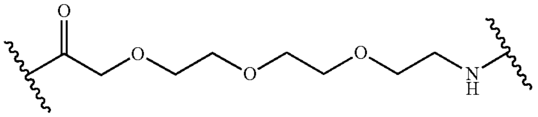 |
| 21 | 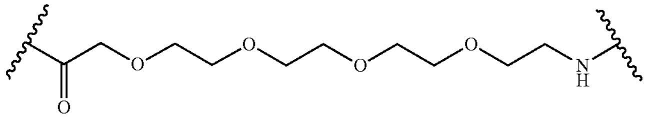 |

i. (S)-3-(1-(2,5-DIMETHOXYPHENYL)-5-METHYL-1H-1,2,3-TRIAZOLE-4-CARBOXAMIDO)-4-(HEXAN-3-YLOXY)BENZOIC ACID (61)

To a solution of compound 8 (500 mg, 1.007 mmol, synthesized according to reported procedures)(Garcia-Maldonado, et al., (2024) *Nat Commun* 2024, 15 (1), 4054) in acetone/water (10/10 mL) was added lithium hydroxide (241 mg, 10.07 mmol) at room temperature. The suspension was stirred overnight. The reaction mixture pH was adjusted by 1N HCl to 4 and extracted with EtOAc (50 mL×2). The EtOAc layer was washed with water, dried with anhydrous $MgSO_4$, and concentrated. The residue was solid and washed by 0° C. $Et_2O$ to give product as a white solid (385.6 mg, 79% yield, 100% purity); $^1$H NMR (500 MHz, DMSO-$d_6$) δ 12.72 (s, 1H), 9.73 (s, 1H), 8.98 (d, J=2.1 Hz, 1H), 7.71 (dd, J=8.6, 2.2 Hz, 1H), 7.29 (d, J=9.2 Hz, 1H), 7.26-7.21 (m, 2H), 7.17 (d, J=3.0 Hz, 1H), 4.60 (t, J=5.8 Hz, 1H), 3.77 (s, 3H), 3.76 (s, 3H), 2.41 (s, 3H), 1.81-1.64 (m, 4H), 1.53-1.34 (m, 2H), 0.96 (t, J=7.4 Hz, 3H), 0.91 (t, J=7.3 Hz, 3H). $^{13}$C NMR (126 MHz, DMSO-$d_6$) δ 166.38, 157.93, 152.47, 149.76, 147.04, 138.58, 136.49, 126.86, 125.35, 122.93, 122.17, 119.48, 116.94, 113.38, 113.30, 111.81, 78.99, 55.74, 55.26, 34.16, 25.27, 17.28, 13.40, 8.40, 8.13. ESI-TOF HRMS: m/z 483.2250 ($C_{25}H_{30}N_4O_6$+$H^+$ requires 483.2238).

ii. 1-(2,5-DIMETHOXYPHENYL)-N-(2-(((S)-HEXAN-3-YL)OXY)-5-(((S)-1-((2S,4R)-4-HYDROXY-2-((4-(4-METHYLTHIAZOL-5-YL)BENZYL)CARBAMOYL)PYRROLIDIN-1-YL)-3,3-DIMETHYL-1-OXOBUTAN-2-YL)CARBAMOYL)PHENYL)-5-METHYL-1H-1,2,3-TRIAZOLE-4-CARBOXAMIDE (16)

(2S,4R)-1-((S)-2-amino-3,3-dimethylbutanoyl)-4-hydroxy-N-(4-(4-methylthiazol-5-yl)benzyl)pyrrolidine-2-carboxamide hydrochloride (62, 53.2 mg, 0.114 mmol) was added to a solution of compound 61 (50 mg, 0.104 mmol), EDCI (29.8 mg, 0.155 mmol), HOBt (wetted with not less than 20% by weight of water, 16.80 mg, 0.124 mmol), and DIEA (40.2 mg, 0.311 mmol) in DMSO (2 mL). The resulting mixture was stirred at room temperature overnight, diluted with water (20 mL), and extracted with EtOAc (20 mL×2). The combined organic phase was washed with saturated aq. $NaHCO_3$, water, and brine, dried with $MgSO_4$, and concentrated. The residue was purified by flash chromatography (0%-100% acetonitrile in water) to give compound 16 as a white solid (44.9 mg, 48% yield, 100% purity). $^1$H NMR (500 MHz, DMSO-$d_6$) δ 9.73 (s, 1H), 8.98 (s, 1H), 8.84 (d, J=2.2 Hz, 1H), 8.60 (t, J=6.1 Hz, 1H), 7.77 (d, J=9.0 Hz, 1H), 7.67 (dd, J=8.6, 2.2 Hz, 1H), 7.45-7.37 (m, 4H), 7.29 (d, J=9.2 Hz, 1H), 7.26-7.18 (m, 2H), 7.17 (d, J=3.1 Hz, 1H), 5.17 (d, J=3.6 Hz, 1H), 4.77 (d, J=9.1 Hz, 1H), 4.60 (p, J=5.7 Hz, 1H), 4.48 (t, J=8.1 Hz, 1H), 4.46-4.36 (m, 2H), 4.32-4.21 (m, 1H), 3.78 (s, 3H), 3.76 (s, 3H), 3.75-3.73 (m, 3H), 2.44 (s, 3H), 2.40 (s, 3H), 2.05 (d, J=9.5 Hz, 1H), 1.92 (ddd, J=12.9, 8.7, 4.6 Hz, 1H), 1.81-1.64 (m, 4H), 1.53-1.33 (m, 2H), 1.04 (s, 9H), 0.96 (t, J=7.4 Hz, 3H), 0.91 (t, J=7.3 Hz, 3H). $^{13}$C NMR (126 MHz, DMSO-$d_6$) δ 172.38, 170.06, 166.45, 158.97, 153.55, 151.92, 149.75, 148.21, 148.11, 139.96, 139.60, 137.61, 131.64, 130.14, 129.17, 127.94, 126.86, 124.17, 124.02, 119.28, 118.00, 114.45, 114.37, 112.70, 79.92, 69.40, 59.30, 57.68, 56.95, 56.81, 56.33, 42.16, 38.40, 36.14, 35.27, 26.97, 26.36, 18.36, 16.42, 14.49, 9.48, 9.22. ESI-TOF HRMS: m/z 895.4141 ($C_{47}H_{59}N_8O_8S$+$H^+$ requires 895.4171).

iii. 1-(2,5-DIMETHOXYPHENYL)-N-(2-(((S)-HEXAN-3-YL)OXY)-5-((5-(((S)-1-((2S,4R)-4-HYDROXY-2-((4-(4-METHYLTHIAZOL-5-YL)BENZYL)CARBAMOYL)PYRROLIDIN-1-YL)-3,3-DIMETHYL-1-OXOBUTAN-2-YL)AMINO)-5-OXOPENTYL)CARBAMOYL)PHENYL)-5-METHYL-1H-1,2,3-TRIAZOLE-4-CARBOXAMIDE (17)

This compound was synthesized by using a procedure similar to that described for compound 16, employing 61 and (2S,4R)-1-((S)-2-(5-aminopentanamido)-3,3-dimethylbutanoyl)-4-hydroxy-N-(4-(4-methylthiazol-5-yl)benzyl) pyrrolidine-2-carboxamide (63) to give compound 17 as a white solid (66.8 mg, 65% yield, 100% purity). $^1$H NMR (500 MHz, DMSO-$d_6$) δ 9.72 (s, 1H), 8.97 (s, 1H), 8.83 (d, J=2.2 Hz, 1H), 8.57 (t, J=6.1 Hz, 1H), 8.36 (t, J=5.7 Hz, 1H), 7.88 (d, J=9.3 Hz, 1H), 7.60 (dd, J=8.6, 2.2 Hz, 1H), 7.42 (d, J=7.9 Hz, 2H), 7.38 (d, J=8.1 Hz, 2H), 7.29 (d, J=9.2 Hz, 1H), 7.22 (dd, J=9.1, 3.1 Hz, 1H), 7.19 (d, J=8.7 Hz, 1H), 7.17 (d, J=3.1 Hz, 1H), 5.14 (d, J=3.7 Hz, 1H), 4.56 (dd, J=12.0, 7.3 Hz, 2H), 4.46-4.40 (m, 2H), 4.35 (s, 1H), 4.21 (dd, J=15.9, 5.4 Hz, 1H), 3.77 (s, 3H), 3.75 (s, 3H), 3.71-3.62 (m, 2H), 3.25 (q, J=6.2 Hz, 2H), 2.44 (s, 3H), 2.42 (s, 3H), 2.36-2.27 (m, 1H), 2.18 (q, J=7.0, 6.2 Hz, 1H), 2.08-1.99 (m, 1H), 1.90 (ddd, J=13.0, 8.6, 4.6 Hz, 1H), 1.79-1.63 (m, 4H), 1.60-1.49 (m, 4H), 1.48-1.35 (m, 2H), 0.96 (t, J=7.5 Hz, 3H), 0.94 (s, 9H), 0.90 (t, J=7.4 Hz, 3H). $^{13}$C NMR (126 MHz, DMSO-$d_6$) δ 172.53, 172.45, 170.20, 166.26, 158.90, 158.87, 153.55, 151.91, 149.52, 148.18, 148.11, 139.97, 139.56, 137.63, 131.64, 130.10, 129.10, 127.88, 127.65, 124.03, 123.58, 119.26, 117.99, 114.45, 114.36, 112.72, 79.88, 69.37, 59.18, 56.86, 56.80, 56.33, 42.12, 38.40, 35.69, 35.29, 35.16, 29.45, 26.86, 26.38, 23.61, 18.36, 16.41, 14.49, 9.48, 9.20. ESI-TOF HRMS: m/z 994.4828 ($C_{52}H_{68}N_9O_9S+H^+$ requires 994.4855).

iv. 1-(2,5-DIMETHOXYPHENYL)-N-(2-(((S)-HEXAN-3-YL)OXY)-5-((2-(2-(2-(((S)-1-((2S,4R)-4-HYDROXY-2-((4-(4-METHYLTHIAZOL-5-YL)BENZYL)CARBAMOYL)PYRROLIDIN-1-YL)-3,3-DIMETHYL-1-OXOBUTAN-2-YL)AMINO)-2-OXOETHOXY)ETHOXY)ETHYL)CARBAMOYL)PHENYL)-5-METHYL-1H-1,2,3-TRIAZOLE-4-CARBOXAMIDE (18)

This compound was synthesized by using a procedure similar to that described for compound 16, employing 61 and (2S,4R)-1-((S)-2-(2-(2-(2-aminoethoxy)ethoxy)acetamido)-3,3-dimethylbutanoyl)-4-hydroxy-N-(4-(4-methylthiazol-5-yl)benzyl)pyrrolidine-2-carboxamide hydrochloride (64) to give compound 18 as a white solid (78.3 mg, 73% yield, 98% purity). $^1$H NMR (500 MHz, DMSO-$d_6$) δ 9.78 (s, 1H), 9.01 (s, 1H), 8.89 (d, J=2.2 Hz, 1H), 8.64 (t, J=6.0 Hz, 1H), 8.45 (t, J=5.7 Hz, 1H), 7.65 (dd, J=8.6, 2.3 Hz, 1H), 7.51 (d, J=9.4 Hz, 1H), 7.44 (s, 4H), 7.35 (d, J=9.2 Hz, 1H), 7.28 (dd, J=9.2, 3.1 Hz, 1H), 7.26-7.19 (m, 2H), 5.23 (d, J=3.4 Hz, 1H), 4.63 (t, J=7.1 Hz, 2H), 4.51 (t, J=8.2 Hz, 1H), 4.43 (dd, J=15.7, 6.1 Hz, 2H), 4.32 (dd, J=15.7, 5.7 Hz, 1H), 4.07-4.00 (m, 2H), 3.83 (s, 3H), 3.81 (s, 3H), 3.77-3.60 (m, 8H), 3.50 (q, J=5.9 Hz, 2H), 2.49 (s, 3H), 2.47 (s, 3H), 2.13-2.07 (m, 1H), 1.96 (ddd, J=13.0, 8.8, 4.5 Hz, 1H), 1.84-1.70 (m, 4H), 1.48 (qdt, J=13.4, 9.4, 6.5 Hz, 2H), 1.05-0.98 (m, 3H), 0.99 (s, 9H), 0.96 (t, J=7.4 Hz, 3H). $^{13}$C NMR (126 MHz, DMSO-$d_6$) δ 172.19, 169.67, 169.10, 166.44, 158.89, 153.54, 151.88, 149.60, 148.21, 148.11, 139.86, 139.57, 137.62, 131.60, 130.18, 129.16, 127.93, 127.88, 127.31, 124.02, 123.63, 119.28, 118.00, 114.45, 114.37, 112.73, 79.90, 70.87, 70.03, 69.82, 69.58, 69.34, 59.20, 57.06, 56.81, 56.33, 56.19, 42.16, 38.39, 36.20, 35.28, 26.65, 26.37, 18.36, 16.39, 14.49, 9.49, 9.20. ESI-TOF HRMS: m/z 1040.4941 ($C_{53}H_{70}N_9O_{11}S+H^+$ requires 1040.4910).

v. 1-(2,5-DIMETHOXYPHENYL)-N-(2-(((S)-HEXAN-3-YL)OXY)-5-((9-(((S)-1-((2S,4R)-4-HYDROXY-2-((4-(4-METHYLTHIAZOL-5-YL)BENZYL)CARBAMOYL)PYRROLIDIN-1-YL)-3,3-DIMETHYL-1-OXOBUTAN-2-YL)AMINO)-9-OXONONYL)CARBAMOYL)PHENYL)-5-METHYL-1H-1,2,3-TRIAZOLE-4-CARBOXAMIDE (19)

This compound was synthesized by using a procedure similar to that described for compound 16, employing 61 and (2S,4R)-1-((S)-2-(9-aminononanamido)-3,3-dimethylbutanoyl)-4-hydroxy-N-(4-(4-methylthiazol-5-yl)benzyl) pyrrolidine-2-carboxamide (65) to give compound 19 as a white solid (70.8 mg, 65% yield, 100% purity). $^1$H NMR (500 MHz, DMSO-$d_6$) δ 9.72 (s, 1H), 8.97 (s, 1H), 8.82 (d, J=2.2 Hz, 1H), 8.57 (t, J=6.1 Hz, 1H), 8.33 (t, J=5.7 Hz, 1H), 7.85 (d, J=9.3 Hz, 1H), 7.59 (dd, J=8.6, 2.3 Hz, 1H), 7.41 (d, J=8.0 Hz, 2H), 7.37 (d, J=8.2 Hz, 2H), 7.29 (d, J=9.2 Hz, 1H), 7.22 (dd, J=9.2, 3.1 Hz, 1H), 7.19 (d, J=8.9 Hz, 1H), 7.17 (d, J=3.1 Hz, 1H), 5.13 (s, 1H), 4.60-4.49 (m, 2H), 4.48-4.39 (m, 2H), 4.35 (s, 1H), 4.21 (dd, J=15.9, 5.5 Hz, 1H), 3.77 (s, 3H), 3.75 (s, 3H), 3.71-3.57 (m, 2H), 3.23 (q, J=6.7 Hz, 2H), 2.44 (s, 3H), 2.41 (s, 3H), 2.26 (dt, J=14.7, 7.6 Hz, 1H), 2.16-2.06 (m, 1H), 2.03 (ddd, J=10.6, 7.9, 2.5 Hz, 1H), 1.90 (ddd, J=12.9, 8.6, 4.6 Hz, 1H), 1.77-1.61 (m, 4H), 1.57-1.34 (m, 6H), 1.27 (t, J=11.6 Hz, 8H), 0.96 (t, J=7.4 Hz, 3H), 0.93 (s, 9H), 0.89 (t, J=7.4 Hz, 3H). $^{13}$C NMR (126 MHz, DMSO-$d_6$) δ 172.59, 172.44, 170.19, 166.24, 158.90, 153.55, 151.91, 149.49, 148.18, 148.11, 139.98, 139.55, 137.63, 131.64, 130.10, 129.10, 127.88, 127.86, 127.69, 124.03, 123.56, 119.25, 117.99, 114.45, 114.36, 112.71, 79.88, 69.34, 59.16, 56.83, 56.74, 56.33, 42.11, 38.42, 35.66, 35.34, 35.29, 29.69, 29.25, 29.13, 26.98, 26.84, 26.38, 25.93, 22.54, 18.36, 16.41, 14.49, 9.48, 9.19. ESI-TOF HRMS: m/z 1050.5504 ($C_{56}H_{76}N_9O_9S+H^+$ requires 1050.5481).

vi. 1-(2,5-DIMETHOXYPHENYL)-N-(2-(((S)-HEXAN-3-YL)OXY)-5-(((S)-13-((2S,4R)-4-HYDROXY-2-((4-(4-METHYLTHIAZOL-5-YL)BENZYL)CARBAMOYL)PYRROLIDINE-1-CARBONYL)-14,14-DIMETHYL-11-OXO-3,6,9-TRIOXA-12-AZAPENTADECYL)CARBAMOYL)PHENYL)-5-METHYL-1H-1,2,3-TRIAZOLE-4-CARBOXAMIDE (20)

This compound was synthesized by using a procedure similar to that described for compound 16, employing 61 and (2S,4R)-1-((S)-14-amino-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide hydrochloride (66) to give compound 20 as a white solid (74.6 mg, 67% yield, 100% purity). $^1$H NMR (500 MHz, DMSO-$d_6$) δ 9.72 (s, 1H), 8.97 (s, 1H), 8.84 (s, 1H), 8.61 (d, J=5.9 Hz, 1H), 8.39 (s, 1H), 7.60 (d, J=8.5 Hz, 1H), 7.41 (d, J=24.8 Hz, 4H), 7.32-7.09 (m, 4H), 5.16 (s, 1H), 4.64-4.55 (m, 2H), 4.55-4.16 (m, 4H), 3.96 (s, 2H), 3.77 (s, 3H), 3.76 (s, 3H), 3.69-3.48 (m, 12H), 3.43-3.38 (m, 2H), 2.43 (s, 3H), 2.41 (s, 3H), 2.10-2.01 (m, 1H), 1.98-1.85 (m, 1H), 1.78-1.61 (m, 4H), 1.49-1.35 (m, 2H), 1.05-0.80 (m, 15H). $^{13}$C NMR (126 MHz, DMSO-$d_6$) δ 172.23, 169.60, 169.08, 166.42, 158.90, 153.54, 151.91, 149.60, 148.21, 148.11, 139.90, 139.56, 137.62, 131.60, 130.16, 129.15, 127.93, 127.88, 127.32, 124.02, 123.62, 119.25, 118.00, 114.45, 114.37, 112.73, 79.90, 70.92, 70.27, 70.13, 70.10, 70.05, 69.46, 69.35, 59.21, 57.04, 56.81, 56.33, 56.16, 42.14, 38.39, 36.18, 35.28, 26.63, 26.37, 18.36, 16.39, 14.49, 9.48, 9.20. ESI-TOF HRMS: m/z 1084.5178 ($C_{55}H_{74}N_9O_{12}S+H^+$ requires 1084.5172).

vii. 1-(2,5-DIMETHOXYPHENYL)-N-(2-(((S)-HEXAN-3-YL)OXY)-5-(((S)-16-((2S,4R)-4-HYDROXY-2-((4-(4-METHYLTHIAZOL-5-YL)BENZYL)CARBAMOYL)PYRROLIDINE-1-CARBONYL)-17,17-DIMETHYL-14-OXO-3,6,9,12-TETRAOXA-15-AZAOCTADECYL)CARBAMOYL)PHENYL)-5-METHYL-1H-1,2,3-TRIAZOLE-4-CARBOXAMIDE (21)

This compound was synthesized by using a procedure similar to that described for compound 16, employing 61 and (2S,4R)-1-((S)-17-amino-2-(tert-butyl)-4-oxo-6,9,12,15-tetraoxa-3-azaheptadecanoyl)-4-hydroxy-N-(4-(4-methylthiazol-5-yl)benzyl)pyrrolidine-2-carboxamide hydrochloride (67) to give compound 21 as a white solid (89.5 mg, 76% yield, 100% purity). $^1$H NMR (500 MHz, DMSO-$d_6$) δ 9.72 (s, 1H), 8.97 (s, 1H), 8.89-8.82 (m, 1H), 8.60 (t, J=6.1 Hz, 1H), 8.39 (t, J=5.6 Hz, 1H), 7.63-7.57 (m, 1H), 7.41 (d, J=20.5 Hz, 5H), 7.29 (d, J=9.2 Hz, 1H), 7.26-7.15 (m, 3H), 5.16 (d, J=3.2 Hz, 1H), 4.56 (d, J=9.9 Hz, 2H), 4.44 (t, J=8.1 Hz, 1H), 4.43-4.33 (m, 1H), 4.25 (dd, J=15.9, 5.6 Hz, 1H), 3.96 (s, 2H), 3.77 (s, 4H), 3.76 (s, 3H), 3.70-3.47 (m, 16H), 3.40 (q, J=5.8 Hz, 2H), 2.43 (s, 3H), 2.41 (s, 3H), 2.06 (dd, J=13.1, 8.0 Hz, 1H), 1.90 (ddd, J=13.1, 8.8, 4.5 Hz, 1H), 1.70 (tq, J=19.5, 7.6 Hz, 4H), 1.49-1.34 (m, 2H), 0.96 (t, J=6.8 Hz, 3H), 0.94 (s, 9H), 0.90 (t, J=7.5 Hz, 3H). $^{13}$C NMR (126 MHz, DMSO-$d_6$) δ 172.24, 169.59, 169.06, 166.41, 158.90, 153.55, 151.91, 149.60, 148.21, 148.11, 139.91, 139.56, 137.62, 131.61, 130.16, 129.15, 127.92, 127.89, 127.33, 124.03, 123.63, 119.24, 118.00, 114.45, 114.36, 112.72, 79.90, 70.91, 70.31, 70.27, 70.21, 70.06, 69.45, 69.35, 59.21, 57.05, 56.81, 56.33, 56.15, 55.38, 42.14, 38.39, 36.18, 35.28, 26.63, 26.37, 18.36, 16.38, 14.49, 9.48, 9.19. ESI-TOF HRMS: m/z 1128.5433 ($C_{57}H_{78}N_9O_{13}S+H^+$ requires 1128.5434).

f. Synthesis of PXR Protac Compounds 22-27 and 29 and 31

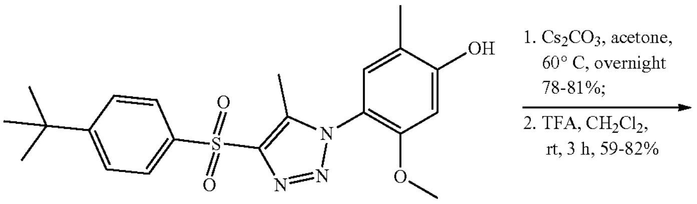

68

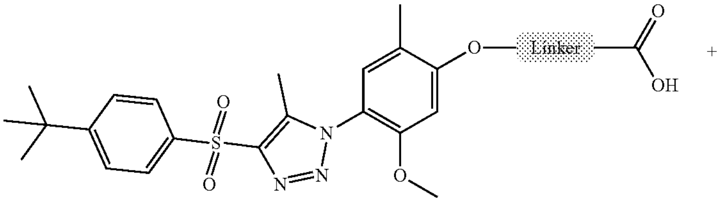

69-76

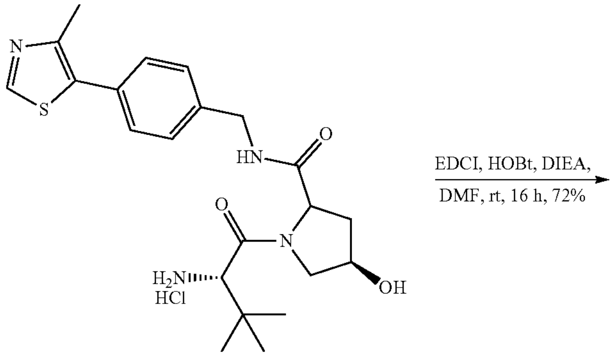

77

-continued
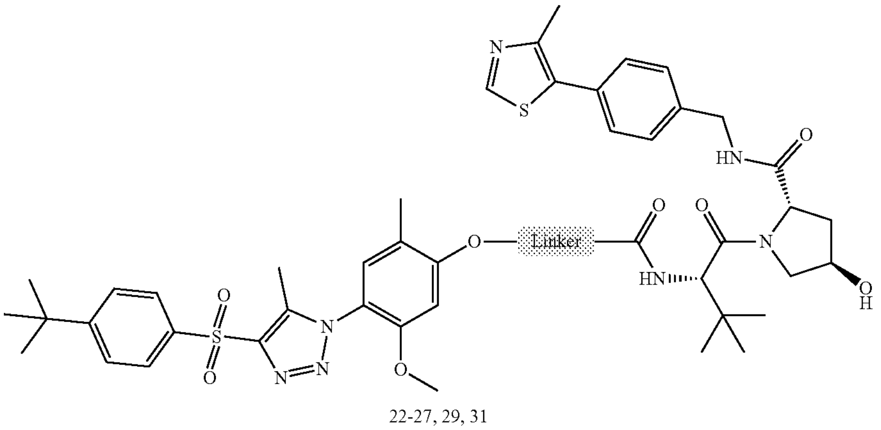
22-27, 29, 31
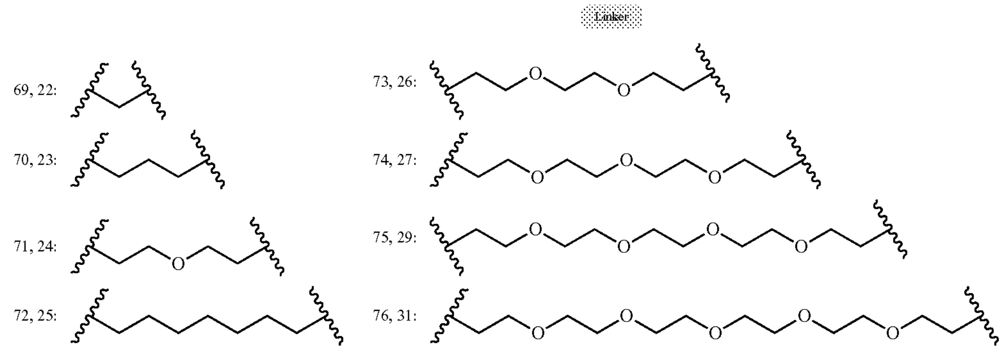
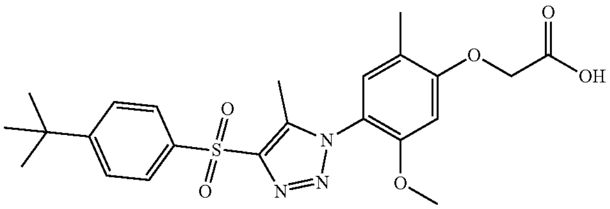
69
+
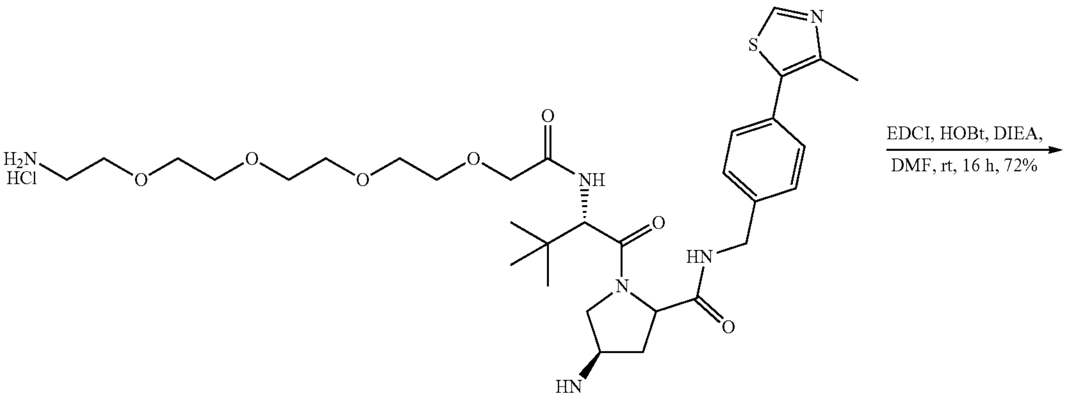
78

-continued

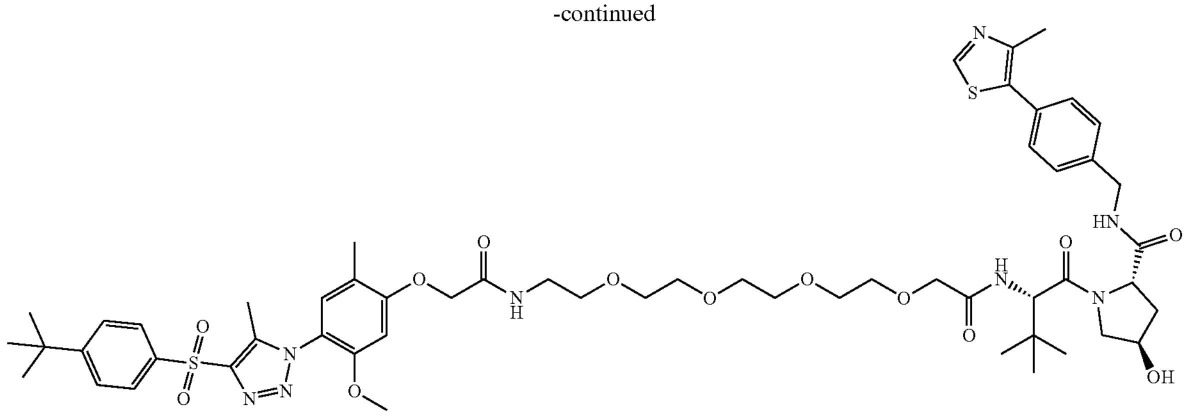

g. Compound 22 i. 2-(4-(4-((4-(TERT-BUTYL)PHENYL)SULFONYL)-5-METHYL-1H-1,2,3-TRIAZOL-1-YL)-5-METHOXY-2-METHYLPHENOXY)ACETIC ACID (69)

To a solution of 68 (1.5 g, 3.61 mmol) in acetone (20 mL) was added potassium carbonate (0.998 g, 7.22 mmol) and tert-butyl 2-bromoacetate (0.586 mL, 3.97 mmol) at room temperature. The suspension was stirred at 60° C. overnight, cooled down, filtered, and washed by DCM (10 mL). The organic phase was concentrated, and DCM (50 mL) was added. Trifluoroacetic acid (20 mL) was added to the mixture and stirred at room temperature for 3 h. The mixture was concentrated and purified by silica gel chromatography (0%-100% EtOAc in hexane) to give product as colorless solid (1.33 g, 78% yield). $^1$H NMR (500 MHz, $CDCl_3$) δ 8.05-7.96 (m, 2H), 7.87 (s, 1H), 7.59-7.52 (m, 2H), 7.07 (s, 1H), 6.46 (s, 1H), 4.78 (s, 2H), 3.72 (s, 3H), 2.40 (s, 3H), 2.21 (s, 3H), 1.33 (s, 9H). $^{13}$C NMR (126 MHz, $CDCl_3$) δ 172.23, 158.46, 157.72, 152.94, 143.87, 138.72, 137.92, 130.10, 127.69, 126.38, 120.13, 116.58, 96.74, 65.39, 56.14, 35.29, 31.06, 15.22, 8.97.

ii. (2S,4R)-1-((S)-2-(2-(4-(4-((4-(TERT-BUTYL)PHENYL)SULFONYL)-5-METHYL-1H-1,2,3-TRIAZOL-1-YL)-5-METHOXY-2-METHYLPHENOXY)ACETAMIDO)-3,3-DIMETHYLBUTANOYL)-4-HYDROXY-N-(4-(4-METHYLTHIAZOL-5 YL)BENZYL)PYRROLIDINE-2-CARBOXAMIDE (22)

Compound 77 (100 mg, 0.214 mmol) was added to a solution of compound 69 (101 mg, 0.214 mmol), EDCI (61.6 mg, 0.321 mmol), HOBt (wetted with not less than 20% by weight of water, 34.7 mg, 0.257 mmol), and DIEA (83 mg, 0.642 mmol) in DMSO (2 mL). The resulting mixture was stirred at room temperature overnight, diluted with water (20 mL), and extracted with EtOAc (20 mL×2). The combined organic phase was washed with saturated aq. $NaHCO_3$, water, and brine, dried with $MgSO_4$, and concentrated. The residue was purified by reversed-phase flash chromatography (0%-100% acetonitrile in water) to give compound 22 as a white solid (144.1 mg, 76% yield, 100% purity). $^1$H NMR (500 MHz, DMSO-$d_6$) δ 8.97 (s, 1H), 8.62 (t, J=6.1 Hz, 1H), 7.94 (dd, J=9.1, 2.8 Hz, 3H), 7.74-7.67 (m, 2H), 7.45-7.35 (m, 4H), 7.31 (s, 1H), 6.82 (s, 1H), 5.14 (d, J=3.3 Hz, 1H), 4.84 (s, 2H), 4.61 (d, J=9.4 Hz, 1H), 4.44 (t, J=8.7 Hz, 2H), 4.35 (s, 1H), 4.23 (dd, J=15.8, 5.5 Hz, 1H), 3.75 (s, 3H), 3.69-3.59 (m, 2H), 2.44 (s, 3H), 2.33 (s, 3H), 2.18 (s, 3H), 2.07-2.03 (m, 1H), 1.90 (ddd, J=13.0, 8.9, 4.4 Hz, 1H), 1.30 (s, 9H), 0.95 (s, 9H). $^{13}$C NMR (126 MHz, DMSO-$d_6$) δ 172.26, 169.54, 167.15, 158.79, 157.82, 153.31, 151.92, 148.19, 143.41, 139.94, 139.27, 138.40, 131.63, 130.15, 129.11, 127.94, 127.65, 127.15, 118.64, 115.65, 97.97, 69.36, 67.44, 59.27, 57.13, 56.74, 56.55, 42.12, 38.39, 36.40, 35.52, 31.16, 26.63, 16.41, 15.35, 9.03. ESI-TOF HRMS: m/z 886.3630 ($C_{45}H_{56}N_7O_8S_2$+$H^+$ requires 886.3626).

h. COMPOUND 23 i. METHYL 4-(4-(4-((4-(TERT-BUTYL)PHENYL)SULFONYL)-5-METHYL-1H-1,2,3-TRIAZOL-1-YL)-5-METHOXY-2-METHYLPHENOXY)BUTANOATE (70A

To a solution of 68 (5 g, 12.03 mmol) in acetone (50 mL) at room temperature was added $K_2CO_3$ (3.33 g, 24.07 mmol) and methyl 4-bromobutanoate (2.178 g, 12.03 mmol). The suspension was stirred at 60° C. overnight. After the reaction mixture was cooled down, water (25 mL) was added, and the suspension was stirred at room temperature overnight. The reaction mixture was concentrated, diluted with water (50 mL), and extracted with EtOAc. The combined organic layer was washed with brine, dried with anhydrous $MgSO_4$, and concentrated. The residue was purified by silica gel chromatography (0%-100% EtOAc in hexane) to give compound 70a as a white solid (5.03 g, 81% yield). $^1$H NMR (500 MHz, $CDCl_3$) δ 8.12-7.91 (m, 2H), 7.62-7.47 (m, 2H), 7.04 (d, J=0.9 Hz, 1H), 6.52 (s, 1H), 4.09 (t, J=6.1 Hz, 2H), 3.76 (s, 3H), 3.70 (s, 3H), 2.57 (t, J=7.1 Hz, 2H), 2.42 (s, 3H), 2.22-2.15 (m, 2H), 2.14 (s, 3H), 1.34 (s, 9H). $^{13}$C NMR (126 MHz, $CDCl_3$) δ 173.52, 159.53, 157.49, 153.02, 143.90, 138.55, 138.16, 129.60, 127.72, 126.28, 119.46, 115.48, 96.08, 67.20, 56.06, 51.76, 35.27, 31.08, 30.32, 24.43, 15.20, 8.98.

ii. 4-(4-(4-((4-(TERT-BUTYL)PHENYL)SULFONYL)-5-METHYL-1H-1,2,3-TRIAZOL-1-YL)-5-METHOXY-2-METHYLPHENOXY)BUTANOIC ACID (70)

To a solution of 70a (5 g, 9.70 mmol) in acetone/$H_2O$ (10/10 mL) at room temperature was added lithium hydroxide (1.161 g, 48.5 mmol). The suspension was stirred at 60° C. overnight. The reaction mixture was cooled down, and water (25 mL) and lithium hydroxide (1.441 g, 60.2 mmol) were added to the reaction mixture. The reaction mixture was stirred at room temperature overnight, concentrated, and diluted with water (50 mL), and the pH was adjusted to <4 by 2N HCl. The aqueous layer was extracted with EtOAc. The combined organic layer was washed with brine, dried with anhydrous $MgSO_4$, and concentrated. The residue was purified by silica gel chromatography (0%-100% EtOAc in hexane) to give product 70 as a white solid (3.85 g, 79% yield); $^1$H NMR (500 MHz, $CDCl_3$) δ 8.05-8.01 (m, 2H), 7.59-7.51 (m, 2H), 7.03 (s, 1H), 6.52 (s, 1H), 4.10 (t, J=6.1 Hz, 2H), 3.75 (s, 3H), 2.63 (t, J=7.1 Hz, 2H), 2.41 (s, 3H), 2.19 (p, J=6.5 Hz, 2H), 2.14 (s, 3H), 1.33 (s, 9H). $^{13}$C NMR (126 MHz, $CDCl_3$) δ 178.50, 159.47, 157.53, 153.02, 143.89, 138.58, 138.12, 129.63, 127.71, 126.30, 119.46, 115.51, 96.08, 67.06, 56.05, 35.28, 31.08, 30.31, 24.20, 15.17, 8.98.

iii. (2S,4R)-1-((S)-2-(4-(4-(4-((4-(TERT-BUTYL)PHENYL)SULFONYL)-5-METHYL-1H-1,2,3-TRIAZOL-1-YL)-5-METHOXY-2-METHYLPHENOXY)BUTANAMIDO)-3,3-DIMETHYLBUTANOYL)-4-HYDROXY-N-(4-(4-METHYLTHIAZOL-5-YL)BENZYL)PYRROLIDINE-2-CARBOXAMIDE (23)

This compound was synthesized by using a procedure similar to that described for compound 22, employing compound 70 and compound 77 to give a white solid (122.9 mg, 63% yield, 98% purity). $^1$H NMR (500 MHz, DMSO-$d_6$) δ 8.98 (s, 1H), 8.56 (t, J=6.1 Hz, 1H), 8.03 (d, J=9.2 Hz, 1H), 7.97-7.90 (m, 2H), 7.75-7.67 (m, 2H), 7.44-7.34 (m, 4H), 7.26 (s, 1H), 6.84 (s, 1H), 5.13 (d, J=3.4 Hz, 1H), 4.57 (d, J=9.3 Hz, 1H), 4.47-4.38 (m, 2H), 4.35 (s, 1H), 4.21 (dd, J=15.9, 5.5 Hz, 1H), 4.17-4.06 (m, 2H), 3.78 (s, 3H), 3.71-3.61 (m, 2H), 2.50-2.43 (m, 1H), 2.44 (s, 3H), 2.42-2.34 (m, 1H), 2.34 (s, 3H), 2.12 (s, 3H), 2.08-1.95 (m, 3H), 1.90 (tt, J=8.6, 4.6 Hz, 1H), 1.31 (s, 9H), 0.93 (s, 9H). $^{13}$C NMR (126 MHz, DMSO-$d_6$) δ 172.41, 172.03, 170.11, 159.83, 157.80, 153.36, 151.93, 148.19, 143.36, 139.98, 139.25, 138.43, 131.63, 130.11, 129.79, 129.11, 127.89, 127.65, 127.15, 118.70, 114.87, 97.47, 69.35, 68.98, 68.17, 59.18, 56.73, 56.30, 42.12, 38.45, 35.72, 35.52, 31.62, 31.17, 26.85, 25.35, 16.42, 15.38, 9.05. ESI-TOF HRMS: m/z 914.3963 ($C_{47}H_{60}N_7O_8S_2$+$H^+$ requires 914.3939).

i. Compound 24 i. 3-(2-(4-(4-((4-(TERT-BUTYL)PHENYL)SULFONYL)-5-METHYL-1H-1,2,3-TRIAZOL-1-YL)-5-METHOXY-2-METHYLPHENOXY)ETHOXY)PROPANOIC ACID (71)

This compound was synthesized by using a procedure similar to that described for compound 70, employing 68 and bromo-PEG1-t-butyl ester to give a white solid (452.9 mg, 71% yield). $^1$H NMR (500 MHz, $CDCl_3$) δ 8.06-7.99 (m, 2H), 7.60-7.52 (m, 2H), 7.02 (d, J=0.9 Hz, 1H), 6.53 (s, 1H), 4.18 (dd, J=5.7, 3.8 Hz, 2H), 3.89-3.86 (m, 2H), 3.85 (t, J=6.1 Hz, 2H), 3.73 (s, 3H), 2.65 (t, J=6.1 Hz, 2H), 2.41 (s, 3H), 2.14 (s, 3H), 1.33 (s, 9H). $^{13}$C NMR (126 MHz, $CDCl_3$) δ 176.52, 159.62, 157.53, 152.93, 143.88, 138.60, 138.13, 129.59, 127.69, 126.30, 119.73, 115.65, 96.64, 69.58, 68.20, 66.61, 56.02, 35.27, 34.88, 31.07, 15.22, 8.97.

ii. (2S,4R)-1-((S)-2-(3-(2-(4-(4-((4-(TERT-BUTYL)PHENYL)SULFONYL)-5-METHYL-1H-1,2,3-TRIAZOL-1-YL)-5-METHOXY-2-METHYLPHENOXY)ETHOXY)PROPANAMIDO)-3,3-DIMETHYLBUTANOYL)-4-HYDROXY-N-(4-(4-METHYLTHIAZOL-5-YL)BENZYL)PYRROLIDINE-2-CARBOXAMIDE (24)

This compound was synthesized by using a procedure similar to that described for compound 22, employing 71 and 77 to give a white solid (166.3 mg, 82% yield, 99% purity). $^1$H NMR (500 MHz, DMSO-$d_6$) δ 8.98 (s, 1H), 8.56 (t, J=6.0 Hz, 1H), 7.96 (dd, J=17.3, 8.9 Hz, 3H), 7.74-7.64 (m, 2H), 7.41 (d, J=8.2 Hz, 2H), 7.38 (d, J=8.3 Hz, 2H), 7.26 (s, 1H), 6.86 (s, 1H), 5.13 (s, 1H), 4.56 (d, J=9.4 Hz, 1H), 4.47-4.39 (m, 2H), 4.35 (s, 1H), 4.27-4.16 (m, 3H), 3.83-3.58 (m, 9H), 2.59 (dt, J=14.1, 6.8 Hz, 1H), 2.44 (s, 3H), 2.42-2.37 (m, 1H), 2.34 (s, 3H), 2.09 (s, 3H), 2.03 (dd, J=13.2, 7.8 Hz, 1H), 1.94-1.81 (m, 1H), 1.30 (s, 9H), 0.92 (s, 9H). $^{13}$C NMR (126 MHz, DMSO-$d_6$) δ 172.39, 170.34, 170.00, 159.83, 157.80, 153.32, 151.92, 148.19, 143.37, 139.97, 139.24, 138.42, 131.63, 130.11, 129.83, 129.11, 127.89, 127.65, 127.15, 118.74, 115.07, 97.87, 69.34, 69.06, 68.74, 67.74, 59.18, 56.86, 56.78, 56.72, 42.11, 38.43, 36.18, 35.83, 35.52, 31.17, 26.80, 16.41, 15.37, 9.05. ESI-TOF HRMS: m/z 944.4052 ($C_{48}H_{62}N_7O_9S_2$+$H^+$ requires 944.4045).

j. Compound 25 i. 8-(4-(4-((4-(TERT-BUTYL)PHENYL)SULFONYL)-5-METHYL-1H-1,2,3-TRIAZOL-1-YL)-5-METHOXY-2-METHYLPHENOXY)OCTANOIC ACID (72)

This compound was synthesized by using a procedure similar to that described for compound 70, employing 68 and 8-bromooctanoate to give a white solid (515.8 mg, 77% yield). $^1$H NMR (500 MHz, $CDCl_3$) δ 8.03 (d, J=8.5 Hz, 2H), 7.56 (d, J=8.4 Hz, 2H), 7.02 (s, 1H), 6.49 (s, 1H), 4.01 (t, J=6.3 Hz, 2H), 3.75 (s, 3H), 2.42 (s, 3H), 2.36 (t, J=7.4 Hz, 2H), 2.14 (s, 3H), 1.84 (p, J=6.6 Hz, 2H), 1.66 (p, J=7.4 Hz, 2H), 1.51 (p, J=7.1 Hz, 2H), 1.42-1.37 (m, 4H), 1.33 (s, 9H). $^{13}$C NMR (126 MHz, $CDCl_3$) δ 179.44, 159.91, 157.49, 152.98, 143.85, 138.59, 138.16, 129.48, 127.70, 126.29, 119.51, 115.19, 96.03, 68.44, 56.01, 35.27, 33.92, 31.07, 29.07, 28.95, 25.90, 24.58, 15.22, 8.99.

ii. (2S,4R)-1-((S)-2-(8-(4-(4-((4-(TERT-BUTYL)PHENYL)SULFONYL)-5-METHYL-1H-1,2,3-TRIAZOL-1-YL)-5-METHOXY-2-METHYLPHENOXY)OCTANAMIDO)-3,3-DIMETHYLBUTANOYL)-4-HYDROXY-N-(4-(4-METHYLTHIAZOL-5-YL)BENZYL)PYRROLIDINE-2-CARBOXAMIDE (25)

This compound was synthesized by using a procedure similar to that described for compound 22, employing 72 and 77 to give a white solid (162.1 mg, 78% yield, 100% purity). $^1$H NMR (500 MHz, DMSO-$d_6$) δ 8.98 (s, 1H), 8.56 (t, J=6.1 Hz, 1H), 7.98-7.90 (m, 2H), 7.86 (d, J=9.3 Hz, 1H), 7.74-7.67 (m, 2H), 7.45-7.35 (m, 4H), 7.25 (s, 1H), 6.83 (s, 1H), 5.12 (d, J=3.1 Hz, 1H), 4.55 (d, J=9.3 Hz, 1H), 4.43 (td, J=8.7, 4.7 Hz, 2H), 4.35 (s, 1H), 4.21 (dd, J=15.9, 5.5 Hz, 1H), 4.11 (t, J=6.4 Hz, 2H), 3.78 (s, 3H), 3.69-3.59 (m, 2H), 2.44 (s, 3H), 2.34 (s, 3H), 2.28 (dt, J=14.7, 7.5 Hz, 1H), 2.13 (dd, J=7.9, 6.2 Hz, 1H), 2.09 (s, 3H), 2.03 (ddd, J=15.5, 8.6, 4.6 Hz, 1H), 1.90 (ddd, J=12.9, 8.6, 4.6 Hz, 1H), 1.76 (p, J=6.5 Hz, 2H), 1.40-1.22 (m, 13H), 0.93 (s, 9H). $^{13}$C NMR (126 MHz, DMSO-$d_6$) δ 172.55, 172.41, 170.17, 159.96, 157.80, 153.37, 151.93, 148.19, 143.35, 139.98, 139.24, 138.42, 131.63, 130.10, 129.76, 129.11, 127.89, 127.64, 127.15, 118.53, 114.80, 97.49, 69.33, 68.61, 59.16, 56.83, 56.71, 42.11, 38.44, 35.70, 35.53, 35.31, 31.17, 29.07, 29.03, 28.89, 26.84, 25.93, 25.84, 16.42, 15.30, 9.05. ESI-TOF HRMS: m/z 970.4560 ($C_{51}H_{68}N_7O_8S_2$+$H^+$ requires 970.4565).

k. Compound 26 i. 3-(2-(2-(4-(4-((4-(TERT-BUTYL)PHENYL) SULFONYL)-5-METHYL-1H-1,2,3-TRIAZOL-1-YL)-5-METHOXY-2-METHYLPHENOXY) ETHOXY)ETHOXY)PROPANOIC ACID (73)

This compound was synthesized by using a procedure similar to that described for compound 69, employing 68 and tert-butyl 3-(2-(2-bromoethoxy)ethoxy)propanoate to give a white solid (473.9 mg, 68% yield). $^1$H NMR (500 MHz, $CDCl_3$) δ 8.05-7.97 (m, 2H), 7.55 (d, J=8.4 Hz, 2H), 7.03 (s, 1H), 6.55 (s, 1H), 4.19 (t, J=4.9 Hz, 2H), 3.89 (t, J=4.8 Hz, 2H), 3.79-3.70 (m, 7H), 3.66 (dd, J=5.9, 3.4 Hz, 2H), 2.62 (t, J=6.2 Hz, 2H), 2.41 (s, 3H), 2.15 (s, 3H), 1.33 (d, J=1.0 Hz, 9H). $^{13}$C NMR (126 MHz, $CDCl_3$) δ 175.98, 159.66, 157.52, 152.96, 143.88, 138.60, 138.14, 129.60, 127.69, 126.30, 119.66, 115.62, 96.63, 70.78, 70.50, 69.71, 68.34, 66.33, 56.04, 35.27, 34.74, 31.07, 15.25, 8.98.

ii. (2S,4R)-1-((S)-2-(3-(2-(2-(4-(4-((4-(TERT-BUTYL)PHENYL)SULFONYL)-5-METHYL-1H-1,2,3-TRIAZOL-1-YL)-5-METHOXY-2-METHYLPHENOXY)ETHOXY)ETHOXY) PROPANAMIDO)-3,3-DIMETHYLBUTANOYL)-4-HYDROXY-N-(4-(4-METHYLTHIAZOL-5-YL) BENZYL)PYRROLIDINE-2-CARBOXAMIDE (26)

This compound was synthesized by using a procedure similar to that described for compound 22, employing 73 and 77 to give a white solid (140.9 mg, 59% yield, 97% purity). $^1$H NMR (500 MHz, DMSO-$d_6$) δ 8.97 (s, 1H), 8.57 (t, J=6.2 Hz, 1H), 7.93 (dd, J=8.6, 6.3 Hz, 3H), 7.70 (d, J=8.6 Hz, 2H), 7.50-7.34 (m, 4H), 7.25 (s, 1H), 6.87 (s, 1H), 5.13 (d, J=3.5 Hz, 1H), 4.55 (d, J=9.4 Hz, 1H), 4.47-4.39 (m, 2H), 4.35 (s, 1H), 4.28-4.17 (m, 3H), 3.79 (d, J=8.0 Hz, 5H), 3.70-3.55 (m, 6H), 3.52 (dt, J=10.1, 4.9 Hz, 2H), 2.55 (dt, J=14.3, 6.9 Hz, 1H), 2.44 (s, 3H), 2.40-2.31 (m, 4H), 2.09 (s, 3H), 2.06-1.99 (m, 1H), 1.90 (ddd, J=12.9, 8.6, 4.6 Hz, 1H), 1.30 (s, 9H), 0.92 (s, 9H). $^{13}$C NMR (126 MHz, DMSO-$d_6$) δ 172.39, 170.39, 170.00, 159.83, 157.81, 153.32, 151.92, 148.18, 143.37, 139.98, 139.24, 138.42, 131.63, 130.11, 129.84, 129.11, 127.89, 127.65, 127.15, 118.69, 115.07, 97.90, 70.48, 70.02, 69.37, 69.34, 68.72, 67.44, 59.18, 56.75, 56.72, 42.11, 38.42, 36.12, 35.84, 35.53, 31.17, 26.79, 16.41, 15.35, 9.05. ESI-TOF HRMS: m/z 988.4264 ($C_{50}H_{66}N_7O_{10}S_2$+$H^+$ requires 988.4307).

l. Compound 27 i. 3-(2-(2-(2-(4-(4-((4-(TERT-BUTYL)PHENYL) SULFONYL)-5-METHYL-1H-1,2,3-TRIAZOL-1-YL)-5-METHOXY-2-METHYLPHENOXY) ETHOXY)ETHOXY)ETHOXY)PROPANOIC ACID (74)

This compound was synthesized by using a procedure similar to that described for compound 69, employing 68 and tert-butyl 3-(2-(2-(2-bromoethoxy)ethoxy)ethoxy)propanoate to give a white solid (473.9 mg, 68% yield). $^1$H NMR (500 MHz, $CDCl_3$) δ 8.06-7.97 (m, 2H), 7.60-7.52 (m, 2H), 7.03 (s, 1H), 6.56 (s, 1H), 4.20 (t, J=4.8 Hz, 2H), 3.90 (dd, J=5.5, 4.0 Hz, 2H), 3.77-3.71 (m, 7H), 3.67 (dd, J=5.8, 3.4 Hz, 2H), 3.65-3.61 (m, 4H), 2.61 (t, J=6.2 Hz, 2H), 2.41 (s, 3H), 2.14 (s, 3H), 1.33 (s, 9H). $^{13}$C NMR (126 MHz, $CDCl_3$) δ 175.62, 159.68, 157.51, 152.96, 143.87, 138.60, 138.14, 129.58, 127.69, 126.30, 119.64, 115.60, 96.64, 70.97, 70.65, 70.40, 70.35, 69.69, 68.34, 66.33, 56.05, 35.27, 34.79, 31.07, 15.26, 8.98.

ii. (2S,4R)-1-((S)-14-(TERT-BUTYL)-1-(4-(4-((4-(TERT-BUTYL)PHENYL)SULFONYL)-5-METHYL-1H-1,2,3-TRIAZOL-1-YL)-5-METHOXY-2-METHYLPHENOXY)-12-OXO-3,6,9-TRIOXA-13-AZAPENTADECAN-15-OYL)-4-HYDROXY-N-(4-(4-METHYLTHIAZOL-5-YL) BENZYL)PYRROLIDINE-2-CARBOXAMIDE (27)

This compound was synthesized by using a procedure similar to that described for compound 22, employing 74 and 77 to give a white solid (152.8 mg, 69% yield, 99% purity). $^1$H NMR (500 MHz, DMSO-$d_6$) δ 8.97 (s, 1H), 8.57 (t, J=6.1 Hz, 1H), 7.93 (t, J=9.4 Hz, 3H), 7.70 (d, J=8.5 Hz, 2H), 7.46-7.35 (m, 4H), 7.26 (s, 1H), 6.88 (s, 1H), 5.13 (d, J=3.6 Hz, 1H), 4.55 (d, J=9.4 Hz, 1H), 4.47-4.39 (m, 2H), 4.35 (s, 1H), 4.29-4.23 (m, 2H), 4.22 (dd, J=16.0, 5.7 Hz, 1H), 3.84-3.75 (m, 5H), 3.68-3.43 (m, 12H), 2.55 (dd, J=14.3, 6.9 Hz, 1H), 2.44 (s, 3H), 2.34 (m, 4H), 2.10 (s, 3H), 2.03 (td, J=9.8, 8.3, 4.6 Hz, 1H), 1.90 (ddd, J=13.0, 8.7, 4.6 Hz, 1H), 1.30 (s, 9H), 0.93 (s, 9H). $^{13}$C NMR (126 MHz, DMSO-$d_6$) δ 172.40, 170.40, 170.00, 159.84, 157.80, 153.33, 151.92, 148.19, 143.37, 139.98, 139.24, 138.43, 131.63, 130.11, 129.84, 129.11, 127.89, 127.65, 127.15, 118.69, 115.08, 97.92, 70.54, 70.32, 70.22, 69.98, 69.36, 69.34, 68.71, 67.42, 59.18, 56.85, 56.75, 56.72, 42.11, 38.42, 36.12, 35.83, 35.52, 31.16, 26.79, 16.41, 15.35, 9.05. ESI-TOF HRMS: m/z 1032.4608 ($C_{52}H_{70}N_7O_{11}S_2$+$H^+$ requires 1032.4569).

m. Compound 29 i. 1-(4-(4-((4-(TERT-BUTYL)PHENYL)SULFONYL)-5-METHYL-1H-1,2,3-TRIAZOL-1-YL)-5-METHOXY-2-METHYLPHENOXY)-3,6,9,12-TETRAOXAPENTADECAN-15-OIC ACID (75)

This compound was synthesized by using a procedure similar to that described for compound 69, employing 68 and tert-butyl 1-bromo-3,6,9,12-tetraoxapentadecan-15-oate to give a white solid (563.8 mg, 70% yield). $^1$H NMR (500 MHz, $CDCl_3$) δ 8.07-8.00 (m, 2H), 7.59-7.53 (m, 2H), 7.04 (s, 1H), 6.56 (s, 1H), 4.21 (t, J=4.8 Hz, 2H), 3.93 (t, J=4.8 Hz, 2H), 3.79-3.73 (m, 7H), 3.70-3.66 (m, 2H), 3.67-3.60 (m, 8H), 2.59 (t, J=6.0 Hz, 2H), 2.42 (s, 3H), 2.15 (s, 3H), 1.34 (s, 9H). $^{13}$C NMR (126 MHz, $CDCl_3$) δ 174.18, 159.64, 157.50, 152.97, 143.89, 138.58, 138.15, 129.61, 127.71, 126.29, 119.64, 115.65, 96.63, 71.04, 70.62, 70.61, 70.48, 70.45, 70.13, 69.68, 68.26, 66.46, 56.06, 35.27, 34.93, 31.08, 15.26, 8.98.

ii. (2S,4R)-1-((S)-17-(TERT-BUTYL)-1-(4-(4-((4-(TERT-BUTYL)PHENYL)SULFONYL)-5-METHYL-1H-1,2,3-TRIAZOL-1-YL)-5-METHOXY-2-METHYLPHENOXY)-15-OXO-3,6,9,12-TETRAOXA-16-AZAOCTADECAN-18-OYL)-4-HYDROXY-N-(4-(4-METHYLTHIAZOL-5-YL)BENZYL)PYRROLIDINE-2-CARBOXAMIDE (29)

This compound was synthesized by using a procedure similar to that described for compound 22, employing 75 and 77 to give a white solid (188.0 mg, 78% yield, 99% purity). $^1$H NMR (500 MHz, DMSO-$d_6$) δ 8.98 (s, 1H), 8.57 (t, J=6.1 Hz, 1H), 7.93 (t, J=10.0 Hz, 3H), 7.70 (d, J=8.3 Hz, 2H), 7.44-7.33 (m, 4H), 7.26 (s, 1H), 6.88 (s, 1H), 5.13 (d, J=3.6 Hz, 1H), 4.55 (d, J=9.3 Hz, 1H), 4.47-4.39 (m, 2H), 4.35 (s, 1H), 4.30-4.25 (m, 2H), 4.21 (dd, J=15.9, 5.5 Hz, 1H), 3.81 (t, J=4.5 Hz, 2H), 3.78 (s, 3H), 3.71-3.41 (m, 16H), 2.59-2.51 (m, 1H), 2.39-2.30 (m, 4H), 2.10 (s, 3H), 2.06-1.99 (m, 1H), 1.95-1.85 (m, 1H), 1.30 (s, 9H), 0.93 (s, 9H). $^{13}$C NMR (126 MHz, DMSO-$d_6$) δ 172.40, 170.40, 170.00, 159.83, 157.80, 153.33, 151.92, 148.19, 143.37, 139.98, 139.24, 138.42, 131.63, 130.11, 129.84, 129.11, 127.89, 127.65, 127.15, 118.69, 115.08, 97.93, 70.54, 70.31, 70.27, 70.18, 69.95, 69.36, 69.34, 68.70, 67.41, 59.18, 56.85, 56.75, 56.72, 42.11, 38.42, 36.12, 35.83, 35.52, 31.17, 26.79, 16.41, 15.34, 9.05. ESI-TOF HRMS: m/z 1076.4827 ($C_{54}H_{74}N_7O_{12}S_2$+$H^+$ requires 1076.4831).

n. Compound 30 i. 1-(4-(4-((4-(TERT-BUTYL)PHENYL)SULFONYL)-5-METHYL-1H-1,2,3-TRIAZOL-1-YL)-5-METHOXY-2-METHYLPHENOXY)-3,6,9,12,15-PENTAOXAOCTADECAN-18-OIC ACID (76)

This compound was synthesized by using a procedure similar to that described for compound 69, employing 68 and tert-butyl 1-bromo-3,6,9,12,15-pentaoxaoctadecan-18-oate to give a white solid (503.9 mg, 59% yield). $^1$H NMR (500 MHz, $CDCl_3$) δ 8.09-7.99 (m, 2H), 7.60-7.52 (m, 2H), 7.03 (d, J=0.9 Hz, 1H), 6.56 (s, 1H), 4.20 (dd, J=5.7, 4.1 Hz, 2H), 3.91 (dd, J=5.5, 4.2 Hz, 2H), 3.76 (d, J=5.8 Hz, 7H), 3.70-3.60 (m, 14H), 2.58 (t, J=6.0 Hz, 2H), 2.41 (s, 3H), 2.15 (d, J=0.7 Hz, 3H), 1.33 (s, 9H). $^{13}$C NMR (126 MHz, $CDCl_3$) δ 174.11, 159.67, 157.50, 152.97, 143.88, 138.57, 138.14, 129.60, 127.71, 126.29, 119.64, 115.63, 96.62, 70.92, 70.65, 70.57, 70.54, 70.48, 70.41, 70.17, 69.68, 68.30, 66.53, 56.06, 35.27, 35.00, 31.08, 15.26, 8.98.

ii. (2S,4R)-1-((S)-2-(TERT-BUTYL)-20-(4-(4-((4-(TERT-BUTYL)PHENYL)SULFONYL)-5-METHYL-1H-1,2,3-TRIAZOL-1-YL)-5-METHOXY-2-METHYLPHENOXY)-4,19-DIOXO-6,9,12,15-TETRAOXA-3,18-DIAZAICOSANOYL)-4-HYDROXY-N-(4-(4-METHYLTHIAZOL-5-YL)BENZYL) PYRROLIDINE-2-CARBOXAMIDE (30)

This compound was synthesized by using a procedure similar to that described for compound 22, employing 69 and 78 to give a white solid (170.5 mg, 72% yield, 98% purity). $^1$H NMR (500 MHz, DMSO-$d_6$) δ 8.97 (s, 1H), 8.60 (t, J=6.1 Hz, 1H), 7.99 (t, J=5.6 Hz, 1H), 7.94 (d, J=8.3 Hz, 2H), 7.70 (d, J=8.3 Hz, 2H), 7.49-7.34 (m, 5H), 7.29 (s, 1H), 6.81 (s, 1H), 5.15 (d, J=3.6 Hz, 1H), 4.69 (s, 2H), 4.56 (d, J=9.6 Hz, 1H), 4.44 (t, J=8.2 Hz, 1H), 4.39 (dd, J=15.9, 6.5 Hz, 1H), 4.35 (s, 1H), 4.25 (dd, J=15.8, 5.7 Hz, 1H), 3.96 (s, 2H), 3.76 (s, 3H), 3.70-3.42 (m, 16H), 3.37-3.28 (m, 2H), 2.44 (s, 3H), 2.35 (s, 3H), 2.17 (s, 3H), 2.08-1.99 (m, 1H), 1.95-1.86 (m, 1H), 1.30 (s, 9H), 0.94 (s, 9H). $^{13}$C NMR (126 MHz, DMSO-$d_6$) δ 172.23, 169.60, 169.05, 167.76, 158.91, 157.82, 153.22, 151.92, 148.21, 143.40, 139.92, 139.24, 138.41, 131.61, 130.16, 130.07, 129.16, 127.93, 127.66, 127.15, 118.99, 115.63, 98.05, 70.90, 70.30, 70.26, 70.21, 70.07, 70.05, 70.00, 69.34, 67.99, 59.21, 57.05, 56.73, 56.15, 42.14, 38.77, 38.40, 36.19, 35.52, 31.16, 26.64, 16.39, 15.45, 9.05. ESI-TOF HRMS: m/z 1119.4860 ($C_{55}H_{75}N_8O_{13}S_2$+$H^+$ requires 1119.4890).

o. COMPOUND 31 i. 1-(4-(4-((4-(TERT-BUTYL)PHENYL)SULFONYL)-5-METHYL-1H-1,2,3-TRIAZOL-1-YL)-5-METHOXY-2-METHYLPHENOXY)-3,6,9,12,15-PENTAOXAOCTADECAN-18-OIC ACID (76)

This compound was synthesized by using a procedure similar to that described for compound 69, employing 68 and tert-butyl 1-bromo-3,6,9,12,15-pentaoxaoctadecan-18-oate to give a white solid (503.9 mg, 59% yield). $^1$H NMR (500 MHz, $CDCl_3$) δ 8.09-7.99 (m, 2H), 7.60-7.52 (m, 2H), 7.03 (d, J=0.9 Hz, 1H), 6.56 (s, 1H), 4.20 (dd, J=5.7, 4.1 Hz, 2H), 3.91 (dd, J=5.5, 4.2 Hz, 2H), 3.76 (d, J=5.8 Hz, 7H), 3.70-3.60 (m, 14H), 2.58 (t, J=6.0 Hz, 2H), 2.41 (s, 3H), 2.15 (d, J=0.7 Hz, 3H), 1.33 (s, 9H). $^{13}$C NMR (126 MHz, $CDCl_3$) δ 174.11, 159.67, 157.50, 152.97, 143.88, 138.57, 138.14, 129.60, 127.71, 126.29, 119.64, 115.63, 96.62, 70.92, 70.65, 70.57, 70.54, 70.48, 70.41, 70.17, 69.68, 68.30, 66.53, 56.06, 35.27, 35.00, 31.08, 15.26, 8.98.

ii. (2S,4R)-1-((S)-20-(TERT-BUTYL)-1-(4-(4-((4-(TERT-BUTYL)PHENYL)SULFONYL)-5-METHYL-1H-1,2,3-TRIAZOL-1-YL)-5-METHOXY-2-METHYLPHENOXY)-18-OXO-3,6,9,12,15-PENTAOXA-19-AZAHENICOSAN-21-OYL)-4-HYDROXY-N-(4-(4-METHYLTHIAZOL-5-YL)BENZYL)PYRROLIDINE-2-CARBOXAMIDE (31)

This compound was synthesized by using a procedure similar to that described for compound 22, employing 76 and 77 to give a white solid (188.0 mg, 78% yield, 100% purity). $^1$H NMR (500 MHz, DMSO-$d_6$) δ 8.98 (s, 1H), 8.57 (t, J=6.1 Hz, 1H), 7.93 (t, J=9.8 Hz, 3H), 7.70 (d, J=8.4 Hz, 2H), 7.52-7.34 (m, 4H), 7.26 (s, 1H), 6.88 (s, 1H), 5.17-5.03 (m, 1H), 4.55 (d, J=9.4 Hz, 1H), 4.47-4.39 (m, 2H), 4.37-4.33 (m, 1H), 4.26 (t, J=4.6 Hz, 2H), 4.21 (dd, J=15.9, 5.5 Hz, 1H), 3.81 (d, J=4.8 Hz, 2H), 3.78 (s, 3H), 3.70-3.42 (m, 20H), 2.54 (dd, J=14.4, 7.0 Hz, 1H), 2.44 (s, 3H), 2.38-2.32 (m, 4H), 2.10 (s, 3H), 2.06-1.99 (m, 1H), 1.90 (ddd, J=12.9, 8.7, 4.6 Hz, 1H), 1.30 (s, 9H), 0.93 (s, 9H). $^{13}$C NMR (126 MHz, DMSO-$d_6$) δ 172.40, 170.40, 170.00, 159.84, 157.80, 153.33, 151.92, 148.19, 143.37, 139.98, 139.24, 138.43, 131.63, 130.11, 129.84, 129.11, 127.89, 127.65, 127.14, 118.69, 115.08, 97.93, 70.55, 70.31, 70.28, 70.26, 70.25, 70.17, 69.94, 69.37, 69.34, 68.70, 67.42, 59.18, 56.85, 56.76, 56.72, 42.11, 38.42, 36.12, 35.84, 35.52, 31.17, 26.79, 16.41, 15.34, 9.04. ESI-TOF HRMS: m/z 1120.5132 ($C_{56}H_{78}N_7O_{13}S_2$+$H^+$ requires 1120.5094).

p. Synthesis of PXR Protac Compounds 28 and 32-35
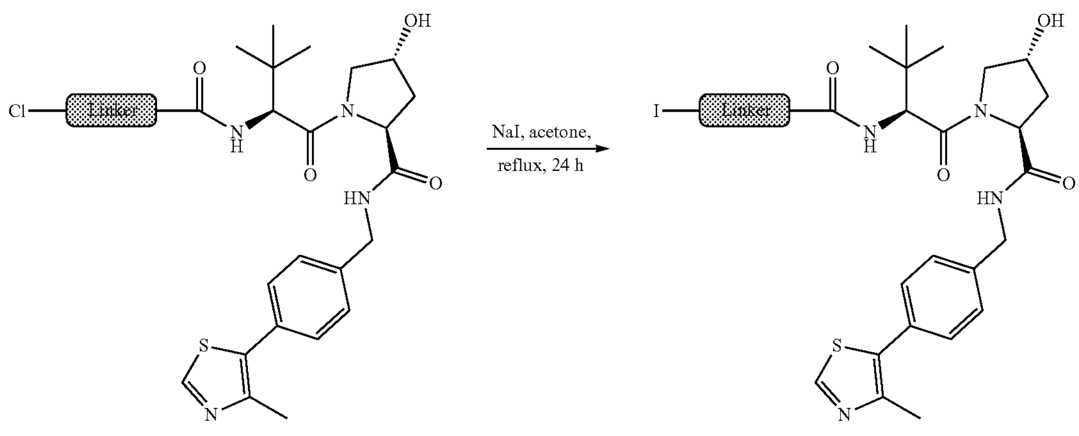
59, 79-81
60, 82-84
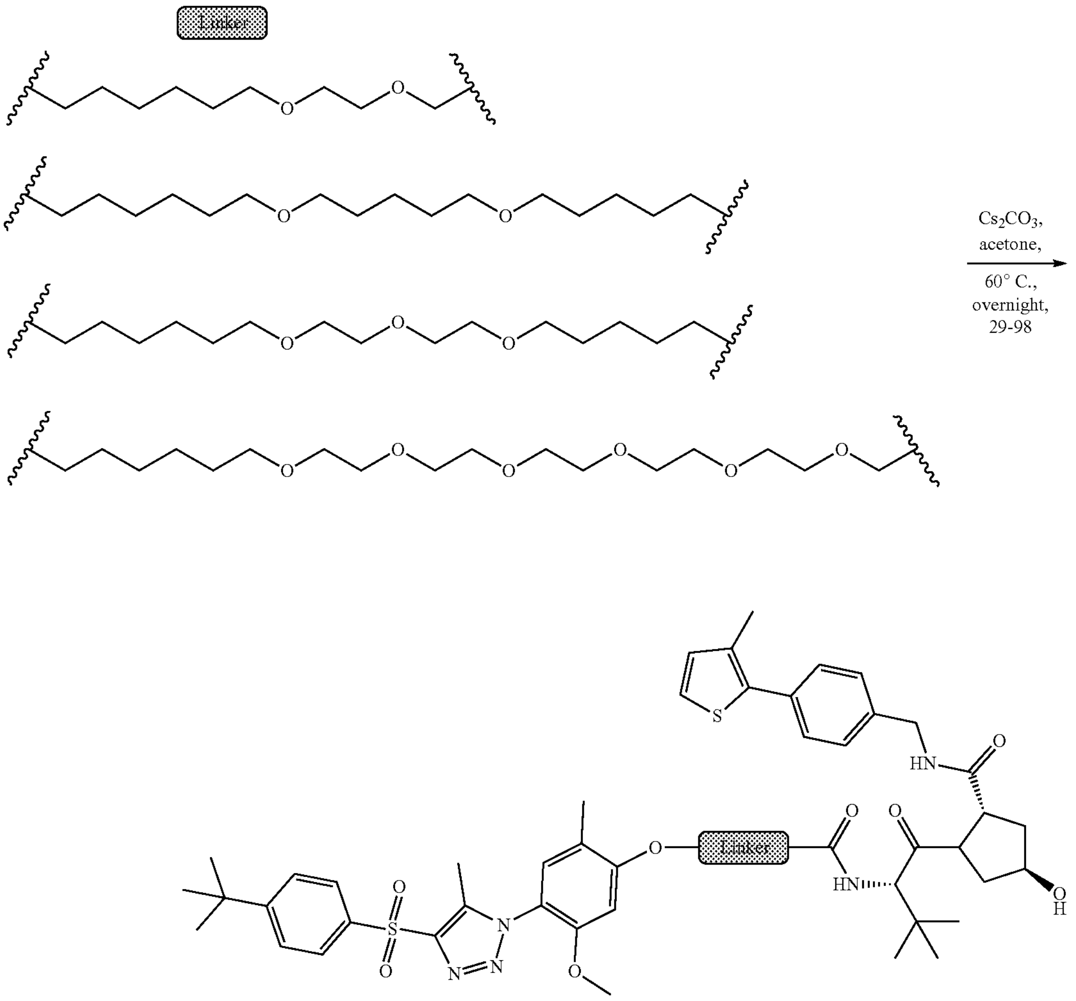
59, 60, 28:
79, 82 32:
80, 83, 33:
81, 84, 34:
28, 32-34 q. Compound 28 i. (2S,4R)-4-HYDROXY-1-((S)-2-(2-(2-((6-IODOHEXYL)OXY)ETHOXY)ACETAMIDO)-3,3-DIMETHYLBUTANOYL)-N-(4-(4-METHYLTHIAZOL-5-YL)BENZYL)PYRROLIDINE-2-CARBOXAMIDE (60)

To a solution of compound 59 (100 mg, 0.154 mmol) in acetone (10 mL) was added NaI (115 mg, 0.768 mmol). The reaction mixture was stirred at 80° C. for 48 h. The solvent was evaporated under reduced pressure, and the residue was purified by reversed-phase flash chromatography (running a gradient of 0%-10% methanol in dichloromethane) to give compound 60 (80 mg, 70% yield). $^{1}$H NMR (500 MHz, $CDCl_3$): δ 8.68 (s, 1H), 7.37-7.32 (m, 4H), 4.75 (t, J=7.85 Hz, 1H), 4.58-4.52 (m, 2H), 4.43 (d, J=8.25 Hz, 1H), 4.33 (dd, J=14.95, 5.30 Hz, 1H), 4.14-4.12 (m, 1H), 3.99 (d, J=8.80 Hz, 1H), 3.73-3.65 (m, 3H), 3.59-3.57 (m, 3H), 3.45 (td, J=6.60, 2.15 Hz, 2H), 3.16 (t, J=7.00 Hz, 2H), 2.61-2.56 (m, 1H), 2.51 (s, 3H), 2.13-2.09 (m, 1H), 1.83-1.77 (m, 2H), 1.61-1.55 (m, 2H), 1.41-1.33 (m, 4H), 0.95 (s, 9H). $^{13}$C NMR (126 MHz, CDCl3) δ 171.71, 170.64, 150.48, 148.57, 138.24, 131.77, 131.09, 129.69, 128.31, 71.52, 71.38, 70.41, 70.32, 69.91, 58.34, 57.49, 56.68, 55.82, 53.57, 43.41, 35.71, 34.67, 33.52, 30.42, 29.45, 26.55, 25.18, 18.79, 17.41, 16.19, 7.24. LCMS: m/z=743.57 $[M+H]^+$.

ii. (2S,4R)-1-((S)-2-(2-(2-((6-(4-(4-((4-(TERT-BUTYL)PHENYL)SULFONYL)-5-METHYL-1H-1,2,3-TRIAZOL-1-YL)-5-METHOXY-2-METHYLPHENOXY)HEXYL)OXY)ETHOXY)ACETAMIDO)-3,3-DIMETHYLBUTANOYL)-4-HYDROXY-N-(4-(4-METHYLTHIAZOL-5-YL)BENZYL)PYRROLIDINE-2-CARBOXAMIDE (28)

To a solution of compound 59 (100 mg, 0.154 mmol) in acetone (10 mL) was added NaI (115 mg, 0.768 mmol). The reaction mixture was stirred under reflux for 24 h, the solvent was removed under vacuum, crude product was dissolved in EtOAc (15 mL) and an aqueous solution of $Na_2SO_3$ (10%, 10 mL), and the organic layer was separated, washed with water (10 mL), dried ($Na_2SO_4$), and evaporated under vacuum. It was used in the next step without any further purification. To the residue was added acetone (5 mL), cesium carbonate (0.100 g, 0.308 mmol), and compound 68 (0.064 g, 0.154 mmol). The suspension was stirred at 60° C. overnight. The reaction mixture was diluted with water (50 mL) and extracted with EtOAc (50 mL×2). The EtOAc layers were washed with water (50 mL), dried with anhydrous $Na_2SO_4$, and concentrated. The residue was purified by C18 silica gel chromatography (0%-100% acetonitrile in water) to give product as white solid [59.8 mg, 38% yield (two steps), 98% purity]. 1H NMR (500 MHz, DMSO-$d_6$) δ 8.97 (s, 1H), 8.59 (t, J=6.1 Hz, 1H), 7.94 (d, J=8.2 Hz, 2H), 7.70 (d, J=8.2 Hz, 2H), 7.46-7.35 (m, 5H), 7.24 (s, 1H), 6.81 (s, 1H), 5.15 (d, J=3.5 Hz, 1H), 4.56 (d, J=9.6 Hz, 1H), 4.47-4.37 (m, 2H), 4.35 (s, 1H), 4.23 (dd, J=15.8, 5.5 Hz, 1H), 4.07 (t, J=6.3 Hz, 2H), 3.96 (s, 2H), 3.77 (s, 3H), 3.67 (dd, J=10.8, 4.1 Hz, 1H), 3.64-3.57 (m, 3H), 3.55-3.50 (m, 2H), 3.47-3.39 (m, 2H), 2.43 (s, 3H), 2.33 (s, 3H), 2.07 (s, 3H), 2.06-2.02 (m, 1H), 1.90 (ddd, J=13.0, 8.8, 4.5 Hz, 1H), 1.74 (p, J=6.6 Hz, 2H), 1.54 (p, J=6.8 Hz, 2H), 1.49-1.33 (m, 4H), 1.30 (s, 9H), 0.94 (s, 9H). 13C NMR (126 MHz, DMSO-$d_6$) δ 171.77, 169.10, 168.56, 159.48, 157.33, 152.89, 151.44, 147.72, 142.88, 139.44, 138.77, 137.96, 131.13, 129.66, 129.28, 128.67, 127.43, 127.17, 126.68, 118.07, 114.33, 96.98, 70.51, 70.40, 69.59, 69.25, 68.88, 68.11, 58.75, 56.57, 56.22, 55.64, 41.65, 37.92, 35.68, 35.06, 30.70, 29.12, 28.57, 26.15, 25.43, 25.37, 15.91, 14.82, 8.57. ESI-TOF HRMS: m/z 1030.4791 ($C_{53}H_{72}N_7O_{10}S_2$+$H^+$ requires 1030.4777).

r. Compound 32

(2S,4R)-1-((S)-2-(6-((5-((6-(4-(4-((4-(tert-Butyl)phenyl)sulfonyl)-5-methyl-1H-1,2,3-triazol-1-yl)-5-methoxy-2-methylphenoxy)hexyl)oxy)pentyl)oxy)hexanamido)-3,3-dimethylbutanoyl)-4-hydroxy-N-(4-(4-methylthiazol-5-yl)benzyl)pyrrolidine-2-carboxamide (32). This compound was synthesized by using a procedure similar to that described for compound 28, employing 68 and 79 to give a white solid (95.3 mg, 63% yield, 99% purity). $^{1}$H NMR (500 MHz, DMSO-$d_6$) δ 8.98 (s, 1H), 8.56 (t, J=6.1 Hz, 1H), 7.97-7.90 (m, 2H), 7.85 (d, J=9.3 Hz, 1H), 7.76-7.65 (m, 2H), 7.45-7.34 (m, 4H), 7.24 (s, 1H), 6.83 (s, 1H), 5.12 (d, J=3.5 Hz, 1H), 4.54 (d, J=9.4 Hz, 1H), 4.43 (td, J=8.7, 4.7 Hz, 2H), 4.35 (q, J=3.4 Hz, 1H), 4.21 (dd, J=15.9, 5.5 Hz, 1H), 4.10 (t, J=6.3 Hz, 2H), 3.78 (s, 3H), 3.70-3.57 (m, 2H), 3.37-3.26 (m, 8H), 2.44 (s, 3H), 2.34 (s, 3H), 2.24 (t, J=7.4 Hz, 1H), 2.12 (d, J=6.3 Hz, 1H), 2.09 (s, 3H), 2.07-1.99 (m, 1H), 1.90 (ddd, J=12.9, 8.6, 4.6 Hz, 1H), 1.77 (p, J=6.6 Hz, 2H), 1.59-1.34 (m, 14H), 1.34-1.20 (m, 13H), 0.93 (s, 9H). $^{13}$C NMR (126 MHz, DMSO-$d_6$) δ 172.50, 172.42, 170.17, 159.96, 157.79, 153.37, 151.91, 148.18, 143.36, 139.98, 139.23, 138.43, 131.64, 130.10, 129.75, 129.10, 127.88, 127.64, 127.14, 118.54, 114.81, 97.46, 70.40, 70.36, 70.32, 69.34, 68.61, 59.16, 56.82, 56.73, 56.70, 42.11, 38.43, 35.68, 35.52, 35.31, 31.16, 29.69, 29.54, 29.47, 29.06, 26.85, 25.93, 25.90, 25.87, 25.78, 22.99, 16.42, 15.29, 9.04. ESI-TOF HRMS: m/z 1128.5881 ($C_{60}H_{86}N_7O_{10}S_2$+$H^+$ requires 1128.5872).

s. Compound 33

(2S,4R)-1-((S)-2-(tert-Butyl)-22-(4-(4-((4-(tert-butyl)phenyl)sulfonyl)-5-methyl-1H-1,2,3-triazol-1-yl)-5-methoxy-2-methylphenoxy)-4-oxo-10,13,16-trioxa-3-azadocosanoyl)-4-hydroxy-N-(4-(4-methylthiazol-5-yl)benzyl)pyrrolidine-2-carboxamide (33). This compound was synthesized by using a procedure similar to that described for compound 28, employing 68 and 80 to give a white solid (71.3 mg, 48% yield, 100% purity). $^{1}$H NMR (500 MHz, DMSO-$d_6$) δ 8.98 (s, 1H), 8.56 (t, J=6.1 Hz, 1H), 7.97-7.87 (m, 2H), 7.85 (d, J=9.3 Hz, 1H), 7.74-7.68 (m, 2H), 7.44-7.34 (m, 4H), 7.25 (s, 1H), 6.83 (s, 1H), 5.11 (d, J=3.5 Hz, 1H), 4.54 (d, J=9.4 Hz, 1H), 4.42 (td, J=9.0, 8.3, 5.0 Hz, 2H), 4.34 (s, 1H), 4.21 (dd, J=15.9, 5.5 Hz, 1H), 4.11 (t, J=6.3 Hz, 2H), 3.78 (s, 3H), 3.71-3.58 (m, 2H), 3.49 (dt, J=6.0, 3.5 Hz, 4H), 3.45 (ddd, J=9.6, 6.0, 3.5 Hz, 4H), 3.39 (t, J=6.6 Hz, 2H), 3.35 (t, J=6.6 Hz, 2H), 2.44 (s, 3H), 2.34 (s, 3H), 2.29-2.21 (m, 1H), 2.12 (t, J=7.2 Hz, 1H), 2.09 (s, 3H), 2.06-1.98 (m, 1H), 1.89 (ddd, J=13.0, 8.6, 4.6 Hz, 1H), 1.77 (p, J=6.4 Hz, 2H), 1.54-1.36 (m, 10H), 1.30 (s, 9H), 1.27-1.22 (m, 2H), 0.93 (s, 9H). $^{13}$C NMR (126 MHz, DMSO-$d_6$) δ 172.49, 172.42, 170.17, 159.96, 157.80, 153.37, 151.92, 148.18, 143.36, 139.98, 139.24, 138.43, 131.64, 130.10, 129.76, 129.10, 127.88, 127.64, 127.14, 118.54, 114.81, 97.47, 70.71, 70.29, 69.98, 69.94, 69.33, 68.60, 59.16, 56.83, 56.73, 56.70, 42.11, 38.43, 35.68, 35.52, 35.30, 31.17, 29.66, 29.42, 29.06, 26.92, 26.85, 25.90, 25.86, 25.78, 16.42, 15.30, 9.05. ESI-TOF HRMS: m/z 1030.4791($C_{59}H_{84}N_7O_{11}S_2$+$H^+$ requires 1130.5665).

t. Compound 34

(2S,4R)-1-((S)-2-(tert-Butyl)-27-(4-(4-((4-(tert-butyl)phenyl)sulfonyl)-5-methyl-1H-1,2,3-triazol-1-yl)-5-methoxy-2-methylphenoxy)-4-oxo-6,9,12,15,18,21-hexaoxa-3-azaheptacosanoyl)-4-hydroxy-N-(4-(4-methylthiazol-5-yl)benzyl)pyrrolidine-2-carboxamide (34). This compound was synthesized by using a procedure similar to that described for compound 28, employing 68 and 81 to give a white solid (85.2 mg, 58% yield, 99% purity). $^1$H NMR (500 MHz, DMSO-$d_6$) δ 8.98 (s, 1H), 8.59 (t, J=6.1 Hz, 1H), 7.98-7.91 (m, 2H), 7.77-7.66 (m, 2H), 7.40 (m, 5H), 7.25 (s, 1H), 6.83 (s, 1H), 5.15 (d, J=3.5 Hz, 1H), 4.56 (d, J=9.5 Hz, 1H), 4.48-4.37 (m, 2H), 4.35 (s, 1H), 4.24 (dd, J=15.7, 5.6 Hz, 1H), 4.10 (t, J=6.3 Hz, 2H), 3.96 (s, 2H), 3.78 (s, 3H), 3.70-3.42 (m, 22H), 3.38 (t, J=6.5 Hz, 2H), 2.44 (s, 2H), 2.34 (s, 3H), 2.09 (s, 3H), 2.04 (d, J=8.0 Hz, 1H), 1.90 (ddd, J=13.0, 8.8, 4.5 Hz, 1H), 1.77 (p, J=6.7 Hz, 2H), 1.49 (dp, J=29.1, 7.1 Hz, 4H), 1.38 (q, J=7.7 Hz, 2H), 1.30 (s, 9H), 0.94 (s, 9H). $^{13}$C NMR (126 MHz, DMSO-$d_6$) δ 172.24, 169.59, 169.05, 159.96, 157.80, 153.37, 151.92, 148.21, 143.36, 139.92, 139.24, 138.43, 131.61, 130.16, 129.76, 129.15, 127.92, 127.64, 127.14, 118.54, 114.81, 97.47, 70.93, 70.71, 70.31, 70.26, 70.22, 70.06, 69.97, 69.35, 68.61, 59.21, 57.05, 56.70, 56.15, 42.14, 38.39, 36.19, 35.52, 31.17, 29.65, 29.05, 26.64, 25.90, 25.86, 16.39, 15.30, 9.04. ESI-TOF HRMS: m/z 1206.5841 ($C_{61}H_{88}N_7O_{14}S_2$+$H^+$ requires 1206.5825).

u. Compound 35

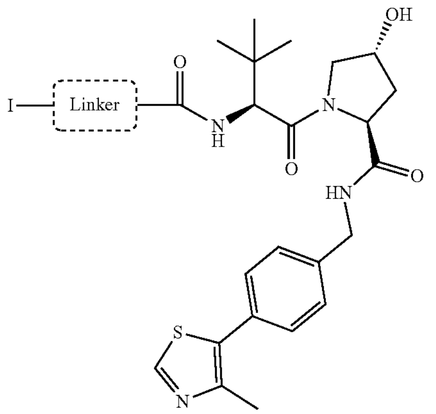

60

+

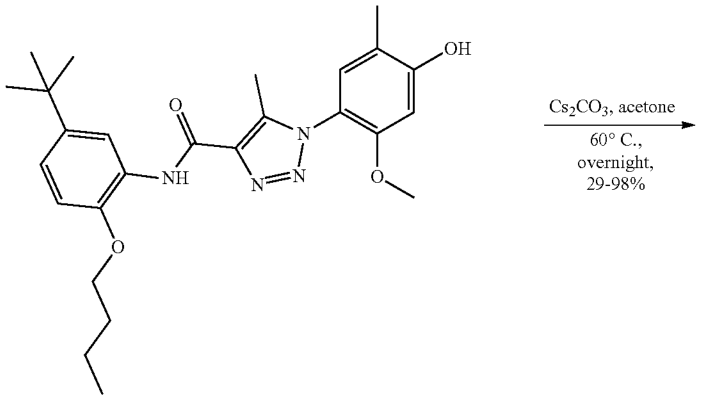

102

-continued

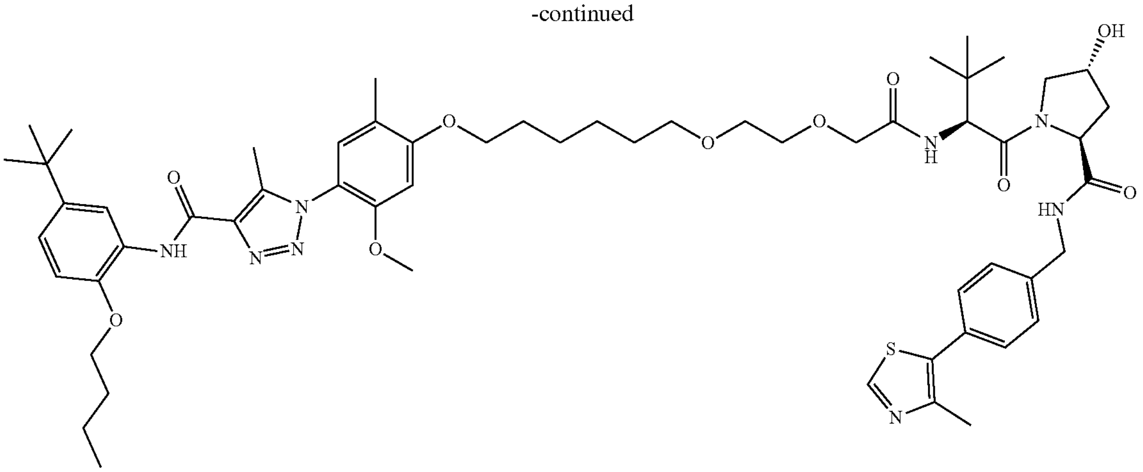

35

N-(2-Butoxy-5-(tert-butyl)phenyl)-1-(4-((6-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)hexyl)oxy)-2-methoxy-5-methylphenyl)-5-methyl-1H-1,2,3-triazole-4-carboxamide (35). To a solution of compound 59 (100 mg, 0.154 mmol) in acetone (10 mL) was added NaI (115 mg, 0.768 mmol). The reaction mixture was stirred under reflux for 24 h, the solvent was removed under vacuum, crude product was dissolved in EtOAc (15 mL) and an aqueous solution of $Na_2SO_3$ (10%, 10 mL), and the organic layer was separated, washed with water (10 mL), dried ($Na_2SO_4$), and evaporated under vacuum. It was used in the next step without any further purification. To the residue was added acetone (5 mL), cesium carbonate (0.100 g, 0.308 mmol), and compound 102 (0.072 g, 0.154 mmol). The suspension was stirred at 60° C. overnight. The reaction mixture was diluted with water (50 mL) and extracted with EtOAc (50 mL×2). The EtOAc layers were washed with water (50 mL), dried with anhydrous $Na_2SO_4$, and concentrated. The residue was purified by C18 silica gel chromatography (0%-100% acetonitrile in water) to give product as a white solid [49.3 mg, 29.5% yield (two steps), 99% purity]. $^1H$ NMR (500 MHz, DMSO-$d_6$) δ 9.64 (s, 1H), 8.97 (s, 1H), 8.60 (t, J=6.1 Hz, 1H), 8.46 (d, J=2.3 Hz, 1H), 7.46-7.33 (m, 5H), 7.25 (s, 1H), 7.09 (dd, J=8.6, 2.4 Hz, 1H), 7.02 (d, J=8.6 Hz, 1H), 6.83 (s, 1H), 5.15 (d, J=3.5 Hz, 1H), 4.57 (d, J=9.6 Hz, 1H), 4.47-4.37 (m, 2H), 4.35 (s, 1H), 4.24 (dd, J=15.8, 5.6 Hz, 1H), 4.14-4.06 (m, 4H), 3.97 (s, 2H), 3.80 (s, 3H), 3.70-3.64 (m, 1H), 3.64-3.58 (m, 3H), 3.56-3.51 (m, 2H), 3.48-3.40 (m, 2H), 2.43 (s, 3H), 2.37 (s, 3H), 2.12 (s, 3H), 2.07-2.03 (m, 1H), 1.90 (ddd, J=13.0, 8.9, 4.5 Hz, 1H), 1.82-1.71 (m, 4H), 1.55 (h, J=7.3, 6.9 Hz, 4H), 1.42 (dh, J=29.4, 7.3 Hz, 3H), 1.28 (s, 9H), 0.99-0.91 (m, 12H). $^{13}C$ NMR (126 MHz, DMSO-$d_6$) δ 171.77, 169.11, 168.57, 159.25, 158.53, 152.91, 151.43, 147.72, 145.34, 142.93, 139.45, 138.92, 137.18, 131.13, 129.67, 129.18, 128.67, 127.44, 126.80, 120.43, 118.01, 116.26, 114.97, 111.48, 97.04, 70.52, 70.41, 69.60, 69.26, 68.88, 68.11, 68.09, 58.75, 56.57, 56.18, 55.65, 41.66, 37.92, 35.68, 34.05, 31.35, 30.78, 29.14, 28.61, 26.16, 25.45, 25.38, 18.68, 15.91, 14.88, 13.70, 8.74. ESI-TOF HRMS: m/z 1081.5803 ($C_{58}H_{81}N_8O_{10}S+H^+$ requires 1081.5791).

v. Compound 36

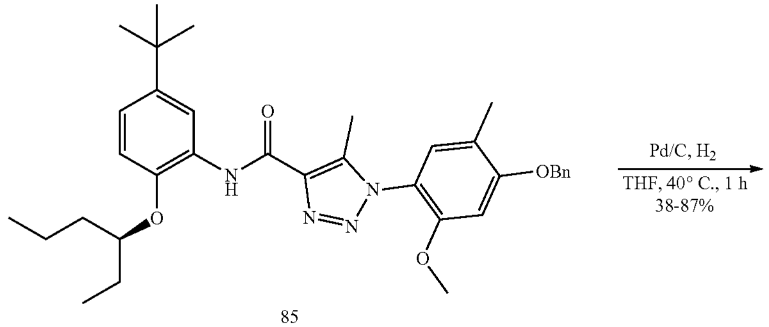

85

-continued

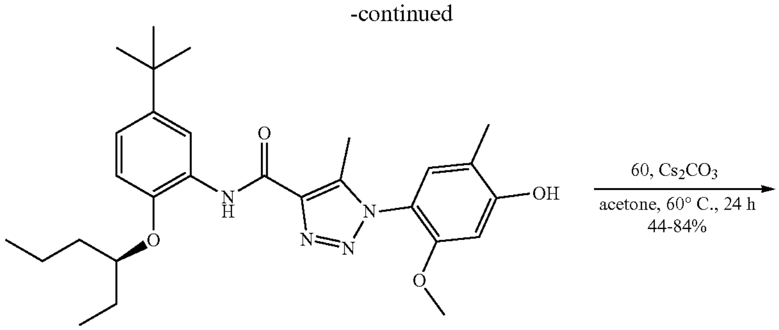

86

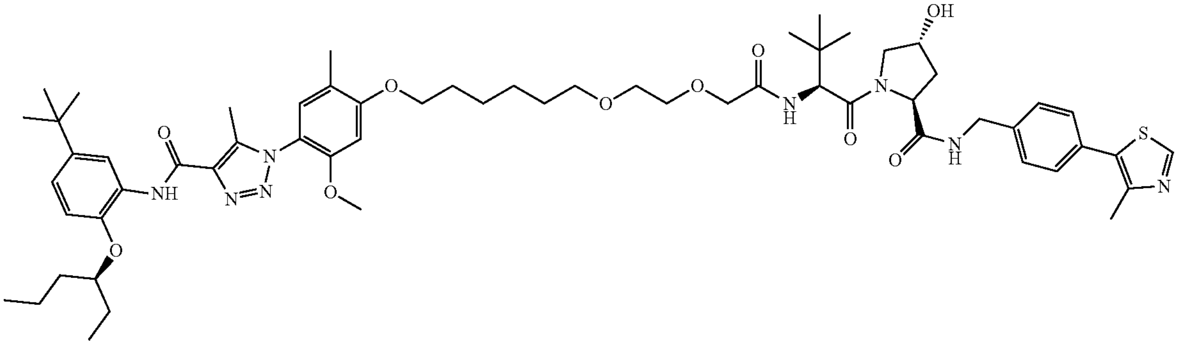

36 i. (S)-1-(4-(BENZYLOXY)-2-METHOXY-5-METHYLPHENYL)-N-(5-(TERT-BUTYL)-2-(HEXAN-3-YLOXY)PHENYL)-5-METHYL-1H-1,2,3-TRIAZOLE-4-CARBOXAMIDE (85)

Compound 85 (35 mg, 38.5% yield) was synthesized by using a procedure similar to that described for compound 51; $^1$H NMR (500 MHz, $CDCl_3$) δ 8.65 (d, J=2.35 Hz, 1H), 7.47 (d, J=6.70 Hz, 2H), 7.42 (t, J=7.85 Hz, 2H), 7.38-7.35 (m, 1H), 7.16 (s, 1H), 7.04 (dd, J=8.55, 2.45 Hz, 1H), 6.84 (d, J=8.55 Hz, 1H), 6.60 (s, 1H), 5.17 (s, 2H), 4.26 (p, J=5.8 Hz, 1H), 3.73 (s, 3H), 2.50 (s, 3H), 2.26 (s, 3H), 1.81-1.64 (m, 4H), 1.53-1.44 (m, 2H), 1.35 (s, 9H), 1.00 (t, J=7.40 Hz, 3H), 0.94 (t, J=7.35 Hz, 3H). $^{13}$C NMR (126 MHz, $CDCl_3$) δ 160.34, 159.23, 152.13, 145.17, 143.70, 139.17, 138.51, 136.64, 129.86, 128.86, 128.56, 128.31, 127.29, 120.09, 119.83, 117.13, 116.58, 112.17, 97.06, 80.41, 70.58, 56.13, 35.63, 34.57, 31.73, 26.69, 18.82, 15.55, 14.36, 9.70, 9.42. LCMS: m/z=585.72 $[M+H]^+$.

ii. (S)—N-(5-(TERT-BUTYL)-2-(HEXAN-3-YLOXY)PHENYL)-1-(4-HYDROXY-2-METHOXY-5-METHYLPHENYL)-5-METHYL-1H-1,2,3-TRIAZOLE-4-CARBOXAMIDE (86)

Compound 86 (4.9 mg, 44.5% yield) was synthesized by using a procedure similar to that described for compound 52; $^1$H NMR (500 MHz, $CD_3OD$) δ 8.53 (d, J=2.35 Hz, 1H), 7.11-7.08 (m, 2H), 6.96-6.93 (m, 1H), 6.64 (s, 1H), 4.35 (p, J=5.75 Hz, 1H), 3.75 (s, 3H), 2.43 (s, 3H), 2.18 (s, 3H), 1.79-1.64 (m, 4H), 1.55-1.43 (m, 2H), 1.33 (s, 9H), 1.02-0.99 (m, 3H), 0.96-0.92 (m, 3H). $^{13}$C NMR (126 MHz, $CD_3OD$) δ 160.94, 159.96, 154.57, 146.54, 144.81, 140.72, 138.95, 130.79, 129.01, 121.88, 118.39, 118.16, 116.18, 113.88, 100.10, 81.58, 56.36, 36.77, 35.27, 31.99, 31.97, 27.66, 19.64, 15.18, 14.55, 9.82, 9.30; ESI-TOF HRMS: m/z 495.2968 ($C_{28}H_{39}N_4O_4$+$H^+$ requires 495.2971).

iii. N-(5-(TERT-BUTYL)-2-(((S)-HEXAN-3-YL)OXY)PHENYL)-1-(4-((6-(2-(2-(((S)-1-((2S,4R)-4-HYDROXY-2-((4-(4-METHYLTHIAZOL-5-YL)BENZYL)CARBAMOYL)PYRROLIDIN-1-YL)-3,3-DIMETHYL-1-OXOBUTAN-2-YL)AMINO)-2-OXOETHOXY)ETHOXY)HEXYL)OXY)-2-METHOXY-5-METHYLPHENYL)-5-METHYL-1H-1,2,3-TRIAZOLE-4-CARBOXAMIDE (36)

To a solution of compound 86 (20 mg, 0.040 mmol) and cesium carbonate (15.81 mg, 0.049 mmol) in acetone (5 mL) was added compound 60 (45.0 mg, 0.061 mmol) at room temperature under $N_2$ atmosphere. The reaction mixture was stirred at 60° C. overnight. The mixture was poured into water (10 mL) and extracted with EtOAc (10 mL×3), and the combined organic layer was dried ($Na_2SO_4$), filtered, and evaporated under reduced pressure. The residue was purified by reversed-phase flash chromatography (running a gradient of 0%-100% acetonitrile in water) to give compound 36, (38 mg, 84% yield, 100% purity). $^1$H NMR (500 MHz, $CD_3OD$): δ 8.85 (s, 1H), 8.53 (d, J=2.40 Hz, 2H), 7.45 (d, J=2.40 Hz, 2H), 7.40 (d, J=2.40 Hz, 1H), 7.14 (m, 1H), 7.10 (dd, J=8.55, 2.40 Hz, 1H), 6.95 (d, J=8.65 Hz, 1H), 6.76 (s, 1H), 4.69 (s, 1H), 4.59-4.55 (m, 2H), 4.51-4.49 (m, 2H), 4.38-4.36 (m, 2H), 4.12-4.08 (m, 2H), 4.04 (d, J=1.55 Hz, 2H), 3.89-3.86 (m, 1H), 3.82 (s, 3H), 3.72-3.70 (m, 2H), 3.64-3.63 (m, 2H), 3.56-3.52 (m, 2H), 2.46 (s, 3H), 2.43 (s, 3H), 2.20-2.16 (m, 4H), 2.11-2.06 (m, 1H), 1.86-1.83 (m, 2H), 1.80-1.74 (m, 3H), 1.69-1.64 (m, 3H), 1.57-1.46 (m, 6H), 1.34 (s, 9H), 1.05 (s, 9H), 1.03-1.00 (m, 3H), 0.95 (t, J=7.35 Hz, 3H). $^{13}$C NMR (126 MHz, $CD_3OD$) δ 174.37, 172.10, 171.69, 161.34, 160.93, 154.83, 152.82, 149.03, 146.58, 144.85, 140.73, 140.24, 138.99, 131.48, 130.38, 130.35, 129.03, 128.92, 121.91, 120.28, 118.18, 116.72, 113.91, 97.56, 81.62, 72.40, 72.33, 71.09, 71.07, 69.56, 60.81, 58.15, 58.10, 56.69, 43.70, 38.95, 37.06, 36.79, 35.29, 31.99, 31.74, 30.68, 30.33, 30.28, 27.69, 27.11, 26.99, 19.66, 15.86, 15.46, 14.55, 9.82, 9.32. ESI-TOF HRMS: m/z 1109.6105 ($C_{60}H_{85}N_8O_{10}S+H^+$ requires 1109.6110).

w. Compound 37

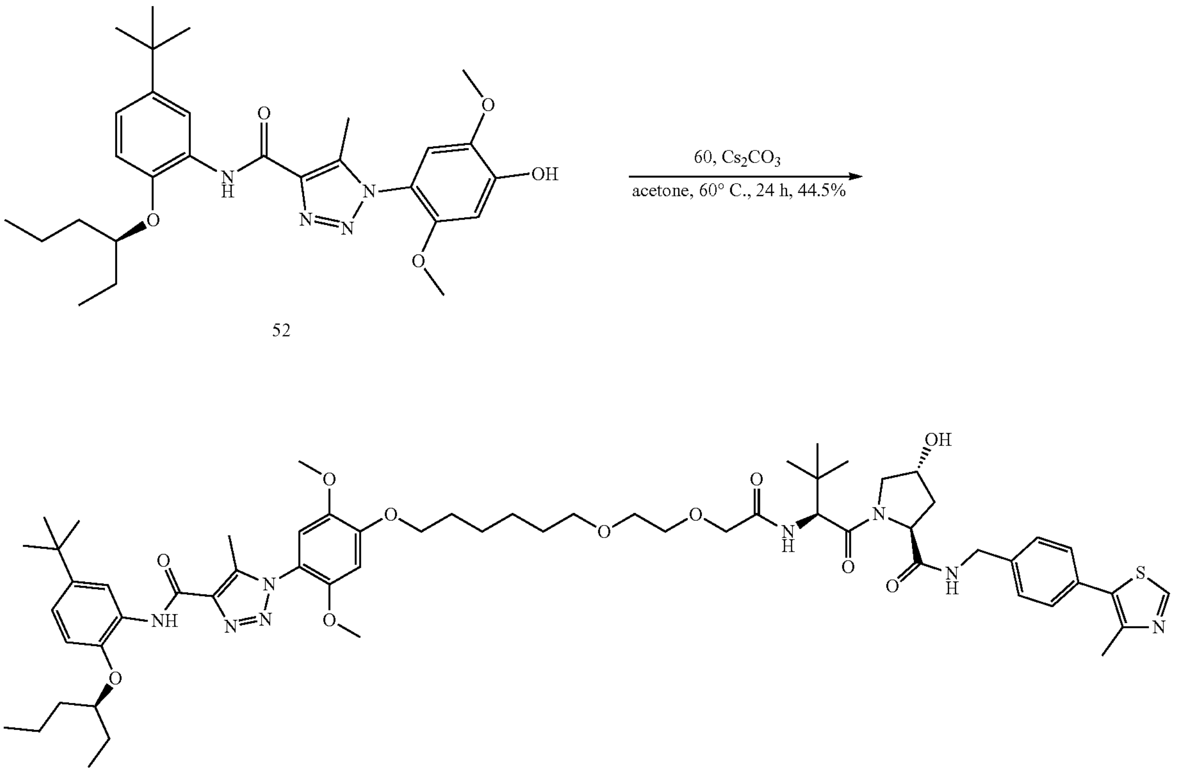

52

37 i. N-(5-(TERT-BUTYL)-2-(((S)-HEXAN-3-YL)OXY)PHENYL)-1-(4-((6-(2-(2-(((S)-1-((2S,4R)-4-HYDROXY-2-((4-(4 METHYLTHIAZOL-5-YL)BENZYL)CARBAMOYL)PYRROLIDIN-1-YL)-3,3-DIMETHYL-1-OXOBUTAN-2-YL)AMINO)-2 OXOETHOXY)ETHOXY)HEXYL)OXY)-2,5-DI-METHOXYPHENYL)-5-METHYL-1H-1,2,3-TRI-AZOLE-4-CARBOXAMIDE (37)

To a solution of 52 (5 mg, 9.79 μmol) and cesium carbonate (3.83 mg, 0.012 mmol) in acetone (5 mL) was added 60 (14.54 mg, 0.020 mmol) at room temperature under $N_2$ atmosphere. The reaction mixture was stirred at 60° C. overnight. The reaction mixture was poured into water (10 mL) and extracted with EtOAc (10 mL×3), and the combined organic layer was dried ($Na_2SO_4$), filtered, and evaporated under reduced pressure. The residue was purified by reversed-phase flash chromatography (running a gradient of 0%-100% acetonitrile in water) to give compound 37 (4.9 mg, 44.5% yield, 99% purity). $^1$H NMR (500 MHz, $CDCl_3$): δ 8.67 (s, 1H), 8.53 (d, J=2.40 Hz, 1H), 7.37-7.32 (m, 4H), 7.04 (dd, J=8.55, 2.40 Hz, 1H), 6.90 (s, 1H), 6.84 (d, J=8.65 Hz, 1H), 6.64 (s, 1H), 4.74 (t, J=7.90 Hz, 1H), 4.58-4.52 (m, 2H), 4.45 (d, J=8.40 Hz, 1H), 4.33 (dd, J=14.95, 5.30 Hz, 1H), 4.26 (p, J=5.85 Hz, 1H), 4.14-4.11 (m, 2H), 4.09-4.04 (m, 2H), 4.00 (d, J=8.85 Hz, 1H), 3.82 (s, 3H), 3.74 (s, 3H), 3.69-3.66 (m, 2H), 3.61-3.58 (m, 2H), 3.48 (td, J=6.70, 2.20 Hz, 2H), 2.61-2.56 (m, 1H), 2.51 (s, 3H), 2.51 (s, 3H), 2.13-2.09 (m, 1H), 1.79-1.74 (m, 3H), 1.68-1.62 (m, 4H), 1.53-1.42 (m, 6H), 1.35 (s, 9H), 1.25 (t, J=7.20 Hz, 2H), 1.00 (t, J=7.45 Hz, 3H), 0.95 (s, 9H), 0.93 (t, J=7.3 Hz, 3H). $^{13}$C NMR (126 MHz, CDCl3) δ 171.64, 171.32, 170.78, 170.69, 159.59, 151.26, 150.44, 148.62, 148.57, 145.15, 143.73, 143.67, 139.35, 138.60, 138.22, 131.73, 131.12, 129.67, 128.49, 128.30, 120.17, 117.12, 115.91, 112.16, 99.10, 80.38, 71.61, 71.36, 70.47, 70.31, 70.01, 69.57, 60.55, 58.39, 57.40, 56.86, 56.73, 56.69, 43.41, 35.80, 35.63, 34.77, 34.57, 31.73, 29.62, 29.23, 26.70, 26.55, 26.05, 26.00, 21.20, 18.82, 16.20, 14.37, 14.34, 9.70, 9.46; ESI-TOF HRMS: m/z 1125.6110 ($C_{60}H_{85}N_8O_{11}S+H^+$ requires 1125.6060).

x. Compound 38

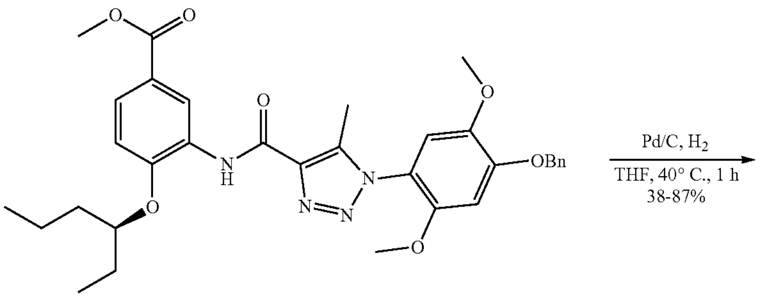

55

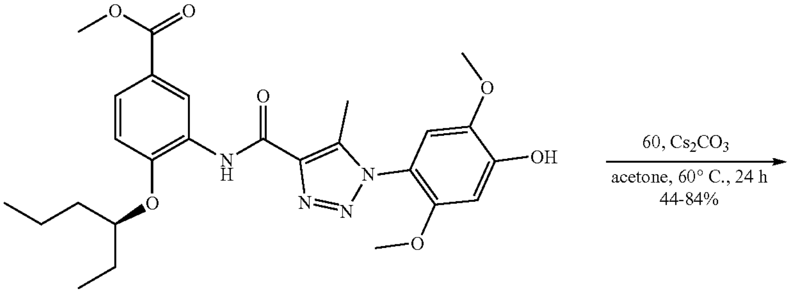

56

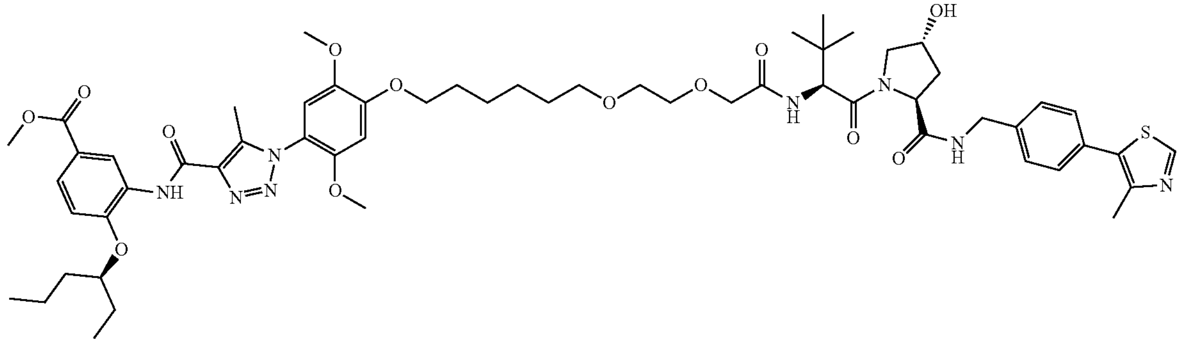

38 i. METHYL (S)-3-(1-(4-(BENZYLOXY)-2,5-DI-METHOXYPHENYL)-5-METHYL-1H-1,2,3-TRI-AZOLE-4-CARBOXAMIDO)-4-(HEXAN-3-YLOXY)BENZOATE (55)

To a solution of 50 (601 mg, 1.627 mmol) in DMF (5 mL) was added HATU (928 mg, 2.441 mmol), and the mixture was stirred at 25° C. for 30 min. Methyl (S)-3-amino-4-(hexan-3-yloxy)benzoate (613 mg, 2.441 mmol) and DIPEA (425 μL, 2.441 mmol) were added to the reaction mixture and stirred at 25° C. for 4 h. LCMS showed the starting material was consumed completely and desired compound was formed. The reaction mixture was poured into brine (10 mL) and extracted with EtOAc (10 mL×3), and the combined organic layer was dried ($Na_2SO_4$), filtered, and evaporated under reduced pressure. The residue was purified by reversed-phase flash chromatography (running a gradient of 0%-100% EtOAc in hexane over 16 min) to give compound 55 (412 mg, 42% yield). $^1$H NMR (500 MHz, $CDCl_3$) δ 7.80 (dd, J=8.55, 2.15 Hz, 1H), 7.48-7.46 (m, 2H), 7.40 (t, J=7.85 Hz, 2H), 7.36-7.33 (m, 1H), 6.94-6.93 (m, 2H), 6.67 (s, 1H), 5.24 (s, 2H), 4.41 (p, J=5.9 Hz, 1H), 3.89 (s, 3H), 3.86 (s, 3H), 3.66 (s, 3H), 2.79 (s, 3H), 1.85-1.76 (m, 3H), 1.74-1.68 (m, 1H), 1.53-1.41 (m, 2H), 1.01 (t, J=7.45 Hz, 3H), 0.94 (t, J=7.35 Hz, 3H). $^{13}$C NMR (126 MHz, $CDCl_3$) δ 167.12, 159.61, 151.05, 150.77, 148.35, 144.00, 139.69, 138.27, 136.38, 128.90, 128.43, 128.30, 127.50, 126.18, 122.57, 120.71, 116.25, 112.19, 111.68, 100.39, 80.62, 71.76, 56.88, 56.53, 52.05, 35.45, 29.83, 26.61, 18.71, 14.27, 9.57, 9.40. LCMS: m/z=603.62 $[M+H]^+$.

ii. METHYL (S)-4-(HEXAN-3-YLOXY)-3-(1-(4-HYDROXY-2,5-DIMETHOXYPHENYL)-5-METHYL-1H-1,2,3-TRIAZOLE-4-CARBOX-AMIDO)BENZOATE (56)

To a solution of 55 (2.39 g, 3.98 mmol) in THF (10 mL) was added Pd/C (2.11 g, 19.9 mmol). The suspension was degassed under vacuum and purged with $H_2$ three times. The mixture was stirred under $H_2$ at 40° C. for 1 h, filtrated from a pad of the celite, and the cake was washed with THF (50 mL). The filtrate was evaporated under reduced pressure, and the residue was purified by reversed-phase flash chromatography (running a gradient of 0%-5% methanol in dichloromethane) to give compound 56 (1.77 g, 87% yield). $^1$H NMR (500 MHz, $CD_3OD$) δ 7.80 (dd, J=8.65, 2.15 Hz, 1H), 7.74 (s, 1H), 7.07 (d, J=8.75, 1H), 6.95 (s, 1H), 6.73 (s, 1H), 4.41 (p, J=5.7 Hz, 1H), 3.89 (s, 3H), 3.84 (s, 3H), 3.74 (s, 3H), 2.47 (s, 3H), 1.86-1.78 (m, 3H), 1.76-1.69 (m, 1H), 1.55-1.43 (m, 2H), 1.02 (t, J=7.45 Hz, 3H), 0.95 (t, J=7.40 Hz, 3H). $^{13}$C NMR (126 MHz, $CD_3OD$) δ 168.25, 160.70, 152.31, 150.99, 150.05, 142.73, 140.89, 138.57, 128.82, 127.19, 123.05, 121.58, 114.98, 112.78, 112.76, 101.49, 81.54, 57.20, 56.68, 54.42, 52.44, 36.30, 27.33, 19.35, 14.44, 9.69; ESI-TOF HRMS: m/z 513.2335 ($C_{26}H_{33}N_4O_7$+$H^+$ requires 513.2349).

iii. METHYL 4-(((S)-HEXAN-3-YL)OXY)-3-(1-(4-((6-(2-(2-(((S)-1-((2S,4R)-4-HYDROXY-2-((4-(4-METHYLTHIAZOL-5-YL)BENZYL)CARBAMOYL)PYRROLIDIN-1-YL)-3,3-DIMETHYL-1-OXOBUTAN-2-YL)AMINO)-2-OXOETHOXY)ETHOXY)HEXYL)OXY)-2,5-DIMETHOXYPHENYL)-5-METHYL-1H-1,2,3-TRIAZOLE-4-CARBOXAMIDO)BENZOATE (38)

Compound 38 (504 mg, 52.7% yield, 100% purity) was synthesized by using a procedure similar to that described for compound 37; $^1$H NMR (500 MHz, $CDCl_3$): δ 9.17 (d, J=2.15 Hz, 1H), 8.67 (s, 1H), 7.80 (dd, J=8.55, 2.15 Hz, 1H), 7.40-7.32 (m, 4H), 6.93 (d, J=8.75 Hz, 1H), 6.89 (s, 1H), 6.64 (s, 1H), 4.72 (t, J=7.85 Hz, 1H), 4.56-4.52 (m, 2H), 4.46-4.40 (m, 2H), 4.33 (dd, J=15.00, 5.30 Hz, 1H), 4.11-4.03 (m, 3H), 3.99 (d, J=8.75 Hz, 1H), 3.89 (s, 3H), 3.82 (s, 3H), 3.75 (s, 3H), 3.68-3.58 (m, 5H), 3.50-3.46 (m, 3H), 2.51-2.50 (m, 6H), 2.13-2.08 (m, 1H), 1.91-1.76 (m, 5H), 1.73-1.60 (m, 4H), 1.54-1.40 (m, 7H), 1.25-1.19 (m, 1H), 1.01 (t, J=7.50 Hz, 3H), 0.95 (s, 9H), 0.94 (t, J=7.35 Hz, 2H); $^{13}$C NMR (126 MHz, $CDCl_3$) δ 171.40, 170.91, 170.58, 167.11, 159.60, 151.31, 151.04, 150.41, 148.54, 143.62, 139.68, 138.24, 138.22, 131.71, 130.99, 129.59, 128.27, 128.17, 126.17, 122.52, 120.69, 115.68, 112.08, 111.66, 98.99, 80.60, 71.57, 71.32, 70.42, 70.22, 69.95, 69.53, 58.61, 57.27, 56.84, 56.77, 56.64, 52.04, 43.30, 36.10, 35.42, 35.03, 29.58, 29.19, 26.58, 26.51, 26.01, 25.96, 18.68, 16.16, 14.25, 9.55, 9.38; ESI-TOF HRMS: m/z 1127.5563 ($C_{58}H_{79}N_8O_{13}S$+$H^+$ requires 1127.5490).

y. Compound 39

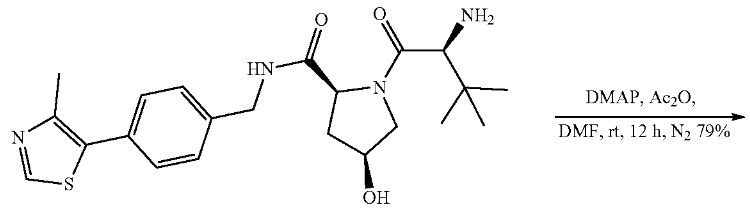

58

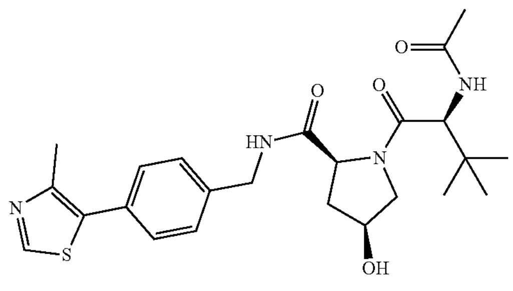

39 i. (2S,4S)-1-((S)-2-ACETAMIDO-3,3-DIIETHYLBUTANOYL)-4-HYDROXY-N-(4-(4-METHYLTHIAZOL-5-YL)BENZYL)PYRROLIDINE-2-CARBOXAMIDE (39)

To a mixture of VHL ligand (58, 48 mg, 0.111 mmol) and DMAP (16 mg, 0.134 mmol) in DMF (5 mL) was added acetic anhydride (13 mL, 0.134 mmol) dropwise under $N_2$ atmosphere. The reaction mixture was stirred at room temperature for 12 h, poured into brine (10 mL) and extracted with EtOAc (10 mL×3), and the combined organic layer was dried ($Na_2SO_4$), filtered, and evaporated under reduced pressure. The residue was purified by reversed-phase flash chromatography (running a gradient of 0%-100% acetonitrile in water over 16 min) to yield compound 39 (42 mg, 79% yield, 97% purity); $^1H$ NMR (500 MHz, $CD_3OD$): δ 8.87 (s, 1H), 7.46-7.40 (m, 4H), 4.52-4.48 (m, 2H), 4.39-4.35 (m, 2H), 4.03 (dd, J=13.25, 6.04 Hz, 1H), 3.69 (dd, J=13.20, 4.80 Hz, 1H), 3.34 (s, 1H), 2.47 (s, 3H), 2.46-2.38 (m, 1H), 2.15 (s, 1H), 1.98 (s, 3H), 1.03 (s, 9H); $^{13}C$ NMR (101 MHz, $CD_3OD$) δ 174.90, 173.41, 172.65, 152.86, 149.06, 140.04, 133.38, 131.61, 130.40, 129.04, 71.50, 60.99, 59.53, 57.61, 43.82, 37.87, 35.87, 26.97, 22.17, 15.81; ESI-TOF HRMS: m/z 473.2207 ($C_{24}H_{33}N_4O_4S+H^+$ requires 473.2222).

z. Compound 40

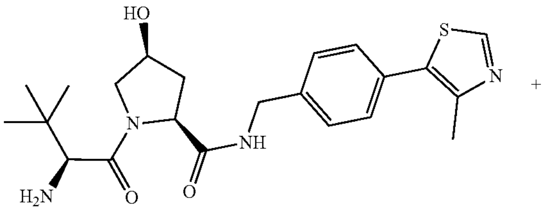

87

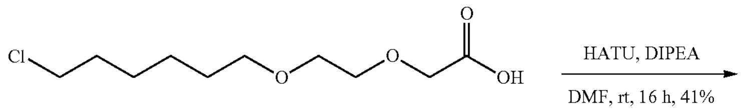

88

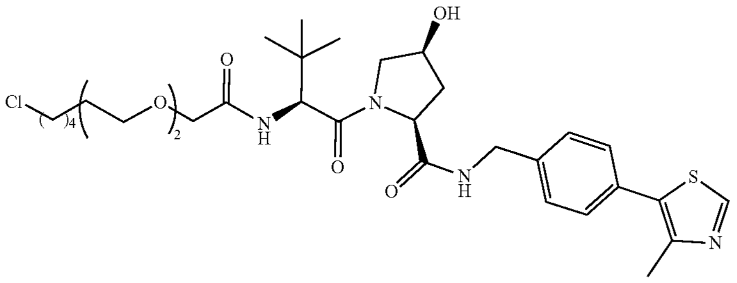

57

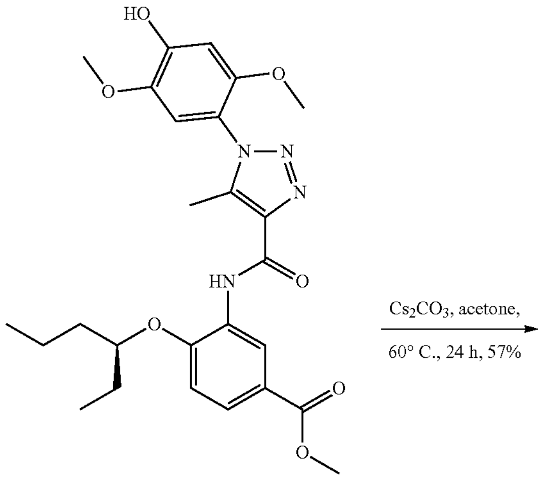

56

-continued

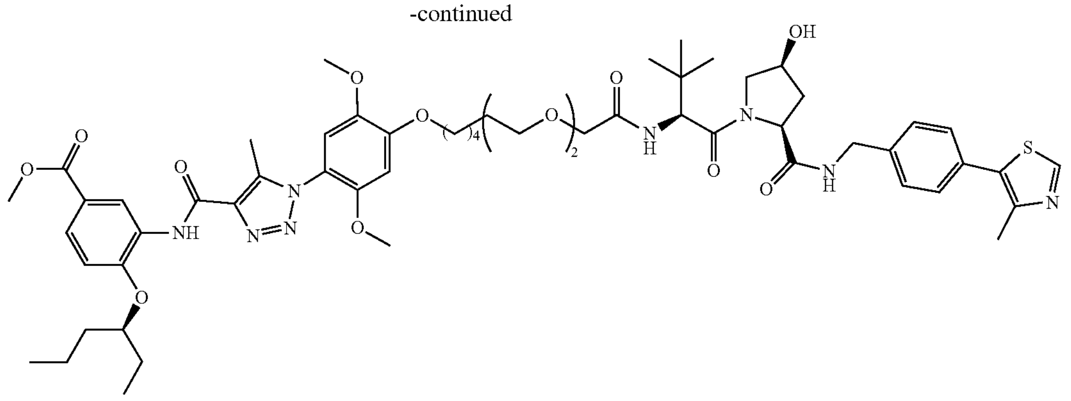

40 i. (2S,4S)-1-((S)-2-(2-(2-((6-CHLOROHEXYL)OXY)ETHOXY)ACETAMIDO)-3,3-DIMETHYLBUTANOYL)-4-HYDROXY-N-(4-(4-METHYLTHIAZOL-5-YL)BENZYL)PYRROLIDINE-2-CARBOXAMIDE (57)

Compound 57 (52 mg, 41.3% yield) was synthesized by using a procedure similar to that described for compound 51; $^1$H NMR (500 MHz, $CDCl_3$): δ 8.69 (s, 1H), 7.51 (t, J=6.15 Hz, 1H), 7.37 (d, J=8.25 Hz, 1H), 7.34 (d, J=8.40 Hz, 1H), 7.18 (d, J=9.00 Hz, 1H), 4.75 (d, J=8.95 Hz, 1H), 4.64 (dd, J=14.90, 7.05 Hz, 1H), 4.52-4.48 (m, 1H), 4.30 (dd, J=15.00, 5.05 Hz, 1H), 4.15 (s, 1H), 4.04-3.92 (m, 2H), 3.81-3.75 (m, 1H), 3.67-3.45 (m, 8H), 2.52 (s, 3H), 2.20-2.14 (m, 1H), 1.79-1.72 (m, 3H), 1.65-1.56 (m, 3H), 1.47-1.33 (m, 4H), 0.93 (s, 9H); $^{13}$C NMR (126 MHz, $CDCl_3$) δ 172.67, 172.01, 170.04, 150.58, 148.65, 137.47, 131.65, 131.38, 129.78, 128.35, 71.74, 71.72, 71.52, 71.38, 71.23, 70.55, 69.94, 69.66, 69.14, 60.03, 58.83, 56.64, 45.18, 45.16, 43.66, 35.10, 35.09, 32.64, 29.50, 26.82, 25.53, 16.17; LCMS: m/z=651.82 [M+H]$^+$.

ii. METHYL 4-(((S)-HEXAN-3-YL)OXY)-3-(1-(4-((6-(2-(2-(((S)-1-((2S,4S)-4-HYDROXY-2-((4-(4-METHYLTHIAZOL-5-YL)BENZYL)CARBAMOYL)PYRROLIDIN-1-YL)-3,3-DIMETHYL-1-OXOBUTAN-2-YL)AMINO)-2-OXOETHOXY)ETHOXY)HEXYL)OXY)-2,5-DIMETHOXYPHENYL)-5-METHYL-1H-1,2,3-TRIAZOLE-4-CARBOXAMIDO)BENZOATE (40)

Compound 40 (9.9 mg, 57% yield, 100% purity) was synthesized by using a procedure similar to that described for compound 37; $^1$H NMR (500 MHz, $CDCl_3$): δ 9.18 (s, 1H), 8.68 (s, 1H), 7.80 (d, J=8.55, 1H), 7.38-7.33 (m, 4H), 6.94 (d, J=8.60 Hz, 1H), 6.90 (s, 1H), 6.64 (s, 1H), 4.73 (d, J=9.00 Hz, 1H), 4.64 (dd, J=14.95, 7.05 Hz, 1H), 4.52 (d, J=9.05 Hz, 1H), 4.49-4.46 (m, 1H), 4.44-4.39 (m, 1H), 4.30 (dd, J=14.95, 5.05 Hz, 1H), 4.08-4.05 (m, 2H), 4.00 (d, J=8.65 Hz, 1H), 3.93 (dd, J=14.95, 5.05 Hz, 1H), 3.89 (s, 3H), 3.82 (s, 3H), 3.75 (s, 3H), 3.68-3.97 (m, 2H), 3.61-3.59 (m, 2H), 3.48 (t, J=6.65 Hz, 2H), 2.51 (s, 6H), 2.36 (d, J=14.2 Hz, 1H), 2.20-2.14 (m, 1H), 1.92-1.86 (m, 2H), 1.83-1.77 (m, 3H), 1.73-1.59 (m, 6H), 1.54-1.42 (m, 6H), 1.01 (t, J=7.35 Hz, 3H), 0.94 (s, 9H), 0.96-0.93 (m, 2H); $^{13}$C NMR (126 MHz, $CDCl_3$) δ 172.71, 171.96, 169.97, 167.14, 159.64, 151.31, 151.07, 150.51, 148.70, 148.56, 143.68, 139.71, 138.29, 137.47, 131.61, 131.41, 129.78, 128.34, 128.31, 126.21, 122.59, 120.72, 115.79, 112.10, 111.69, 99.03, 80.64, 71.62, 71.37, 71.25, 70.61, 70.03, 69.58, 60.04, 58.82, 56.85, 56.68, 56.60, 52.08, 43.66, 35.47, 35.15, 29.64, 29.23, 26.63, 26.46, 26.07, 26.01, 18.73, 16.22, 14.29, 9.60, 9.42; ESI-TOF HRMS: m/z 1127.5533 ($C_{58}H_{79}N_8O_{13}S+H^+$ requires 1127.5490).

aa. Intermediate Compound 92

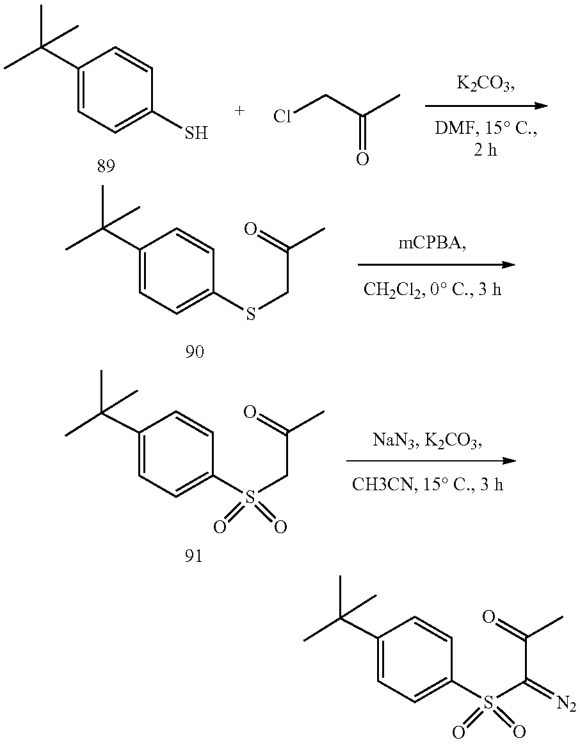

iii. 1-((4-(TERT-BUTYL)PHENYL)THIO)PROPAN-2-ONE (90)

To a solution of compound 89 (500 g, 3.01 mol) and 1-chloropropan-2-one (301 g, 3.26 mol) in DMF (3.33 L)

was added $K_2CO_3$ (831 g, 6.01 mol), and the mixture was stirred at 15° C. for 2 h. LCMS showed compound 89 was consumed completely. The reaction mixture was poured into water (1.50 L) and extracted with EtOAc (1.50 L×2). The combined organic phase was dried over anhydrous $Na_2SO_4$ and concentrated under reduced pressure to give compound 90 (640 g, 2.88 mol, 95.7% yield) as a yellow oil. The mixture was used in the next step without further purification; MS (ESI) m/z=223.1 $[M+H]^+$.

iv. 1-((4-(TERT-BUTYL)PHENYL)SULFONYL)PROPAN-2-ONE (91)

To a solution of compound 90 (320 g, 1.44 mol) in $CH_2Cl_2$ (3.36 L), m-CPBA (613 g, 3.02 mol, 85.0% purity) was added over the course of 3 h at 0° C., then the mixture was stirred at −20° C. for 3 h. LCMS showed compound 90 was consumed completely. $K_2CO_3$ (198 g, 1.44 mol) was added to the mixture at 0° C., and the mixture was stirred at 25° C. for 12 h. The mixture was filtered and concentrated under reduced pressure, and the crude product was purified by column chromatography of silica gel (10:1 petroleum ether:EtOAc) to give compound 91 (300 g, 1.18 mol, 81.9% yield) as a yellow solid; $^1H$ NMR (400 MHz, $CDCl_3$) δ 7.81-7.79 (d, J=8.8 Hz, 2H), 7.58-7.56 (d, J=8.4 Hz, 2H), 4.14 (s, 2H), 2.42 (s, 3H), 1.34 (s, 9H); MS (ESI) m/z=255.1 $[M+H]^+$.

v. 1-((4-(TERT-BUTYL)PHENYL)SULFONYL)-1-DIAZOPROPAN-2-ONE (92)

To a solution of compound 91 (40.0 g, 157 mmol), $K_2CO_3$ (86.9 g, 629 mmol), $NaN_3$ (11.3 g, 174 mmol), and acetonitrile (300 mL) in water (400 mL) was added 3-chlorosulfonylbenzoic acid (38.1 g, 172 mmol) at 15° C. The mixture was stirred at 25° C. for 3 h. LCMS showed the starting material was consumed completely and desired compound was formed. The mixture was poured into water (400 mL) and extracted with EtOAc (300 mL×2), and the organic phase was concentrated under reduced pressure. The residue was purified by column chromatography (SiO2, 3:1 petroleum ether:EtOAc) to give compound 92 (158 g, 94.5 mmol, 60.1% yield) as a yellow solid; $^1H$ NMR (400 MHz, $CDCl_3$) δ 7.90-7.85 (m, 2H), 7.60-7.58 (m, 2H), 2.31 (s, 3H), 1.36 (s, 9H); MS (ESI) m/z=281.1 $[M+H]^+$.

bb. Intermediate Compound 98

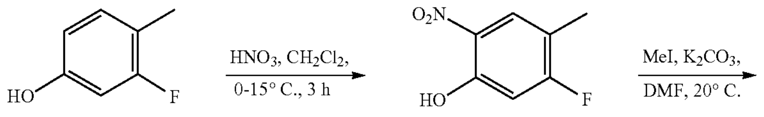

93 94

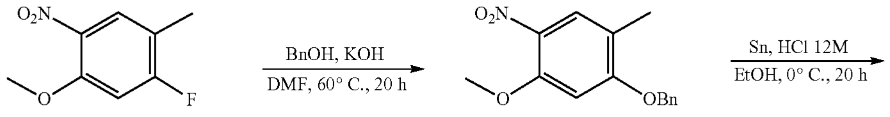

95 96

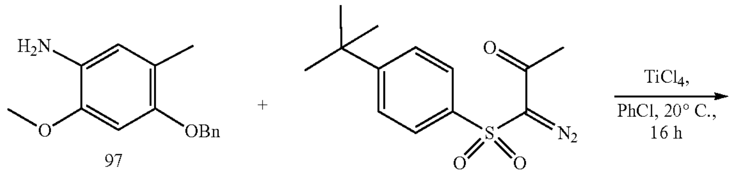

97 92

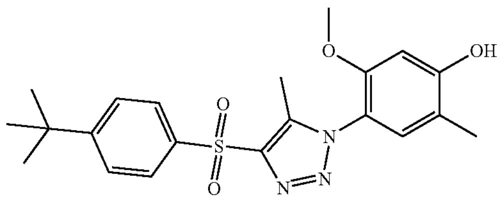

98 i. 5-FLUORO-4-METHYL-2-NITROPHENOL (94)

To a solution of compound 93 (150 g, 1.19 mol) in $CH_2Cl_2$ (3 L), was added $HNO_3$ (151 g, 1.59 mol, 108 mL, 66% purity) dropwise at 0° C. The mixture was stirred at 15° C. for 3 h. TLC (10:1 petroleum ether:EtOAc) showed the starting material was consumed completely. The mixture was washed with water (1 L×2), brine (1 L), dried over $Na_2SO_4$, and evaporated under reduced pressure. The crude product was purified by column chromatography of silica gel (10:1 petroleum ether:EtOAc, $R_f$=0.680) to give compound 94 (146 g, 853 mmol, 71.74% yield) as a yellow solid; $^1H$ NMR (400 MHz, $CDCl_3$) δ 10.6 (s, 1H), 8.03-7.90 (m, 1H), 6.84-6.78 (m, 1H), 2.26 (s, 3H).

ii. 1-FLUORO-5-METHOXY-2-METHYL-4-NITROBENZENE (95)

To a solution of compound 94 (146 g, 853 mmol) and $K_2CO_3$ (141 g, 1.02 mol) in DMF (1.5 L) was added iodomethane (145 g, 1.02 mol, 63.74 mL). The mixture was stirred at 20° C. for 3 h. TLC (10:1 petroleum ether:EtOAc, $R_f$=0.50) showed the starting material was consumed completely and the desired compound was formed. The mixture was used in the next step without purification.

iii. 1-(BENZYLOXY)-5-METHOXY-2-METHYL-4-NITROBENZENE (96)

To solution of compound 95 (157 g, 847 mmol) in DMF (1.50 L) were added phenyl methanol (183 g, 1.70 mol) and KOH (142 g, 2.54 mol). The mixture was stirred at 60° C. for 20 h. TLC (10:1 petroleum ether:EtOAc) showed the starting material was consumed completely. The mixture was poured into water (200 mL) under stirring, then the solid was collected by filtration. The crude product was triturated with MeOH (2 L) at 25° C. for 50 min and filtered, and the cake was collected to give compound 96 (372 g, 1.36 mol, 80.27% yield) as a yellow solid; $^1H$ NMR (400 MHz, $CDCl_3$) δ 7.86 (s, 1H), 7.45-7.34 (m, 5H), 6.51 (s, 1H), 5.18 (s, 2H), 3.91 (s, 3H), 2.23 (s, 3H).

iv. 4-(BENZYLOXY)-2-METHOXY-5-METHYLANILINE (97)

To a solution of compound 96 (186 g, 680) and λ2-stannane (807 g, 6.81 mol) in EtOH (2 L) was added HCl (12 M, 623.89 mL) at 0° C., and the mixture was stirred for 20 h. LCMS showed the starting material was consumed completely and desired compound was formed. The mixture was evaporated under reduced pressure, the residue was poured into ice water (2 L) under stirring, and the solid was collected by filtration. The solid was suspended in $CH_2Cl_2$ (2 L), and the pH was adjusted to 9~10 with aq. $Na_2CO_3$ solution. The mixture was filtrated, and the cake was washed with $CH_2Cl_2$ (1 L). The combined organic layer was washed with brine (1 L), dried over $Na_2SO_4$, and evaporated under reduced pressure. The crude product was purified by column chromatography of silica gel (2:1 petroleum ether:EtOAc, $R_f$=0.41) to give compound 97 (240 g, 986 mmol, 72.4% yield) as a brown solid; $^1H$ NMR (400 MHz, DMSO-$d_6$) δ 7.47-7.33 (m, 5H), 6.57 (s, 1H), 6.50 (s, 1H), 5.00 (s, 2H), 3.80 (s, 3H), 3.79-3.41 (m, 2H), 2.18 (s, 3H); MS (ESI) m/z=244.2 $[M+H]^+$.

v. 4-(4-((4-(TERT-BUTYL)PHENYL)SULFONYL)-5-METHYL-1H-1,2,3-TRIAZOL-1-YL)-5-METHOXY-2-METHYLPHENOL (98)

To a solution of compound 92 (53 g, 189 mmol) and compound 97 (50.6 g, 207 mmol) in chlorobenzene (500 mL) was added $TiCl_4$ (53.7 g, 283 mmol). The mixture was stirred at 20° C. for 16 h. LCMS showed the starting material was consumed completely and desired MS was formed. The mixture was poured into ice cold aq. $NaHCO_3$ (500 mL) and extracted with EtOAc (500 mL×2), and the combined organic layer was washed with NaCl (300 mL) and concentrated under reduced pressure. The residue was purified by column chromatography ($SiO_2$, 3:1 petroleum ether:EtOAc) to give compound 98 (15 g, 36.1 mmol, 19.1% yield) as a pink solid; $^1H$ NMR (400 MHz, DMSO-$d_6$) δ 10.1 (s, 1H), 7.94-7.92 (d, J=4.0 Hz, 2H), 7.71-7.69 (m, 2H), 7.16 (s, 1H), 6.66 (s, 1H), 3.68 (s, 3H), 2.33 (s, 3H), 2.06 (s, 3H), 1.30 (s, 9H); MS (ESI) m/z=416.0 $[M+H]^+$.

cc. Compound 102

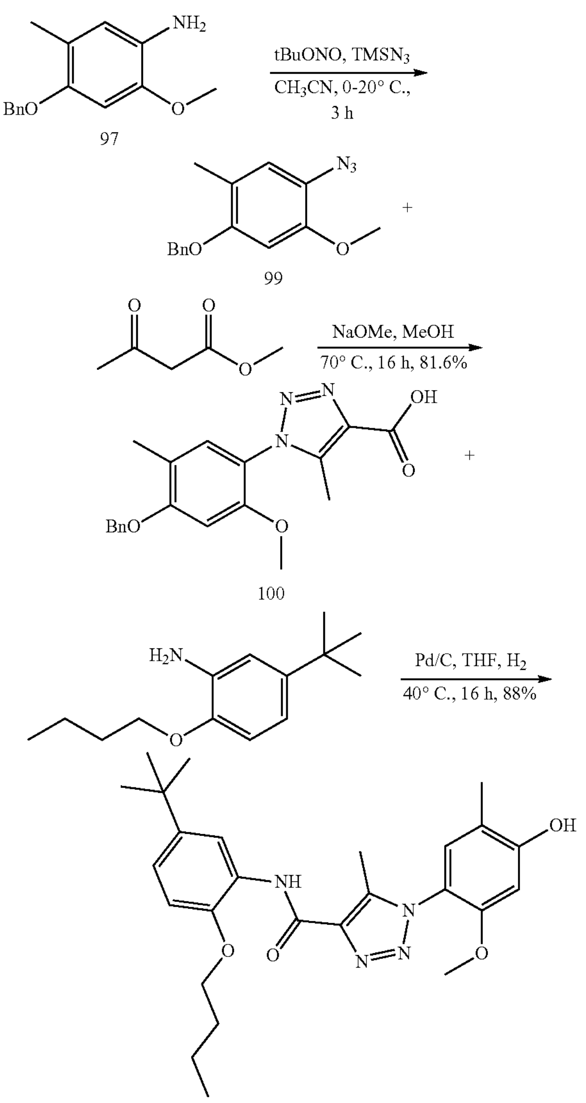

97

99

100

102 vi. 1-AZIDO-4-(BENZYLOXY)-2-METHOXY-5-METHYLBENZENE (99)

To a solution of compound 97 (120 g, 493 mmol) in acetonitrile (1.2 L) was added t-BuONO (90.0 g, 873 mmol, 104 mL) at 0° C., and then $TMSN_3$ (85.2 g, 739 mmol, 97.3 mL) in acetonitrile (600 mL) dropwise at 0° C. The mixture was stirred at 20° C. for 3 h. LCMS showed the starting material was consumed completely. The mixture was poured into ice water (500 mL) and extracted with EtOAc (2 L×3). The combined organic layer was washed with brine (500 mL), dried over anhydrous $Na_2SO_4$, and evaporated under reduced pressure. The mixture was purified by column chromatography of silica gel (petroleum ether: EtOAc=1:0 to 5:1) to give compound 99 (86.0 g, 313 mmol, 63.4% yield, 98% purity) as a brown solid; $^1$H NMR (400 MHz, $CDCl_3$) δ 7.52-7.34 (m, 5H), 6.81 (s, 1H), 6.50 (s, 1H), 5.07 (s, 2H), 3.82 (s, 3H), 2.20 (s, 3H).

vii. 1-(4-(BENZYLOXY)-2-METHOXY-5-METHYLPHENYL)-5-METHYL-1H-1,2,3-TRIAZOLE-4-CARBOXYLIC ACID (100)

To a solution of compound 99 (42.0 g, 156 mmol) and methyl 3-oxobutanoate (38.2 g, 329 mmol, 35.3 mL) in MeOH (500 mL) was added $CH_3ONa$ (42.1 g, 780 mmol), and the mixture was stirred at 70° C. for 16 h. LCMS showed the starting material was consumed completely. The combined mixture was evaporated under reduced pressure. The residue was dissolved in water (1.5 L), and the pH was adjusted to 3-4 with aq. HCl (12 M). The solid was collected by filtration, and the cake was washed with water (500 mL). The solid was purified by trituration in EtOAc (500 mL) to give compound 100 (100 g, 254 mmol, 81.6% yield, 90.0% purity) as a brown solid; $^1$H NMR (400 MHz, DMSO-$d_6$) δ 7.52 (d, J=7.2 Hz, 2H), 7.43 (t, J=7.2 Hz, 2H), 7.36 (t, J=7.2 Hz, 1H), 7.25 (s, 1H), 6.99 (s, 1H), 5.28 (s, 2H), 3.79 (s, 3H), 2.28 (s, 3H), 2.17 (s, 3H); MS (ESI) m/z=354.1 $[M+H]^+$.

viii. 1-(4-(BENZYLOXY)-2-METHOXY-5-METHYLPHENYL)-N-(2-BUTOXY-5-(TERT-BUTYL)PHENYL)-5-METHYL-1H-1,2,3-TRIAZOLE-4-CARBOXAMIDE (101)

To a solution of compound 100 (80.0 g, 226 mmol) and HATU (129 g, 339 mmol) in DMF (1.2 L) was added $Et_3N$ (45.8 g, 452 mmol, 63.0 mL), and the mixture was stirred at 20° C. for 30 min. 2-butoxy-5-tert-butyl-aniline (61.1 g, 276 mmol, synthesized according to reported procedures)(Li, Y.; et al., (2022) *J Med Chem* 65 (24), 16829-16859) was added, and the mixture was stirred at 25° C. for 4 h. LCMS showed the starting material was consumed completely. The mixture was poured into ice water (2.5 L), and the solid was collected by filtration. The solid was purified by trituration in MeOH (1.5 L) and filtration to give compound 101 (110 g, 193 mmol, 85.3% yield, 97.8% purity) as a white solid; $^1$H NMR (400 MHz, $CDCl_3$) δ 9.82 (br.s, 1H), 8.65 (d, J=2.4 Hz, 1H), 7.49-7.37 (m, 5H), 7.16 (s, 1H), 7.07 (dd, $J_1$=8.4 Hz, $J_2$=2.4 Hz, 1H), 6.86 (d, J=8.8 Hz, 1H), 6.61 (s, 1H), 5.18 (s, 2H), 4.08 (t, J=6.4 Hz, 2H), 3.74 (s, 3H), 2.51 (s, 3H), 2.27 (s, 3H), 1.90-1.85 (m, 2H), 1.63-1.57 (m, 2H), 1.36 (s, 9H), 1.01 (t, J=7.2 Hz, 3H); MS (ESI) m/z=557.3 $[M+H]^+$.

ix. N-(2-BUTOXY-5-(TERT-BUTYL)PHENYL)-1-(4-HYDROXY-2-METHOXY-5-METHYLPHENYL)-5-METHYL-1H-1,2,3-TRIAZOLE-4-CARBOXAMIDE (102)

To a solution of compound 101 (60.0 g, 107 mmol) in THF (900 mL) was added Pd/C (5 g, 10% purity) under argon protected atmosphere. The suspension was degassed under vacuum and purged with $H_2$ three times. The mixture was stirred under $H_2$ (30 psi) at 40° C. for 16 h. TLC (5:1 petroleum ether:EtOAc, $R_f$=0.31) showed the starting material was consumed completely. The mixture was filtrated from a pad of the celite, and the cake was washed with THF (1 L). The crude was purified by column chromatography of silica gel (100% THF) to give compound 102 (92.0 g, 191 mmol, 88.8% yield, 97.1% purity) as a brown solid; $^1$H NMR (400 MHz, DMSO-$d_6$) δ 9.82 (s, 1H), 8.65 (d, J=2.4 Hz, 1H), 7.10-7.07 (m, 2H), 6.88-6.85 (d, J=2.4 Hz, 1H), 6.56 (s, 1H), 4.10-4.07 (t, J=2.8 Hz, 2H), 3.62 (s, 3H), 2.49 (s, 3H), 2.21 (s, 3H), 1.91-1.84 (m, 2H), 1.61-1.55 (m, 2H), 1.34 (s, 9H), 1.01 (t, J=7.2 Hz, 3H); MS (ESI) m/z=467.2 $[M+H]^+$.

A list of exemplary compounds is shown in Table 1 below. Compounds were prepared using the synthetic methods described herein.

TABLE 1

| Compound Number | Structure |
|---|---|
| 13 | 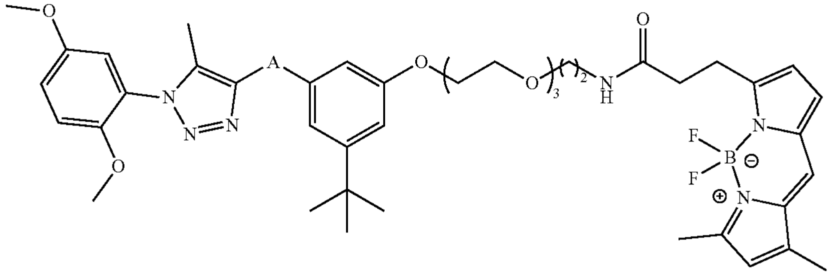 |

TABLE 1-continued
| Compound Number | Structure |
|---|---|
| 14 | 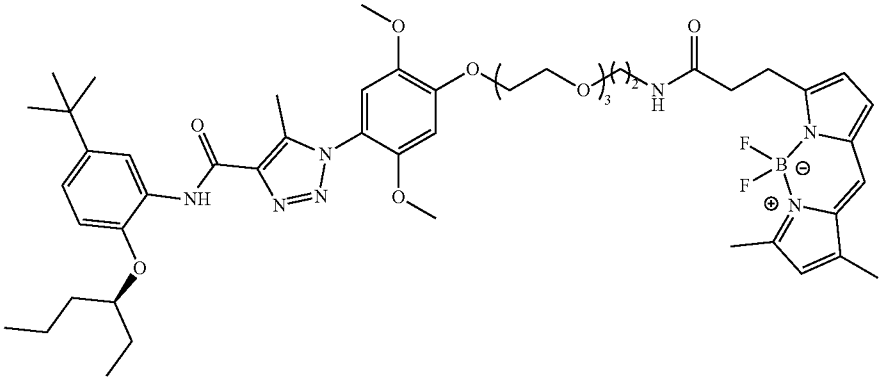 |
| 15 | 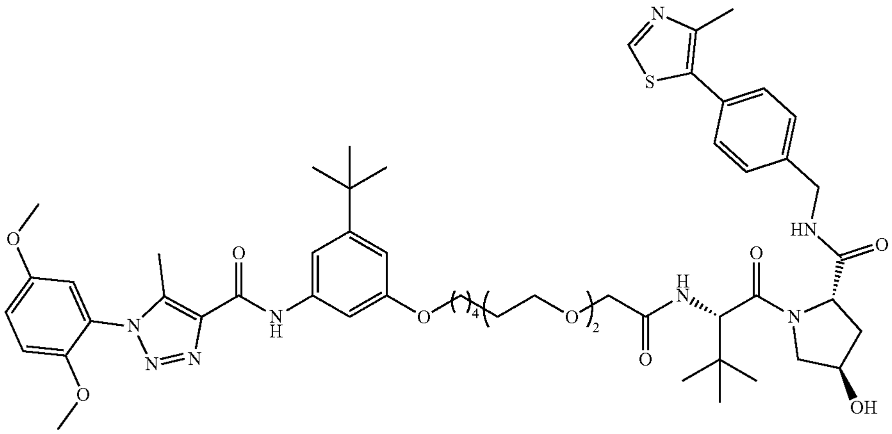 |
| 16 | 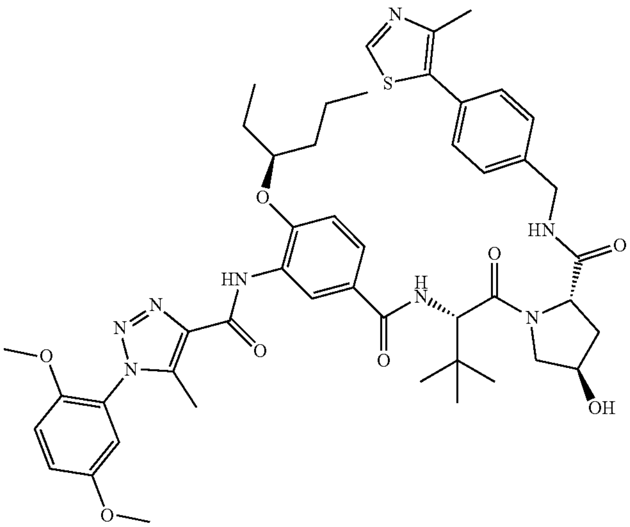 [SMILES: CCC[C@H](CC)Oc1ccc(C(=O)N[C@H](C(=O)N2C[C@H](O)C[C@H]2C(=O)NCc2ccc(-c3scnc3C)cc2)C(C)(C)C)cc1NC(=O)c1nnn(-c2cc(OC)ccc2OC)c1C] |

TABLE 1-continued
| Compound Number | Structure |
|---|---|
| 17 | 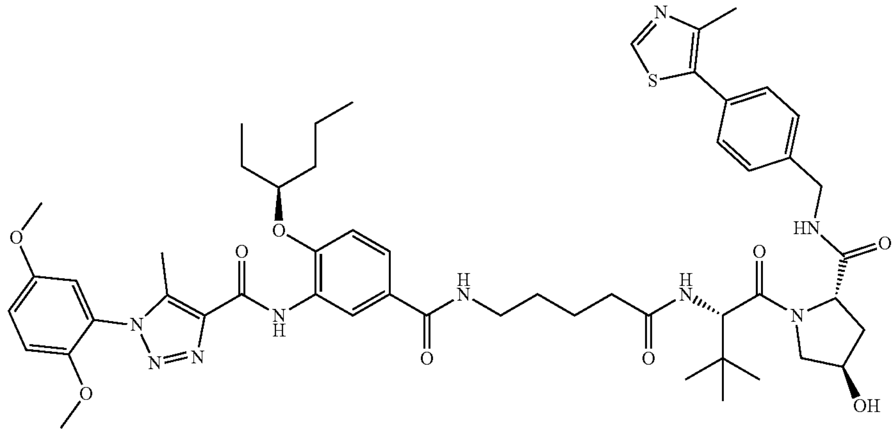 [SMILES: CCC[C@H](CC)Oc1ccc(C(=O)NCCCCC(=O)N[C@H](C(=O)N2C[C@H](O)C[C@H]2C(=O)NCc2ccc(-c3scnc3C)cc2)C(C)(C)C)cc1NC(=O)c1nnn(-c2cc(OC)ccc2OC)c1C] |
| 18 | 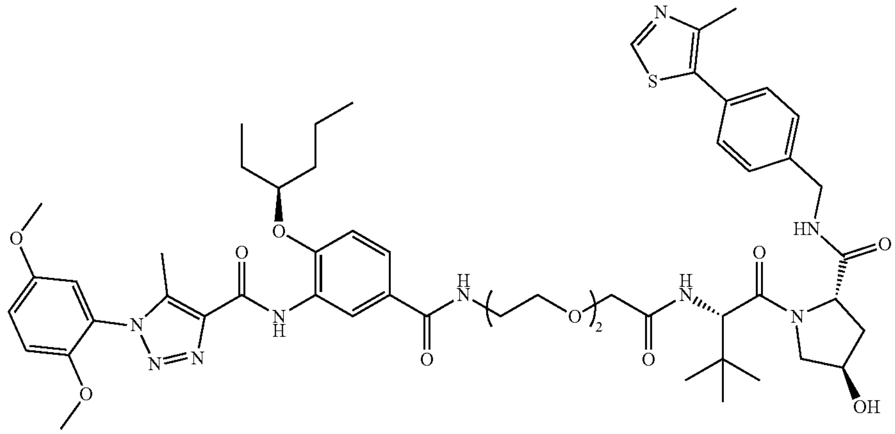 |
| 19 | 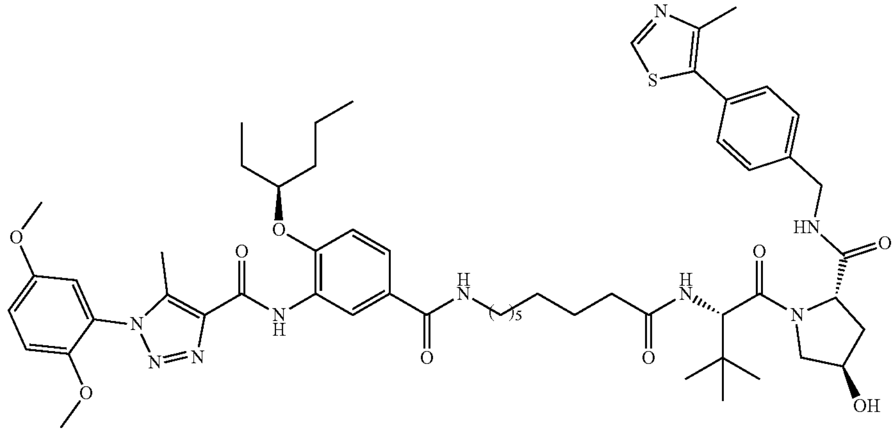 |

TABLE 1-continued
| Compound Number | Structure |
|---|---|
| 20 | 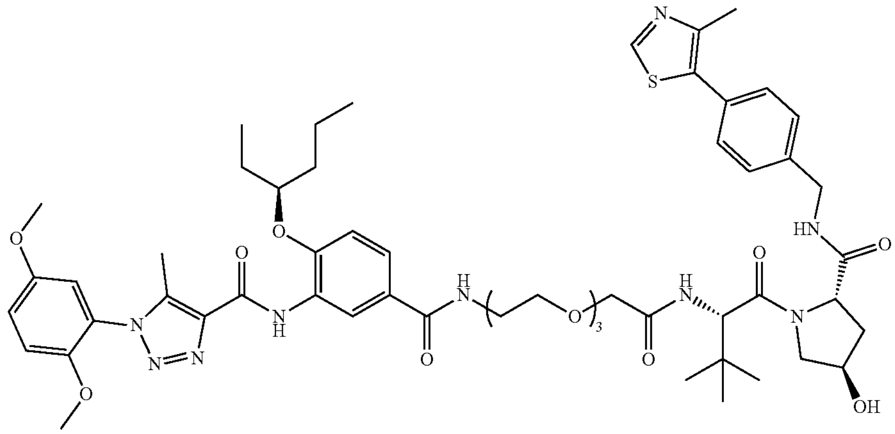 |
| 21 | 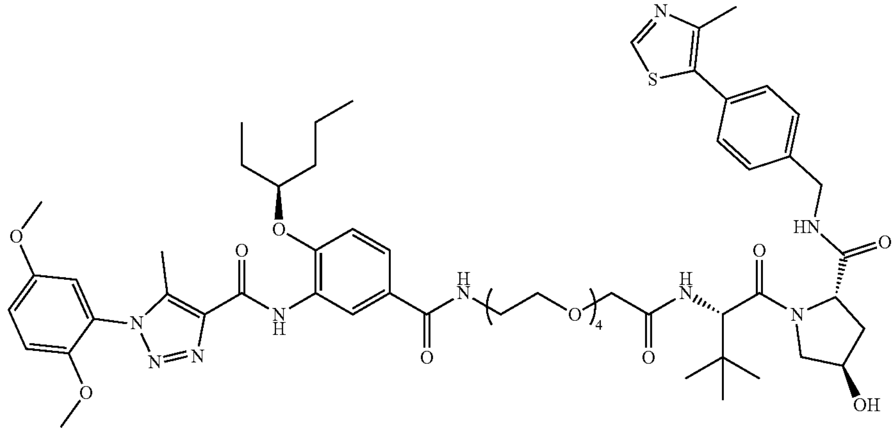 |
| 22 | 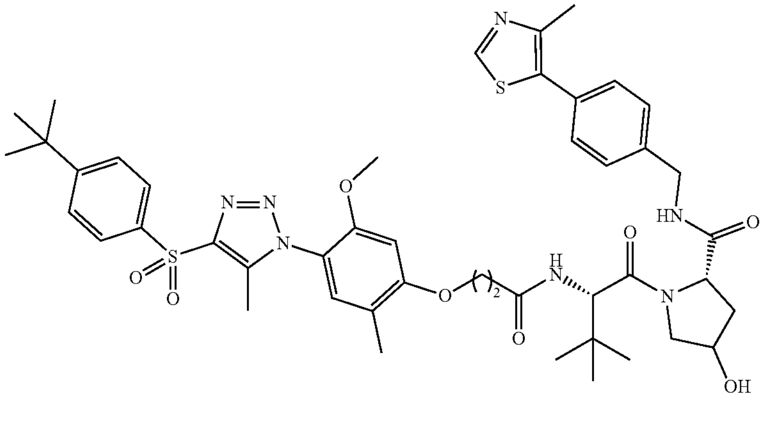 |

TABLE 1-continued
| Compound Number | Structure |
| --- | --- |
| 23 | 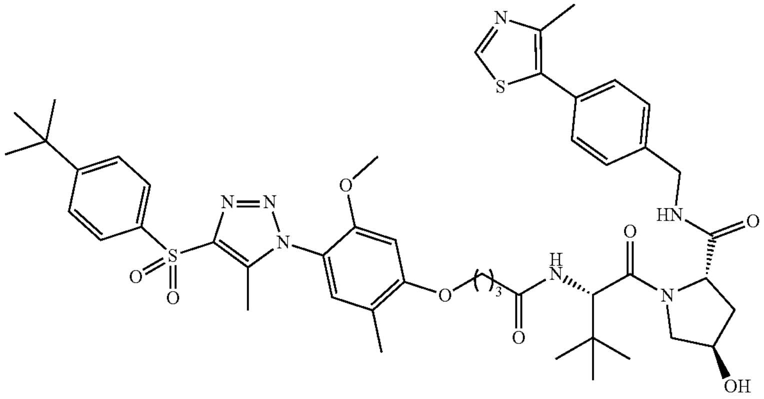 |
| 24 | 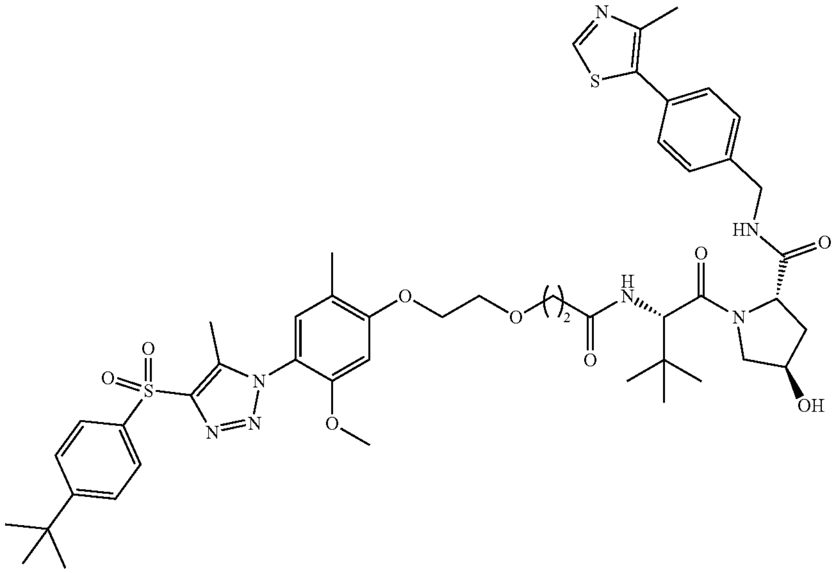 |
| 25 | 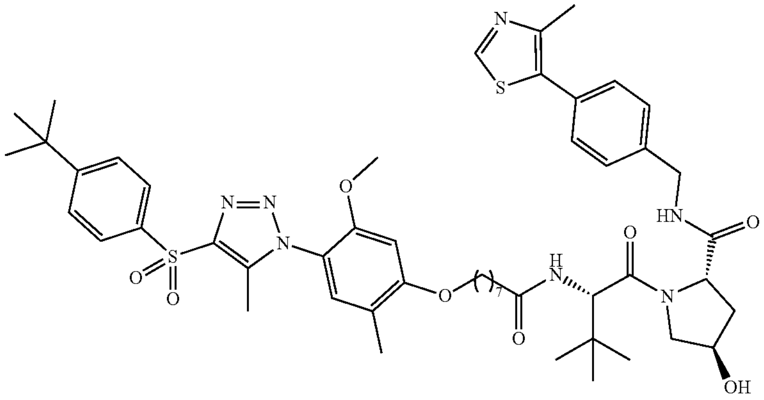 |

TABLE 1-continued
| Compound Number | Structure |
|---|---|
| 26 | 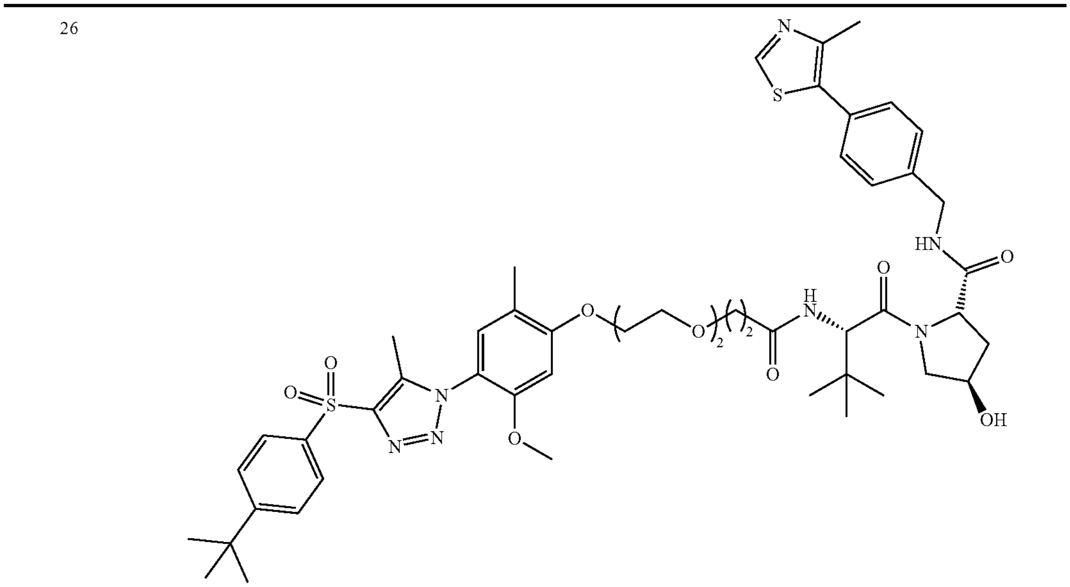 |
| 27 | 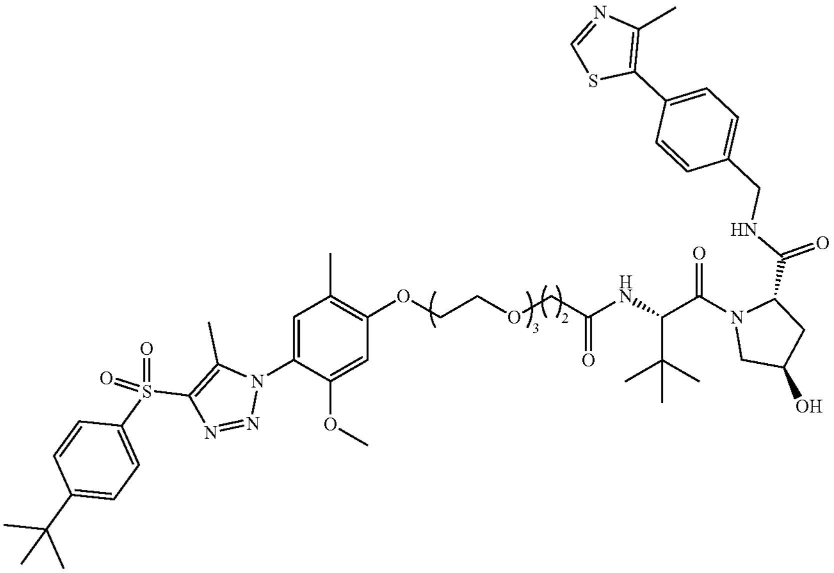 |
| 28 | 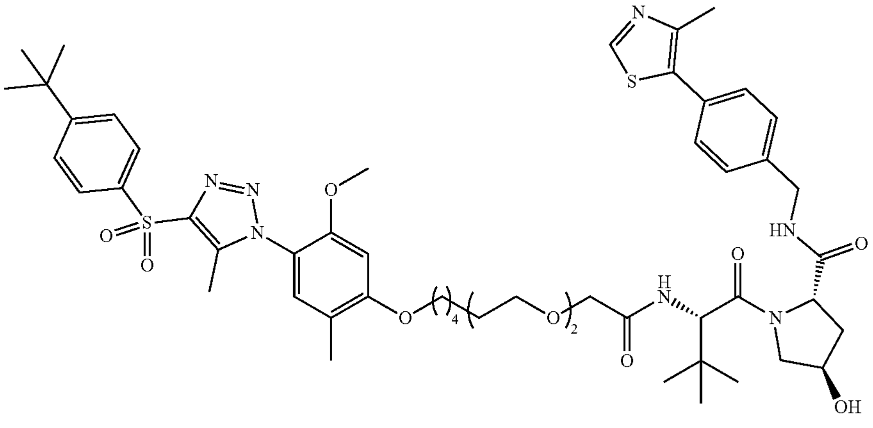 |

TABLE 1-continued
| Compound Number | Structure |
|---|---|
| 29 | 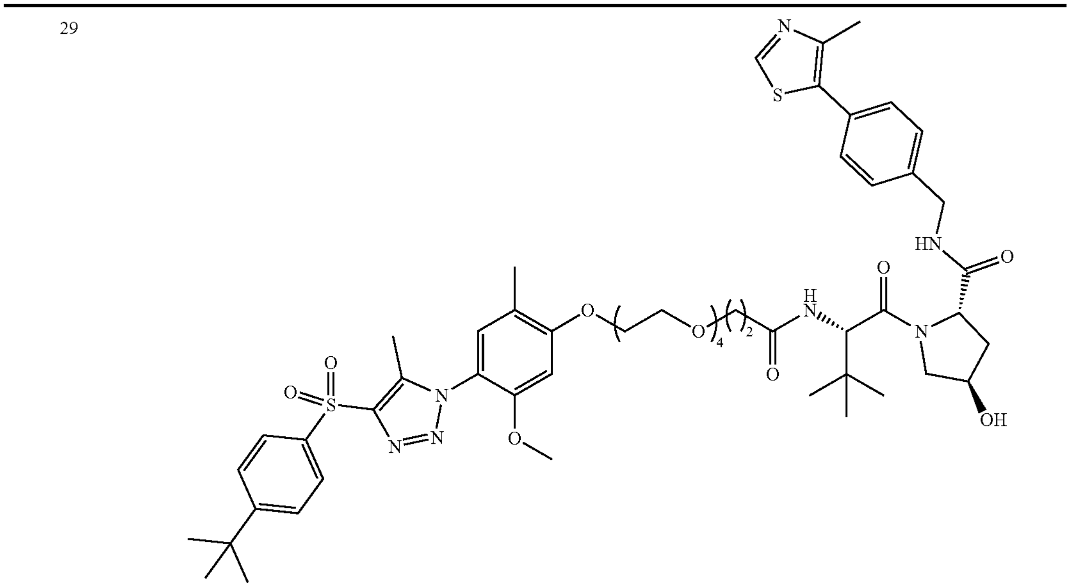 |
| 30 | 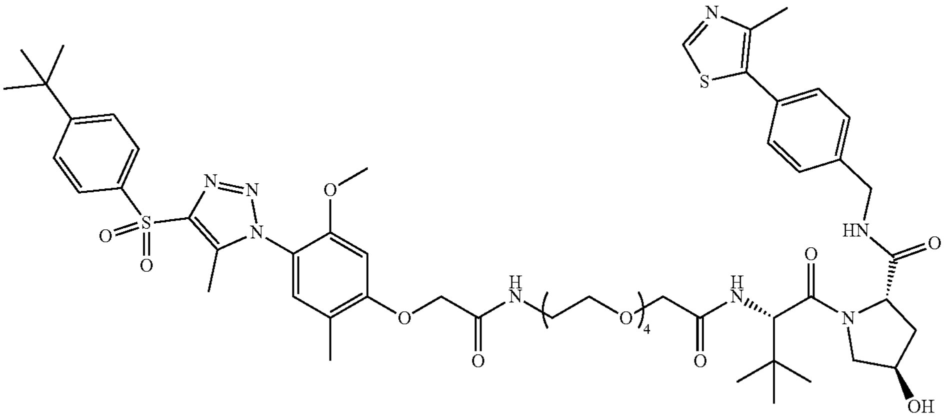 |
| 31 | 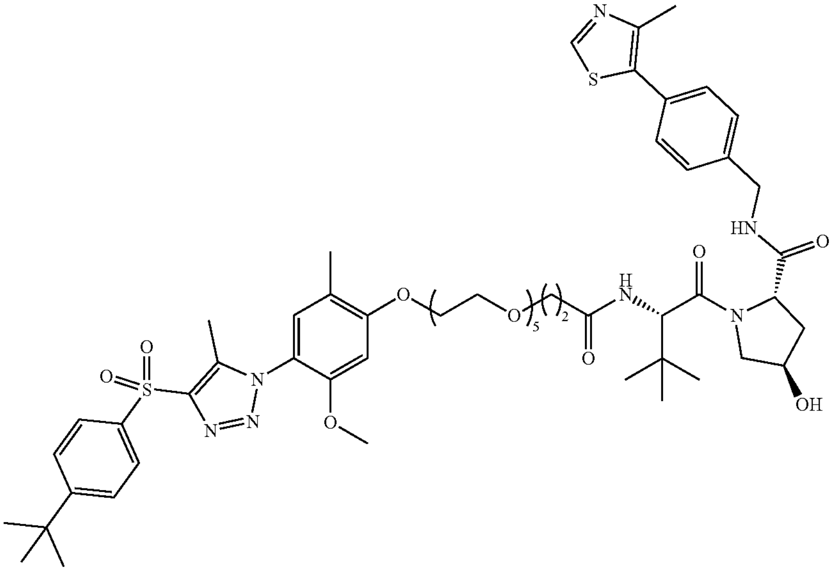 |

TABLE 1-continued
| Compound Number | Structure |
|---|---|
| 32 | 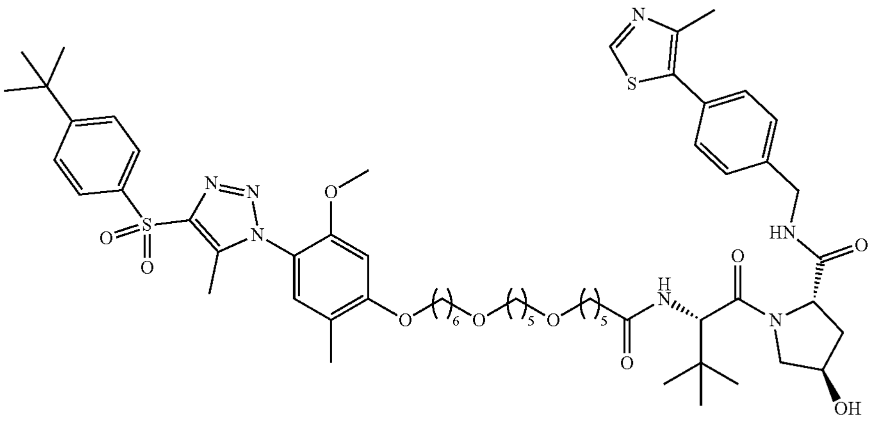 |
| 33 | 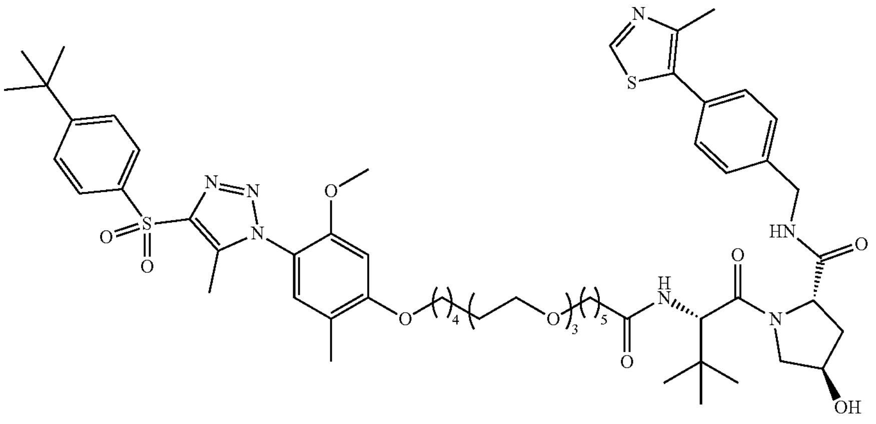 |
| 34 | 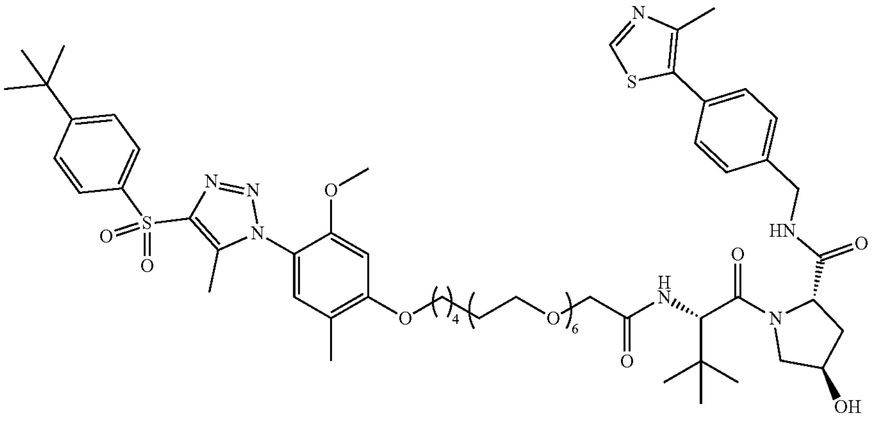 |

TABLE 1-continued
| Compound Number | Structure |
| --- | --- |
| 35 | 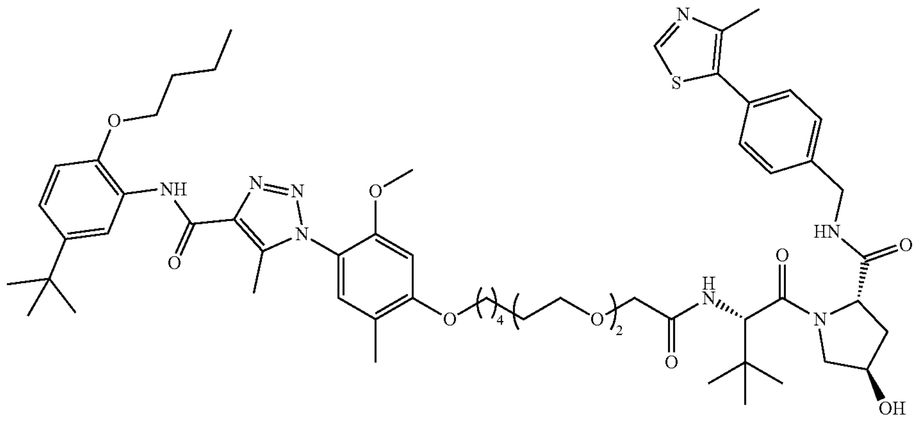 |
| 36 | 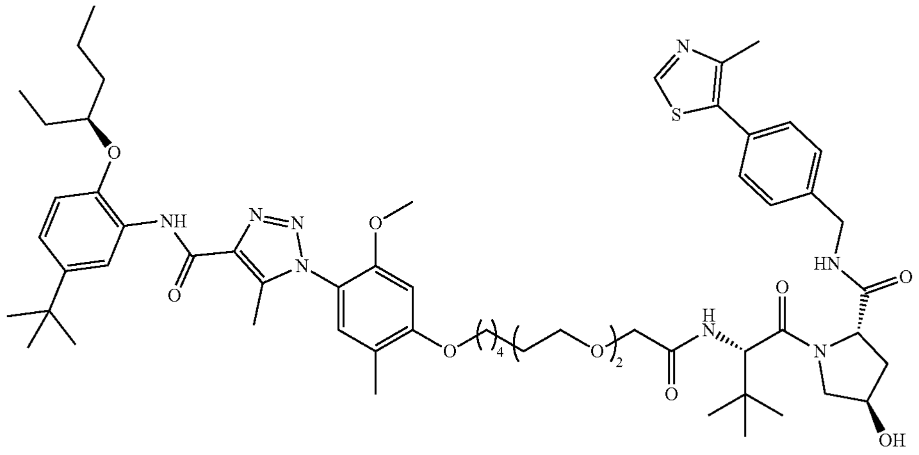 |
| 37 | 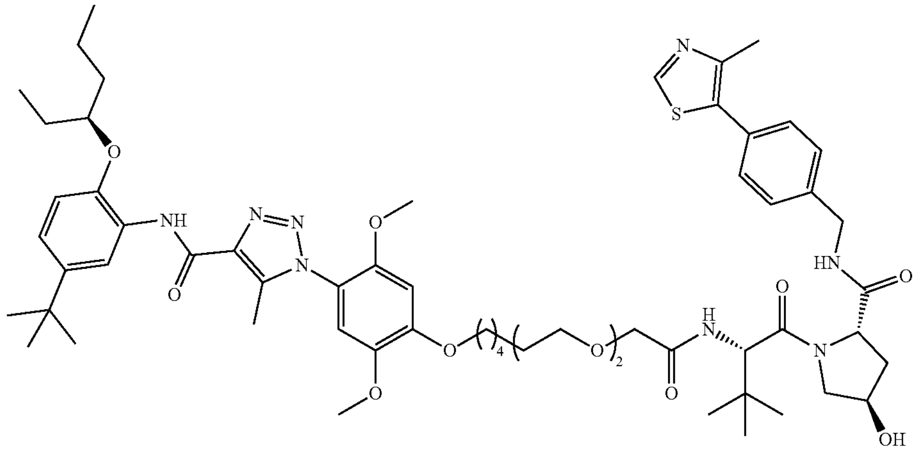 |

TABLE 1-continued

| Compound Number | Structure |
|---|---|
| 38 | 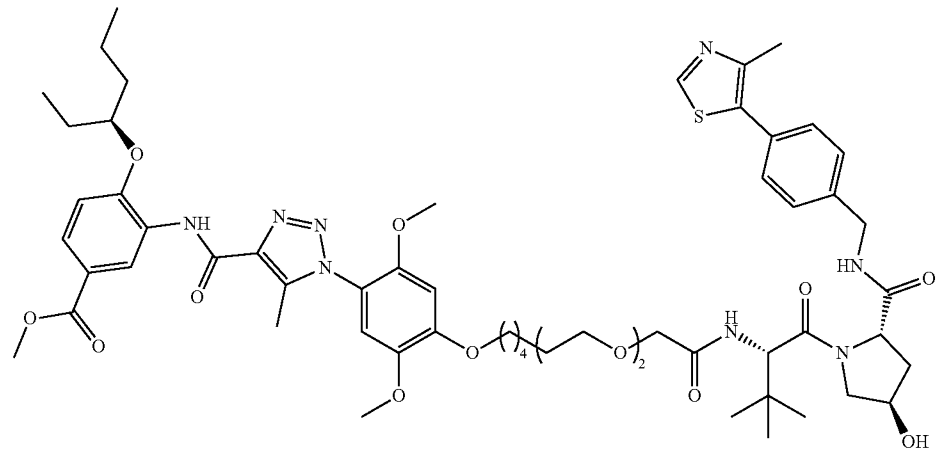 |
| 40 | 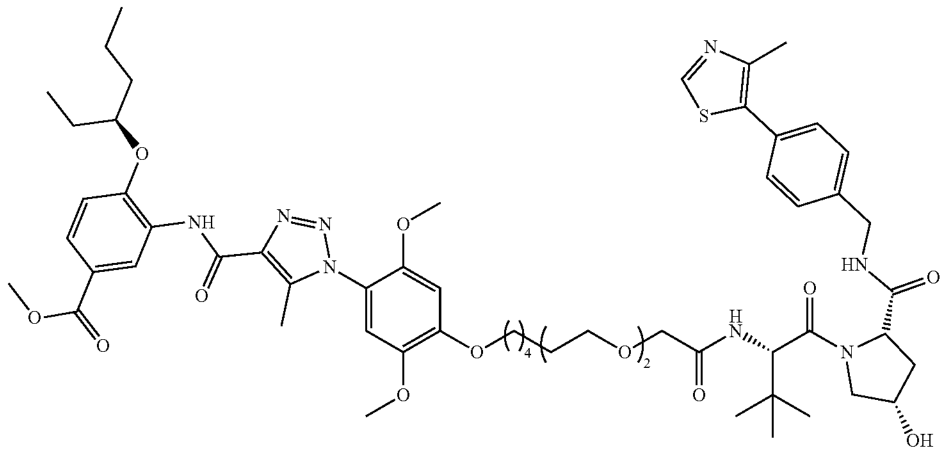 |

2. BIOLOGY METHODS a. Cell Culture, Plasmids, and Reagents

HepG2/C3A cells were obtained from the American Type Culture Collection (ATCC, cat. #CRL-3581) and maintained in Eagle's Minimum Essential Medium (ATCC, cat. #30-2003) with 10% FBS (Cytiva, cat. #SH30396.03). SNU—C4 cells were obtained from the Korean Cell Line Bank (KCLB, cat. #0000C4). SNU—C4 3×FLAG-PXR KI cells containing a 3×FLAG tag fused to the N-terminus of endogenous PXR were generated using CRISPR/Cas9 technology and have been described (Huber, A. D.; et al., (2022) *ACS Med Chem Lett* 13 (8), 1311-1320). SNU—C4 HiBiT-PXR KI cells containing a HiBiT tag fused to the N-terminus of endogenous PXR were similarly generated and have been described (Florke Gee, et al., (2023) *Acta Pharm Sin B* 13 (11), 4523-4534). Parental SNU—C4 and the CRISPR/Cas9 derivatives were maintained in RPMI-1640 medium (ATCC, cat. #30-2001) with 10% FBS. *Cells* were incubated in a humidified atmosphere at 37° C. with 5% $CO_2$ and routinely verified to be *mycoplasma* free by using the MycoProbe *Mycoplasma* Detection Kit (R&D Systems, cat. #CUL001B). *Cell* counts were obtained with a Countess II Automated Cell Counter using trypan blue staining. The "assay media" used for relevant experiments below was phenol red-free DMEM (Thermo Fisher Scientific, cat. #21063029) supplemented with 5% charcoal/dextran-treated FBS (Cytive, cat. #SH30068.03).

The pcDNA3-FLAG-PXR expression plasmid and pGL3-CYP3A4-luc containing firefly luciferase under the control of a PXR-responsive CYP3A4 promoter have been previously described (Goodwin, B.; et al., (1999) *Mol Pharmacol* 56 (6), 1329-1339; Lin, W.; et al., (2008) *J Biol Chem* 283 (45), 30650-30657). DMSO was purchased from Fisher Scientific (cat. #BP231-100), and paclitaxel was purchased from LC Laboratories (cat. #P-9600). Rifampicin (cat. #R3501) and MG132 (cat. #474790) were purchased from Sigma-Aldrich. T0901317 (cat. #HY-10626) and MLN4924 (cat. #HY-70062) were purchased from MedChemExpress. The PXR ligands SPA70, SJB7, SJPYT-328, and SJPYT-331 were synthesized as previously described (Lin, W.; et al., (2017) *Nat Commun* 8 (1), 741; Garcia-Maldonado, E.; et al., (2024) *Nat Commun* 15 (1), 4054). LanthaScreen Terbium (Tb)-anti-glutathione S-transferase (GST, cat. #PV3550), Alexa Fluor 488-anti-GST (cat. #MA4-004-A488), LanthaScreen Elite Tb-anti-His (cat. #PV5895), and GST-PXR LBD protein (cat. #PV4841) were purchased from Thermo Fisher Scientific. Purifications of GST-tagged VCB (Lin, W.; et al., (2021) *ACS Omega* 6 (1), 680-695) and His-tagged PXR LBD (Lin, W.; et al., (2023) *Proc Natl Acad*

*Sci USA* 120 (10), e2217804120; Huber, A. D.; et al., (2024) *Nucleic Acids Res* 52 (4), 1661-1676) have been described previously.

b. TR-FRET PXR LBD Ligand Binding Assays

The assay buffer composition was 50 mM Tris (pH 7.5), 0.002% Pluronic F-127, 0.01% bovine serum albumin (BSA), and 0.05 mM dithiothreitol (DTT). For fluorescent probe $K_D$ determination, 15 μL assay buffer containing 3 nM Tb-anti-GST and 3 nM GST-PXR LBD was added to the wells of black low-volume 384-well assay plates (Revvity cat. #6008260). An Echo 655T Acoustic Liquid Handler (Beckman Coulter Life Sciences) was used to dispense 15 nL/well of stock probe dilutions in DMSO and an additional 15 nL/well of either DMSO or 20 mM T0901317. The final DMSO concentration was 0.2% in all wells, with 0.1% from fluorescent probes and 0.1% from either DMSO or 20 mM T0901317 stock. The final probe concentration range was 122.1 μM to 4 μM in the absence or presence of 20 μM T0901317 to confirm that the probe can be displaced from the ligand binding pocket. The plates were shaken at 900 rpm (80×g) on an IKA MTS 2/4 digital microtiter shaker for 1 min then centrifuged at 1,000 rpm (201×g) for 30 s in an Eppendorf 5810 centrifuge equipped with an A-4-62 swing-bucket rotor. The plates were protected from light exposure and incubated for 90 min at room temperature. After incubation, the TR-FRET signal from each well was collected with a PHERAstar FS Microplate Reader (BMG Labtech) using 340 nm excitation, 520 and 490 nm emissions, a 100-μs delay, and a 200-μs integration time. The measured relative fluorescence units (RFU) were normalized for each well using equation 1, $$\text{Signal} = \frac{RFU \text{ at } 520 \text{ nm}}{RFU \text{ at } 490 \text{ nm}} \times 10^4$$

For ligand competition assays, 15 μL assay buffer containing 3 nM Tb-anti-GST, 3 nM GST-PXR LBD, and 30 nM fluorescent probe was added to the wells of black low-volume 384-well assay plates. An Echo 655T Acoustic Liquid Handler was used to dispense 45 nL/well of DMSO or stock test compound dilutions for a final total DMSO concentration of 0.4%. DMSO alone and 10 μM T0901317 (diluted from 45 nL of 3.33 mM stock) were included in each plate to serve as negative and positive controls, respectively. Plates were shaken, centrifuged, incubated, and measured as above. The measured RFU were normalized for each well using equation 1 and then normalized to control wells using equation 2, $$TR-FRET \text{ Signal } (\%) = 100 \times \left(1 - \frac{(\text{Signal}_{Test\ Compound} - \text{Signal}_{T0901317})}{(\text{Signal}_{DMSO} - \text{Signal}_{T0901317})}\right)$$

c. TR-FRET PXR LBD-VCB Complex Formation Assays

As above, the assay buffer composition was 50 mM Tris (pH 7.5), 0.002% Pluronic F-127, 0.01% BSA, and 0.05 mM DTT. For assessment of complex formation, 7.5 μL assay buffer containing 24 nM GST-VCB and 12 nM Alexa Fluor 488-anti-GST was added to the wells of black low-volume 384-well assay plates. An Echo 655T Acoustic Liquid Handler was used to dispense 45 nL/well of DMSO or stock compound dilutions in DMSO. Then, 7.5 μL assay buffer containing 6 nM His-PXR LBD and 6 nM Tb-anti-His was dispensed. The final concentrations were 12 nM GST-VCB, 6 nM Alexa Fluor 488-anti-GST, 3 nM His-PXR LBD, 3 nM Tb-anti-His, and 0.3% DMSO. Plates were shaken, centrifuged, incubated, and measured as above, and data were normalized using equation 1. The complex inhibition assays were similarly performed but with 45 nL/well DMSO or stock competitor dilutions and 15 nL/well 41.2 μM 37 or 38. This resulted in 0.4% DMSO and 41.2 nM 37 or 38 in each well. The concentration was chosen as the point at which the PROTAC induced ~90% complex.

d. SNU—C4 HIBIT-PXR KI Degradation Assays

SNU—C4 HiBiT-PXR KI cells suspended in assay media were plated in white tissue culture-treated 384-well plates (Revvity, cat. #6007680, $1\times10^4$ cells/well in 25 μL media). The following day, an Echo 655T Acoustic Liquid Handler was used to dispense 75 nL/well of DMSO or stock PROTAC dilutions. For single-compound dose responses, the final DMSO concentration was 0.3%. For experiments containing two compounds, 25 nL/well of 10 mM stock competitor compound was also added, resulting in a final DMSO concentration of 0.4%, 1 μM PROTAC, and 10 μM competitor. The plates were incubated at 37° C. for the indicated time points, and the Nano-Glo HiBiT Lytic Detection System (Promega, cat. #N3040) and an EnVision microplate reader (Revvity) were used to measure HiBiT signal. DMSO-treated SNU—C4 HiBiT-PXR KI cells served as positive controls, and DMSO-treated parental SNU—C4 cells served as negative controls. The measured relative light units (RLU) were used to calculate percent HiBiT signal for each well with equation 3, $$\%\ HiBiT \text{ Signal} = 100 \times \frac{(RLU_{Test\ Compound} - RLU_{Negative\ Control})}{(RLU_{Positive\ Control} - RLU_{Negative\ Control})}$$

Figure 7:
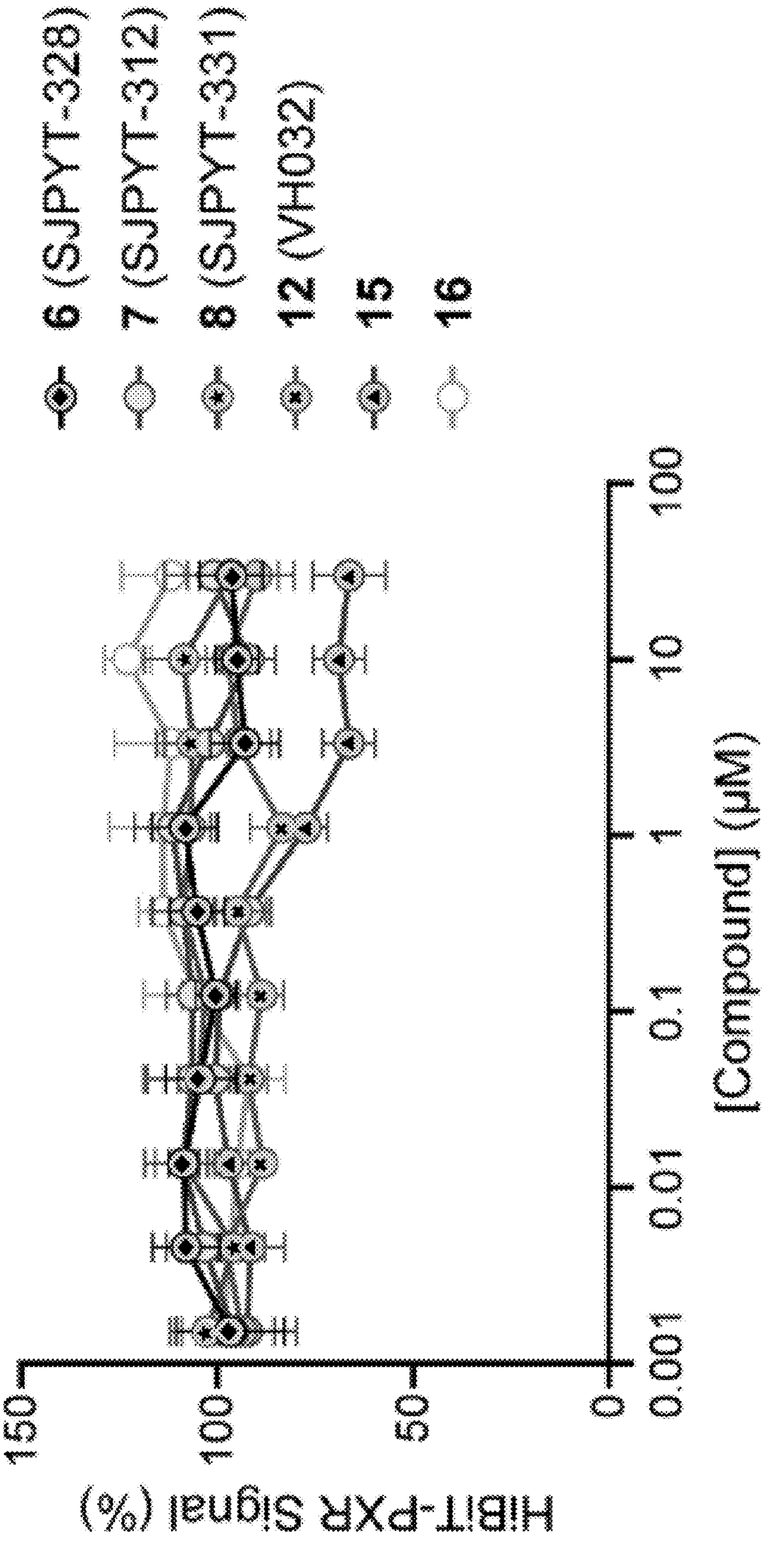
FIG. 7 shows representative data of HiBiT-PXR degradation by PROTACs.
Figure 7:
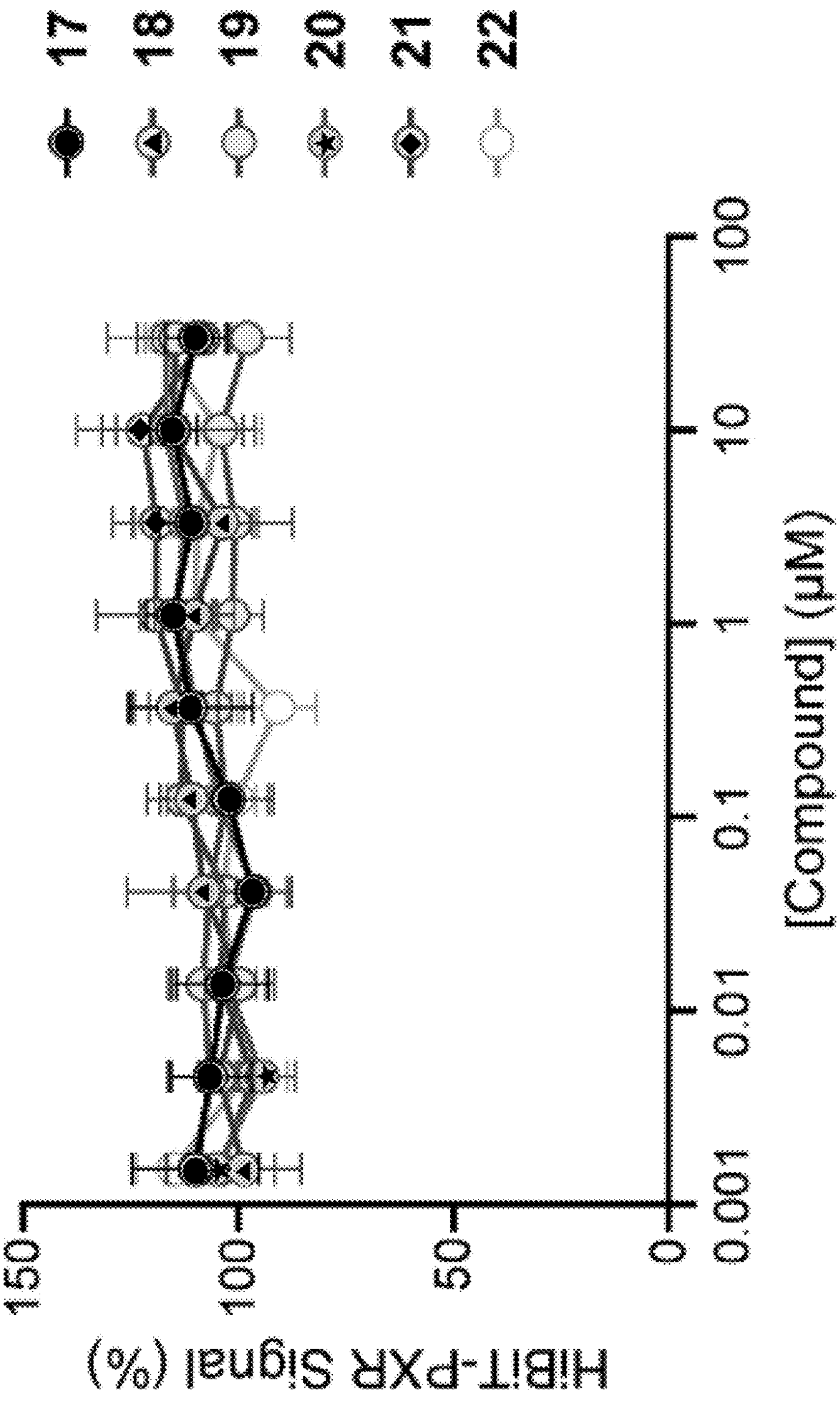
Figure 7:
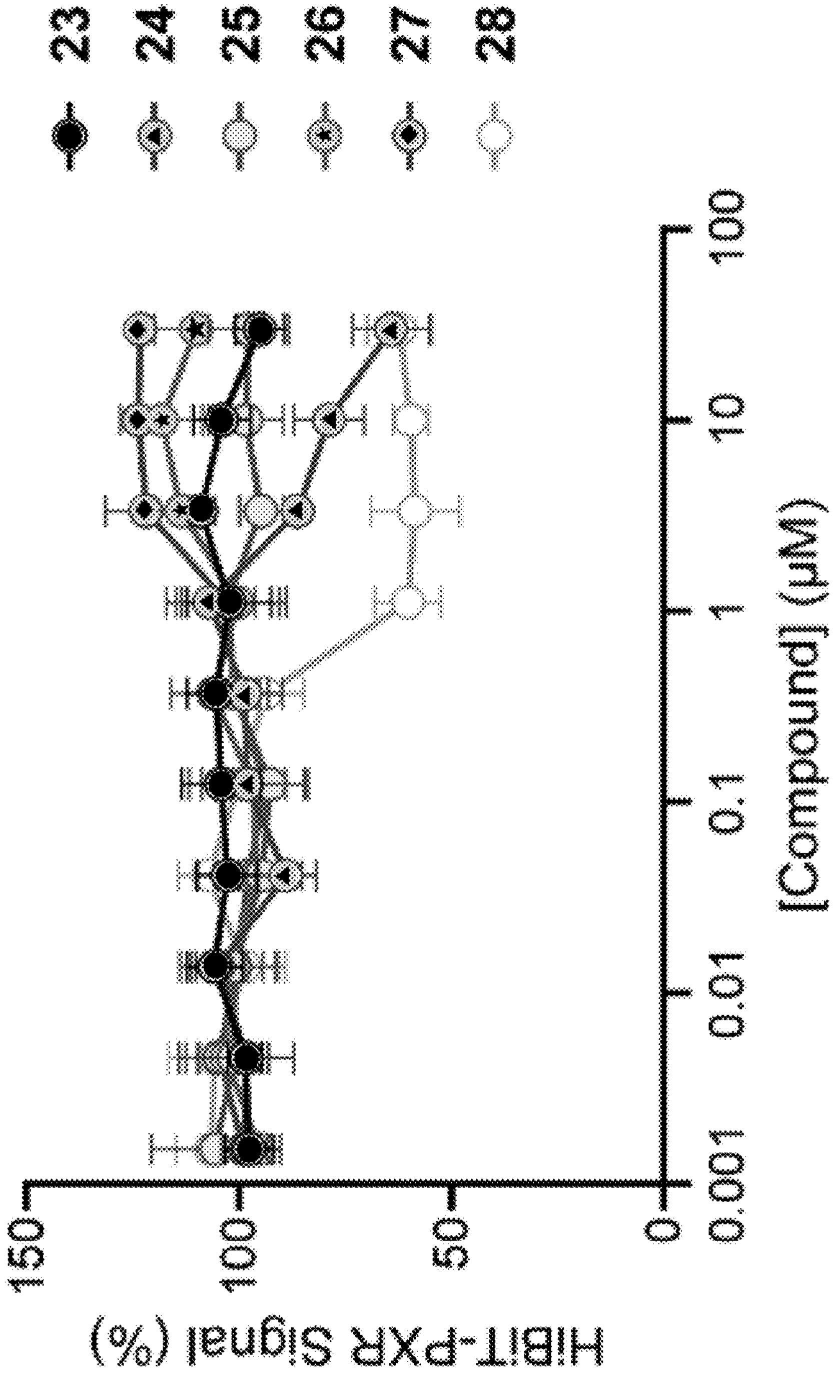
Figure 7:
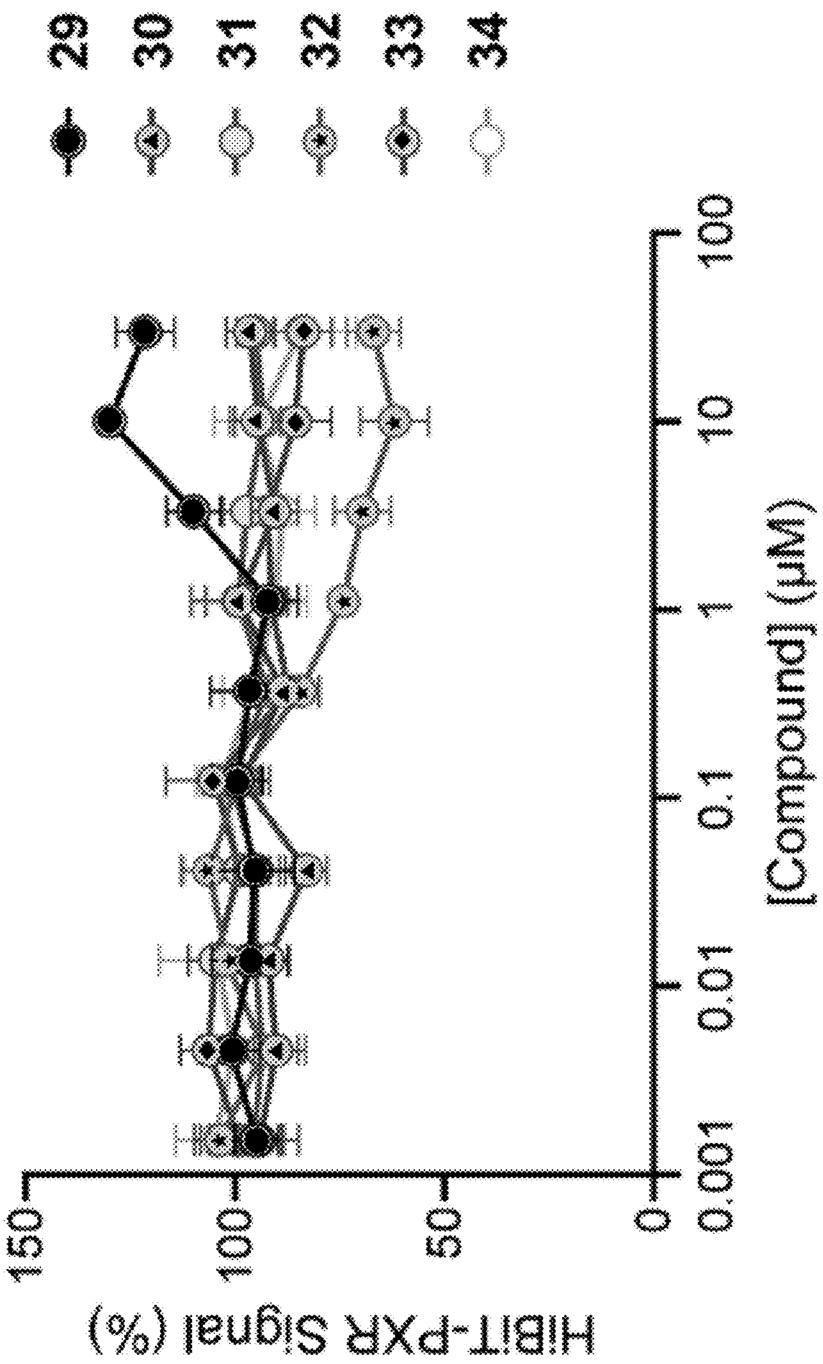
Figure 7:
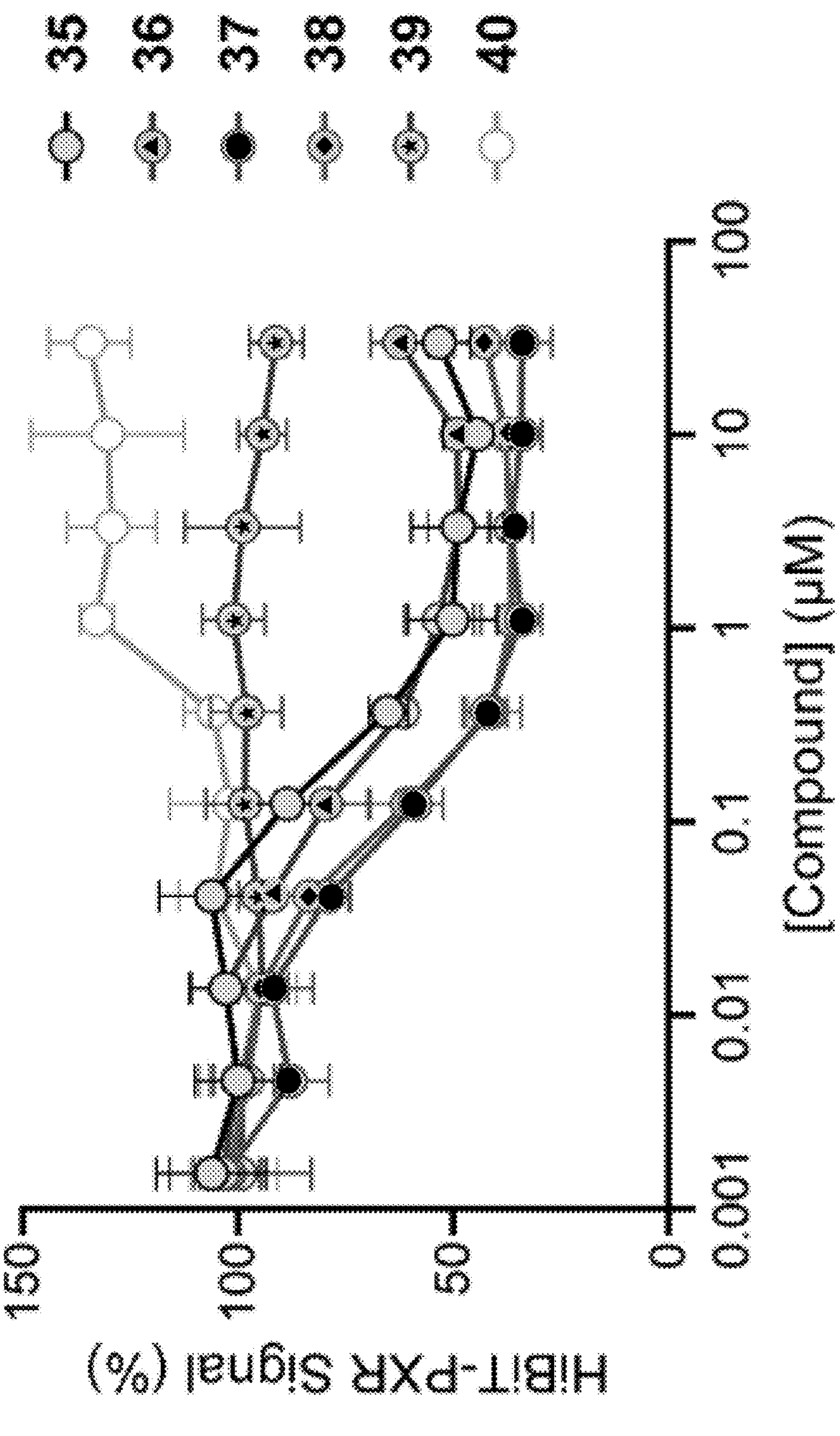

The curves for all compounds are shown in FIG. 7.

e. Western Blotting

SNU—C4 3×FLAG-PXR KI cells were plated in tissue culture-treated 12-well plates (Corning, cat. #3512, $1\times10^6$ cells/well in 1 mL assay media). The following day, DMSO or compounds were added to result in 0.5% DMSO and the indicated compound concentrations. At the indicated time points, cells were washed with DPBS, trypsinized, pelleted by centrifugation, and lysed in 50 μL radioimmunoprecipitation assay (RIPA) buffer [50 mM Tris (pH 8.0), 150 mM NaCl, 1% NP-40, 0.5% sodium deoxycholate, 0.1% SDS] supplemented with Halt Protease Inhibitor Cocktail (Thermo Fisher Scientific, cat. #78429). Protein in the lysate was quantified with the Pierce BCA Protein Assay Kit (Thermo Fisher Scientific, cat. #23227), and 50 μg was diluted with NuPAGE LDS Sample Buffer (Thermo Fisher Scientific, cat. #NP0007), heated at 95° C. for 5 min, and loaded into NuPAGE 4-12% Bis-Tris gels (Thermo Fisher Scientific). Separated proteins were transferred to nitrocellulose membranes using the iBlot 2 Dry Blotting System (Thermo Fisher Scientific). Membranes were blocked with TBST [50 mM Tris (pH 7.4), 150 mM NaCl, 0.1% Tween 20] containing 5% milk for 1 h at room temperature. Antibodies against FLAG (Sigma-Aldrich, cat. #F3165, 1:2,000 dilution) and β-Actin (Cell Signaling Technology, cat. #4967, 1:2,000 dilution) were bound overnight at 4° C. in TBST containing 5% milk. Membranes were washed with TBST three times for 10 min each, and IRDye 800CW Goat anti-Mouse IgG Secondary Antibody (LI-COR, cat. #926-32210, 1:10,000 dilution) and IRDye 680LT Goat anti-Rabbit IgG Secondary Antibody (LI-COR, cat. #926-68021, 1:10,000 dilution) were added in TBST containing 5% milk for 1 h at room temperature. Membranes were washed as above and imaged with an Odyssey CLx imaging system (LI-COR). Bands were quantified with Image Studio Lite Software (LI-COR) and normalized as FC relative to DMSO controls.

f. PXR Transactivation Assays

Assays were performed similarly as previously described with minor modifications (Huber, A. D.; et al., (2021) *Cell Mol Life Sci* 78 (1), 317-335; Lin, W.; et al (2020) *Mol Pharmacol* 97 (3), 180-190; Wang, Y. M.; et al (2015) *Biochem Pharmacol* 96 (4), 357-368). HepG2 cells ($7.5\times10^5$/well) were plated in six-well tissue culture-treated plates (Corning, cat. #353046). The following day, cells were co-transfected with 2 μg/well pGL3-CYP3A4-luc and 100 ng/well pcDNA3-FLAG-PXR using Lipofectamine 3000 (Thermo Fisher Scientific, cat. #L3000015). After 24 h, cells were trypsinized and suspended in assay media, and $1\times10^4$ cells/well in 25 μL media were added to white tissue culture-treated 384-well plates. An Echo 655T Acoustic Liquid Handler was used to dispense 75 nL/well of DMSO or stock compounds, resulting in 0.3% DMSO and the indicated concentrations of chemicals. For wells containing two compounds, the final DMSO of all wells was 0.4% with the indicated concentrations of compounds. After 24 h, the steadylite plus Reporter Gene Assay System (Revvity, cat. #6066751) and EnVision microplate reader were used to measure firefly luciferase activity. Cells treated with 5 μM rifampicin served as positive controls, and DMSO-treated cells served as negative controls. The measured RLU were normalized for each well using equation 4.

$$PXR\text{ Activity }(\%) = 100\times\frac{(RLU_{Test\ Compound} - RLU_{Negative\ Control})}{(RLU_{Postive\ Control} - RLU_{Negative\ Control})}$$

g. Quantitative Reverse Transcription Polymerase Chain Reaction (Rt-QPCR)

SNU—C4 cells were plated in tissue culture-treated 12-well plates ($1.5\times10^5$ cells/well in 1 mL RPMI with 10% FBS) and grown for seven days with fresh media added every 2-3 days. Cells were washed with DPBS, and 800 μL assay media containing 0.5% DMSO and the indicated concentrations of compounds was added. After 24 h, cells were washed with DPBS, total RNA was isolated with Maxwell 16 LEV SimplyRNA Tissue Kits (Promega, cat. #AS1280), and cDNA was generated from 1 μg of RNA with the SuperScript VILO cDNA Synthesis Kit (Thermo Fisher Scientific, cat. #11754050). RT-qPCR was conducted with 2 μL of cDNA using TaqMan Fast Advanced Master Mix (Thermo Fisher Scientific, cat. #4444557) in an Applied Biosystems 7500 Fast or QuantStudio 5 Real-Time PCR System. TaqMan gene expression assays specific for CYP3A4 (assay ID Hs00604506_ml), PXR (assay ID Hs01114267_ml), and RNA18S (assay ID Hs03928990_g1) were purchased from Thermo Fisher Scientific. Fold induction values were calculated according to the $2^{-\Delta\Delta Ct}$ method, where ΔCt represents the differences in cycle threshold numbers between the target gene and reference gene and ΔΔCt represents the relative change in these differences between the control and treatment groups (Livak, K. J.; et al., (2001) *Methods* 25 (4), 402-408). RNA18S was used as the reference gene for relative quantification of other genes.

h. Cytotoxicity Assays

An Echo 655T Acoustic Liquid Handler was used to dispense 75 nL/well of DMSO or PROTAC dilution into white tissue culture-treated 384-well plates. For 24 h cytotoxicity, 25 μL assay media containing $1\times10^4$ cells was added to each well to match the conditions for the degradation assays. For 72 h cytotoxicity, 25 μL RPMI with 10% FBS containing $2.5\times10^3$ cells was added to each well to match normal growth conditions. These volumes resulted in 0.3% final DMSO in each well. After 24 h or 72 h, the CellTiter-Glo Luminescent Cell Viability Assay (Promega, cat. #G7572) and an EnVision microplate reader were used to assess cytotoxicity. DMSO wells with cells served as positive controls, and wells without cells served as negative controls. The percent cell viability for each well was calculated using equation 5, $$\%\text{ Cell Viability} = 100\times\frac{(RLU_{Test\ Compound} - RLU_{Negative\ Control})}{(RLU_{Postive\ Control} - RLU_{Negative\ Control})}$$

Figure 8:
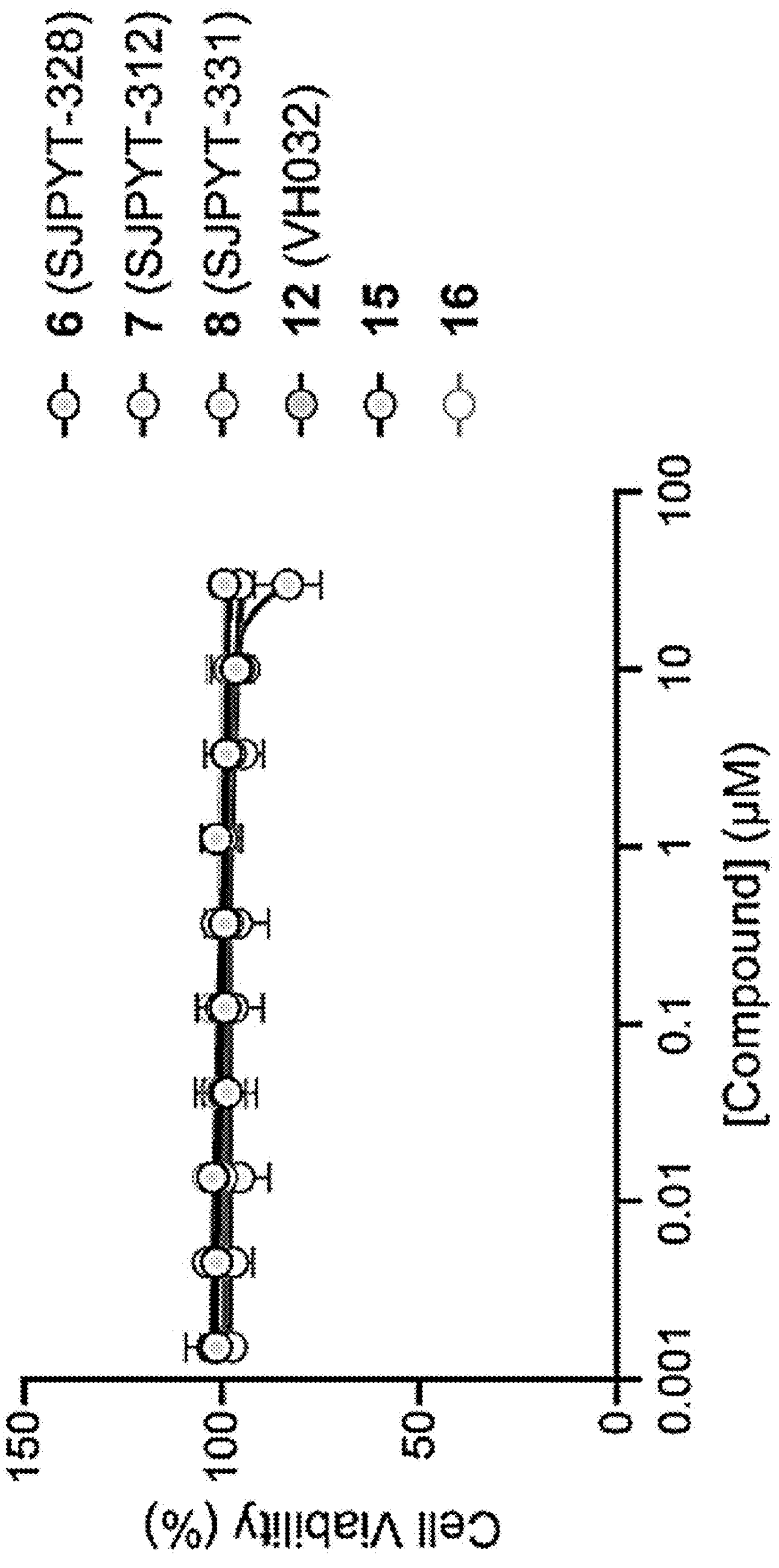
FIG. 8 shows representative data illustrating disclosed PROTACs are not cytotoxic at 24 h.
Figure 8:
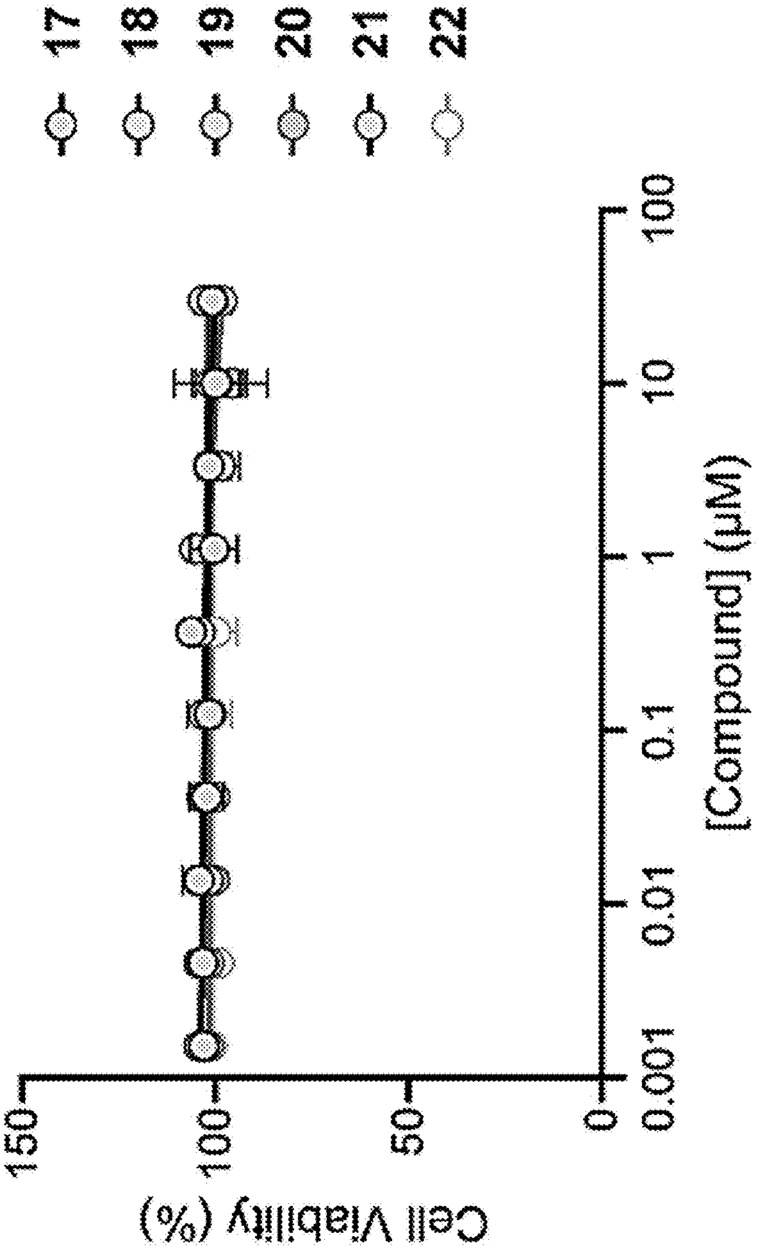
Figure 8:
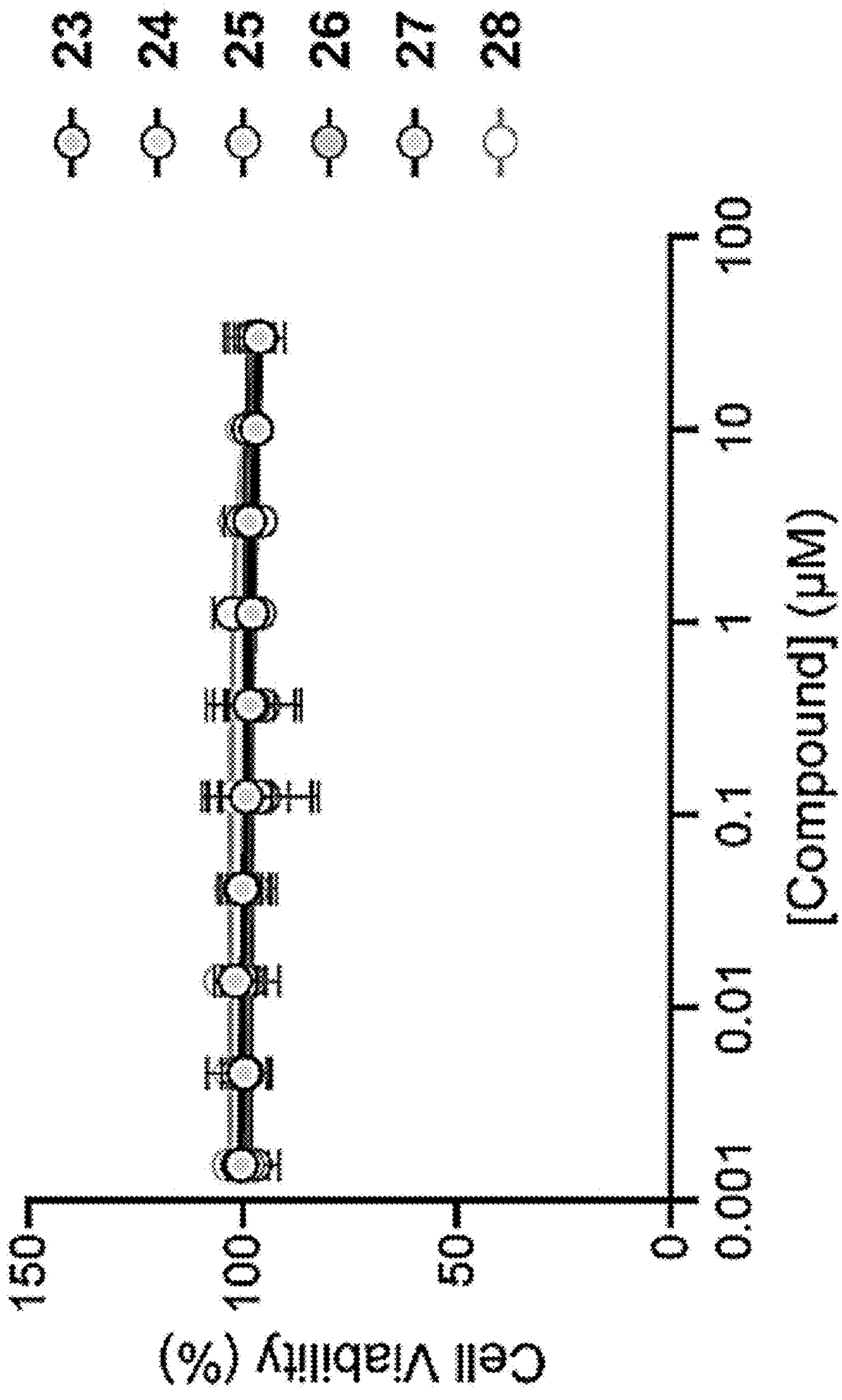
Figure 8:
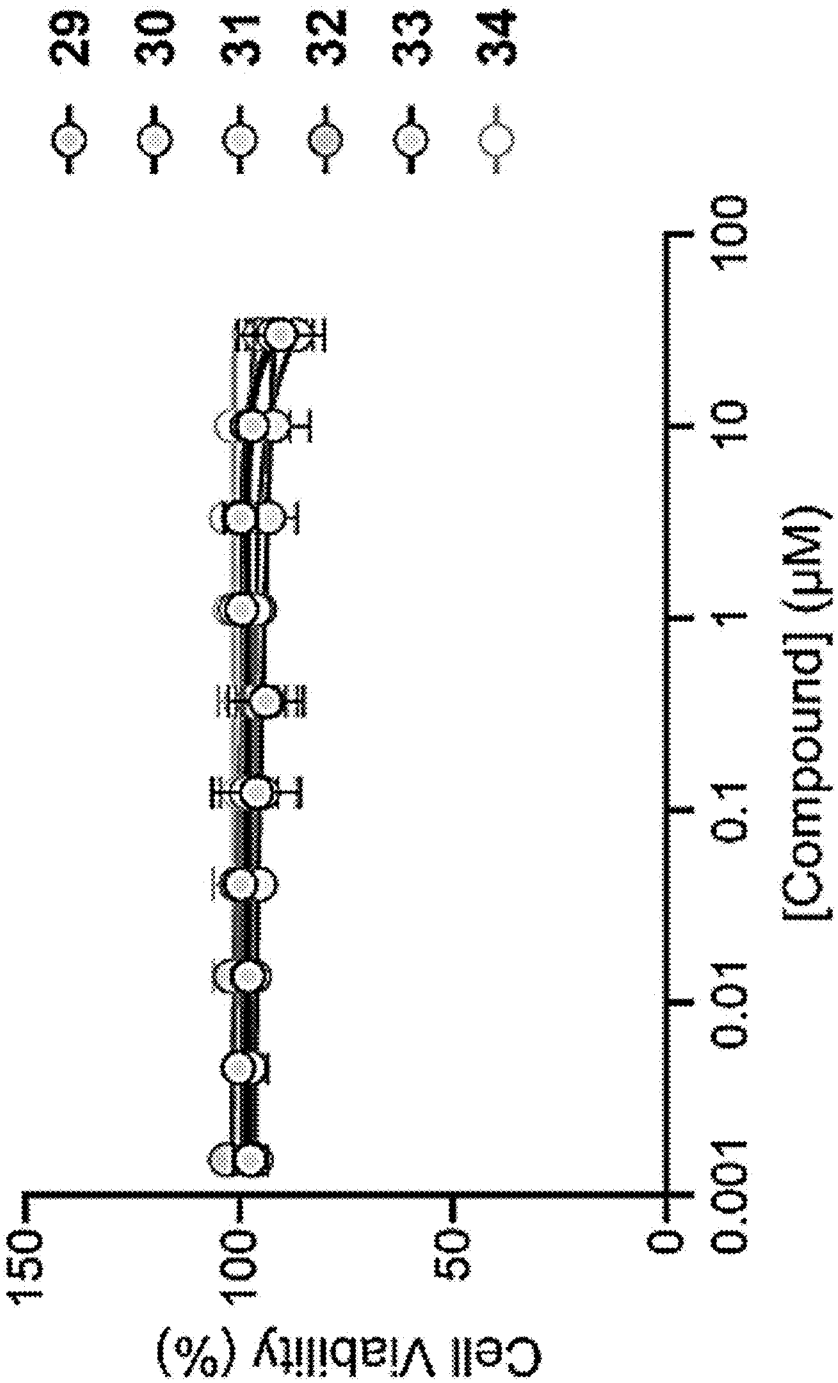
Figure 8:
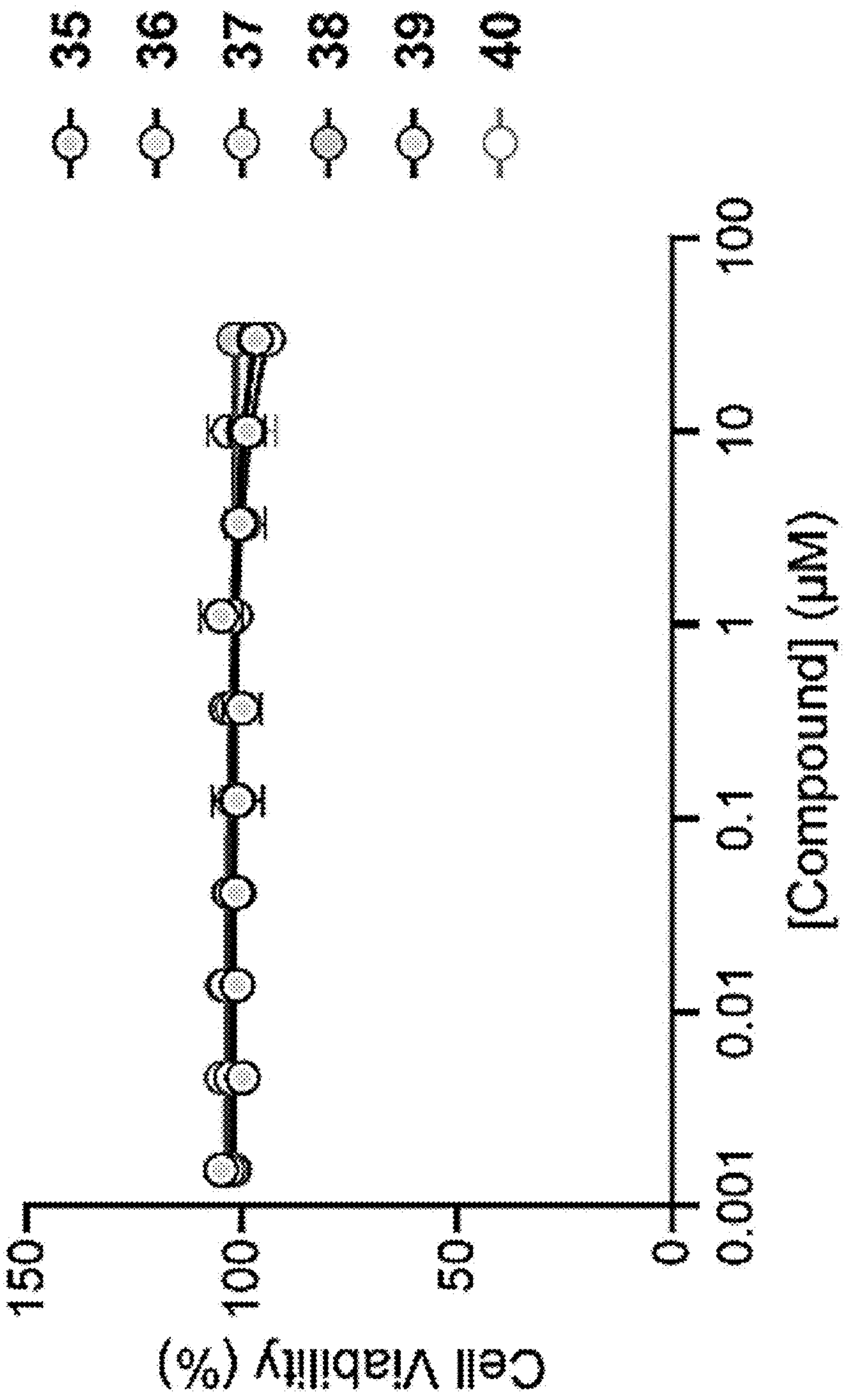
Figure 9:
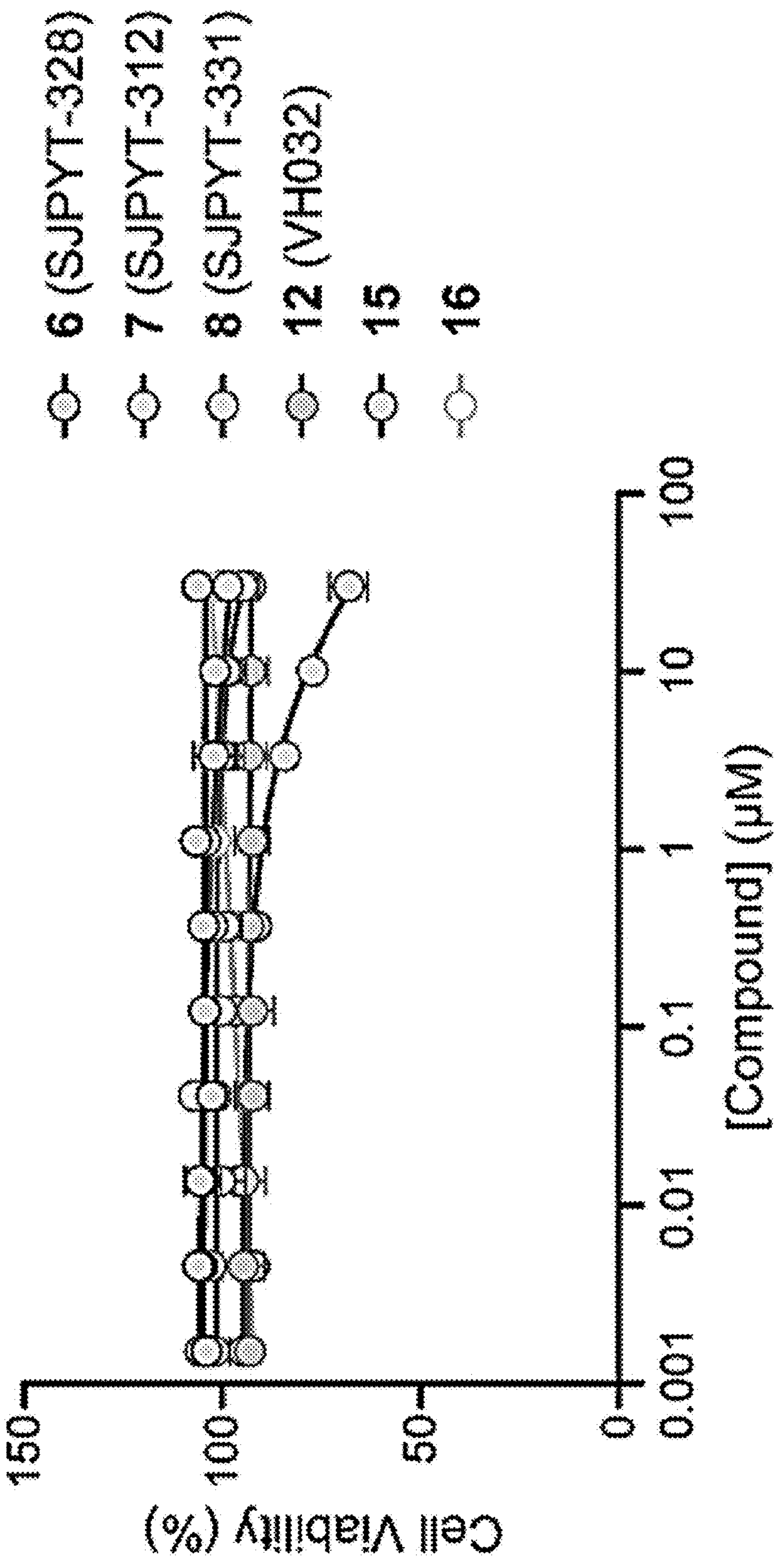
FIG. 9 shows representative data illustrating disclosed PROTACs are not cytotoxic at 72 h.
Figure 9:
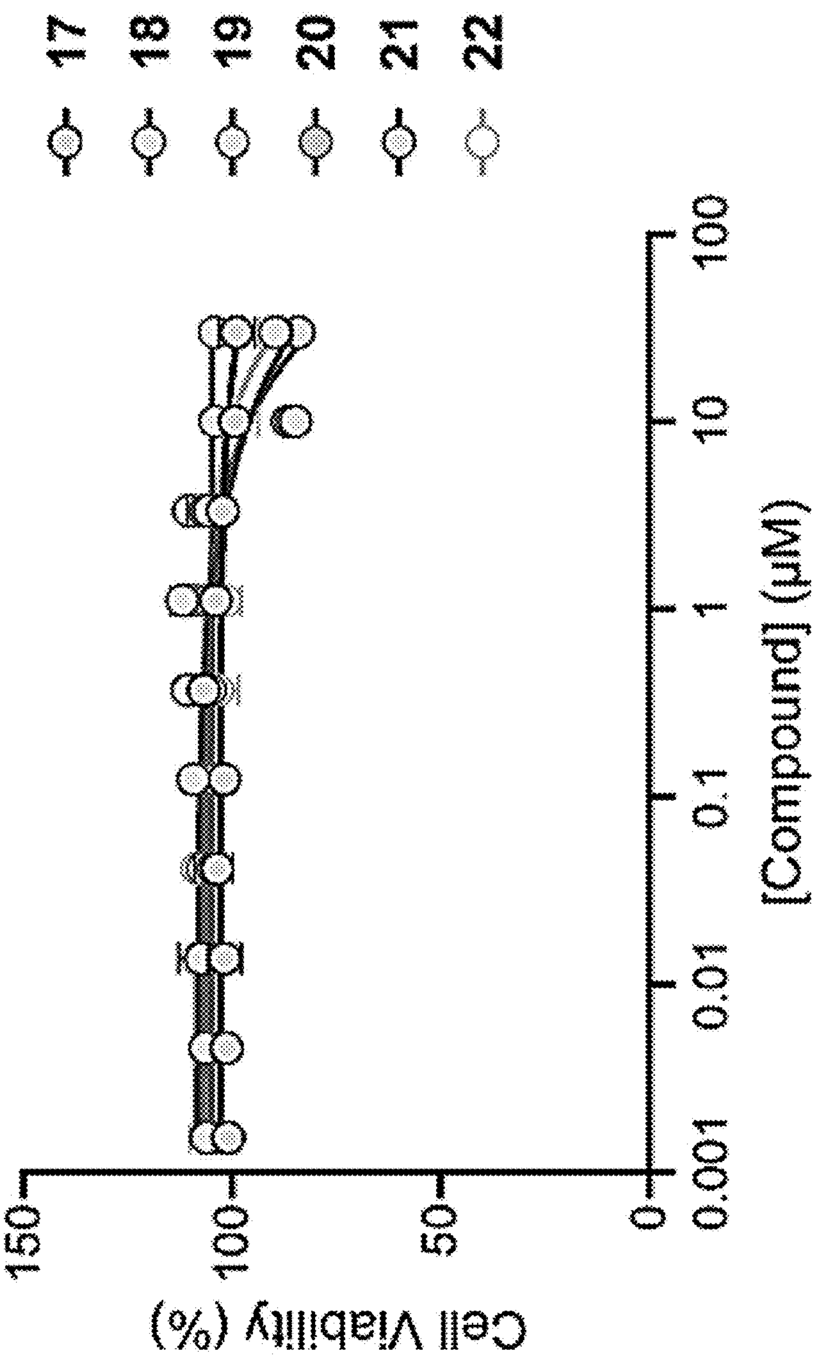
Figure 9:
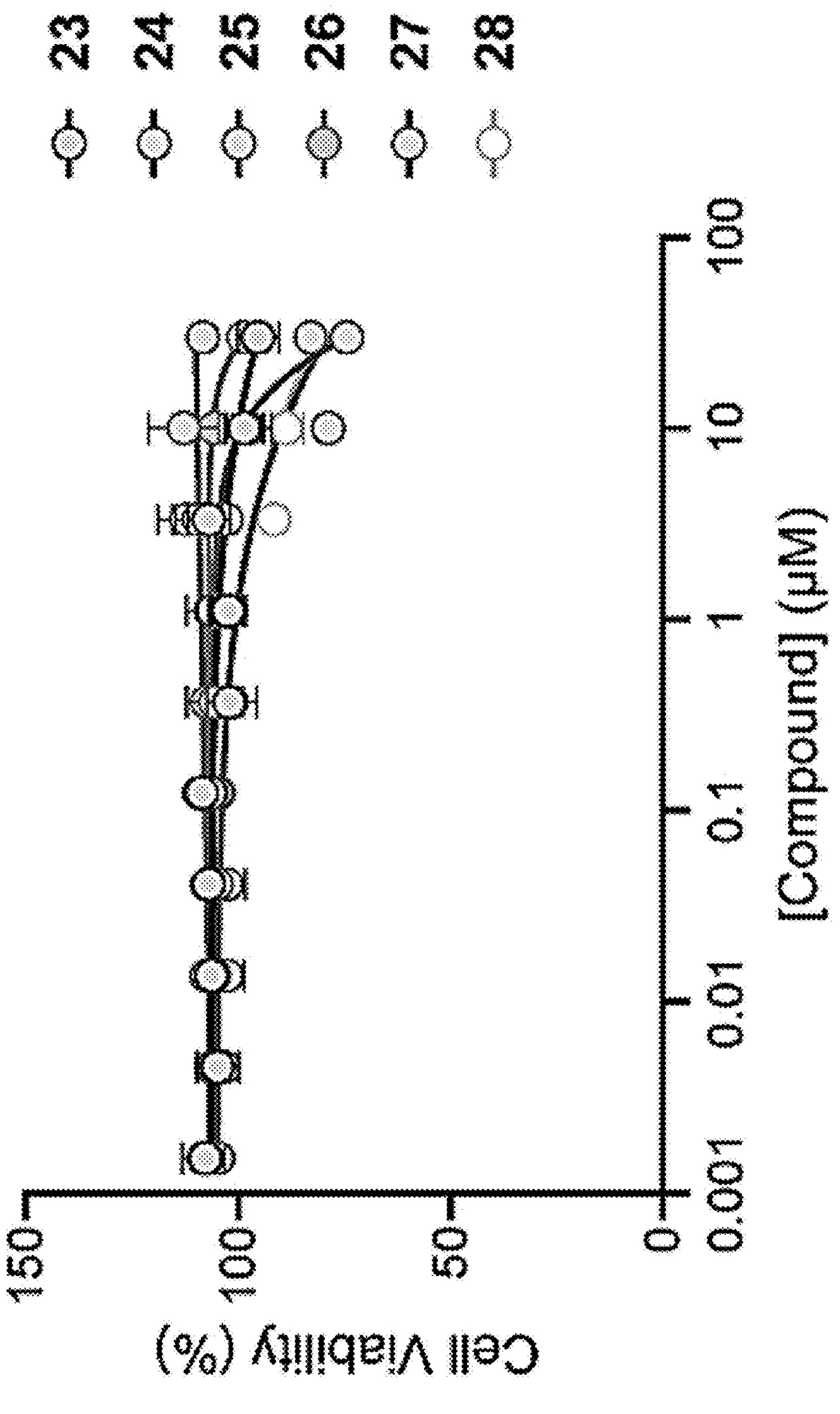
Figure 9:
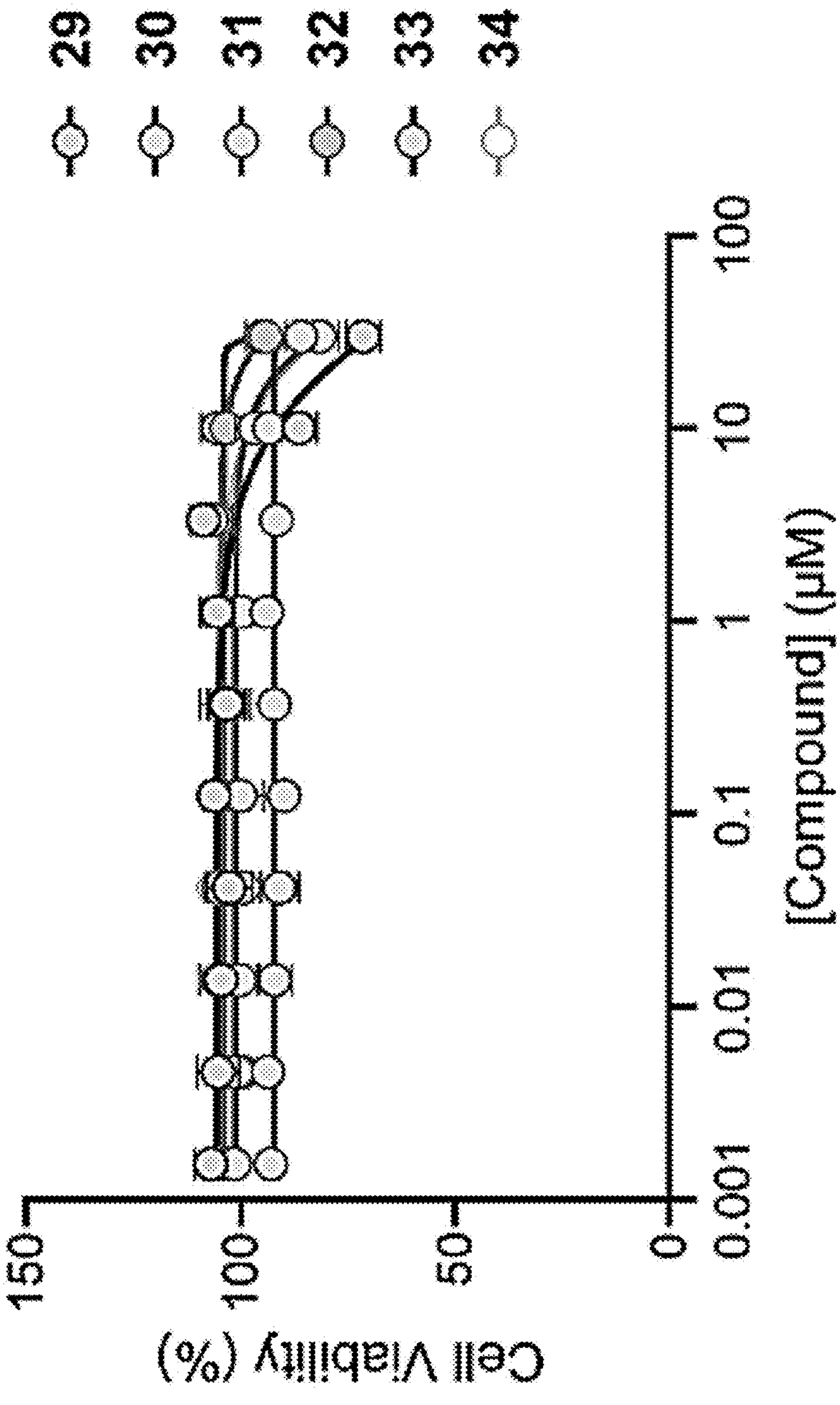
Figure 9:
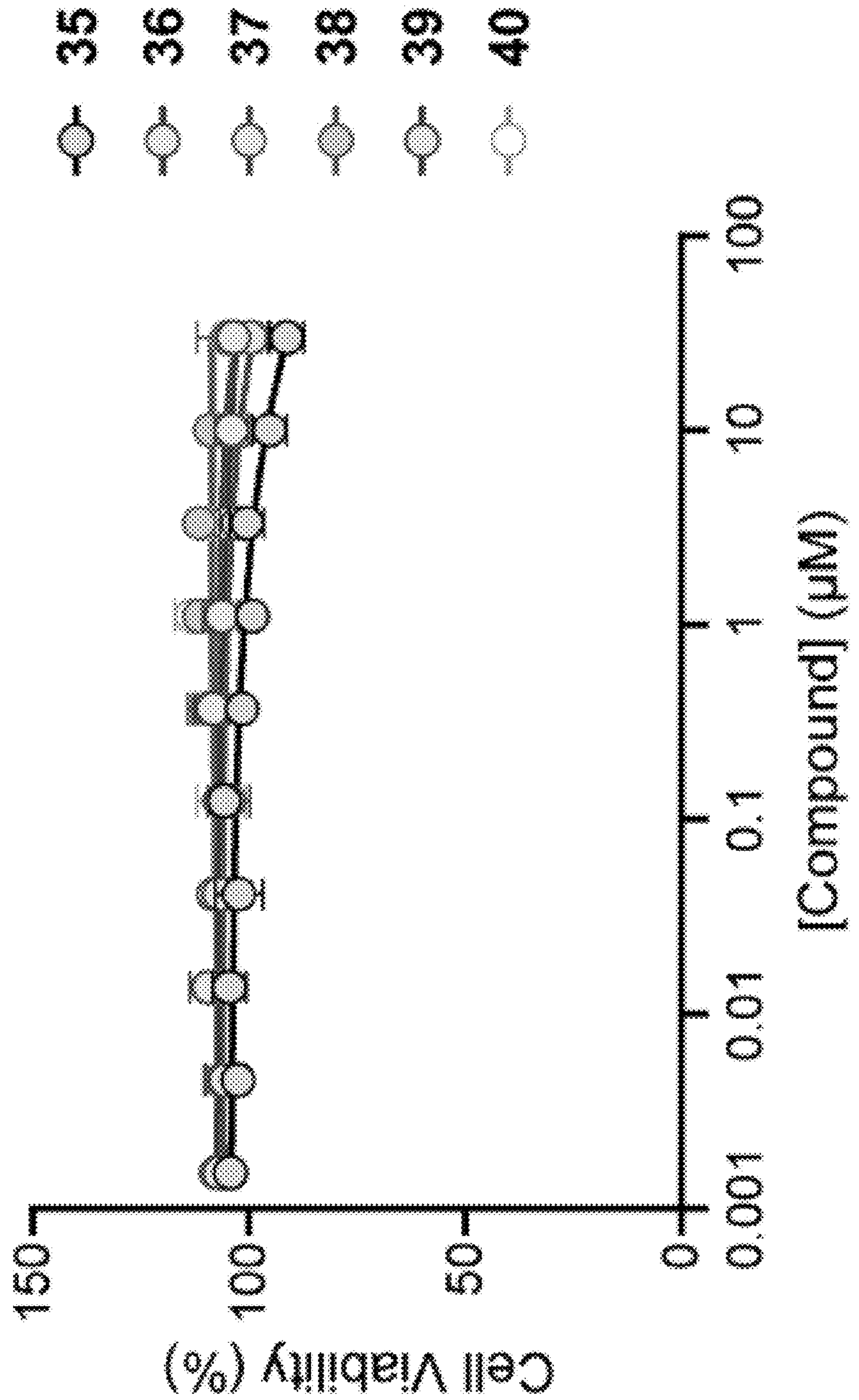

The resulting curves for all compounds are shown in FIG. 8 and FIG. 9.

For PROTAC/paclitaxel combinations, 75 nL paclitaxel dilution and 25 nL DMSO or PROTAC stock was added to wells. SNU—C4 cells ($2.5\times10^3$/well in 25 μL RPMI with 10% FBS) were added to the 384-well plates, resulting in 0.4% DMSO and the indicated concentrations of paclitaxel with or without PROTAC. After 72 h compound treatment, cell viability was measured as above.

3. RESULTS AND DISCUSSION a. Structure-Guided Design of PXR-Linker-E3 Directionality

Previous attempts at generating PXR PROTACs yielded CRBN-mediated molecular glue degraders of GSPT1 (Huber, A. D.; et al., (2022) *ACS Med Chem Lett* 13 (8), 1311-1320. DOI: 10.1021/acsmedchemlett.2c00223). Further study suggested that PXR degradation may be difficult due to the large distance between the buried ligand binding pocket and the protein surface, precluding the use of short linkers to recruit the E3 ligase (Huber, A. D., et al, (2024) *Structure* 32 DOI: 10.1016/j.str.2024.09.016). However, the ligand binding pocket is malleable, offering potential opportunities for PROTACs to function through protein remodeling. Because PXR binds vastly diverse ligands (FIG. 1A and FIG. 1B), structures of PXR bound to different ligand scaffolds were analyzed to identify a starting point for PROTAC derivatization (FIG. 2A and FIG. 2B). Binding of the agonist T0901317 results in a compact, buried pocket (Xue, Y.; et al., (2007) *Bioorg Med Chem* 15 (5), 2156-2166), but the extended analog T0-BP displaces alpha helix 2 (α2), introducing a pore (FIG. 2A) (Lin, W.; et al., (2023) *Proc Natl Acad Sci USA* 120 (10), e2217804120). The α2 region is flexible to such an extent that it is even unobserved in certain crystal structures, such as PXR LBD bound to the agonist sjb7 (FIG. 2A)(Lin, W.; et al., (2017) *Nat Commun* 8 (1), 741. DOI: 10.1038/s41467-017-00780-5). Unlike T0901317 and T0-BP, SJB7 and related analogs also puncture the PXR surface above α12 (FIG. 2B)(Lin, W.; et al., (2017) *Nat Commun* 8 (1), 741. DOI: 10.1038/s41467-017-00780-5; Garcia-Maldonado, E.; et al., (2024) *Nat Commun* 15 (1), 4054. DOI: 10.1038/s41467-024-48472-1). Thus, the sulfonyl-based SJB7 and related amide-linked scaffolds offer two solvent-accessible points for potential linker connection: α2 (site 1) and α12 (site 2) (FIG. 2C).

Figure 2A:
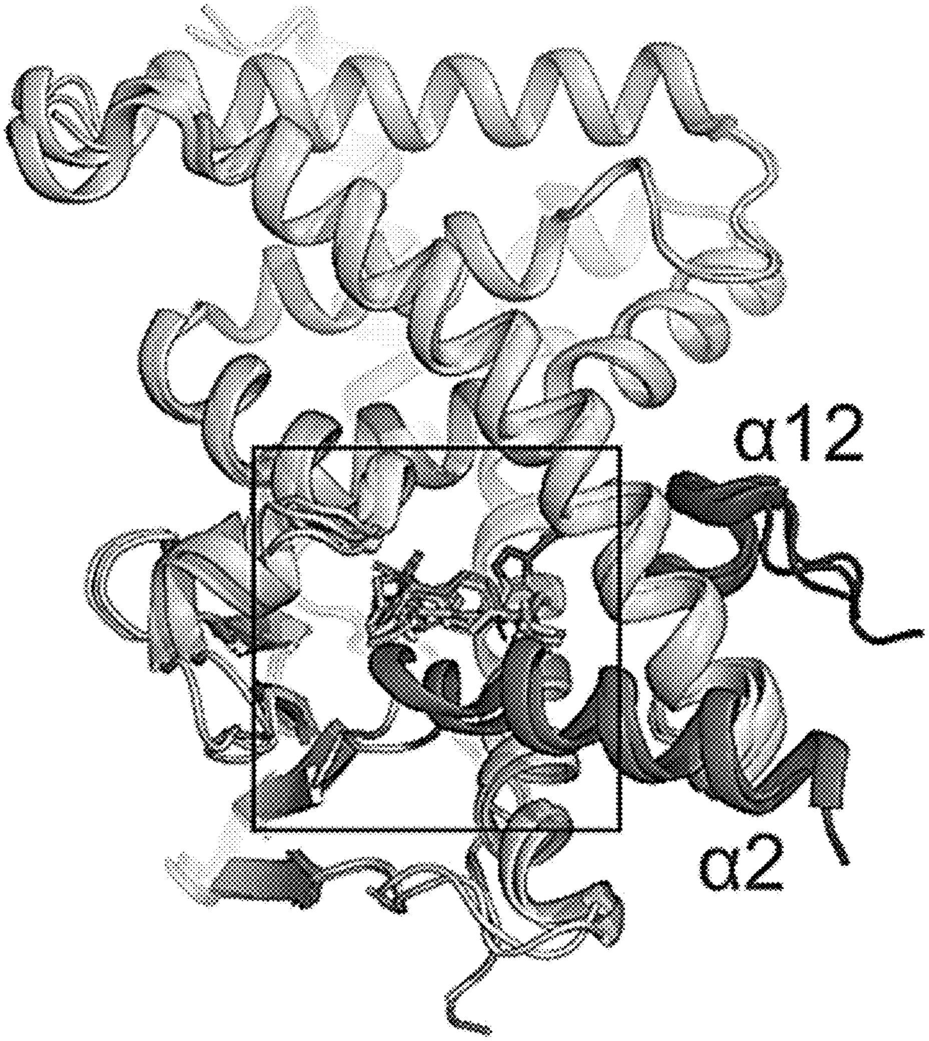
FIG. 2A-D show representative crystal structures of PXR ligand binding domain and representative binding data of compounds 13 and 14.
Figure 2A:
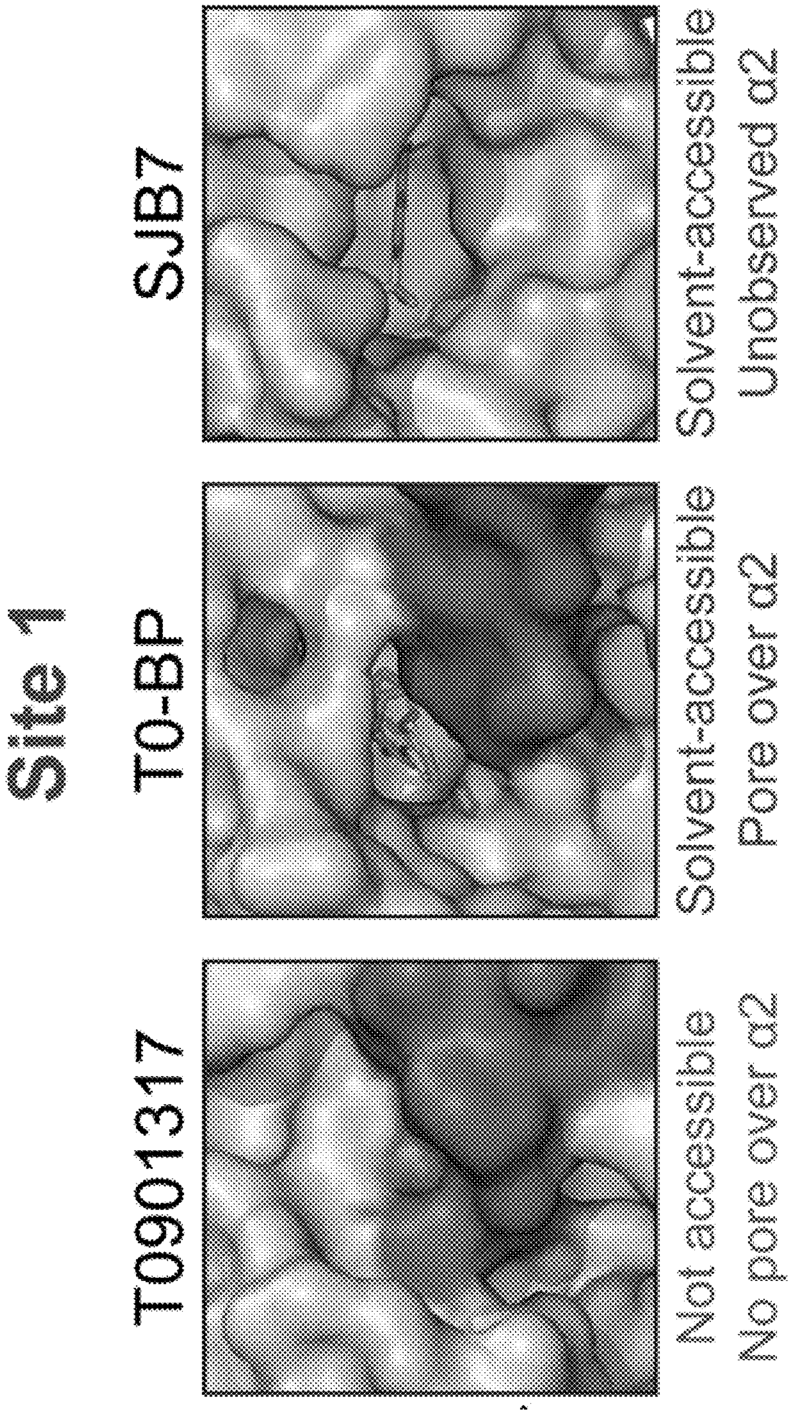
Figure 2B:
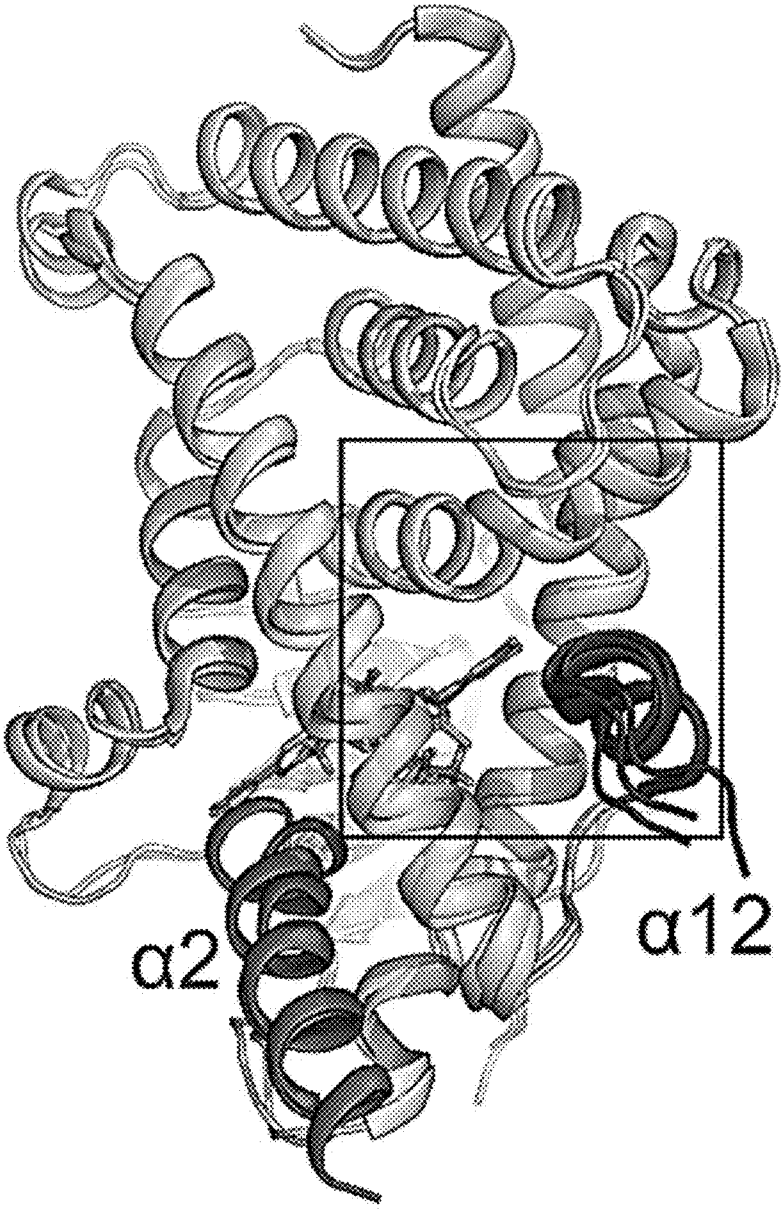
Figure 2B:
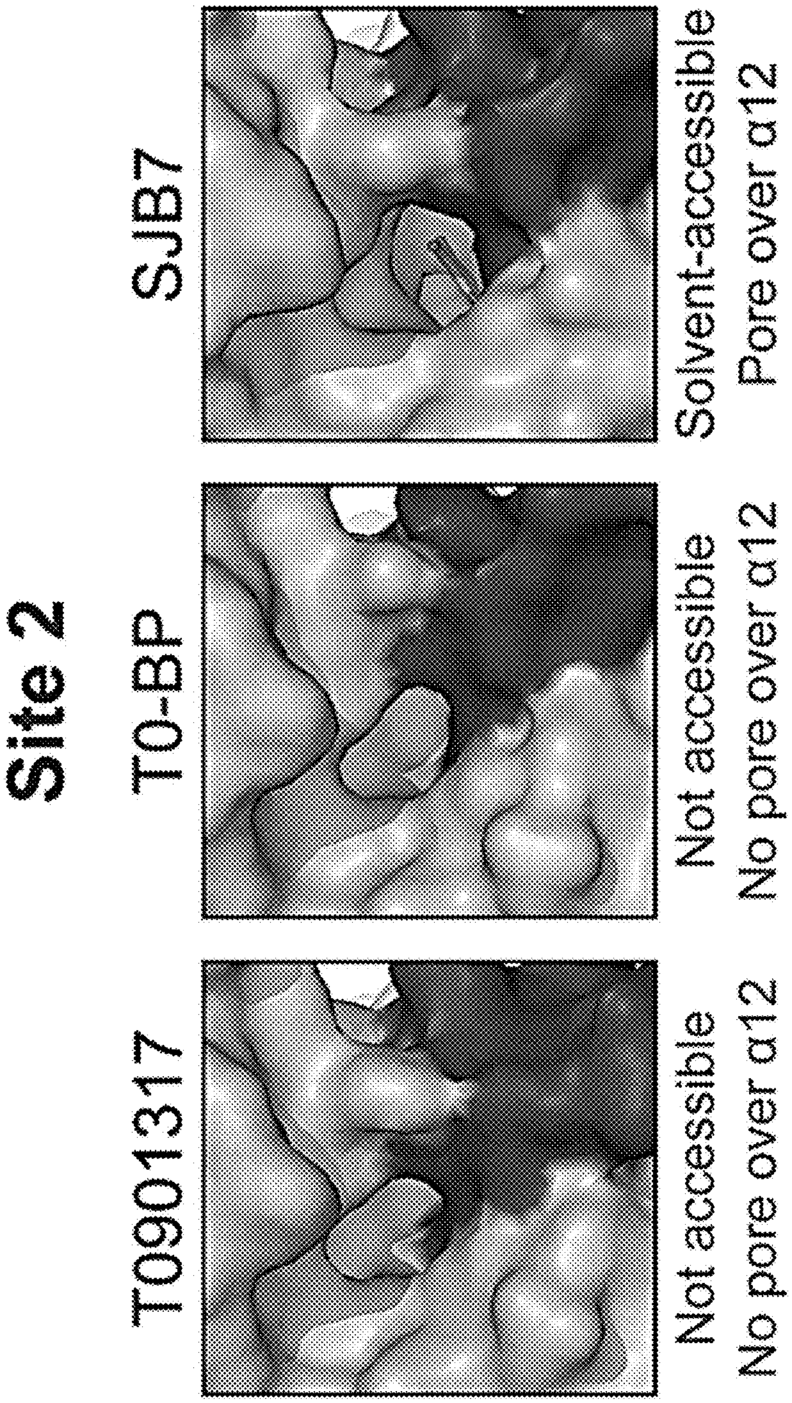
Figure 2C:
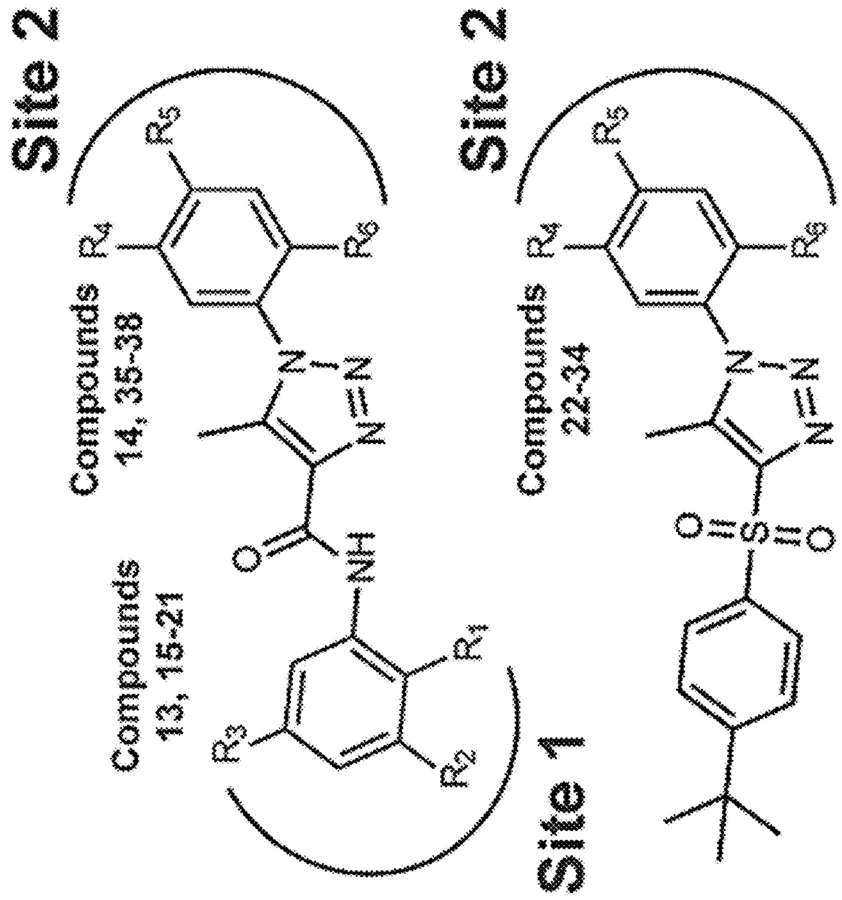
Figure 2D:
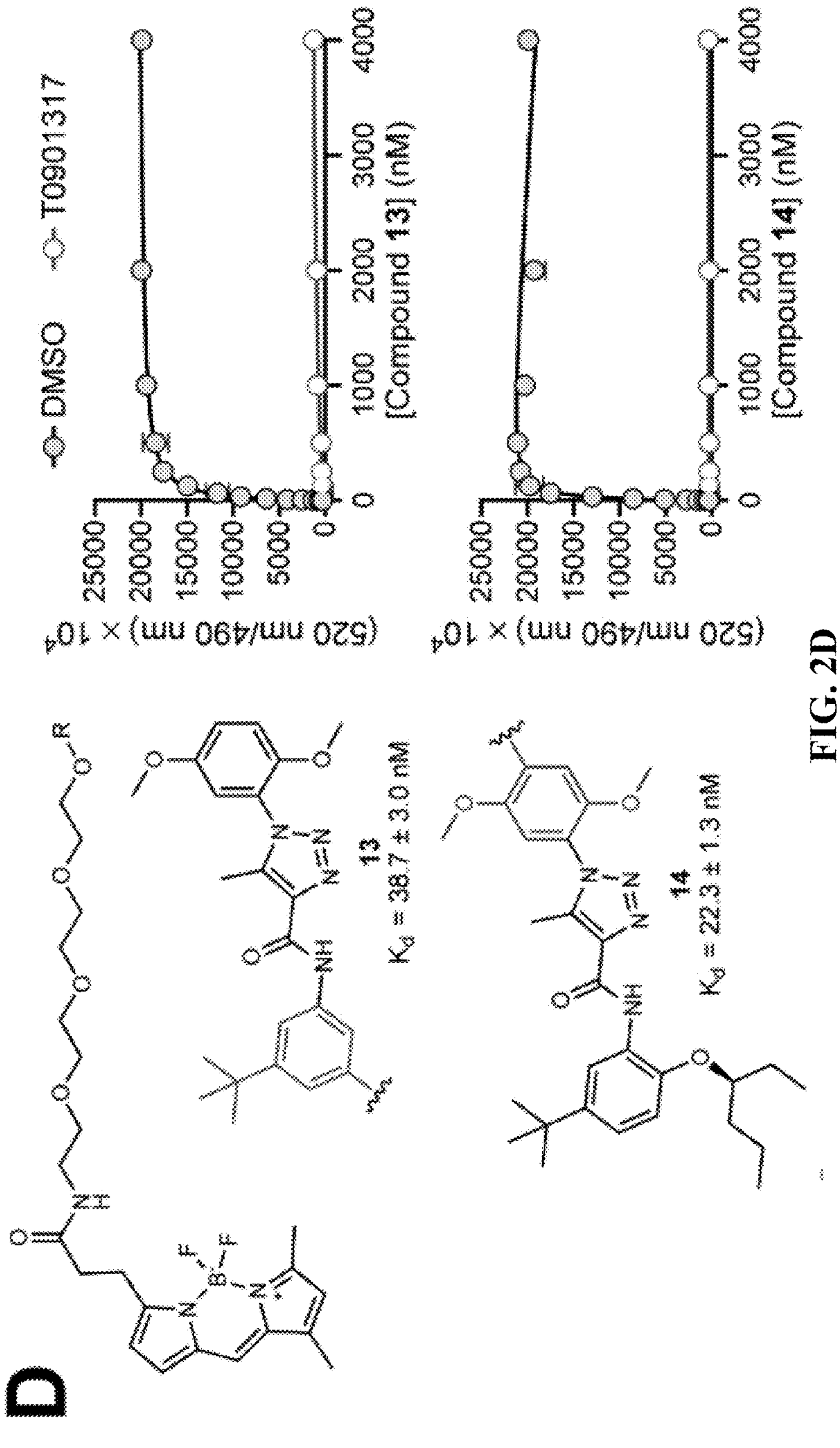

To verify that attachment of a linker to site 1 or site 2 of the sulfonyl-based SJB7 and related amide-linked scaffolds does not result in loss of PXR binding, two fluorescent probes, 13 and 14 were synthesized and tested their binding to fluorescently labeled PXR LBD by a time-resolved fluorescence resonance energy transfer (TR-FRET) assay. Site 1 was tested with 13 (in which fluorescent dye BODIPY FL is attached to site 1), and site 2 was tested with 14 (in which BODIPY FL is attached to site 2) (FIG. 2D). Both probes bound PXR LBD with comparable affinity, with apparent dissociation constants ($K_D$) of 38.7 nM (13) and 22.3 nM (14). Without wishing to be bound by theory, both sites appeared to be viable for linkage to E3 ligands. Because of the previously observed CRBN-mediated GSPT1 off-target effects (Huber, A. D.; et al., (2022) *ACS Med Chem Lett* 13 (8), 1311-1320), VHL was selected as the E3 ligase substrate receptor and utilized VH032 as the E3 ligand (Galdeano, C.; et al., (2014) *J Med Chem* 57 (20), 8657-8663).

Figure 1B:
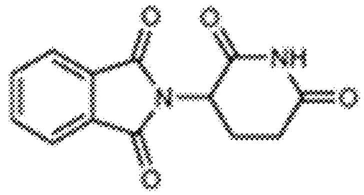
Figure 1B:
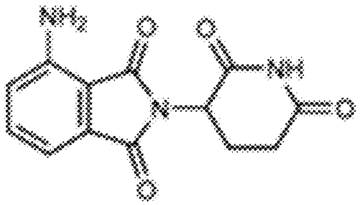
Figure 1B:
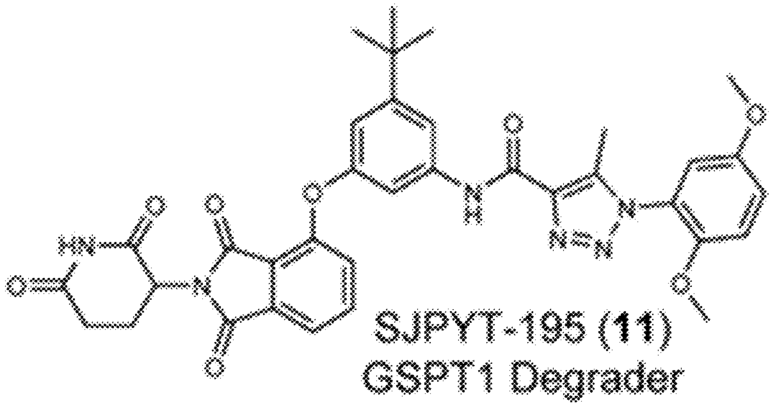
Figure 1B:
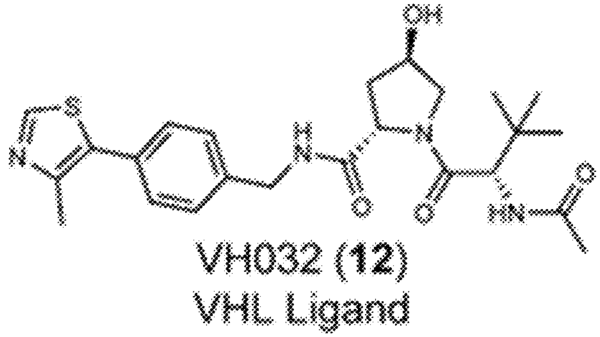

FIG. 1A shows representative PXR ligands with antagonists indicated and FIG. 1B shows representative chemical structures of CRBN ligands, a thalidomide-PXR ligand-conjugated GSPT1 degrader, and the VHL ligand VH032. FIG. 2A-D shows the PXR PROTAC design strategy. FIG. 2A and FIG. 2B show the overlaid crystal structures of PXR LBD bound to T0901317 (PDB ID 209I), T0-BP (PDB ID 8FPE), or SJB7 (PDB ID 5X0R). The surface views show where PROTAC linkers may protrude from the binding pocket. α2 and α12 are highlighted. FIG. 2C shows the general scaffolds for the amide- and sulfonyl-based PXR ligands. FIG. 2D shows the fluorescent probes were synthesized to protrude over α2 (site 1, compound 13) or α12 (site 2, compound 14). The probes were tested for binding affinity to fluorescently labeled PXR LBD by TR-FRET assay in the absence or presence of 20 M T0901317 to confirm displacement from the ligand binding pocket.

b. Site 1 Conjugates Weakly Reduce PXR Protein Level

Compounds 15-21 were conjugated at site 1 of the amide-linked scaffolds with the VHL ligand VH032 using variable linker lengths, compositions, and connection positions, Table 2, FIG. 7). Of the seven compounds, only 15 reduced PXR protein level after 24 h treatment, but weakly, with half-maximal degradation concentration ($DC_{50}$) of 886 nM and maximal degradation ($D_{max}$) of 33.1%. To reflect both $DC_{50}$ and $D_{max}$, as well as potential hook effects, area under the curve (AUC) was calculated, in which higher values indicate more potent and/or complete degradation, values near zero indicate no activity, and negative values indicate protein stabilization rather than degradation. 15 had an AUC of 61.1 compared to 33.8 for the control unconjugated VH032. 15 also showed little cytotoxicity with both 24 h and 72 h treatment (FIG. 8 and FIG. 9).

TABLE 2

EVALUATION OF SITE 1 CONNECTION BETWEEN PXR AND VHL LIGANDS

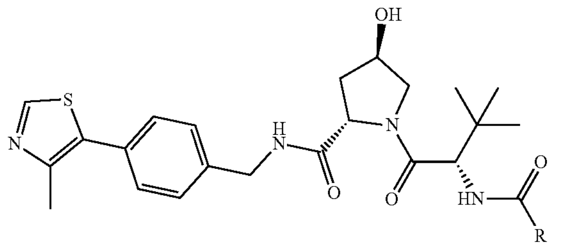

| Compound | $DC_{50}$ (nM)[a] | $D_{max}$ (%) | AUC | 24 h $CC_{50}$ (μM)[b] | 72 h $CC_{50}$ (μM) |
|---|---|---|---|---|---|
| SJPYT-328 (6) | >30,000 | ND[c] | −8.89 ± 11 | >30 (99.3 ± 2.0) | >30 (106 ± 3.3) |
| SJPYT-312 (7) | >30,000 | ND | −17.7 ± 23 | >30 (95.7 ± 2.6) | >30 (98.7 ± 1.8) |
| SJPYT-331 (8) | >30,000 | ND | −20.1 ± 11 | >30 (95.6 ± 3.9) | >30 (94.9 ± 4.0) |
| VH032 (12) | >30,000 | ND | 33.8 ± 7.0 | >30 (99.6 ± 3.6) | >30 (93.0 ± 1.6) |
| 15 SJPYT-149 (12 atoms) | 886 ± 280 | 33.1 ± 2.9 | 61.1 ± 15 | >30 (83.2 ± 8.4) | >30 (68.2 ± 4.8) |
| 16 SJPYT-348 (0 atoms) | >30,000 | ND | −26.9 ± 18 | >30 (99.9 ± 3.5) | >30 (101 ± 3.2) |
| 17 SJPYT-349 (6 atoms) | >30,000 | ND | −34.9 ± 23 | >30 (101 ± 2.0) | >30 (98.9 ± 4.4) |

TABLE 2-continued

EVALUATION OF SITE 1 CONNECTION BETWEEN PXR AND VHL LIGANDS

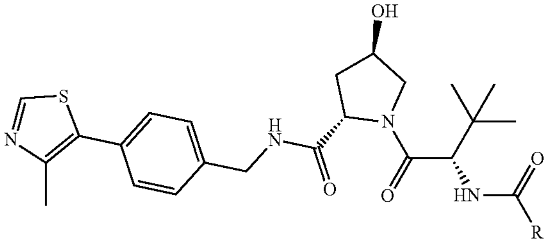

| Compound | $DC_{50}$ (nM)[a] | $D_{max}$ (%) | AUC | 24 h $CC_{50}$ (μM)[b] | 72 h $CC_{50}$ (μM) |
|---|---|---|---|---|---|
| 18 SJPYT-351 (9 atoms) | >30,000 | ND | −35.3 ± 21 | >30 (103 ± 3.5) | >30 (89.7 ± 3.3) |
| 19 SJPYT-350 (10 atoms) | >30,000 | ND | −20.1 ± 30 | >30 (102 ± 2.9) | >30 (104 ± 3.8) |
| 20 SJPYT-352 (12 atoms) | >30,000 | ND | −29.6 ± 34 | >30 (98.3 ± 2.4) | >30 (89.1 ± 2.5) |
| 21 SJPYT-353 (15 atoms) | >30,000 | ND | −46.3 ± 23 | >30 (100 ± 4.7) | >30 (84.1 ± 1.7) |

a$DC_{50}$, $D_{max}$, and AUC were determined by 24 h treatment of SNU-C4 HiBiT-PXR KI cells, which were generated by fusing a HiBiT tag to the N-terminus of endogenous PXR by CRISPR/Cas9. Values represent mean ± SD from four replicates.

[b]The 50% cytotoxic concentration ($CC_{50}$) was determined by treating SNU-C4 HiBiT-PXR KI cells for 24 h or 72 h followed by CellTiter-Glo Luminescent Cell Viability Assay. Values are derived from four replicates, and the percentage of cells remaining at the highest concentration (30 μM) is shown in parentheses (mean ± SD).

[c]ND (not determined): $D_{max}$ could not be determined due to no observed HiBiT-PXR degradation.

c. Site 2 Conjugates More Potently Reduce PXR Protein Level

Linkage of VH032 to site 1 yielded the weak degrader 15 and six inactive compounds (Table 2). To determine if site 1 should be further explored or if site 2 is a better starting point, compounds 22-34 with site 2 conjugation of the PXR ligand SJB7 to VH032 were synthesized and tested (Table 3, FIG. 7). Of the 13 compounds, two exhibited PXR degradation activity (28 and 32), which was the same hit rate as the site 1 analogs. Though the $DC_{50}$, $D_{max}$, and AUC for 15, 28, and 32 were all relatively similar among compounds, 28 had a higher $D_{max}$ (41.4%) than 15 (33.1%). Interestingly, aliphatic chains were preferred over PEG linkers, as the 12-atom PEG linker of 27 fully lost degradation activity compared to the 12-atom $PEG_2$-$C_6$ linker of 28. Furthermore, there appeared to be a critical linker length, as the 8-atom alkyl linker of 25 was inactive while the 12- and 19-atom linkers of 28 and 32, respectively, showed degradation.

TABLE 3

EVALUATION OF SITE 2 CONNECTION BETWEEN PXR AND VHL LIGANDS.

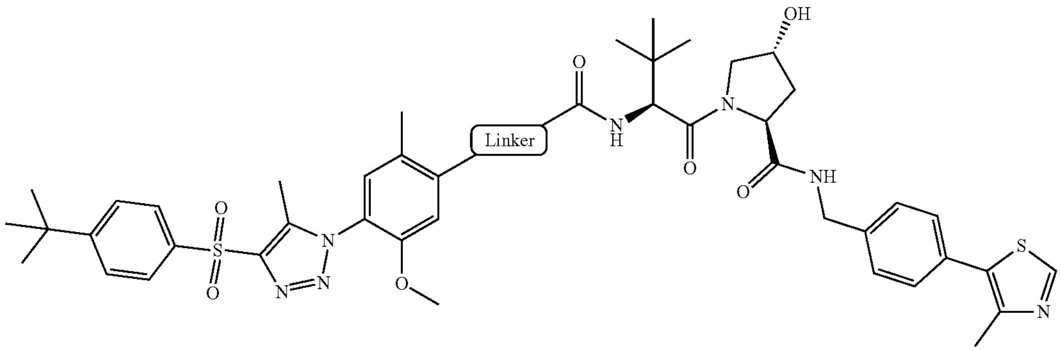 [SMILES: COc1cc(C)c(C)cc1-n1nnc(S(=O)(=O)c2ccc(C(C)(C)C)cc2)c1C ; CC(=O)N[C@H](C(=O)N1C[C@H](O)C[C@H]1C(=O)NCc1ccc(-c2scnc2C)cc1)C(C)(C)C]

| Compound | $DC_{50}$ (nM) | $D_{max}$ (%) | AUC | 24 h $CC_{50}$ (μM) | 72 h $CC_{50}$ (μM) |
|---|---|---|---|---|---|
| 22 SJPYT-339 (2 atoms) | >30,000 | ND | −16.9 ± 6.6 | >30 (99.1 ± 2.6) | >30 (89.6 ± 3.9) |

TABLE 3-continued

EVALUATION OF SITE 2 CONNECTION BETWEEN PXR AND VHL LIGANDS.

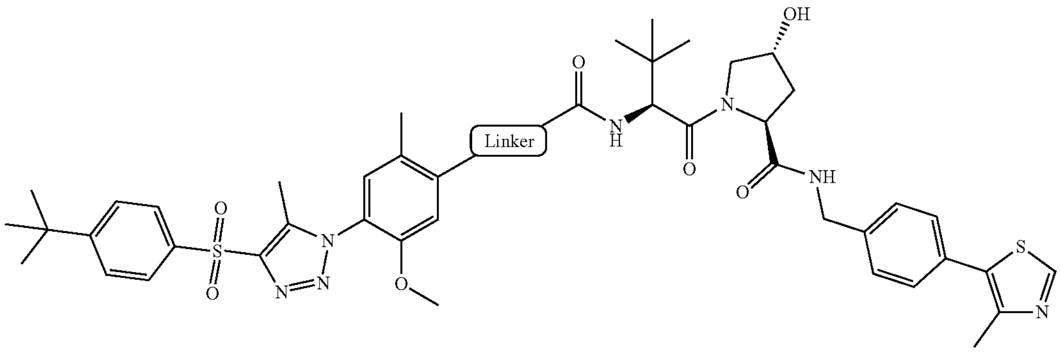

| Compound | $DC_{50}$ (nM) | $D_{max}$ (%) | AUC | 24 h $CC_{50}$ (μM) | 72 h $CC_{50}$ (μM) |
|---|---|---|---|---|---|
| 23 SJPYT-340 (4 atoms) | >30,000 | ND | −15.4 ± 11 | >30 (96.1 ± 2.3) | >30 (95.4 ± 4.8) |
| 24 SJPYT-342 (6 atoms) | >30,000 | ND | 27.0 ± 17 | >30 (95.6 ± 5.5) | >30 (74.6 ± 3.2) |
| 25 SJPYT-341 (8 atoms) | >30,000 | ND | 5.48 ± 15.7 | >30 (97.4 ± 4.7) | >30 (108 ± 3.6) |
| 26 SJPYT-343 (9 atoms) | >30,000 | ND | −19.1 ± 22 | >30 (98.5 ± 6.1) | >30 (98.9 ± 3.2) |
| 27 SJPYT-344 (12 atoms) | >30,000 | ND | −27.9 ± 24 | >30 (98.2 ± 5.3) | >30 (83.1 ± 2.8) |
| 28 SJPYT-294 (12 atoms) | 550 ± 270 | 41.4 ± 6.4 | 61.9 ± 22 | >30 (95.7 ± 1.2) | >30 (83.1 ± 2.9) |
| 29 SJPYT-345 (15 atoms) | >30,000 | ND | −14.5 ± 17 | >30 (90.5 ± 10) | >30 (71.5 ± 4.1) |
| 30 SJPYT-347 (17 atoms) | >30,000 | ND | 32.5 ± 8.1 | >30 (92.3 ± 4.4) | >30 (86.0 ± 3.3) |
| 31 SJPYT-346 (18 atoms) | >30,000 | ND | 18.2 ± 13 | >30 (86.8 ± 4.1) | >30 (81.6 ± 4.5) |
| 32 SJPYT-338 (19 atoms) | 472 ± 120 | 34.3 ± 2.6 | 58.4 ± 13 | >30 (95.4 ± 2.6) | >30 (94.3 ± 4.6) |
| 33 SJPYT-336 (19 atoms) | >30,000 | ND | 18.4 ± 20 | >30 (91.3 ± 7.1) | >30 (95.4 ± 2.9) |
| 34 SJPYT-337 (24 atoms) | >30,000 | ND | 13.6 ± 25 | >30 (97.9 ± 3.3) | >30 (82.2 ± 1.7) |

Of note, this series of analogs used the sulfonyl-based PXR ligand rather than the amide-linked scaffold utilized in 15. The amide substitution coupled with additional hydrophobic moieties on the site 1 phenyl ring results in higher PXR binding affinity due to optimized hydrogen bonding and hydrophobic interactions within the PXR ligand binding pocket (Li, Y.; et al., (2022) *J Med Chem* 65 (24), 16829-16859; Garcia-Maldonado, E.; et al., (2024) *Nat Commun* 15 (1), 4054). SJB7 was replaced with a corresponding amide analog that has ~10-fold higher affinity (Li, Y.; et al., (2022) *J Med Chem* 65 (24), 16829-16859) and observed a significant enhancement in degradation activity (compound 35, Table 4, FIG. 7). Altering the $R_1$ carbon chain on the site 1 phenyl ring had little impact on degradation efficiency (compound 36), but substituting the $R_3$ methyl for methoxy on the site 2 phenyl ring enhanced all degradation parameters (compound 37). Replacement of the tert-butyl at site 1 with a more hydrophilic group had no further effect on activity (compound 38).

Figure 3A:
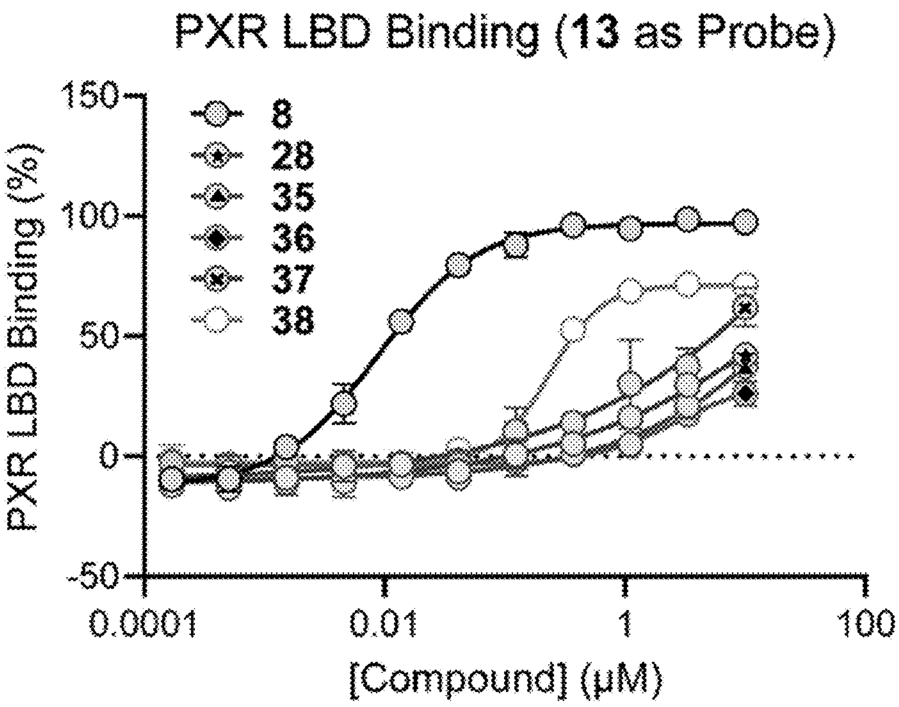
FIG. 3A-D show representative PROTAC binding affinity compounds to the PXR ligand binding domain and representative crystal structures of PXR LBD bound to coactivator SRC-1 and PROTAC precursors.
Figure 3B:
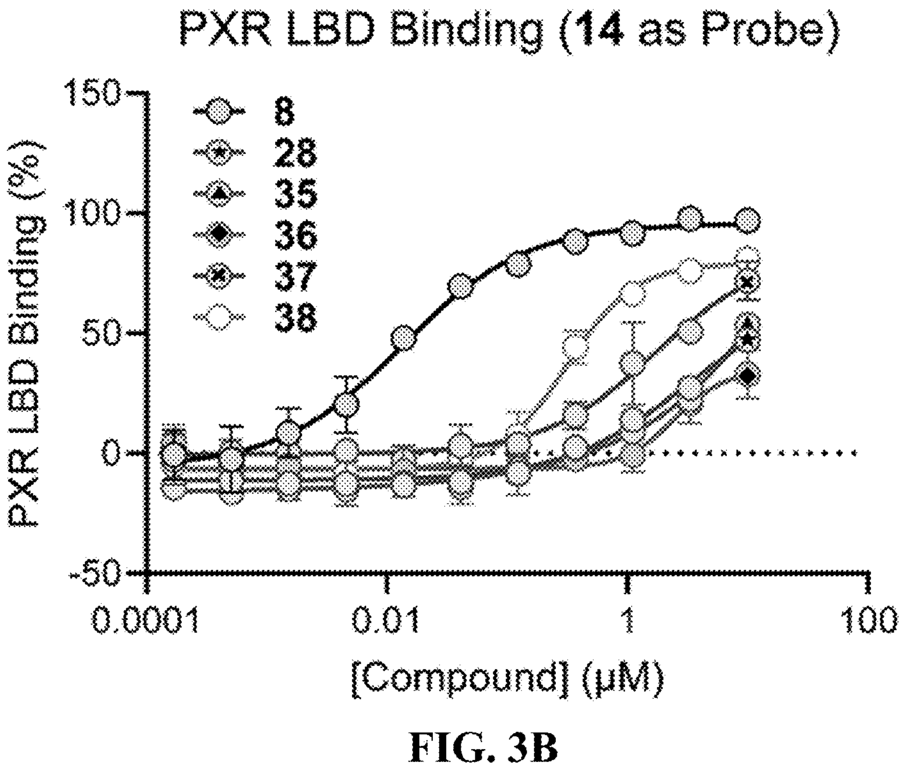
Figure 3C:
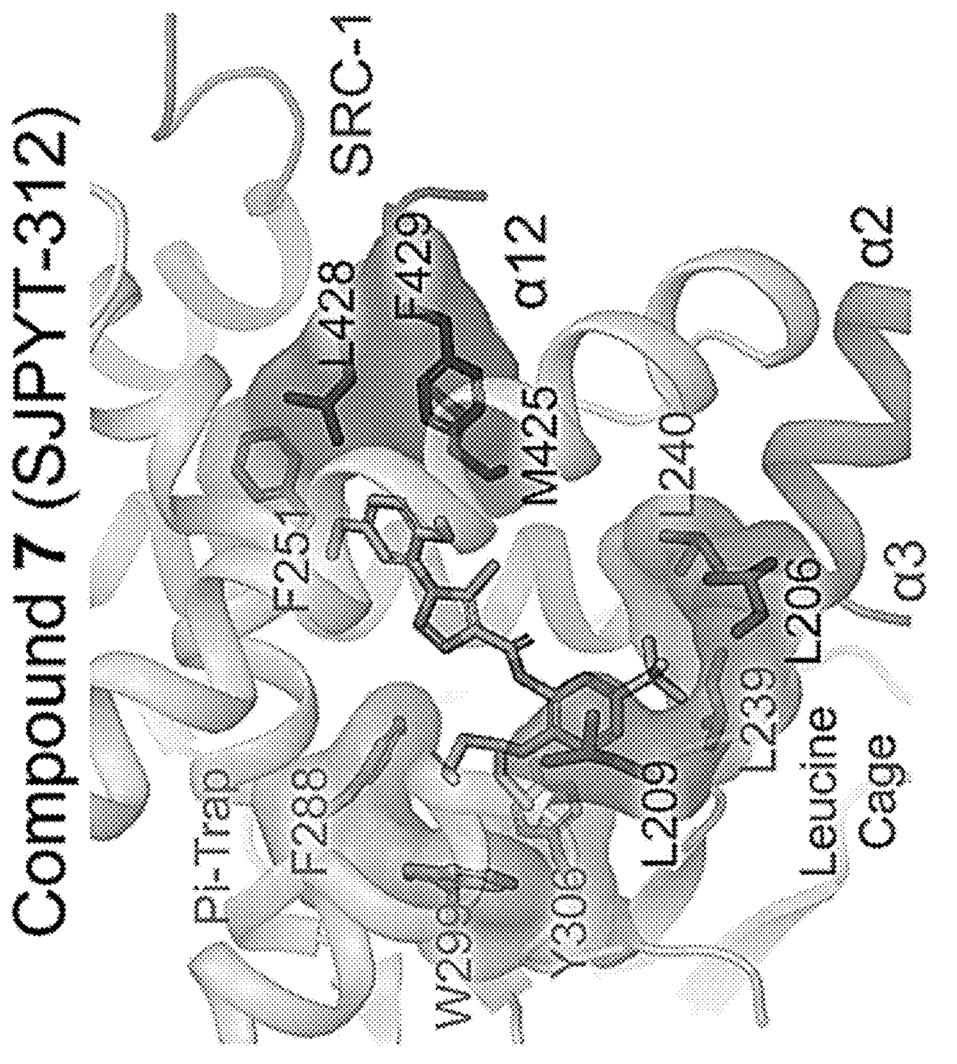
Figure 3D:
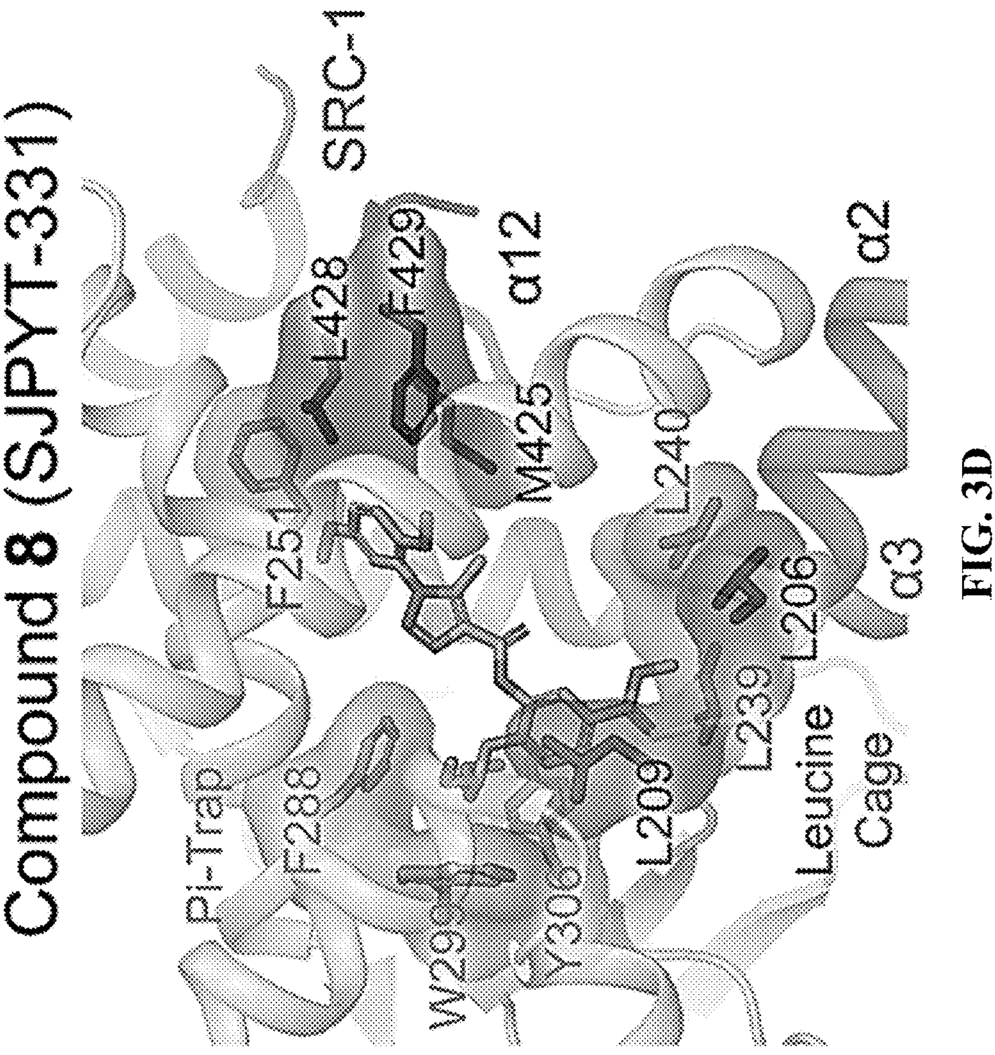

The PROTACs were tested for PXR binding affinity in a TR-FRET assay that measures displacement of the fluorescent probe 13 or 14 from the ligand binding pocket (FIG. 2D, FIG. 3A and FIG. 3B). Notably, all compounds had substantially lower affinity than the representative parental antagonist 8 (SJPYT-331) but were still able to achieve potent degradation. Among the PROTACs, 37 and 38 had the highest affinity (FIG. 3A-B), suggesting that degradation activity may be partially correlated with binding affinity. However, the observation that 38 has a markedly higher affinity than 37 while having equal degradation efficiency indicates that degradation activity is not fully attributable to binding affinity. Without wishing to be bound by theory, the results show that various site 1 ring substitutions can alter PXR binding, where the ring resides deep within the ligand binding pocket buried among hydrophobic residues (FIG. 3C and FIG. 3D)(Garcia-Maldonado, E.; et al., (2024) *Nat Commun* 15 (1), 4054). Interestingly, simply changing the site 2 methyl group (36) to a methoxy (37) drastically increased degradation efficiency, possibly due to more optimized interactions at the site 2/linker/α12 interface (FIG. 3C and FIG. 3D).

4D). Interestingly, although the two top compounds (37 and 38) had similar potencies at 24 hours post-treatment, 38 had a much faster onset of activity (FIG. 4E-G). Without wishing to be bound by theory, this suggests that the two PROTACs may act by distinct mechanisms or may have differing routes of cell entry, although the precise reason is unclear. Furthermore, 37 and 38 had improved degradation parameters when assayed by western blot ($DC_{50}$=~50 nM and $D_{max}$=~80%, FIG. 4G) compared to HiBiT ($DC_{50}$=~85 nM and $D_{max}$=~65%, Table 4). Thus, these two PROTACs indeed potently reduce the level of PXR protein.

TABLE 4

EVALUATION OF PXR LIGAND MODIFICATIONS ON SITE 2 POTENCY.

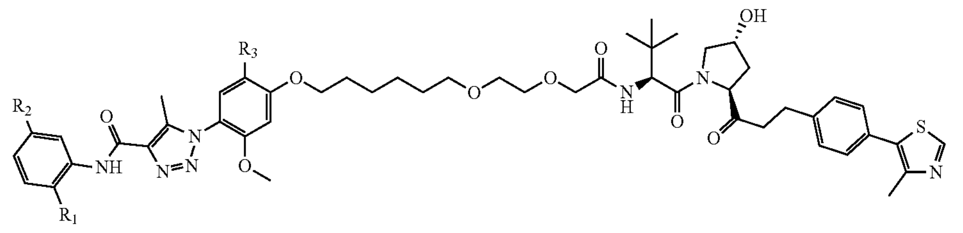

| Compound | $DC_{50}$ (nM) | $D_{max}$ (%) | AUC | 24 h $CC_{50}$ (μM) | 72 h $CC_{50}$ (μM) |
|---|---|---|---|---|---|
| 35 SJPYT-292 (12 atoms) | 232 ± 67 | 52.9 ± 10 | 102 ± 32 | >30 (96.7 ± 2.1) | >30 (91.2 ± 3.9) |
| 36 SJYHJ-036 (12 atoms) | 146 ± 50 | 50.8 ± 8.0 | 110 ± 19 | >30 (93.9 ± 3.3) | >30 (104 ± 2.4) |
| 37 SJYHJ-026 (12 atoms) | 86.6 ± 20 | 66.4 ± 4.1 | 175 ± 6.7 | >30 (97.4 ± 1.3) | >30 (99.5 ± 4.0) |
| 38 SJYHJ-040 (12 atoms) | 85.1 ± 30 | 63.9 ± 4.4 | 163 ± 18 | >30 (102 ± 1.8) | >30 (105 ± 7.5) |

FIG. 3A-D show PROTAC binding affinity for PXR LBD. FIG. 3A and FIG. 3B show the indicated compounds were tested for displacement of fluorescent probes 13 or 14 from the PXR ligand binding pocket by TR-FRET assay. Data were normalized to wells containing DMSO only (0%) and 10 μM T0901317 (100%). FIG. 3C and FIG. 3D show the crystal structures of PXR LBD bound to coactivator SRC-1 and PROTAC precursors (FIG. 3C) SJPYT-312 (PDB ID 8SVQ) or (FIG. 3D) SJPYT-331(PDB ID 8SVT). The site 1 ring of each ligand is buried in the hydrophobic pi-trap and leucine cage while the site 2 ring extends towards the mobile α12. Modifications of the site 2 ring may affect the arrangement of surrounding residues, leading to different orientations of the PROTAC linkers.

d. Confirmation of PXR Degradation Activity

Figure 4A:
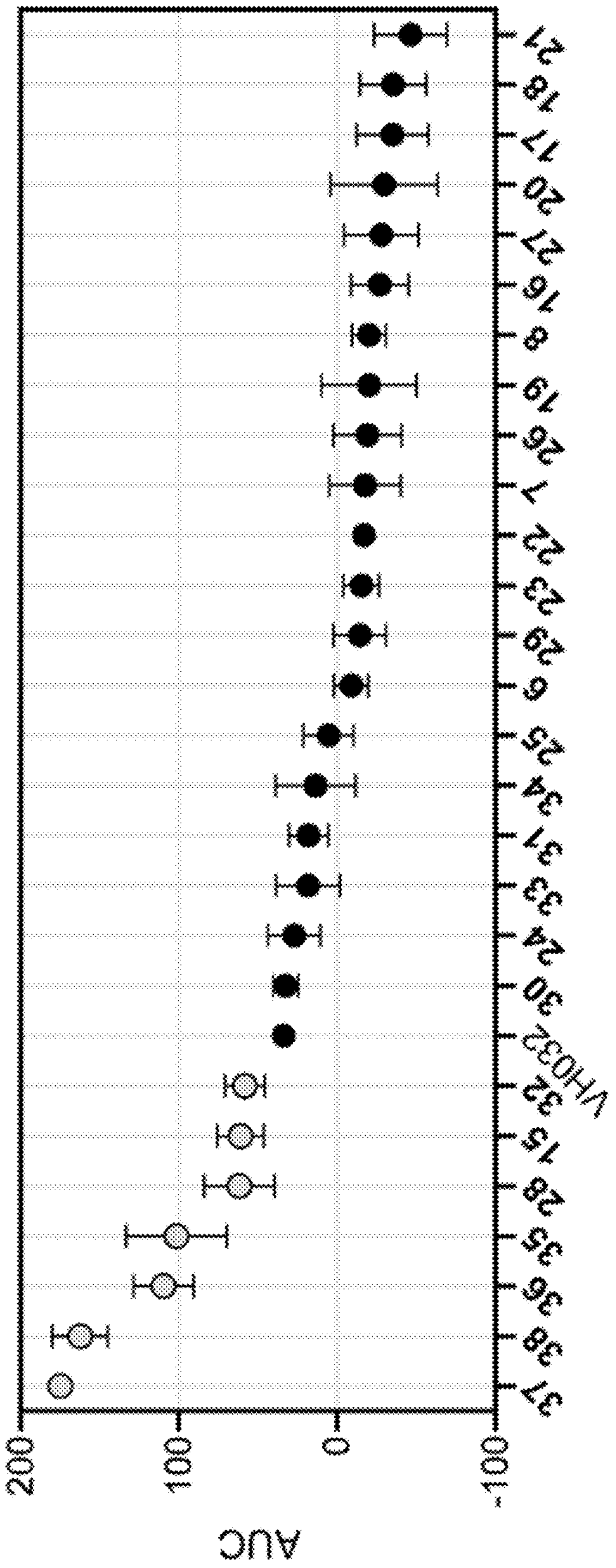
FIG. 4A-G show representative data illustrating confirmation of PROTAC activities for exemplary compounds.
Figure 4B:
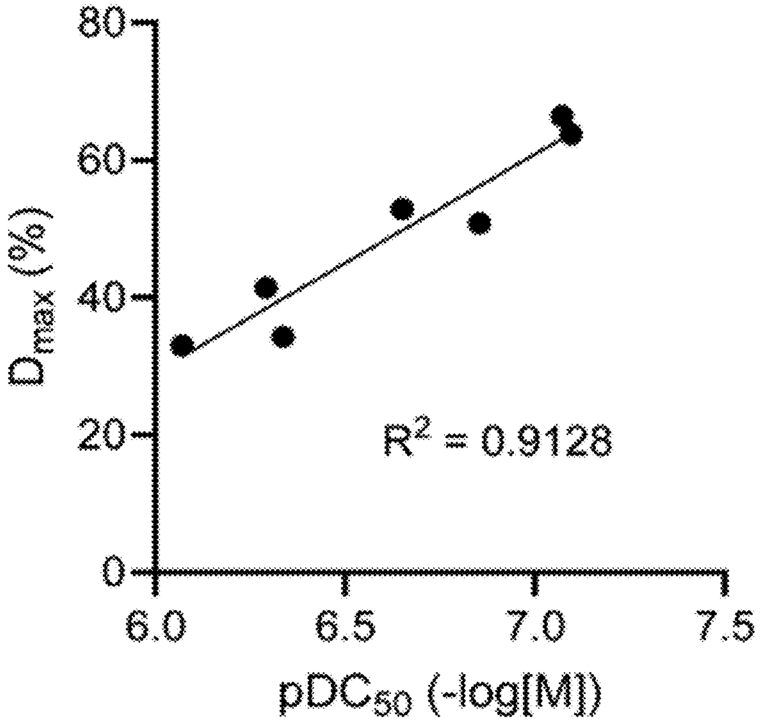
Figure 4C:
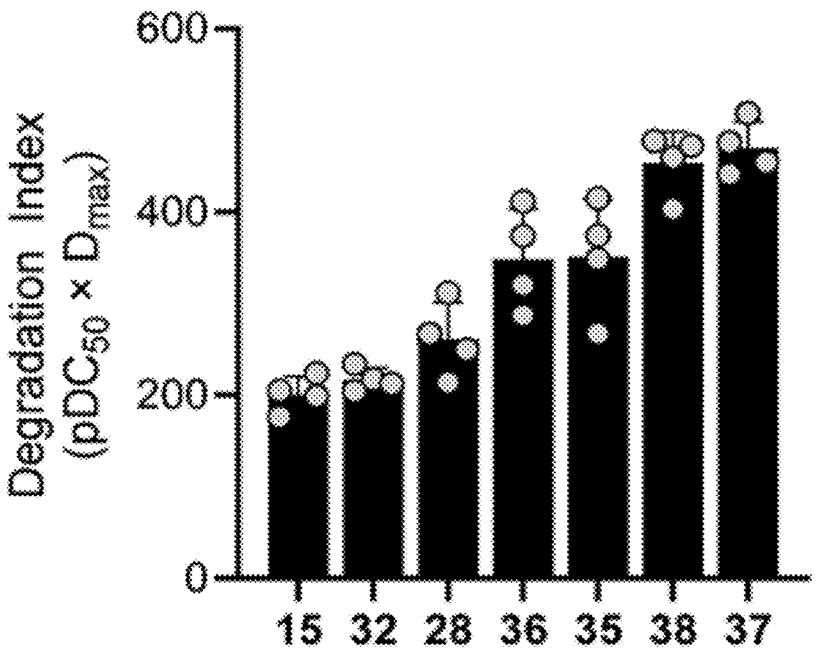

Because prior PXR degraders to use as comparative controls are lacking, three parameters were relied on to guide the SAR ($DC_{50}$, $D_{max}$, and AUC), with the AUC of VH032 used as a cutoff to identify degraders (FIG. 4A). To gain a fuller understanding of true degradation activity, $DC_{50}$ was converted to $pDC_{50}$ (negative log of $DC_{50}$ in molar), and a linear relationship with $D_{max}$ was observed for our set of PROTACs (FIG. 4B). A "degradation index" was generated by multiplying the $pDC_{50}$ and $D_{max}$ for each compound, which was then used to more accurately rank the molecules' activities (FIG. 4C). The five site 2 conjugates with $PEG_2$-$C_6$ linker were found to be most efficacious, and their ranked activities were confirmed by western blot (FIG.

Figure 4D:
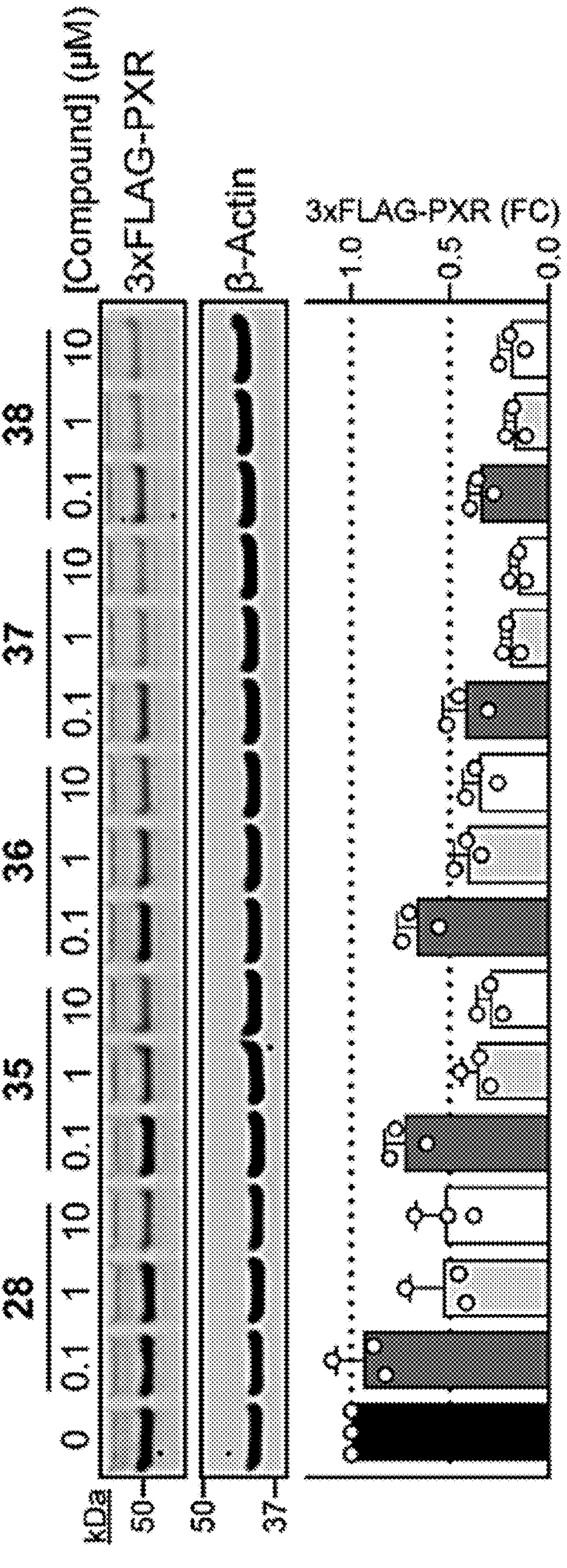
Figure 4E:
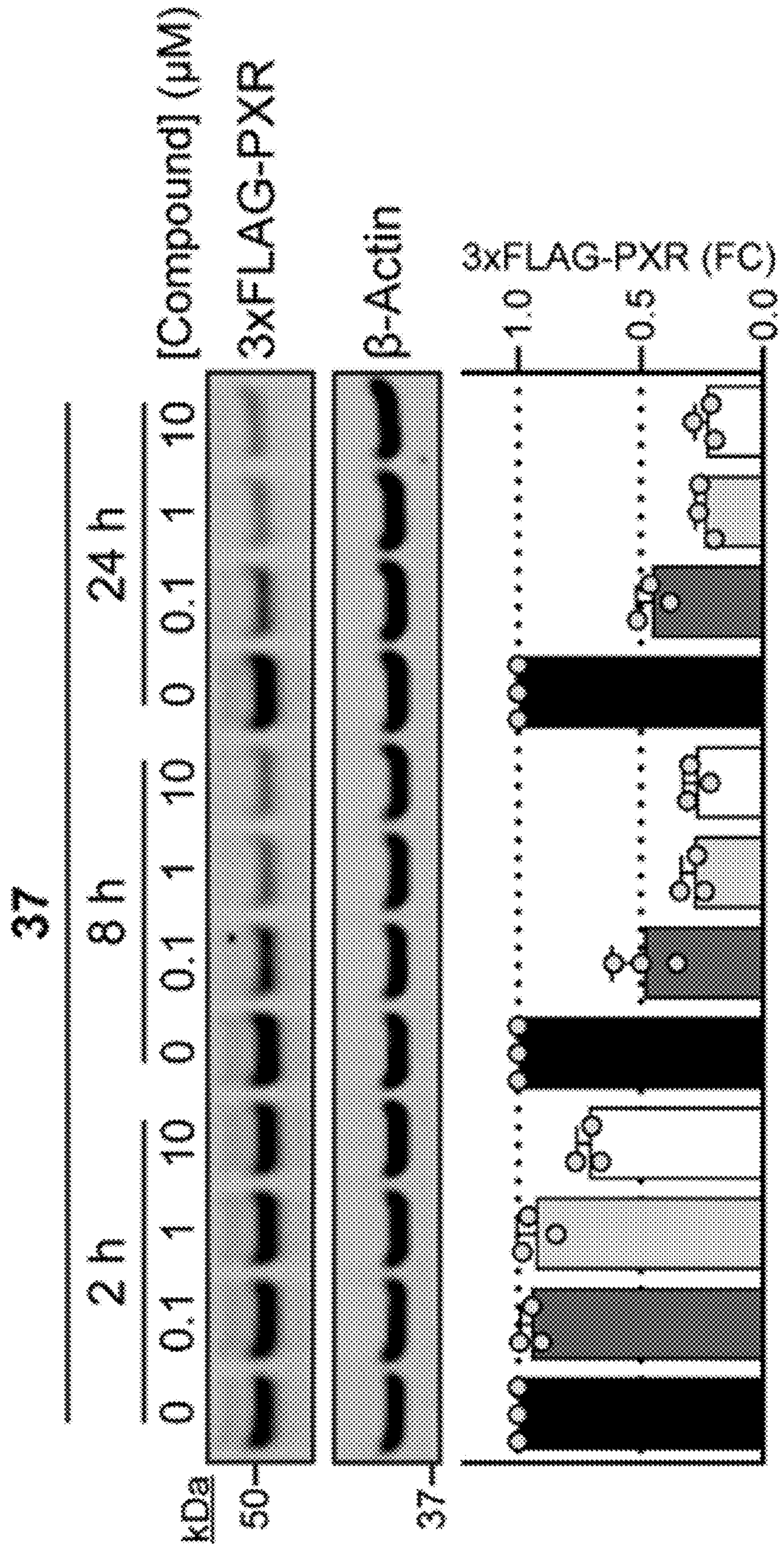
Figure 4E:
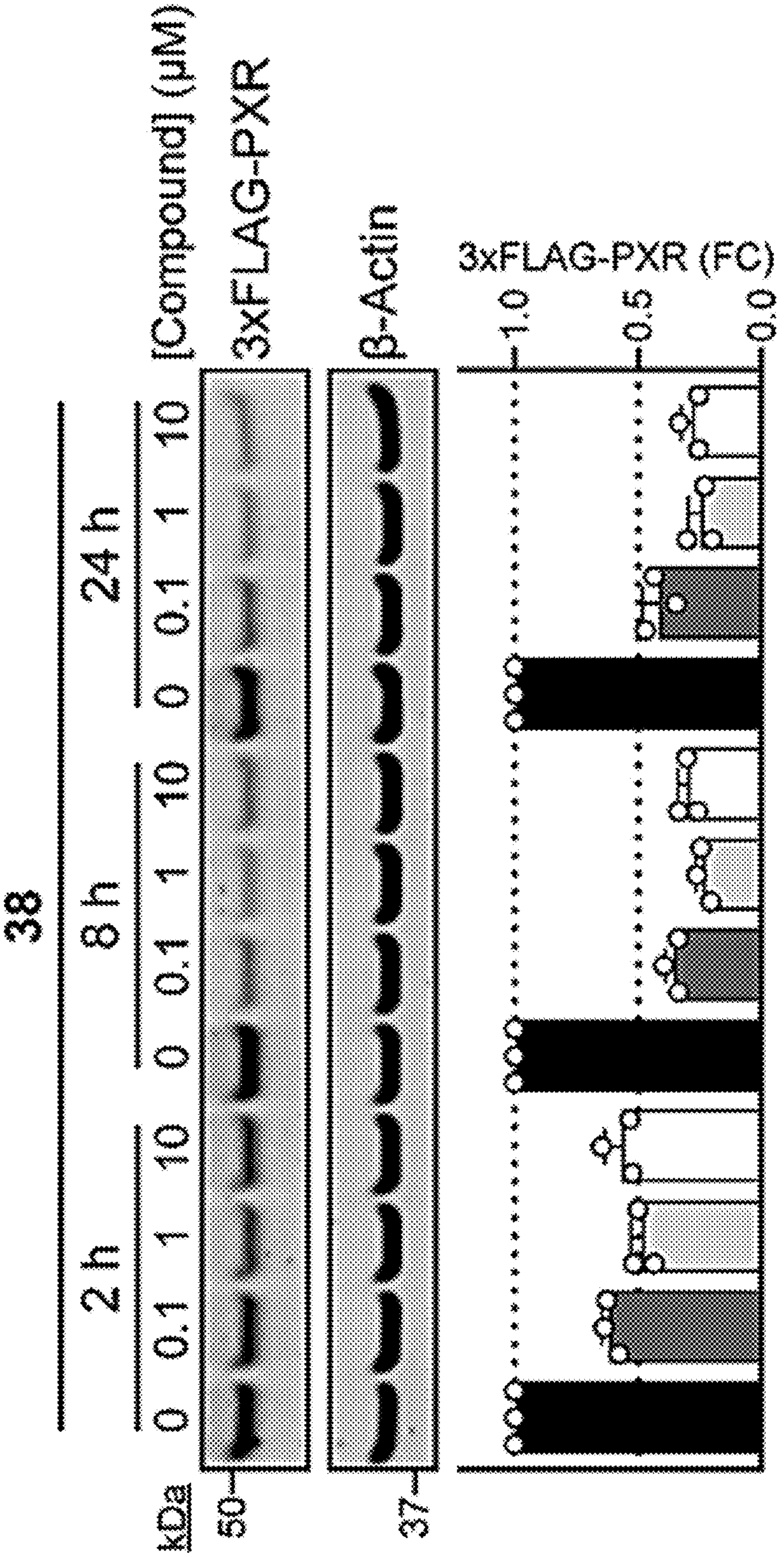
Figure 4F:
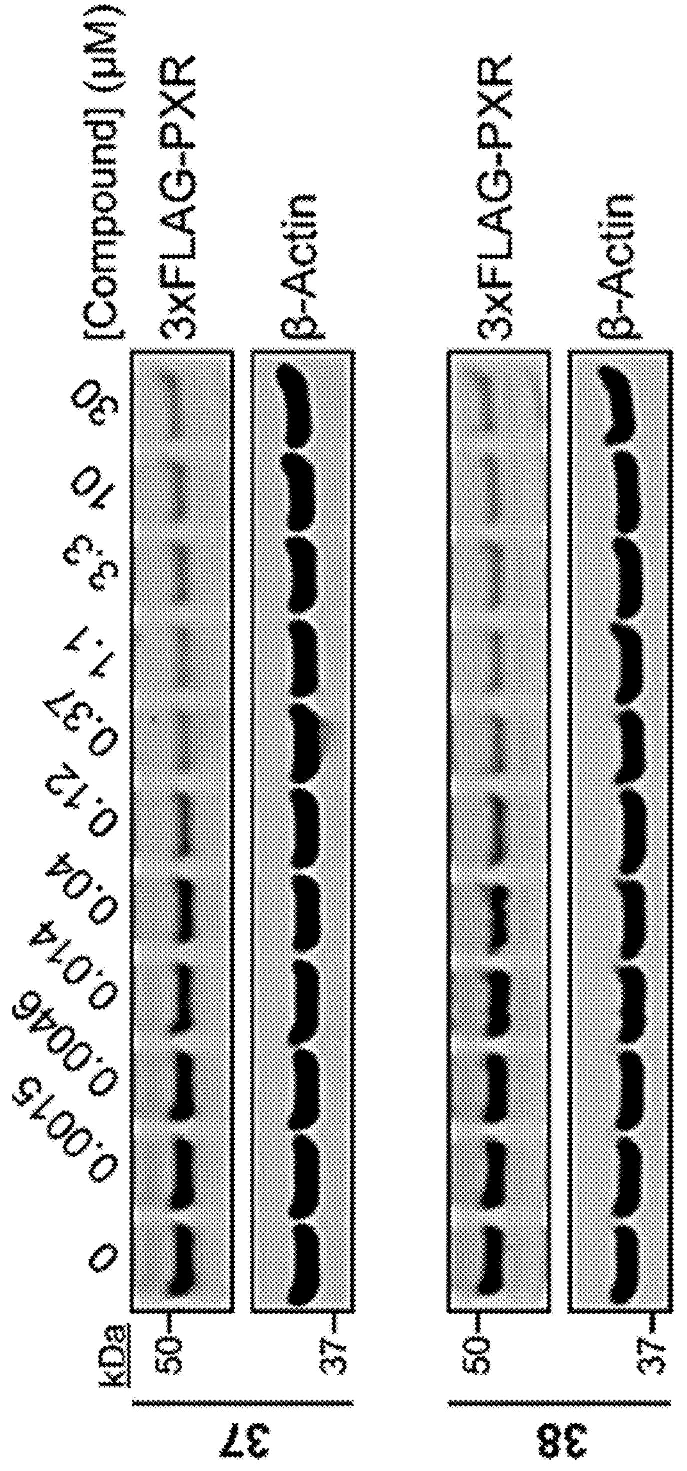
Figure 4G:
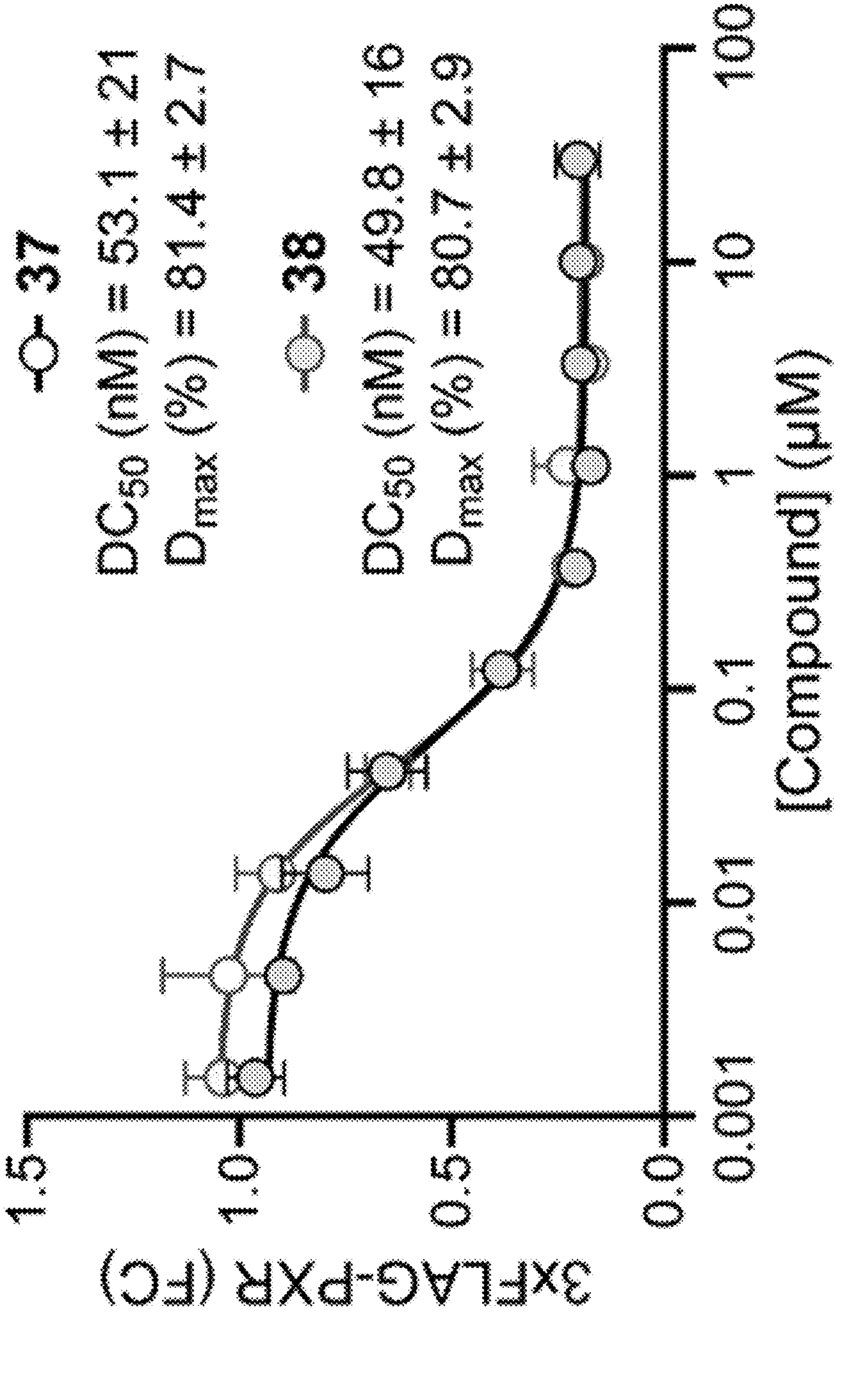

FIG. 4A-G shows the confirmation of PROTAC activities. FIG. 4A shows the AUC derived from HiBiT-PXR degradation 24 hours post-treatment. FIG. 4B shows the $pDC_{50}$ for each of the seven hit compounds plotted against the $D_{max}$. FIG. 4C shows the degradation index of each compound calculated by multiplying $pDC_{50}$ by $D_{max}$. FIG. 4D shows SNU—C4 3×FLAG-PXR KI cells treated with the indicated compounds for 24 h and subjected to western blot. FC, fold change relative to DMSO. FIG. 4E shows SNU—C4 3×FLAG-PXR KI cells treated with compound 37 or 38 at the indicated concentrations for 2, 8, or 24 h and subjected to western blot. FIG. 4F and FIG. 4G show SNU—C4 3×FLAG-PXR KI cells treated with compound 37 or 38 for 24 h and subjected to western blot.

e. PXR Degradation Requires a PXR-PROTAC-VHL Complex

Figure 5A:
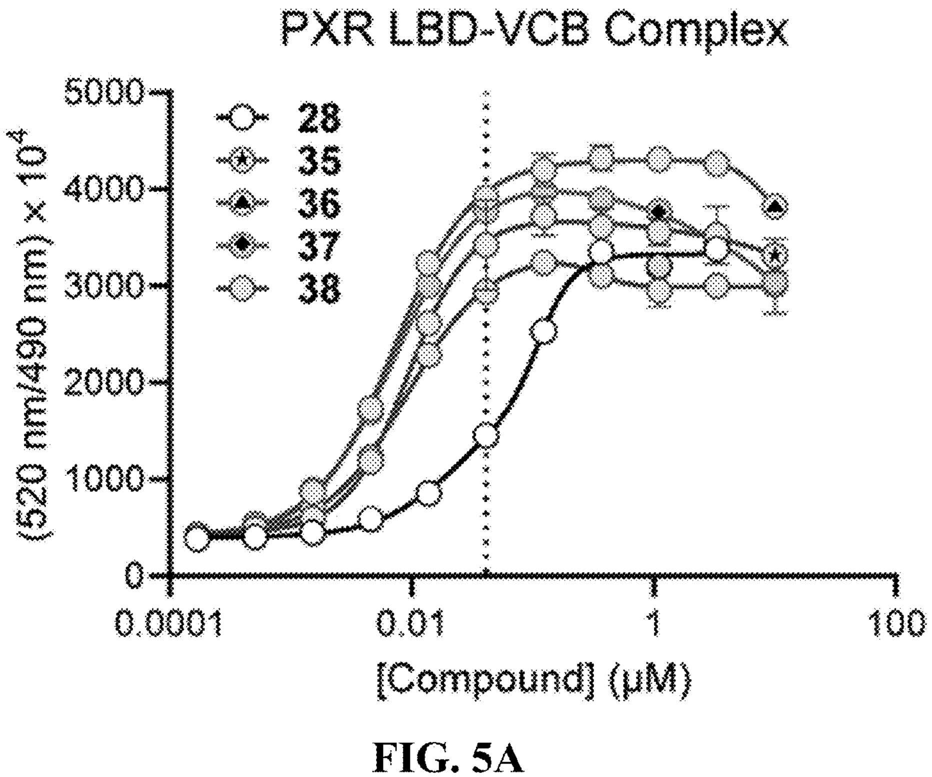
FIG. 5A-G show representative data illustrating PXR degradation requires a PXR-PROTAC-VHL complex.
Figure 5B:
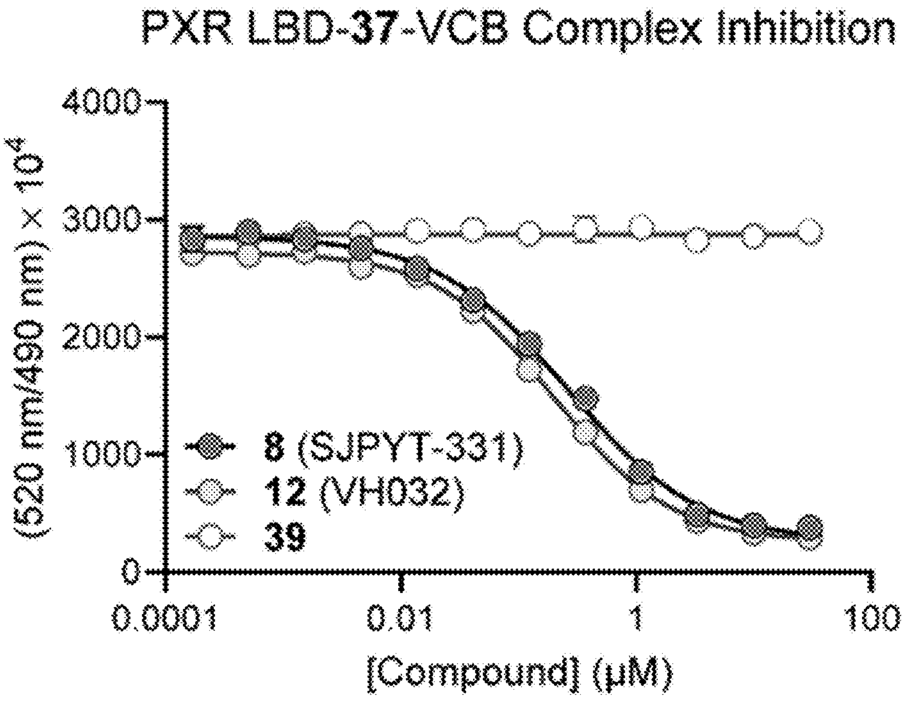
Figure 5C:
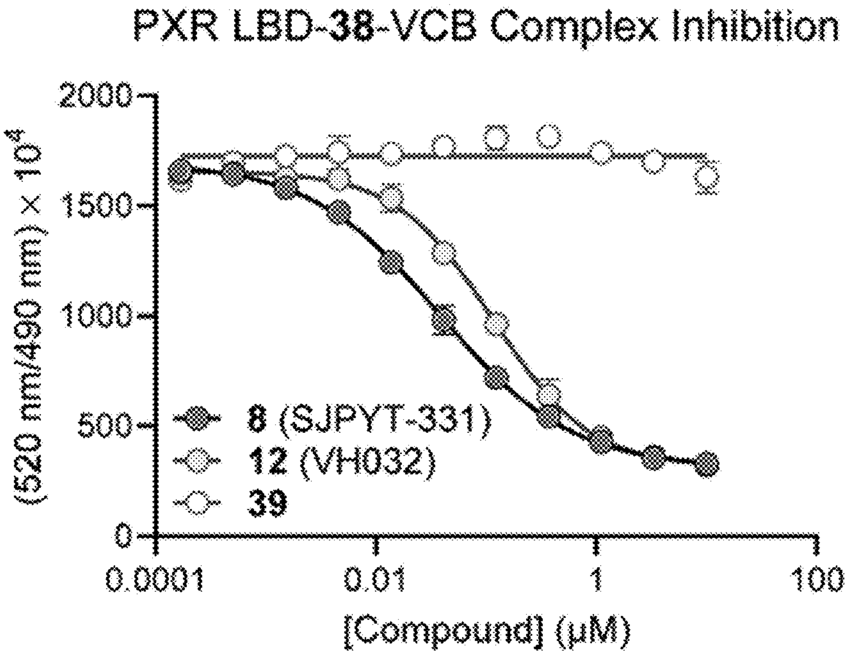
Figure 5D:
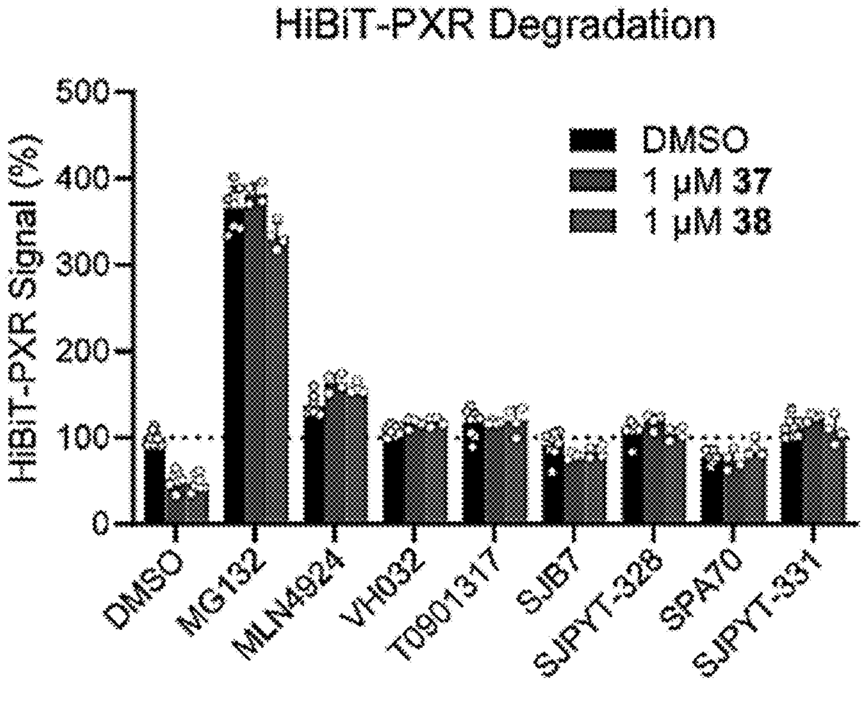
Figure 5E:
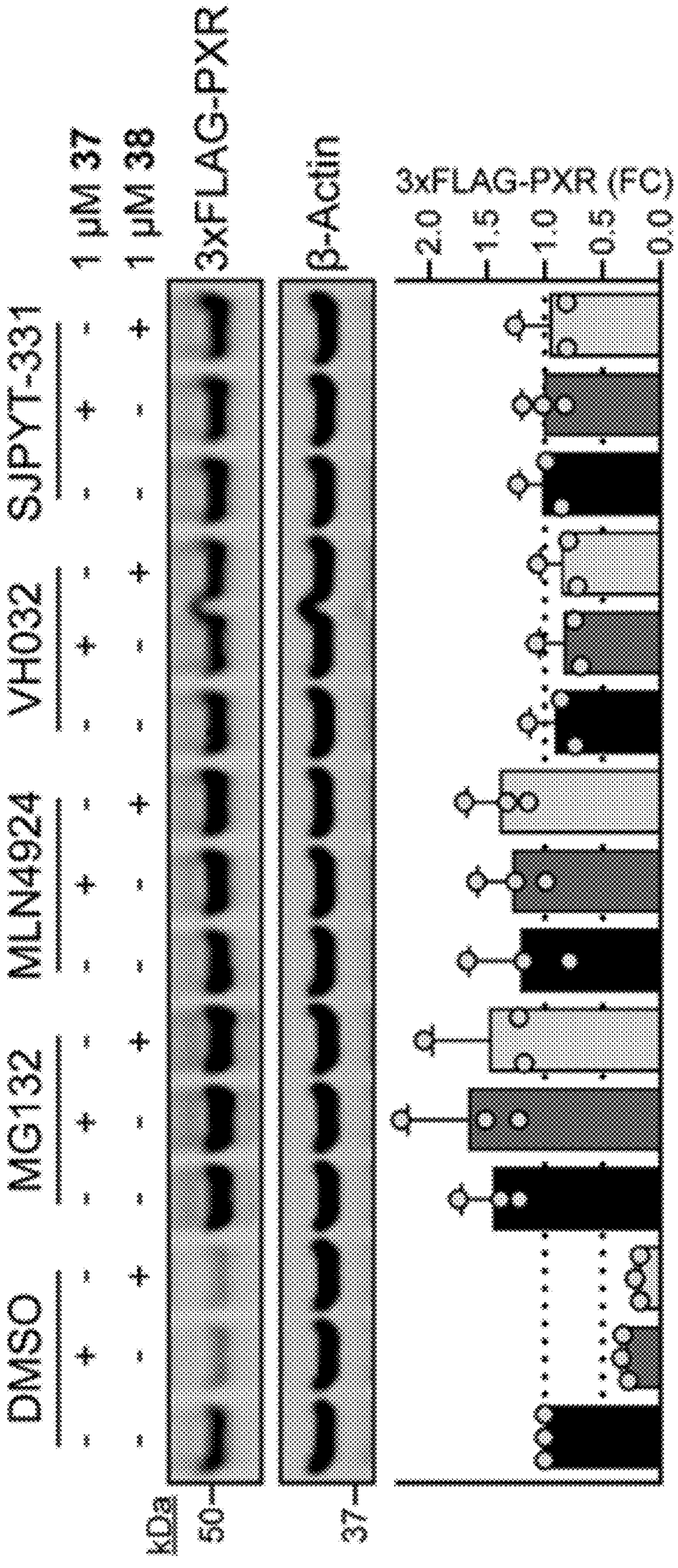
Figure 5F:
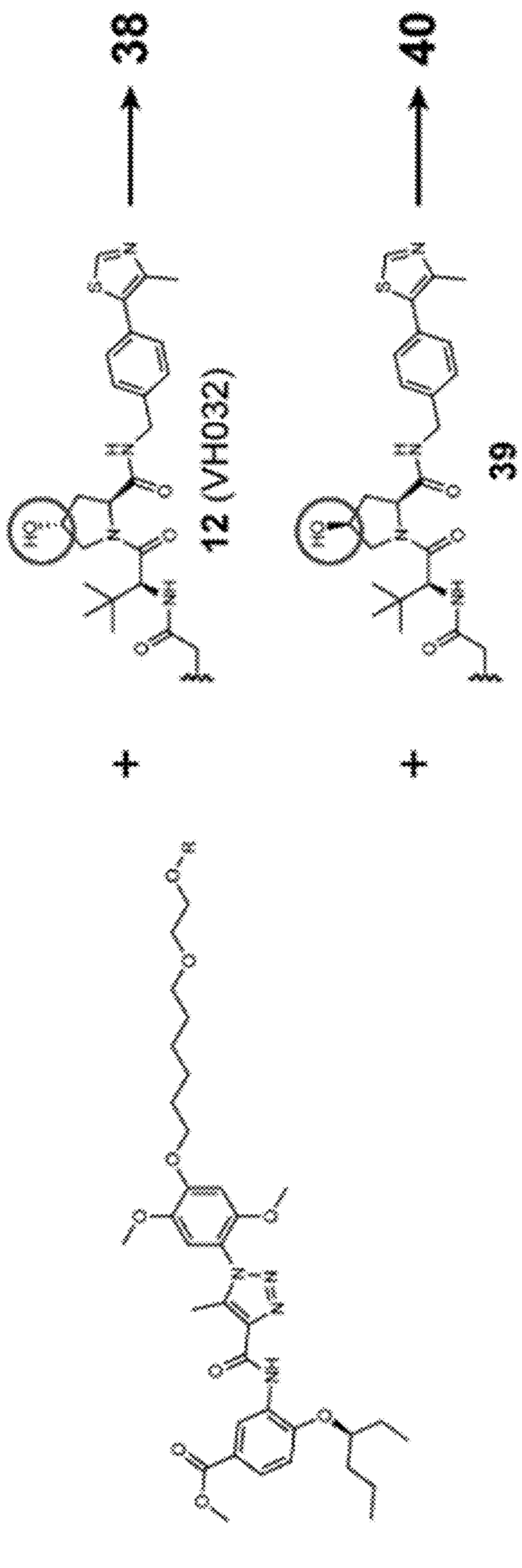
Figure 5G:
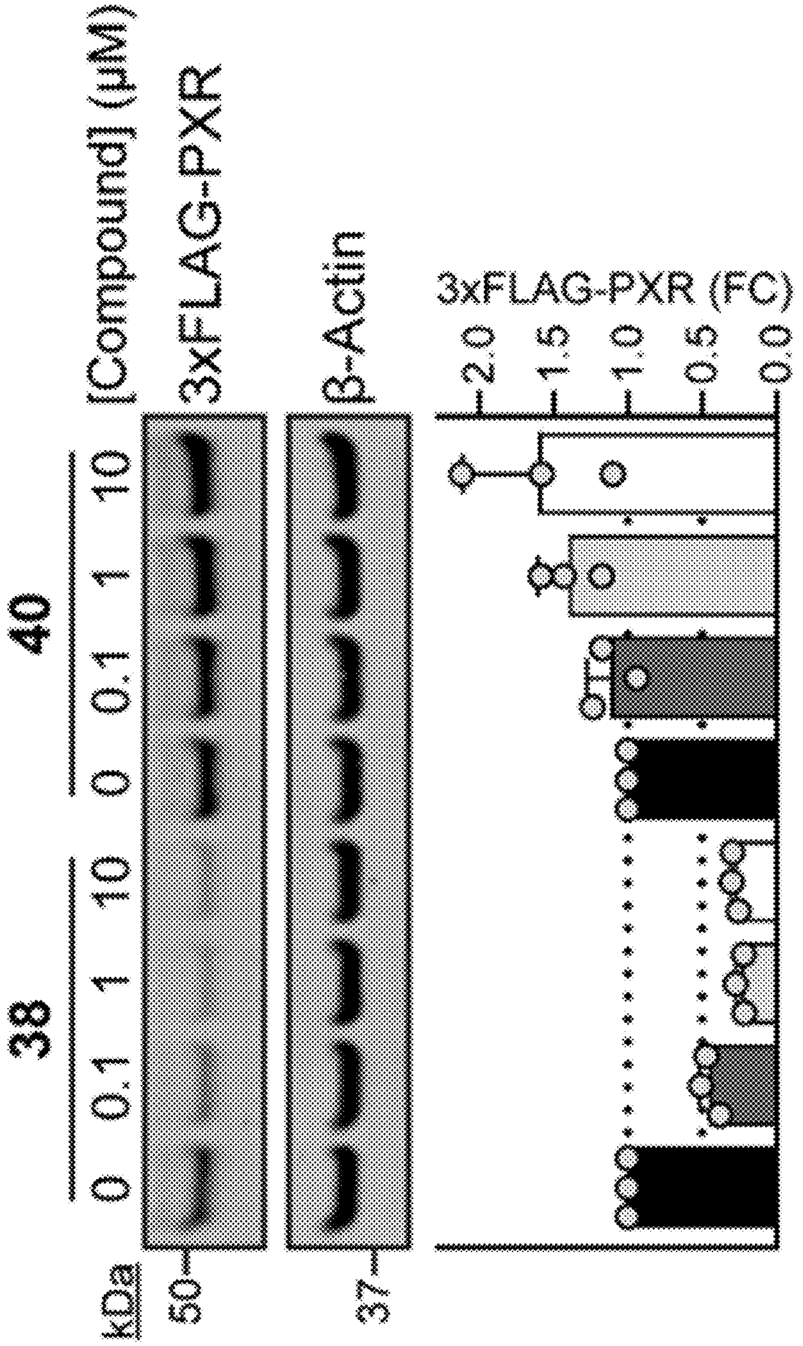

To ascertain that the observed PXR degradation was due to PROTAC-induced $CRL2^{VHL}$ recruitment, a series of characterizations was conducted. First, it was found that the compounds induced interaction between purified PXR LBD and VHL/elongin B/elongin C (VCB) with the expected hook effect as concentrations increased (FIG. 5A). Next, we observed that ligands for both PXR and VHL can inhibit PXR LBD-VCB interaction while the VHL-inactive (S,S,S) epimer (39) had no effect (FIG. 5B and FIG. 5C). In cells, PXR degradation was blocked by PXR ligands, the VHL ligand VH032, the proteasome inhibitor MG132, and the neddylation inhibitor MLN4924 (FIG. 5D and FIG. 5E). Furthermore, an analog of 38 with VH032 replaced by the VHL-inactive (S,S,S) epimer (40) fully lost the ability to degrade PXR (FIG. 5F, FIG. 5G, and FIG. 7). Together, these results show that the PROTACs decrease PXR protein by the expected mechanism of induced proteasomal degradation.

FIG. 5A-G shows PXR degradation requires a PXR-PROTAC-VHL complex. FIG. 5A shows the interaction of PXR LBD with VCB in the presence of PROTACs assessed by TR-FRET assay. The vertical dotted line indicates the concentration of 37 and 38 that is used in (FIG. 5B and FIG. 5C) for competition assays (41.2 nM). FIG. 5B and FIG. 5C shows the inhibition of PXR LBD-VCB complex in the presence of 41.2 nM (FIG. 5B) 37 or (FIG. 5C) 38 assessed by TR-FRET assay. The PXR ligand SJPYT-331 and the VHL ligand VH032 dose-dependently reduce complex formation while the VHL-inactive (S,S,S) epimer 39 has no effect. FIG. 5D shows SNU—C4 HiBiT-PXR KI cells treated with DMSO or 10 μM competitor with or without 1 μM 37 or 38 for 8 h. FIG. 5E shows SNU—C4 3×FLAG-PXR KI cells treated with DMSO or 10 μM competitor with or without 1 μM 37 or 38 for 8 h and subjected to western blot. FIG. 5F shows the design of the VHL-inactive (S,S,S) epimer 39 and its linkage to the PXR ligand to create the negative control PROTAC 40. FIG. 5G shows SNU—C4 3×FLAG-PXR KI cells treated with the indicated concentrations of 38 or 40 for 24 h and subjected to western blot.

f. PROTACS Reduce Agonist-Induced PXR Activity and Sensitize Colon Cancer Cells to Chemotherapy PXR upregulates the expression of drug metabolism- and transport-related genes, such as CYP3A4, upon activation by foreign chemicals. Using a reporter with firefly luciferase under the control of the CYP3A4 promoter, it was found that 38 reduces PXR activation by the antibiotic rifampicin, the potent chemical tool compound T0901317, and the chemotherapy paclitaxel (FIG. 6A-D). In the absence of PXR agonist, 38 also reduced the basal PXR activity on the CYP3A4 promoter (FIG. 6D). The inhibitory effect of 38 was also observed when induction of endogenous CYP3A4 was assessed in SNU—C4 colorectal cancer cells (FIG. 6E, left panel). Importantly, 38 had no effect on the RNA level of PXR itself, although it did reduce PXR RNA in the presence of paclitaxel, likely due to the enhanced cytotoxic effects of paclitaxel (FIG. 6E, right panel). Paclitaxel is metabolized by a "suicide" mechanism in which it activates PXR (Harmsen, S.; et al., (2009) *Cancer Chemother Pharmacol* 64 (1), 35-43) and is metabolized by the downstream enzyme product CYP3A4 (Martinez, C.; et al., (2002) Br *J Cancer* 87 (6), 681-686). Consequently, PXR and CYP3A4 inhibition have been shown to enhance the anticancer activity of paclitaxel (Lin, W.; et al., (2017) *Nat Commun* 8 (1), 741; Niu, X.; et al., (2022) *Cells* 11 (19); Martinez, C.; et al., (2002)*Br J Cancer* 87 (6), 681-686; Masuyama, H.; et al., (2016) *Int J Oncol* 49 (3), 1211-1220). SNU—C4 cells were treated with paclitaxel for 72 h and found that cotreatment with 38 enhances the cytotoxic effect by 3.3-fold (FIG. 6F), indicating that PXR degradation has potential therapeutic benefit when combined with PXR-activating drugs.

Figure 6A:
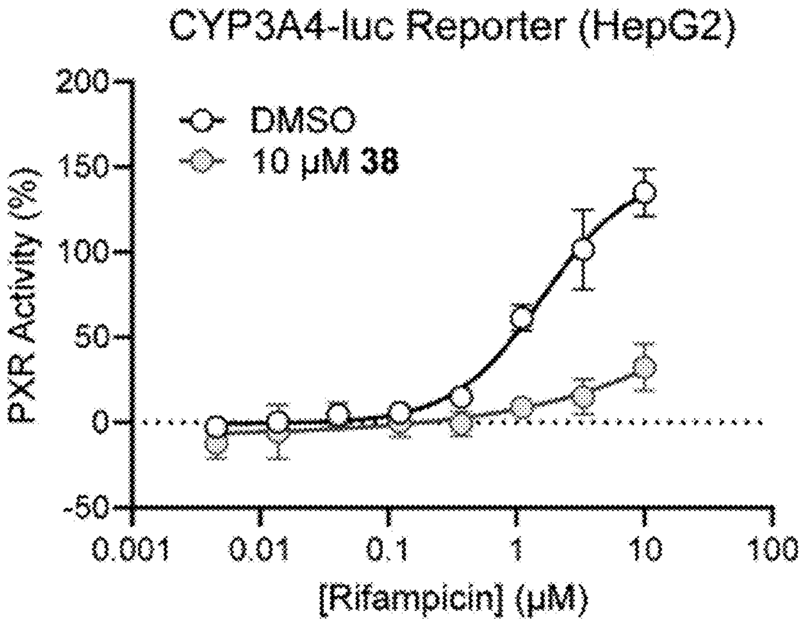
FIG. 6A-F show representative data illustrating PROTACs reduces agonist-induced PXR activity and sensitizes colon cancer cells to paclitaxel.
Figure 6B:
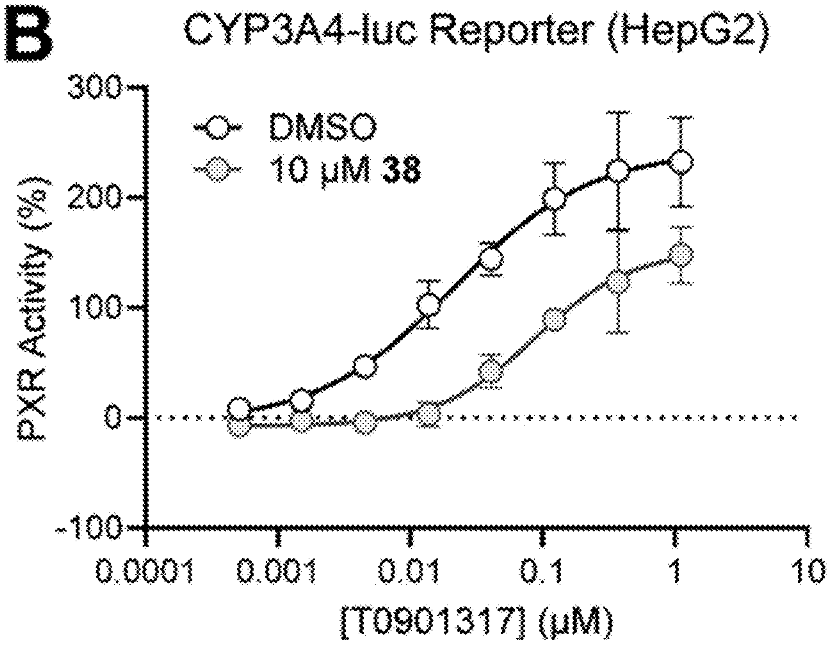
Figure 6C:
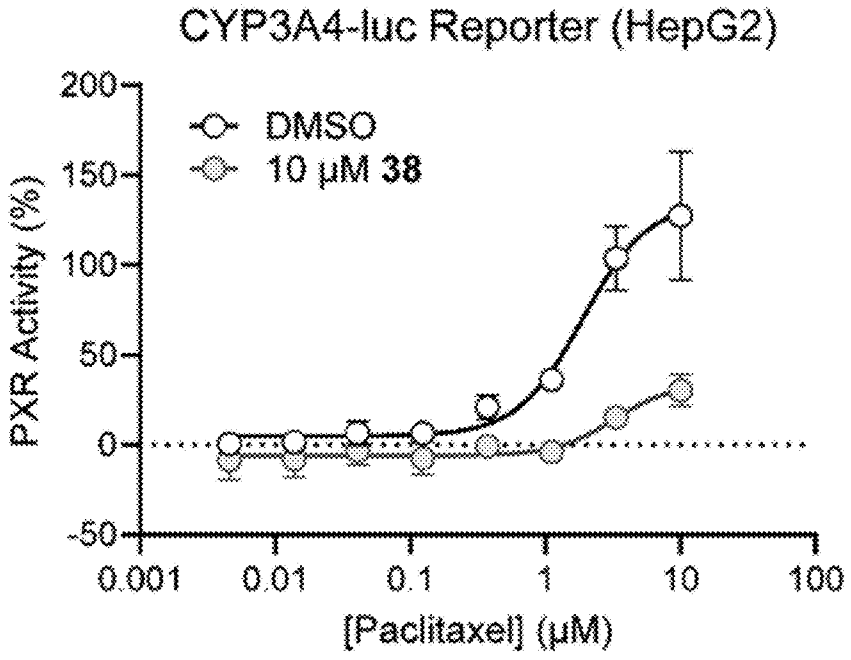
Figure 6D:
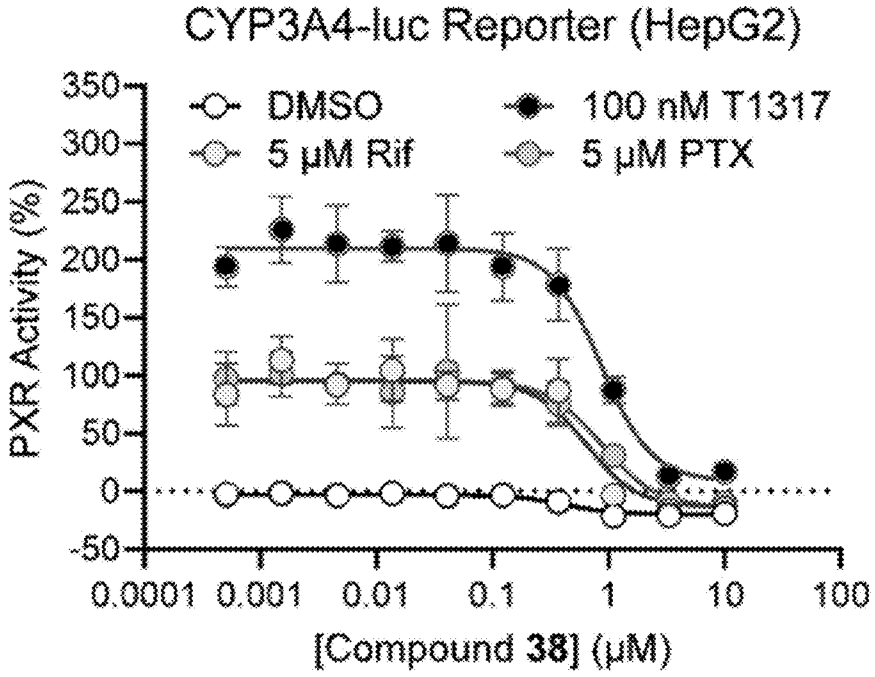
Figure 6E:
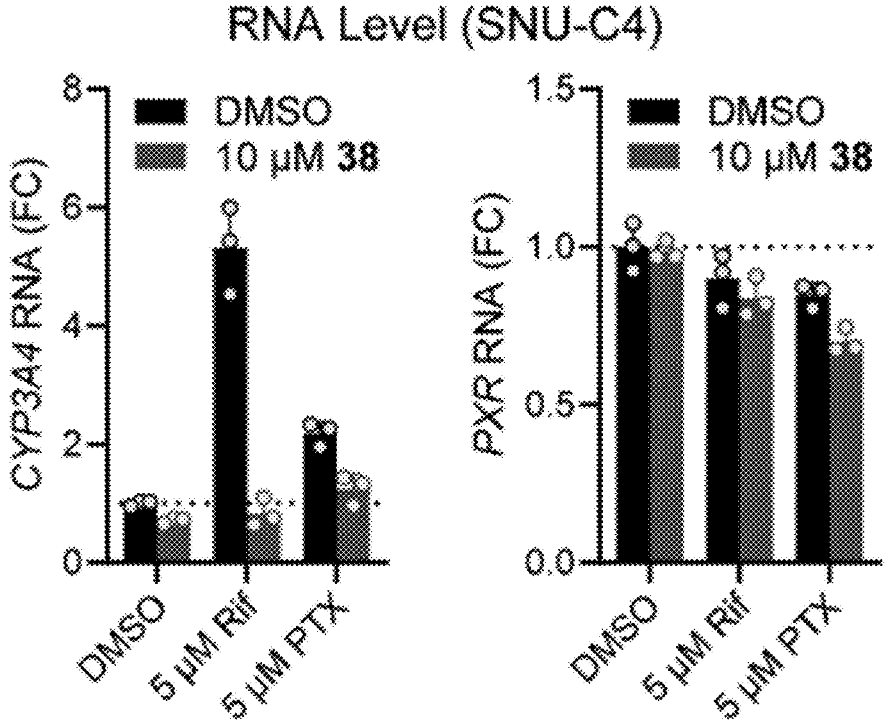
Figure 6F:
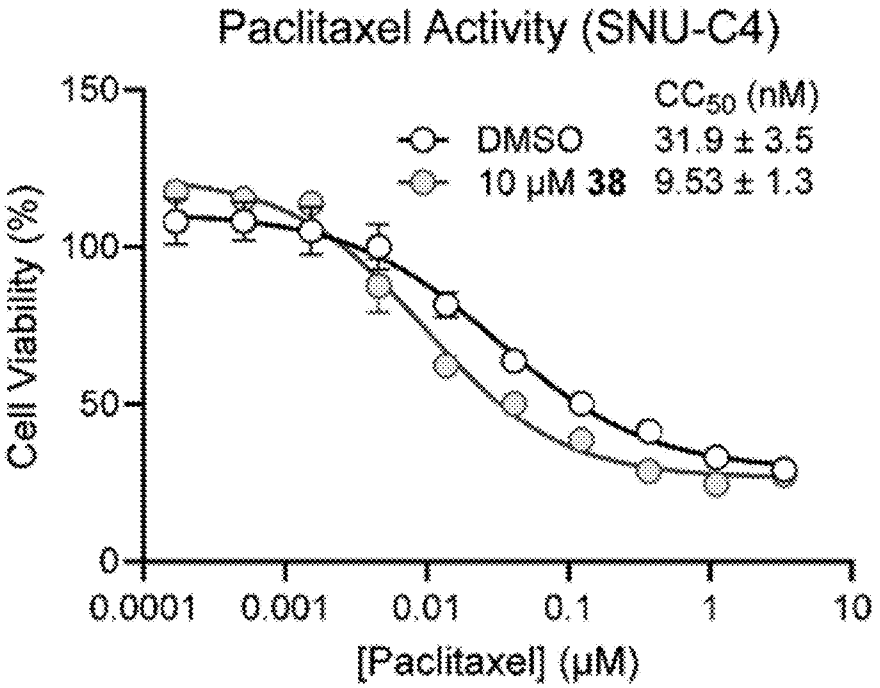

FIG. 6A-F shows that PROTACs reduce agonist-induced PXR activity and sensitize colon cancer cells to paclitaxel. FIG. 6A-D show HepG2 cells transfected with PXR-expressing plasmid and a plasmid encoding firefly luciferase under the control of a PXR-responsive CYP3A4 promoter (pGL3-CYP3A4-luc), treated with compounds for 24 h, and assessed for luciferase activity. Data were normalized to wells containing DMSO only (0%) and 5 μM rifampicin (100%). In FIG. 6A-C, cells were treated with a dose response of agonist in the absence or presence of 10 μM 38. In FIG. 6D, cells were treated with a dose response of 38 in the absence or presence of 5 μM rifampicin (Rif), 100 nM T0901317 (T1317), or 5 μM paclitaxel (PTX). FIG. 6E shows SNU—C4 cells treated with DMSO, 5 μM rifampicin, or 5 μM paclitaxel in the absence or presence of 10 μM 38 for 24 h. RNA was extracted and subjected to reverse transcription-quantitative polymerase chain reaction (RT-qPCR) to measure expression of CYP3A4 (left panel) or PXR (right panel). Data were normalized to 18S RNA and represent FC relative to the DMSO control for each gene. FIG. 6E shows SNU—C4 cells treated with a dose response of paclitaxel in the absence or presence of 10 μM 38 for 72 h and assessed for cell viability.

5. CONCLUSIONS

Physiological detoxification systems protect the body from chemical harm but hinder the safety and efficacy of medicines by promoting excretion or generating metabolites that may be impotent or toxic. PXR is a drug-activated transcription factor that controls expression of drug-metabolizing enzymes and drug transporters and is thus a key component of the detoxification machinery. To explore PXR degradation as a strategy to mitigate drug metabolism events, a suitable location had to be identified to extend a linker from the PXR ligand bound deep within the solvent-inaccessible pocket. Using PXR ligands linked to fluorescent probes at positions that would protrude over α2 (compound 13) or α12 (compound 14), it was found that both sites were amenable to compound binding. Initial PROTACs designed according to the two protrusions (compound 15 at α2 and compound 28 at α12) validated both sites as amenable to degradation, but the protein loss was relatively weak. Optimization of the PXR ligand in compound 28 led to more potent degradation that was correlated with PXR binding affinity, with compounds 37 and 38 having approximate $DC_{50}$ of 50 nM and $D_{max}$ of 80% by western blot. Importantly, the PROTACs reduced PXR activation by known chemical agonists and resulted in higher anticancer activity of paclitaxel. This study provides a framework for the design and optimization of degraders that may reduce PXR-mediated metabolic liabilities.

L. REFERENCES (1) Wouters, O. J.; McKee, M.; Luyten, J. Estimated Research and Development Investment Needed to Bring a New Medicine to Market, 2009-2018. *JAMA* 2020, 323 (9), 844-853. DOI: 10.1001/jama.2020.1166 From NLM Medline.

(2) Dowden, H.; Munro, J. Trends in clinical success rates and therapeutic focus. *Nat Rev Drug Discov* 2019, 18 (7), 495-496. DOI: 10.1038/d41573-019-00074-z From NLM PubMed-not-MEDLINE.

(3) DiMasi, J. A.; Grabowski, H. G.; Hansen, R. W. Innovation in the pharmaceutical industry: New estimates of R&D costs. *J Health Econ* 2016, 47, 20-33. DOI: 10.1016/j.jhealeco.2016.01.012 From NLM Medline.

(4) Wienkers, L. C.; Heath, T. G. Predicting in vivo drug interactions from in vitro drug discovery data. *Nat Rev*

*Drug Discov* 2005, 4 (10), 825-833. DOI: 10.1038/nrd1851 From NLM Medline.

(5) Honig, P. K.; Wortham, D. C.; Zamani, K.; Conner, D. P.; Mullin, J. C.; Cantilena, L. R. Terfenadine-ketoconazole interaction. Pharmacokinetic and electrocardiographic consequences. *JAMA* 1993, 269 (12), 1513-1518. From NLM Medline.

(6) Yun, C. H.; Okerholm, R. A.; Guengerich, F. P. Oxidation of the antihistaminic drug terfenadine in human liver microsomes. Role of cytochrome P-450 3A(4) in N-dealkylation and C-hydroxylation. *Drug Metab Dispos* 1993, 21 (3), 403-409. From NLM Medline.

(7) Honig, P. K.; Woosley, R. L.; Zamani, K.; Conner, D. P.; Cantilena, L. R., Jr. Changes in the pharmacokinetics and electrocardiographic pharmacodynamics of terfenadine with concomitant administration of erythromycin. *Clin Pharmacol Ther* 1992, 52 (3), 231-238. DOI: 10.1038/clpt.1992.135 From NLM Medline.

(8) Zeldin, R. K.; Petruschke, R. A. Pharmacological and therapeutic properties of ritonavir-boosted protease inhibitor therapy in HIV-infected patients. *J Antimicrob Chemother* 2004, 53 (1), 4-9. DOI: 10.1093/jac/dkh029 From NLM Medline.

(9) Mahase, E. Covid-19: Pfizer's paxlovid is 89% effective in patients at risk of serious illness, company reports. *BMJ* 2021, 375, n2713. DOI: 10.1136/bmj.n2713 From NLM PubMed-not-MEDLINE.

(10) Tseng, A.; Hughes, C. A.; Wu, J.; Seet, J.; Phillips, E. J. Cobicistat Versus Ritonavir: Similar Pharmacokinetic Enhancers But Some Important Differences. *Ann Pharmacother* 2017, 51 (11), 1008-1022. DOI: 10.1177/1060028017717018 From NLM Medline.

(11) Bertilsson, G.; Heidrich, J.; Svensson, K.; Asman, M.; Jendeberg, L.; Sydow-Backman, M.; Ohlsson, R.; Postlind, H.; Blomquist, P.; Berkenstam, A. Identification of a human nuclear receptor defines a new signaling pathway for CYP3A induction. *Proc Nat Acad Sci USA* 1998, 95 (21), 12208-12213. DOI: 10.1073/pnas.95.21.12208 From NLM Medline.

(12) Blumberg, B.; Sabbagh, W., Jr.; Juguilon, H.; Bolado, J., Jr.; van Meter, C. M.; Ong, E. S.; Evans, R. M. SXR, a novel steroid and xenobiotic-sensing nuclear receptor. *Genes Dev* 1998, 12 (20), 3195-3205. DOI: 10.1101/gad.12.20.3195 From NLM Medline.

(13) Lehmann, J. M.; McKee, D. D.; Watson, M. A.; Willson, T. M.; Moore, J. T.; Kliewer, S. A. The human orphan nuclear receptor PXR is activated by compounds that regulate CYP3A4 gene expression and cause drug interactions. *J Clin Invest* 1998, 102 (5), 1016-1023. DOI: 10.1172/JCI3703 From NLM Medline.

(14) Kliewer, S. A.; Moore, J. T.; Wade, L.; Staudinger, J. L.; Watson, M. A.; Jones, S. A.; McKee, D. D.; Oliver, B. B.; Willson, T. M.; Zetterstrom, R. H.; et al. An orphan nuclear receptor activated by pregnanes defines a novel steroid signaling pathway. *Cell* 1998, 92 (1), 73-82. DOI: 10.1016/s0092-8674 (00)80900-9 From NLM Medline.

(15) Lin, W.; Wang, Y. M.; Chai, S. C.; Lv, L.; Zheng, J.; Wu, J.; Zhang, Q.; Wang, Y. D.; Griffin, P. R.; Chen, T. SPA70 is a potent antagonist of human pregnane X receptor. *Nat Commun* 2017, 8 (1), 741. DOI: 10.1038/s41467-017-00780-5 From NLM Medline.

(16) Li, Y.; Lin, W.; Wright, W. C.; Chai, S. C.; Wu, J.; Chen, T. Building a Chemical Toolbox for Human Pregnane X Receptor Research: Discovery of Agonists, Inverse Agonists, and Antagonists Among Analogs Based on the Unique Chemical Scaffold of SPA70. *J Med Chem* 2021, 64 (3), 1733-1761. DOI: 10.1021/acs.jmedchem.0c02201 From NLM Medline.

(17) Li, Y.; Lin, W.; Chai, S. C.; Wu, J.; Annu, K.; Chen, T. Design and Optimization of 1H-1,2,3-Triazole-4-carboxamides as Novel, Potent, and Selective Inverse Agonists and Antagonists of PXR. *J Med Chem* 2022, 65 (24), 16829-16859. DOI: 10.1021/acs.jmedchem.2c01640 From NLM Medline.

(18) Garcia-Maldonado, E.; Huber, A. D.; Chai, S. C.; Nithianantham, S.; Li, Y.; Wu, J.; Poudel, S.; Miller, D. J.; Seetharaman, J.; Chen, T. Chemical manipulation of an activation/inhibition switch in the nuclear receptor PXR. *Nat Commun* 2024, 15 (1), 4054. DOI: 10.1038/s41467-024-48472-1 From NLM Medline.

(19) Xie, Y.; Xu, M.; Deng, M.; Li, Z.; Wang, P.; Ren, S.; Guo, Y.; Ma, X.; Fan, J.; Billiar, T. R.; et al. Activation of Pregnane X Receptor Sensitizes Mice to Hemorrhagic Shock-Induced Liver Injury. *Hepatology* 2019, 70 (3), 995-1010. DOI: 10.1002/hep.30691 From NLM Medline.

(20) Niu, X.; Wu, T.; Yin, Q.; Gu, X.; Li, G.; Zhou, C.; Ma, M.; Su, L.; Tang, S.; Tian, Y.; et al. Combination of Paclitaxel and PXR Antagonist SPA70 Reverses Paclitaxel-Resistant Non-Small Cell Lung Cancer. *Cells* 2022, 11 (19). DOI: 10.3390/cells11193094 From NLM Medline.

(21) Huber, A. D.; Wright, W. C.; Lin, W.; Majumder, K.; Low, J. A.; Wu, J.; Buchman, C. D.; Pintel, D. J.; Chen, T. Mutation of a single amino acid of pregnane X receptor switches an antagonist to agonist by altering AF-2 helix positioning. *Cell Mol Life Sci* 2021, 78 (1), 317-335. DOI: 10.1007/s00018-020-03505-y From NLM Medline.

(22) Huber, A. D.; Li, Y.; Lin, W.; Galbraith, A. N.; Mishra, A.; Porter, S. N.; Wu, J.; Florke Gee, R. R.; Zhuang, W.; Pruett-Miller, S. M.; et al. SJPYT-195: A Designed Nuclear Receptor Degrader That Functions as a Molecular Glue Degrader of GSPT1. *ACS Med Chem Lett* 2022, 13 (8), 1311-1320. DOI: 10.1021/acsmedchemlett.2c00223 From NLM PubMed-not-MEDLINE.

(23) Xue, Y.; Chao, E.; Zuercher, W. J.; Willson, T. M.; Collins, J. L.; Redinbo, M. R. Crystal structure of the PXR-T1317 complex provides a scaffold to examine the potential for receptor antagonism. *Bioorg Med Chem* 2007, 15 (5), 2156-2166. DOI: 10.1016/j.bmc.2006.12.026 From NLM Medline.

(24) Lin, W.; Huber, A. D.; Poudel, S.; Li, Y.; Seetharaman, J.; Miller, D. J.; Chen, T. Structure-guided approach to modulate small molecule binding to a promiscuous ligand-activated protein. *Proc Natl Acad Sci USA* 2023, 120 (10), e2217804120. DOI: 10.1073/pnas.2217804120 From NLM Medline.

(25) Galdeano, C.; Gadd, M. S.; Soares, P.; Scaffidi, S.; Van Molle, I.; Birced, I.; Hewitt, S.; Dias, D. M.; Ciulli, A. Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. *J Med Chem* 2014, 57(20), 8657-8663. DOI: 10.1021/jm5011258 From NLM Medline.

(26) Harmsen, S.; Meijerman, I.; Beijnen, J. H.; Schellens, J. H. Nuclear receptor mediated induction of cytochrome P450 3A4 by anticancer drugs: a key role for the pregnane X receptor. *Cancer Chemother Pharmacol* 2009, 64 (1), 35-43. DOI: 10.1007/s00280-008-0842-3 From NLM Medline.

(27) Martinez, C.; Garcia-Martin, E.; Pizarro, R. M.; Garcia-Gamito, F. J.; Agundez, J. A. Expression of paclitaxel-inactivating CYP3A activity in human colorectal cancer: implications for drug therapy. *Br J Cancer* 2002, 87 (6), 681-686. DOI: 10.1038/sj.bjc.6600494 From NLM Medline.

(28) Masuyama, H.; Nakamura, K.; Nobumoto, E.; Hiramatsu, Y. Inhibition of pregnane X receptor pathway contributes to the cell growth inhibition and apoptosis of anticancer agents in ovarian cancer cells. *Int J Oncol* 2016, 49 (3), 1211-1220. DOI: 10.3892/ijo.2016.3611 From NLM Medline.

(29) Florke Gee, R. R.; Huber, A. D.; Wu, J.; Bajpai, R.; Loughran, A. J.; Pruett-Miller, S. M.; Chen, T. The F-box-only protein 44 regulates pregnane X receptor protein level by ubiquitination and degradation. *Acta Pharm Sin B* 2023, 13 (11), 4523-4534. DOI: 10.1016/j.apsb.2023.07.014 From NLM PubMed-not-MEDLINE.

(30) Goodwin, B.; Hodgson, E.; Liddle, C. The orphan human pregnane X receptor mediates the transcriptional activation of CYP3A4 by rifampicin through a distal enhancer module. *Mol Pharmacol* 1999, 56 (6), 1329-1339. DOI: 10.1124/mol.56.6.1329 From NLM Medline.

(31) Lin, W.; Wu, J.; Dong, H.; Bouck, D.; Zeng, F. Y.; Chen, T. Cyclin-dependent kinase 2 negatively regulates human pregnane X receptor-mediated CYP3A4 gene expression in HepG2 liver carcinoma cells. *J Biol Chem* 2008, 283 (45), 30650-30657. DOI: 10.1074/jbc.M806132200 From NLM Medline.

(32) Lin, W.; Li, Y.; Yang, L.; Chen, T. Development of BODIPY FL VH032 as a High-Affinity and Selective von Hippel-Lindau E3 Ligase Fluorescent Probe and Its Application in a Time-Resolved Fluorescence Resonance Energy-Transfer Assay. *ACS Omega* 2021, 6 (1), 680-695. DOI: 10.1021/acsomega.0c05221 From NLM PubMed-not-MEDLINE.

(33) Huber, A. D.; Poudel, S.; Wu, J.; Miller, D. J.; Lin, W.; Yang, L.; Bwayi, M. N.; Rimmer, M. A.; Gee, R. R. F.; Seetharaman, J.; et al. A bromodomain-independent mechanism of gene regulation by the BET inhibitor JQ1: direct activation of nuclear receptor PXR. *Nucleic Acids Res* 2024, 52 (4), 1661-1676. DOI: 10.1093/nar/gkad1175 From NLM Medline.

(34) Lin, W.; Bwayi, M.; Wu, J.; Li, Y.; Chai, S. C.; Huber, A. D.; Chen, T. CITCO Directly Binds to and Activates Human Pregnane X Receptor. *Mol Pharmacol* 2020, 97 (3), 180-190. DOI: 10.1124/mol.119.118513 From NLM Medline.

(35) Wang, Y. M.; Chai, S. C.; Lin, W.; Chai, X.; Elias, A.; Wu, J.; Ong, S. S.; Pondugula, S. R.; Beard, J. A.; Schuetz, E. G.; et al. Serine 350 of human pregnane X receptor is crucial for its heterodimerization with retinoid X receptor alpha and transactivation of target genes in vitro and in vivo. *Biochem Pharmacol* 2015, 96 (4), 357-368. DOI: 10.1016/j.bcp.2015.06.018 From NLM Medline.

(36) Livak, K. J.; Schmittgen, T. D. Analysis of relative gene expression data using real-time quantitative PCR and the 2(-Delta Delta C(T)) Method. *Methods* 2001, 25 (4), 402-408. DOI: 10.1006/meth.2001.1262 From NLM Medline.

It will be apparent to those skilled in the art that various modifications and variations can be made without departing from the scope or spirit of this disclosure. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A compound having a structure represented by a formula:

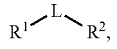

wherein L is a linker;

wherein $R^1$ is a residue of a pregnane X receptor (PXR) ligand; and wherein $R^2$ is a residue of a Cereblon (CRBN) ligand or a residue of a von Hippel-Lindau protein (pVHL) ligand, or a pharmaceutically acceptable salt thereof.

2. The compound of claim 1, wherein $R^2$ is the residue of the pVHL ligand.

3. The compound of claim 2, wherein the residue of the pVHL ligand has a structure selected from:

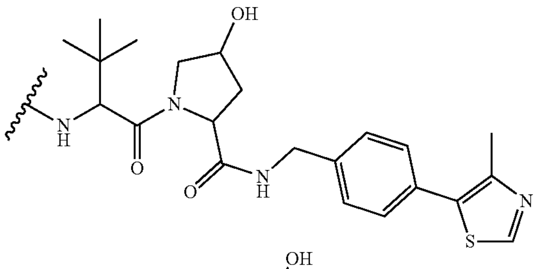

and

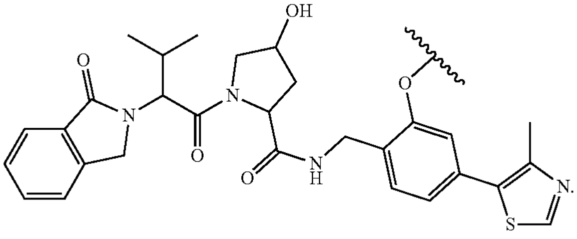

4. The compound of claim 2, wherein the residue of the pVHL ligand has a structure represented by a formula:

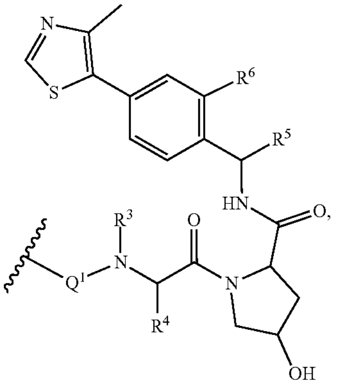

wherein $Q^1$ is selected from *—C(O)—**, *—OC(O)—**, *—$C(R^{20a})(R^{20b})C(O)$—**, *—$OC(R^{20a})(R^{20b})C(O)$—**, *—$C(R^{20a})(R^{20b})C(O)C$(cyclopropyl)C(O)—**, *—$C(R^{20a})(R^{20b})C(O)N(R^{21a})CH_2CH(R^{21b})C(O)$—**, *—C (C3-C4 cycloalkyl)C(O)—**, *—NH($CH_2CH_2O$)$_q$$CH_2$C(O)—**, *—NH$CH_2$C(cyclopropyl)C(O)—**, and *—$CH_2$C(O)N($R^{22}$)CH($R^{23}$)C(O)—**, wherein * denotes a bond connected to -L- and ** denotes a bond connected to —N($R^3$)—;

wherein q is selected from 1, 2, 3, 4, 5, and 6;

wherein each of $R^{20a}$ and $R^{20b}$ is independently selected from hydrogen and C1-C4 alkyl;

or wherein each of $R^{20a}$ and $R^{20b}$ are covalently bound, and, together comprise a C3-C4 cycloalkyl or a C2-C3 heterocycloalkyl;

or wherein $R^{20}$ is covalently bound to $R^3$, and, together with the intermediate atoms, comprises a 5-membered heterocycle;

wherein $R^4$ is selected from C1-C4 alkyl, C1-C4 hydroxyalkyl, and $C_6H_5$;

or wherein each of $R^3$ and $R^4$ are covalently bound, and, together with the intermediate atoms, comprise a 5- or 6-membered heterocycle having 0 or 1 —OH group;

or wherein each of $R^3$ and $R^{20a}$, when present, are covalently bound, and, together with the intermediate atoms, comprise a 5-membered heterocycle;

wherein $R^5$ is selected from hydrogen and methyl; and wherein $R^6$ is selected from hydrogen, —OH, and C1-C4 alkyl halide.

5. The compound of claim 1, wherein the compound is selected from:

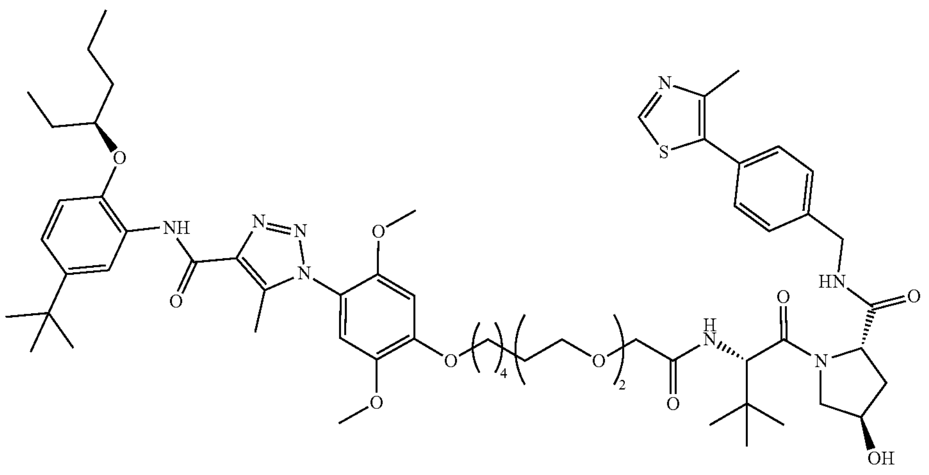

and

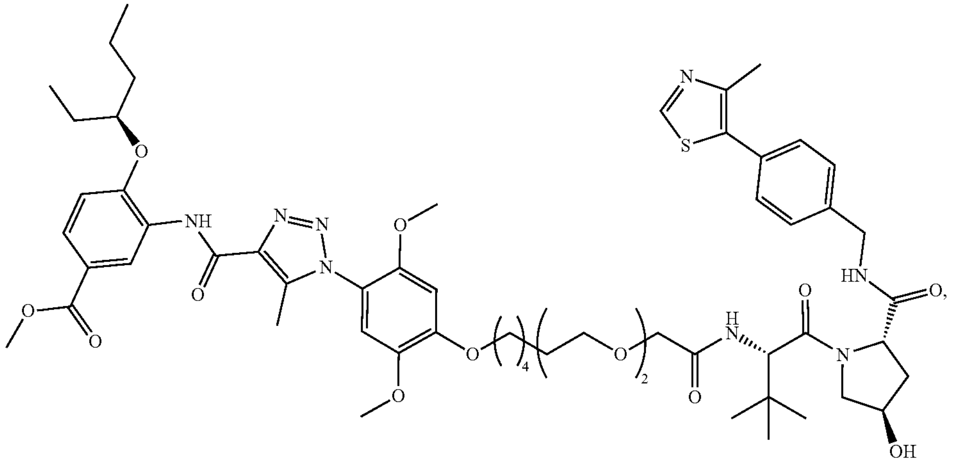

wherein each of $R^{21a}$ and $R^{21b}$ are covalently bound, and, together with the intermediate atoms, comprise a 4-membered heterocycle;

wherein $R^{22}$ is hydrogen; and wherein $R^{23}$ is selected from C1-C4 alkyl, —$CH_2C_6H_5$, and —$C_6H_5$;

or wherein each of $R^{22}$ and $R^{23}$ are covalently bound, and, together with the intermediate atoms, comprise an 10-membered heterocycloalkyl;

wherein $R^3$ is selected from hydrogen and C1-C4 alkyl; and or a pharmaceutically acceptable salt thereof.

6. A pharmaceutical composition comprising an effective amount of claim 1, or a pharmaceutically acceptable salt thereof, and a pharmaceutically acceptable carrier.

7. The compound of claim 4, wherein $Q^1$ is *—C($R^{10a}$)($R^{10b}$)C(O)—**.

8. The compound of claim 1, wherein L is selected from *-(C3-C24 alkylene)-**, *-(C3-C24 alkoxy)-**, *—($CH_2CH_2O$)$_n$—**, *—($CH_2CH_2O$)$_n$(C1-C4 alkyl)-**, and a structure selected from:

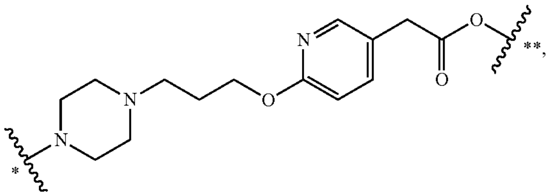

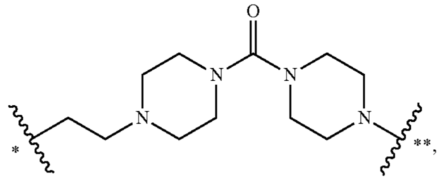

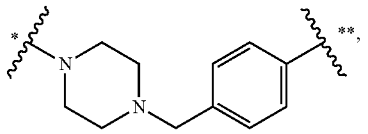

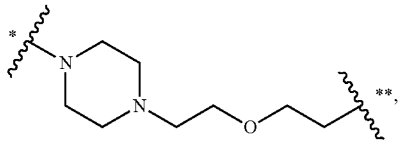

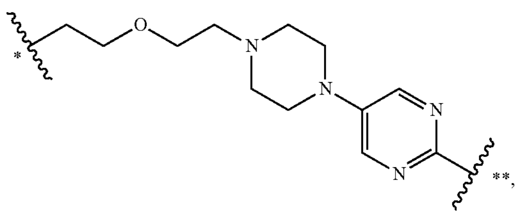

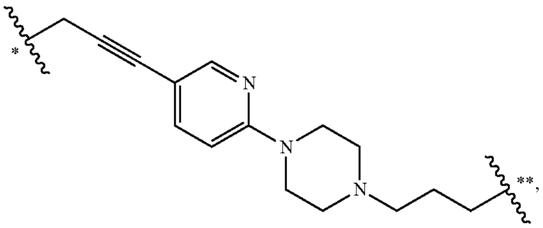

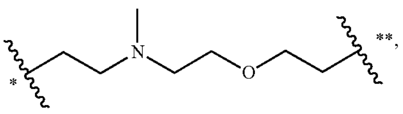

and

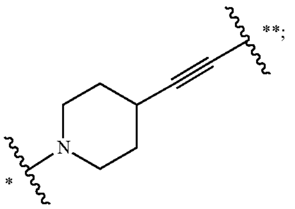

wherein * denotes a bond connected to $R^1$ and ** denotes a bond connected to $R^2$, and wherein n is selected from 2, 3, 4, 5, 6, 7, and 8.

9. The compound of claim 8, wherein L is *—$(CH_2CH_2O)_n$—**.

10. The compound of claim 1, wherein the residue of the PXR ligand has a structure represented by a formula:

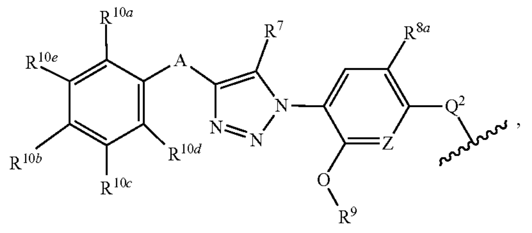

wherein A is selected from *—$SO_2$—**, *—$NR^{24}C(O)$—**, *—$N(R^{24})C(O)NR^{25}$—** *—$C(O)NR^{24}$—**, *—$SO_2NR^{24}$—**, and *—$NR^{24}SO_2$—**, wherein * denotes a bond connected to the triazole and ** denotes a bond connected to the phenyl;

wherein each of $R^{24}$ and $R^{25}$ is independently selected from hydrogen and C1-C4 alkyl;

wherein $Q^2$ is selected from *—O—**, *—O(C1-C8 alkylene)-**, *—$OCH_2C(O)NH$—**, and *—C(O)NH—**, wherein * denotes a bond connected to the phenyl and ** denotes a bond connected to -L-;

wherein Z is selected from N and CH;

wherein $R^7$ is selected from hydrogen and C1-C4 alkyl;

wherein $R^{8a}$ is selected from hydrogen, halogen, C1-C4 alkyl, C1-C4 haloalkyl, C1-C4 alkoxy, and C1-C4 haloalkoxy;

wherein $R^9$ is C1-C4 alkyl; and wherein each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, C1-C8 alkylamino, and —$CO_2$(C1-C4 alkyl).

11. The compound of claim 10, wherein A is selected from *—$C(O)NR^{24}$—** and *—$SO_2NR^{24}$—**.

12. The compound of claim 10, wherein the compound has a structure represented by a formula:

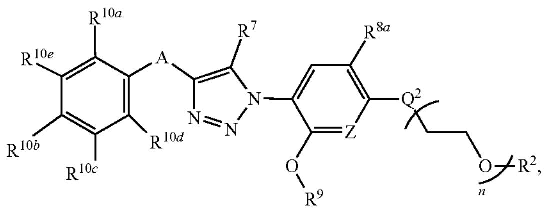

wherein n is selected from 2, 3, 4, 5, 6, 7, and 8, or a pharmaceutically acceptable salt thereof.

13. The compound of claim 1, wherein the compound has a structure represented by a formula:

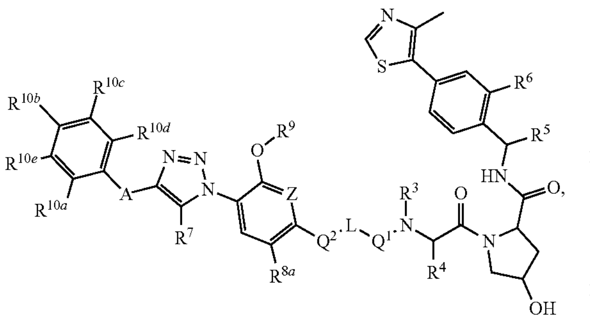

wherein A is selected from *—$SO_2$—**, *—$NR^{24}C(O)$—**, *—$N(R^{24})C(O)NR^{25}$—** *—$C(O)NR^{24}$—**, *—$SO_2NR^{24}$—**, and *—$NR^{24}SO_2$—**, wherein * denotes a bond connected to the triazole and ** denotes a bond connected to the phenyl;

wherein each of $R^{24}$ and $R^{25}$ is independently selected from hydrogen and C1-C4 alkyl;

wherein $Q^1$ is selected from *—C(O)—**, *—OC(O)—**, *—$C(R^{20a})(R^{20b})C(O)$—**, *—$OC(R^{20a})(R^{20b})C(O)$—**, *—$C(R^{20a})(R^{20b})C(O)C$(cyclopropyl)C(O)—**, *—$C(R^{20a})(R^{20b})C(O)N(R^{21a})CH_2CH(R^{21b})C(O)$—**, *—C(C3-C4 cycloalkyl)C(O)—**, *—$NH(CH_2CH_2O)_qCH_2C(O)$—**, *—$NHCH_2C$(cyclopropyl)C(O)—**, and *—$CH_2C(O)N(R^{22})CH(R^{23})C(O)$—**, wherein * denotes a bond connected to -L- and ** denotes a bond connected to —$N(R^3)$—;

wherein q is selected from 1, 2, 3, 4, 5, and 6;

wherein each of $R^{20a}$ and $R^{20b}$ is independently selected from hydrogen and C1-C4 alkyl;

or wherein each of $R^{20a}$ and $R^{20b}$ are covalently bound, and, together comprise a C3-C4 cycloalkyl or a C2-C3 heterocycloalkyl;

or wherein $R^{20}$ is covalently bound to $R^3$, and, together with the intermediate atoms, comprises a 5-membered heterocycle;

wherein each of $R^{21a}$ and $R^{21b}$ are covalently bound, and, together with the intermediate atoms, comprise a 4-membered heterocycle;

wherein $R^{22}$ is hydrogen; and wherein $R^{23}$ is selected from C1-C4 alkyl, —$CH_2C_6H_5$, and —$C_6H_5$;

or wherein each of $R^{22}$ and $R^{23}$ are covalently bound, and, together with the intermediate atoms, comprise an 10-membered heterocycloalkyl;

wherein $Q^2$ is selected from *—O—**, *—O(C1-C8 alkylene)-**, *—$OCH_2C(O)NH$—**, and *—C(O)NH—**, wherein * denotes a bond connected to the phenyl and ** denotes a bond connected to -L-;

wherein Z is selected from N and CH;

wherein $R^3$ is hydrogen or C1-C4 alkyl; and wherein $R^4$ is a C1-C4 alkyl, C1-C4 hydroxyalkyl, or $C_6H_5$;

or wherein each of $R^3$ and $R^4$ are covalently bound, and, together with the intermediate atoms, comprise a 5- or 6-membered heterocycle having 0 or 1 —OH group;

or wherein each of $R^3$ and $R^{10}$, when present, are covalently bound, and, together with the intermediate atoms, comprise a 5-membered heterocycle;

wherein $R^5$ is hydrogen or methyl;

wherein $R^6$ is hydrogen, —OH, or C1-C4 alkyl halide;

wherein $R^7$ is selected from hydrogen and C1-C4 alkyl;

wherein $R^{8a}$ is selected from hydrogen, halogen, C1-C4 alkyl, C1-C4 haloalkyl, C1-C4 alkoxy, and C1-C4 haloalkoxy;

wherein $R^9$ is C1-C4 alkyl; and wherein each of $R^{10a}$, $R^{10b}$, $R^{10c}$, $R^{10d}$, and $R^{10e}$ is independently selected from hydrogen, halogen, —CN, —$NH_2$, —OH, —$NO_2$, C1-C8 alkyl, C2-C8 alkenyl, C1-C8 haloalkyl, C1-C8 cyanoalkyl, C1-C8 hydroxyalkyl, C1-C8 haloalkoxy, C1-C8 alkoxy, C1-C8 alkylamino, (C1-C8)(C1-C8) dialkylamino, C1-C8 alkylamino, and —$CO_2$(C1-C4 alkyl), or a pharmaceutically acceptable salt thereof.

14. The compound of claim 13, wherein the compound has a structure represented by a formula:

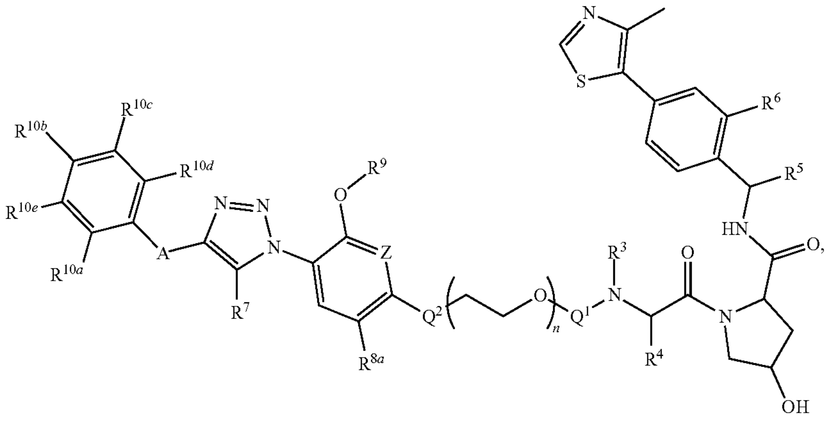

wherein n is selected from 2, 3, 4, 5, 6, 7, and 8, or a pharmaceutically acceptable salt thereof.

15. The compound of claim 1, wherein the compound is selected from:
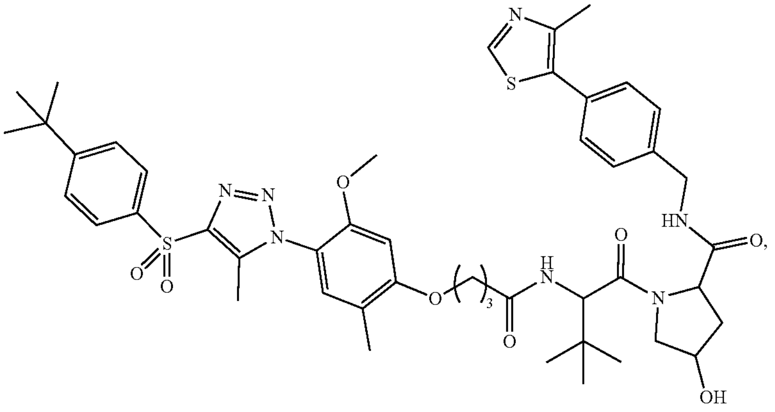
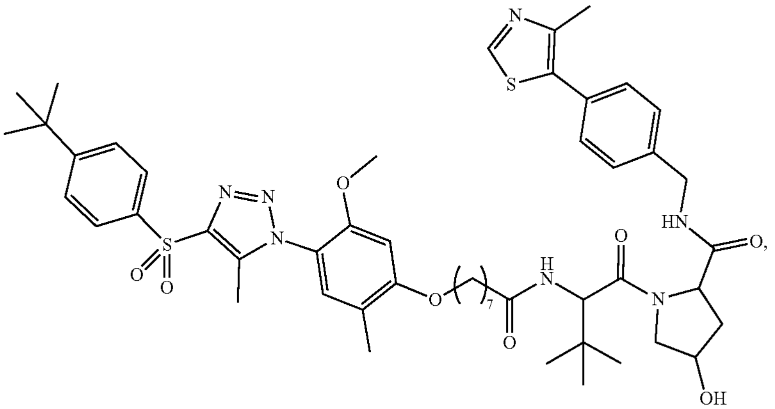
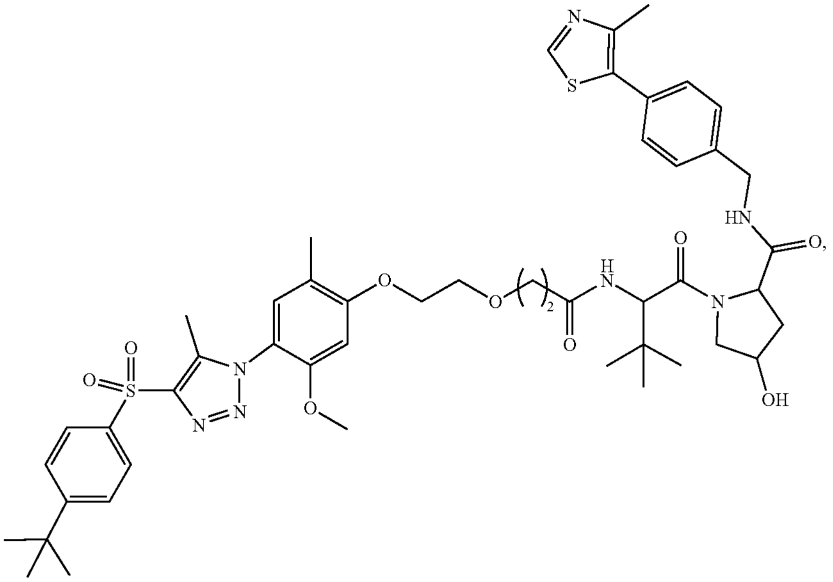

-continued
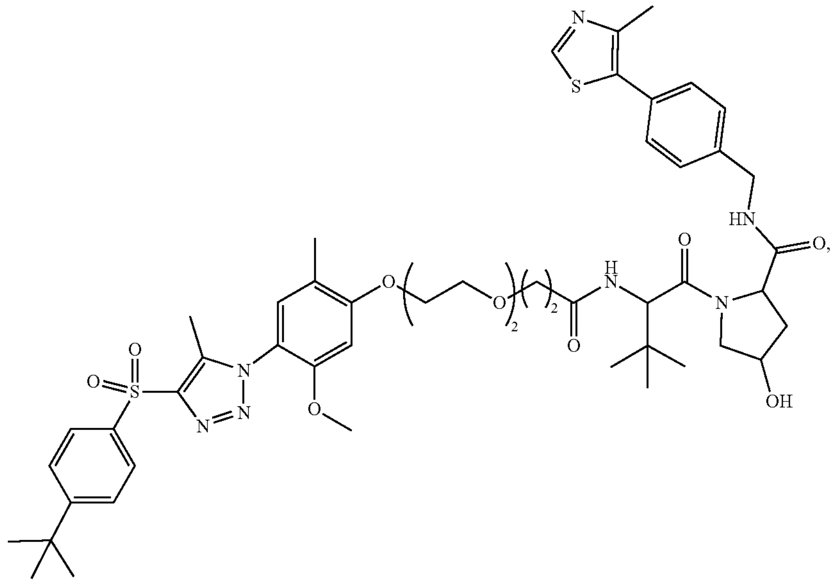
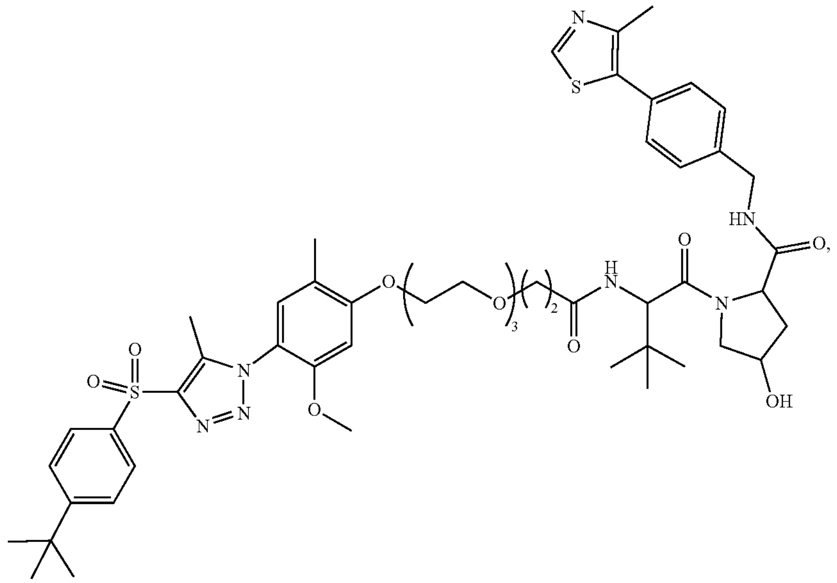

-continued
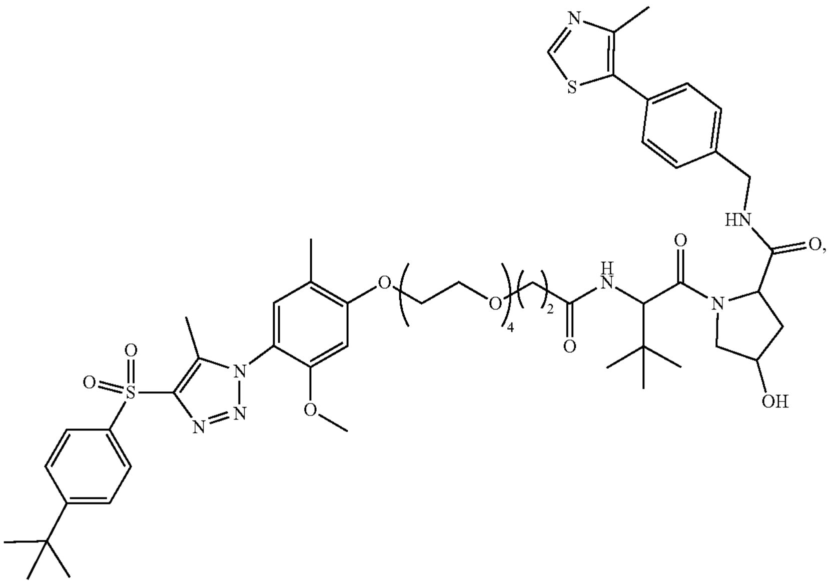
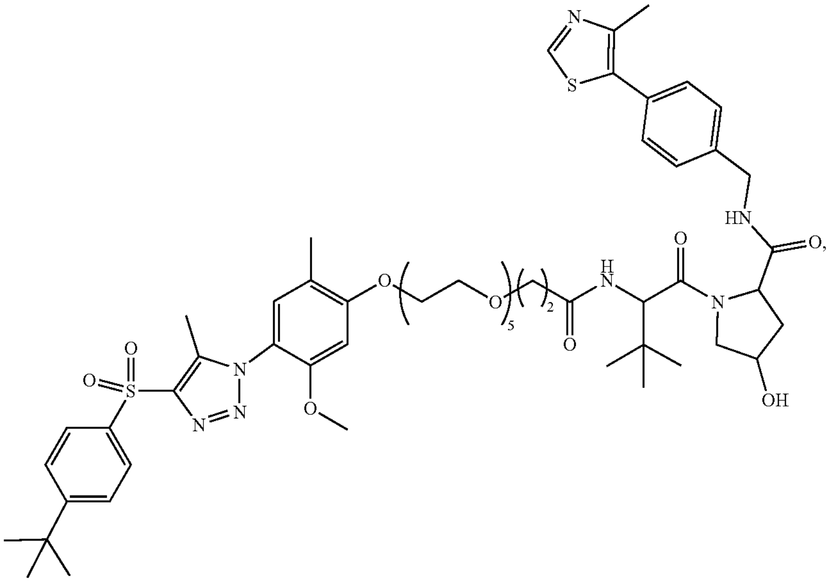
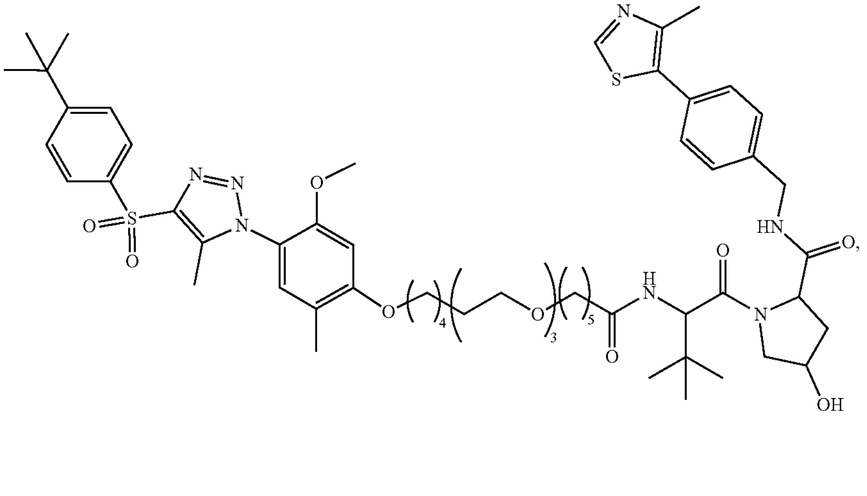

-continued
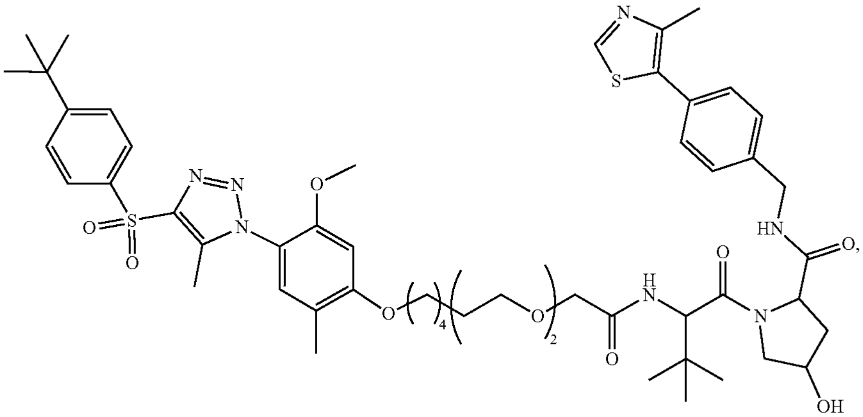
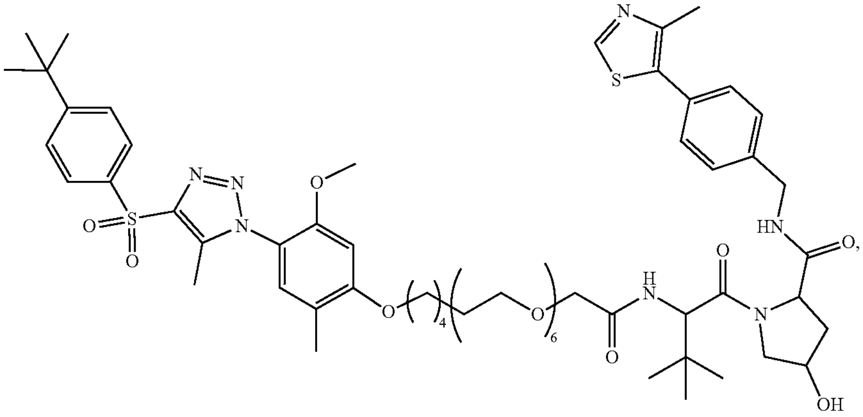
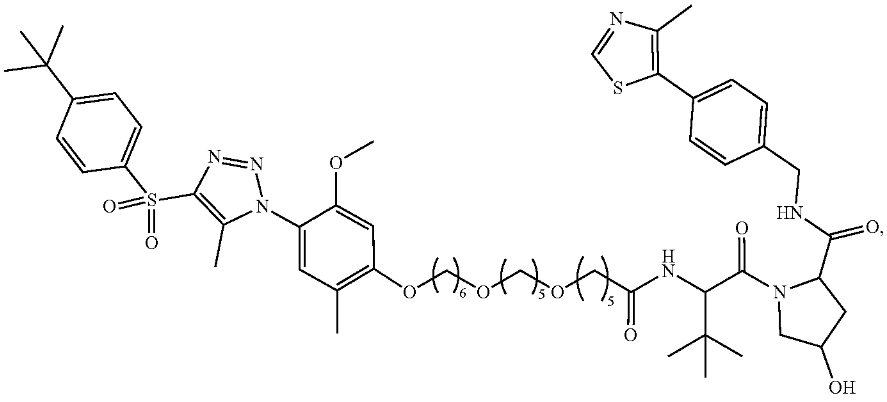
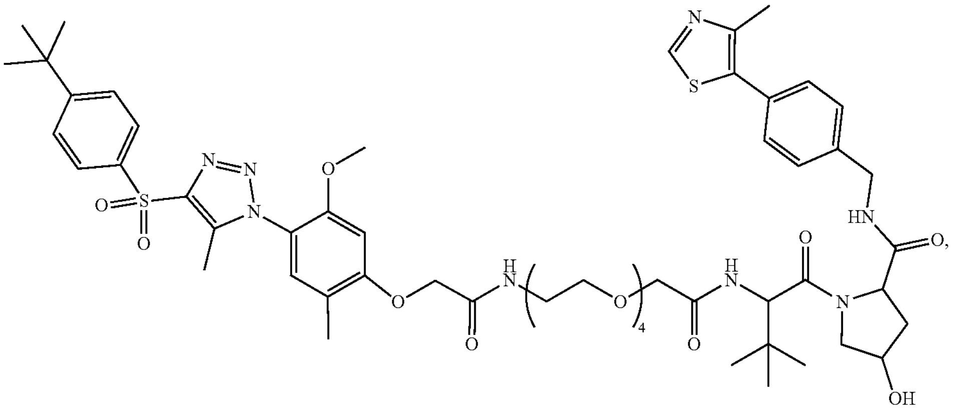

-continued
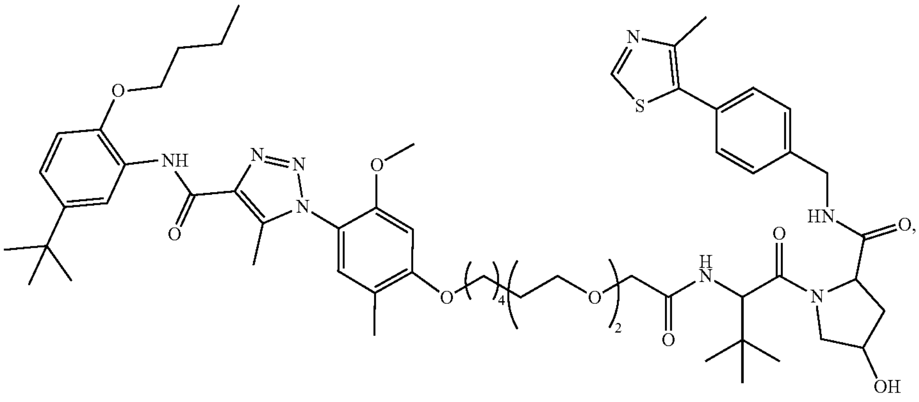
,
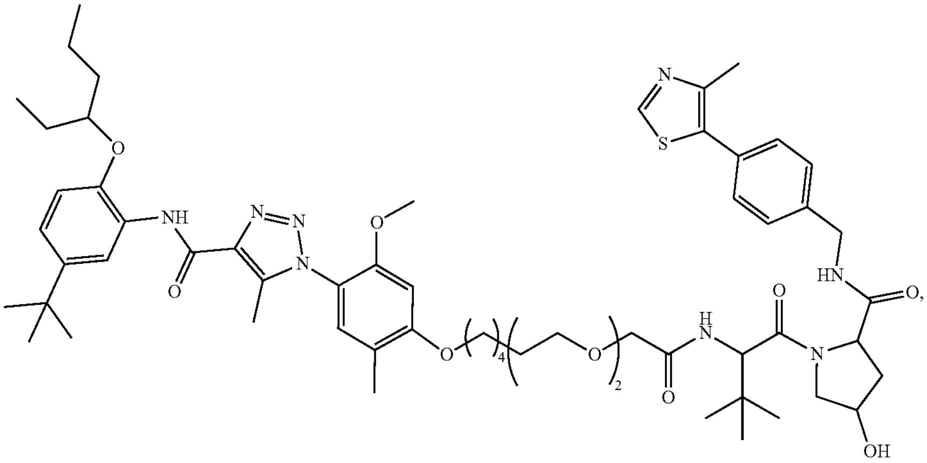
,
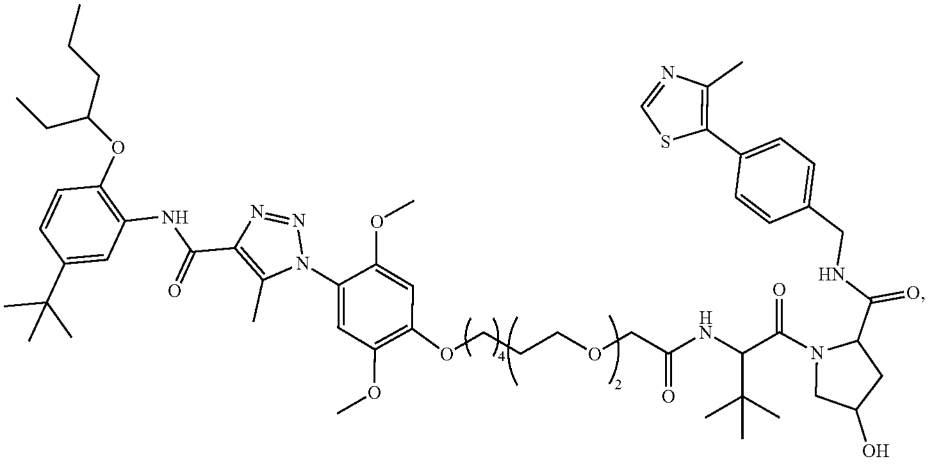
, and

-continued
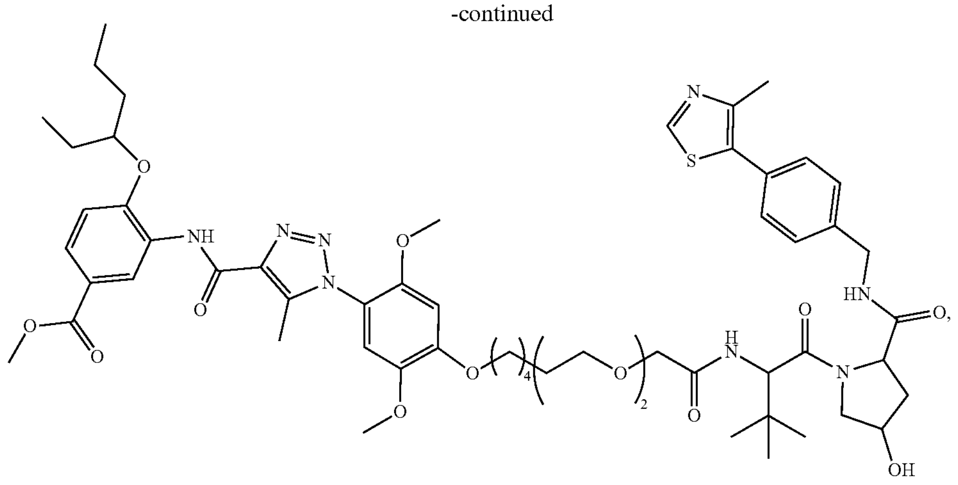
or a pharmaceutically acceptable salt thereof.
* * * * *